(12) United States Patent
Tan et al.

(10) Patent No.: US 11,180,492 B2
(45) Date of Patent: Nov. 23, 2021

(54) ANTI-PARASITIC COMPOUNDS AND USES THEREOF

(71) Applicants: Memorial Sloan-Kettering Cancer Center, New York, NY (US); The Regents of the University of California, Oakland, CA (US); University of Central Florida Research Foundation, Inc., Orlando, FL (US); The Broad Institute, Inc., Cambridge, MA (US)

(72) Inventors: Derek Shieh Tan, New York, NY (US); Corinne N. Foley, New York, NY (US); Gustavo Moura-Letts, New York, NY (US); James McKerrow, New York, NY (US); Sivaraman Dandapani, Wakefield, MA (US); Rahul Edwankar, New York, NY (US); Alyssa Verano, New York, NY (US); Debopam Chakrabarti, Winter Springs, FL (US); Bracken Roberts, Oviedo, FL (US)

(73) Assignees: University of Central Florida Research Foundation, Inc., Orlando, FL (US); The Regents of the University of California, Oakland, CA (US); Memorial Sloan-Kettering Cancer Center, New York, NY (US); The Broad Institute, Inc., Cambridge, MA (US)

( * ) Notice: Subject to any disclaimer, the term of this patent is extended or adjusted under 35 U.S.C. 154(b) by 0 days.

(21) Appl. No.: 16/070,137

(22) PCT Filed: Jan. 17, 2017

(86) PCT No.: PCT/US2017/013755
§ 371 (c)(1),
(2) Date: Jul. 13, 2018

(87) PCT Pub. No.: WO2017/124087
PCT Pub. Date: Jul. 20, 2017

(65) Prior Publication Data
US 2019/0002463 A1    Jan. 3, 2019

Related U.S. Application Data

(60) Provisional application No. 62/384,653, filed on Sep. 7, 2016, provisional application No. 62/279,401, filed on Jan. 15, 2016.

(51) Int. Cl.
*C07D 471/04* (2006.01)
*A61P 33/00* (2006.01)
*A61P 33/06* (2006.01)

(52) U.S. Cl.
CPC ............ *C07D 471/04* (2013.01); *A61P 33/00* (2018.01); *A61P 33/06* (2018.01)

(58) Field of Classification Search
CPC ......... C07D 471/04; A61P 33/00; A61P 33/06
(Continued)

(56) References Cited

U.S. PATENT DOCUMENTS

2004/0038973 A1 * 2/2004 Nahra ................. C07D 209/46
514/243
2014/0296531 A1 10/2014 Pudhom et al.

FOREIGN PATENT DOCUMENTS

| EP | 1746097 B1 | 1/2010 | |
| WO | WO-2015089327 A1 * | 6/2015 | ........... C07D 471/04 |
| WO | WO 2016/172261 A1 | 10/2016 | |

OTHER PUBLICATIONS

Trost; Org. Lett., 2007, 1473-1476. (Year: 2007).*

(Continued)

*Primary Examiner* — Daniel R Carcanague
(74) *Attorney, Agent, or Firm* — Wolf, Greenfield & Sacks, P.C.

(57) ABSTRACT

The present disclosure provides compounds of Formula (I'), Formula (II), and Formula (III). The compounds described herein may useful in treating and/or preventing protozoan infections in a subject in need thereof, treating and/or preventing trypanosomal infections (e.g., *Trypanosoma cruzi* (*T. cruzi*) or *Trypanosoma brucei* infections) and/or plasmodial infections in a subject in need thereof, treating and/or preventing diseases in a subject in need thereof (e.g., Chagas disease, malaria, and/or sleeping sickness), and may be useful in treating and/or preventing infectious diseases in a subject in need thereof. Also provided in the present disclosure are pharmaceutical compositions, kits, methods, and uses including a compound described herein.

(Continued)

-continued

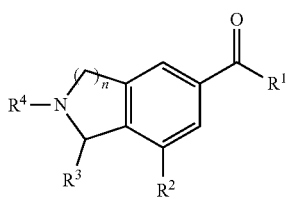

(III)

29 Claims, 9 Drawing Sheets

(58) Field of Classification Search
USPC .......................................................... 514/300
See application file for complete search history.

(56) References Cited

OTHER PUBLICATIONS

Moura-Letts; PNAS 2011, 108 (17), pp. 6745-6750, and supporting information p. S1-S189. (Year: 2011).*
Chemical Abstracts STN Registry Database, Entry for RN 1414845-33-2, entered STN: Dec. 14, 2012. (Year: 2012).*
Chemical Abstracts STN Registry Database, Entry for RN 1414845-43-4, entered STN: Dec. 14, 2012. (Year: 2012).*
Chemical Abstracts STN Registry Database, Entry for RN 1414845-44-5, entered STN: Dec. 14, 2012. (Year: 2012).*
National Center for Biotechnology Information. PubChem Compound Database; CID=56835569, https://pubchem.ncbi.nlm.nih.gov/compound/56835569 (accessed Jan. 25, 2019). Create Date: Mar. 13, 2012. (Year: 2012).*
National Center for Biotechnology Information. PubChem Compound Database; CID=56835583, https://pubchem.ncbi.nlm.nih.gov/compound/56835583 (accessed Jan. 25, 2019). Create Date: Mar. 13, 2012. (Year: 2012).*
National Center for Biotechnology Information. PubChem Compound Database; CID=56835584, https://pubchem.ncbi.nlm.nih.gov/compound/56835584 (accessed Jan. 25, 2019). Create Date: Mar. 13, 2012. (Year: 2012).*
National Center for Biotechnology Information. PubChem Database. MLS003269600, Source=MLSMR, SID=121286056, available on May 18, 2011 https://pubchem.ncbi.nlm.nih.gov/substance/121286056 (accessed on Jun. 14, 2019). (Year: 2011).*
National Center for Biotechnology Information. PubChem Database. BRD-K28061285-001-01-9, Source=Broad Institute, SID=161005166, available on Mar. 15, 2014 https://pubchem.ncbi.nlm.nih.gov/substance/161005166 (accessed on Jun. 14, 2019) (Year: 2014).*
Chemical Abstracts STN Registry Database, Entry for RN 1414845-32-1, entered STN: Dec. 14, 2012. (Year: 2012).*
Chemical Abstracts STN Registry Database, Entry for RN 1414845-35-4, entered STN: Dec. 14, 2012. (Year: 2012).*
Chemical Abstracts STN Registry Database, Entry for RN 1414845-36-5, entered STN: Dec. 14, 2012. (Year: 2012).*
Chemical Abstracts STN Registry Database, Entry for 1414845-38-7, entered STN: Dec. 14, 2012. (Year: 2012).*
Chemical Abstracts STN Registry Database, Entry for 1414845-39-8, entered STN: Dec. 14, 2012. (Year: 2012).*
Chemical Abstracts STN Registry Database, Entry for 1414845-41-2, entered STN: Dec. 14, 2012. (Year: 2012).*
Boger; J. Org. Chem. 1989, 54, 714-718. (Year: 1989).*
National Center for Biotechnology Information. PubChem Database. MLS003487533, Source=MLSMR, SID=124753802, https://pubchem.ncbi.nlm.nih.gov/substance/124753802 (accessed on Jan. 6, 2020). Date Available: Aug. 3, 2011. (Year: 2011).*

National Center for Biotechnology Information. PubChem Database. CID=53299818, https://pubchem.ncbi.nlm.nih.gov/compound/53299818 (accessed on Jan. 6, 2020). Create Date Aug. 3, 2011. (Year: 2011).*
National Center for Biotechnology Information. PubChem Database. CID=53299845, https://pubchem.ncbi.nlm.nih.gov/compound/53299845 (accessed on Jan. 6, 2020). Create Date Aug. 3, 2011. (Year: 2011).*
National Center for Biotechnology Information. PubChem Database. CID=54649330, https://pubchem.ncbi.nlm.nih.gov/compound/54649330 (accessed on Jan. 6, 2020). Create Date Dec. 20, 2011. (Year: 2011).*
National Center for Biotechnology Information. PubChem Database. CID=54649433, https://pubchem.ncbi.nlm.nih.gov/compound/54649433 (accessed on Jan. 6, 2020). Create Date Dec. 20, 2011. (Year: 2011).*
National Center for Biotechnology Information. PubChem Database. CID=54649368, https://pubchem.ncbi.nlm.nih.gov/compound/54649368 (accessed on Jan. 7, 2020). Create Date Dec. 20, 2011. (Year: 2011).*
National Center for Biotechnology Information. PubChem Database. CID=51361352, https://pubchem.ncbi.nlm.nih.gov/compound/51361352 (accessed on Jan. 7, 2020). Create Date May 18, 2011. (Year: 2011).*
National Center for Biotechnology Information. PubChem Database. CHEBI:102279, Source=ChEBI, SID=85307876, Available Nov. 19, 2009, https://pubchem.ncbi.nlm.nih.gov/substance/85307876 (accessed on May 29, 2020) (Year: 2009).*
National Center for Biotechnology Information. PubChem Database. MLS003367994, Source=MLSMR, SID=121286413, Available May 18, 2011, https://pubchem.ncbi.nlm.nih.gov/substance/121286413 (accessed on May 29, 2020) (Year: 2011).*
National Center for Biotechnology Information. PubChem Database. BRD-K15752674-001-02-5, Source=Broad Institute, SID=144198985, Available Sep. 28, 2012, https://pubchem.ncbi.nlm.nih.gov/substance/144198985 (accessed on May 29, 2020) (Year: 2012).*
Sainz; J. Org. Chem. 2005, 70, 24, 10086-10095 and S1-S4. DOI: 10.1021/jo0518304 (Year: 2005).*
Buysens; Tetrahedron, 1996, 52, 9161-9178. (Year: 1996).*
Bonaga; Chem. Commun., 2004, 2394-2395, with supplemental material, 23 pages. (Year: 2004).*
Carly; Tetrahedron 2001, 57, 4203-4212. (Year: 2001).*
National Center for Biotechnology Information. "PubChem Compound Summary for CID 53299837" PubChem, https://pubchem.ncbi.nlm.nih.gov/compound/53299837. Accessed Nov. 2, 2020. Create Date Aug. 3, 2011. (Year: 2011).*
Chemical Abstracts STN Registry Database, record for RN 1346789-00-1, entered on Dec. 1, 2011. (Year: 2011).*
Chemical Abstracts STN Registry Database, record for RN 1256822-81-7, entered on Dec. 16, 2010. (Year: 2010).*
National Center for Biotechnology Information. PubChem Compound Summary for CID 60192566. https://pubchem.ncbi.nlm.nih.gov/compound/60192566. Create Date Sep. 28, 2012. (Year: 2012).*
Saito; Tetrahedron Letters (2007), 48(39), 6852-6855. (Year: 2007).*
Stolle; Tetrahedron (1992), 48(9), 1643-1656. (Year: 1992).*
Chemical Abstracts STN Registry Database, record for RN 1346926-02-0, entered on Dec. 1, 2011. (Year: 2011).*
Chemical Abstracts STN Registry Database, record for RN 1349743-04-9, entered on Dec. 6, 2011. (Year: 2011).*
PubChem AID 624255. BioAssay record. Jun. 4, 2012.
PubChem AID 624280. Bio Assay record. Aug. 6, 2013.
PubChem AID 1159554. Bio Assay record. Sep. 22, 2015.
PubChem SID 131445833. Substance Record. Dec. 20, 2011.
PubChem SID 134962318. Substance Record. Mar. 13, 2012.
PubChem SID 131445766. Substance Record. Dec. 20, 2011.
PubChem SID 144198206. Substance Record. Sep. 28, 2012.
PubChem CID 130230303. Compound Summary. Oct. 10, 2017.
PubChem CID 60183770. Compound Summary. Sep. 28, 2012.
Bauer et al., The tert-butylsulfinamide lynchpin in transition-metal-mediated multiscaffold library synthesis. Org Lett. May 7, 2010;12(9):2084-7. doi: 10.1021/ol100574y.

(56) References Cited

OTHER PUBLICATIONS

PubChem SID 162653720. 2013. Retrieved on Apr. 11, 2017. https://pubchem.ncbi.nlm.nih.gov/substance/162653720#section=Top>.
PubChem SID 164121711. 2013. Retrieved on Feb. 15, 2017 https://pubchem.ncbi.nlm.nih.gov/substance/164121711#section=Top>.
PubChem SID 218001288. 2014. Retrieved on Feb. 15, 2017. https://pubchem.ncbi.nhn.nih.gov I substance/218001288#section=top>.
[No Author Listed] PubChem Structure No. CID70789993 Search Results: Similarity Tab. https://pubchem.ncbi.nlm.nih.gov/#query=CID70789993%20structure&tab=similarity [last accessed Sep. 19, 2019]. 21 pages.
[No Author Listed] PubChem Structure No. CID54649433 Search Results: Similarity Tab. https://pubchem.ncbi.nlm.nih.gov/#query=CID54649433 structure&tab=similarity [last accessed May 21, 2020]. 6 pages.
[No Author Listed] PubChem Structure No. CID54649433 Search Results: Similarity Tab. https://pubchem.ncbi.nlm.nih.gov/#query=CID54649433 structure&tab=similarity [last accessed May 19, 2020]. 6 pages.
[No Author Listed] PubChem Structure No. CID54649433 Search Results: Same, Connectivity. https://ncbi.nlm.nih.gov/pccompound?cmd=Link&LinkName=pccompound_pccompound_sameconnectivity_pulldown&from_uid=54649433 [last accessed May 19, 2020]. 1 page.

* cited by examiner

ANTI-PARASITIC COMPOUNDS AND USES THEREOF

RELATED APPLICATIONS

This application is a national stage filing under 35 U.S.C. § 371 of international PCT application, PCT/US2017/013755, filed Jan. 17, 2017, which claims priority under 35 U.S.C. § 119(e) to U.S. Provisional Applications, U.S. Ser. No. 62/279,401, filed Jan. 15, 2016, and U.S. Ser. No. 62/384,653, filed Sep. 7, 2016, each of which is incorporated herein by reference.

GOVERNMENT SUPPORT

This invention was made with government support under grant numbers CA062948, GM076267, HG005032, CA104685, CA008748, AI122326, and AI128517 awarded by the National Institutes of Health. The government has certain rights in the invention.

BACKGROUND OF THE INVENTION

Chagas disease, caused by the protozoan parasite *Trypanosoma cruzi* (*T. cruzi*), is a major cause of heart failure in Central and South America, leading to 12,000 deaths per year. Infected individuals are also increasingly detected in non-endemic areas due to emigration. In the United States in particular, at least 300,000 individuals are currently infected. However, there are no FDA-approved drugs currently available. The two drugs currently used in Latin America, nifurtimox and benznidazole, are limited by side effects, treatment duration, and route of administration. There is therefore a need for new treatments against protozoan infections including *T. cruzi* infections and Chagas disease.

Malaria, another parasitic disease, causes 300 million clinical cases and about a million deaths each year, (see WHO "World malaria report," World Health Organization, 2011, www.who.int/malaria/publications/world malaria report/en/), but the drugs that are available for treatment are rapidly losing their efficacy because of widespread prevalence of drug resistant parasites. (see Rieckmann, K. H., "The chequered history of malaria control: are new and better tools the ultimate answer?" *Ann. Trop. Med. Parasitol.* 2006, 100, 647-662; Greenwood, D. "Conflicts of interest: the genesis of synthetic antimalarial agents in peace and war," *J. Antimicrob. Chemother.* 1995, 36, 857-872, www.ncbi.nlm.nih.gov/pubmed/8626269; Murray et al., "Global malaria mortality between 1980 and 2010: a systematic analysis," *Lancet,* 2012, 379, 413-431). There is therefore a need for new treatments against protozoan infections including trypanosomal infections (e.g., Chagas disease, African sleeping sickness) and plasmodial infections (e.g., malaria).

SUMMARY OF THE INVENTION

Described herein are anti-parasitic compounds. In one aspect, described herein are compounds of Formula (I'), Formula (II), Formula (III), and pharmaceutically acceptable salts, solvates, hydrates, polymorphs, co-crystals, tautomers, stereoisomers, isotopically labeled derivatives, and prodrugs thereof. The compounds described herein may be useful in treating infectious disease, particularly in treating parasitic disease. The compounds described herein may be useful in treating parasitic infections, particularly protozoan infections, and also bacterial infections. The compounds described herein may be useful in treating trypanosomal infections (e.g. *T. cruzi* infections) and/or treating plasmodial infections (e.g., malaria). The compounds described herein may be anti-parasitic compounds, particularly anti-trypanosomal and/or anti-plasmodial compounds. The compounds may be useful in treating parasitic infections in a subject in need thereof, treating protozoan infections in a subject in need thereof, treating trypanosomal infections (e.g., *Trypanosoma cruzi* (*T. cruzi*) infections) in a subject in need thereof, and/or treating plasmodial infections (e.g., malaria) in a subject in need thereof, treating an infectious disease in a subject in need thereof (e.g., Chagas disease, sleeping sickness, and/or malaria), preventing an infectious disease in a subject at risk of developing an infectious disease, preventing a protozoan infection in a subject at risk of developing a protozoan infection, preventing a trypanosomal infection in a subject at risk of developing a trypanosomal infection (e.g., *T. cruzi* or *Trypanosoma brucei* infections), preventing a plasmodial infection in a subject at risk of developing a plasmodial infection, preventing a protozoan infection in a subject at risk of developing a protozoan infection (e.g., trypanosomal infection from *T. cruzi* or *Trypanosoma brucei*, and/or plasmodial infections), preventing diseases in a subject in need thereof (e.g., Chagas disease, malaria, and/or sleeping sickness), preventing infectious diseases in a subject in need thereof, and as research tools (e.g., for studying trypanosomal infections (e.g., studying *T. cruzi* infections) and/or, plasmodial infections in a subject, biological sample, tissue, or cell). Also provided are pharmaceutical compositions, kits, methods, and uses including a compound described herein.

In one aspect, the present disclosure provides compounds of Formula (I'):

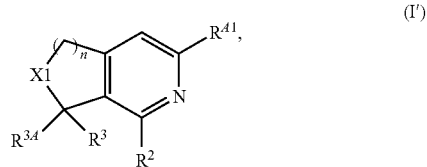

(I')

and pharmaceutically acceptable salts, solvates, hydrates, polymorphs, co-crystals, tautomers, stereoisomers, isotopically labeled derivatives, and prodrugs thereof, wherein n, X1, $R^{41}$, $R^2$, $R^3$, and $R^{3A}$ are as defined herein.

In some embodiments, the present disclosure provides compounds of Formula (I'-A):

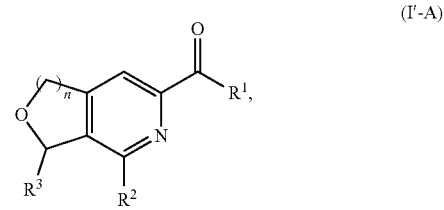

(I'-A)

and pharmaceutically acceptable salts, solvates, hydrates, polymorphs, co-crystals, tautomers, stereoisomers, isotopically labeled derivatives, and prodrugs thereof, wherein n, $R^1$, $R^2$, and $R^3$ are as defined herein.

In some embodiments, the present disclosure provides compounds of Formula (I'-B):

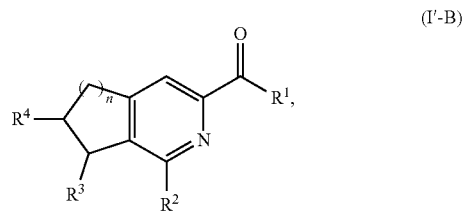

(I'-B)

and pharmaceutically acceptable salts, solvates, hydrates, polymorphs, co-crystals, tautomers, stereoisomers, isotopically labeled derivatives, and prodrugs thereof, wherein n, $R^1$, $R^2$, $R^3$, and $R^4$ are as defined herein.

In some embodiments, the present disclosure provides compounds of Formula (I'-C):

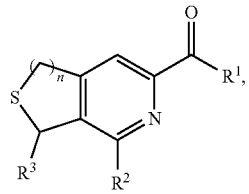
(I'-C)

and pharmaceutically acceptable salts, solvates, hydrates, polymorphs, co-crystals, tautomers, stereoisomers, isotopically labeled derivatives, and prodrugs thereof, wherein n, $R^1$, $R^2$, and $R^3$ are as defined herein.

In one aspect, the present disclosure provides compounds of Formula (I):

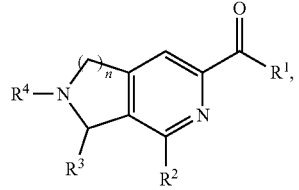
(I)

and pharmaceutically acceptable salts, solvates, hydrates, polymorphs, co-crystals, tautomers, stereoisomers, isotopically labeled derivatives, and prodrugs thereof, wherein n, $R^1$, $R^2$, $R^3$, and $R^4$ are as defined herein.

Exemplary compounds of Formula (I') and (I) include, but are not limited to:

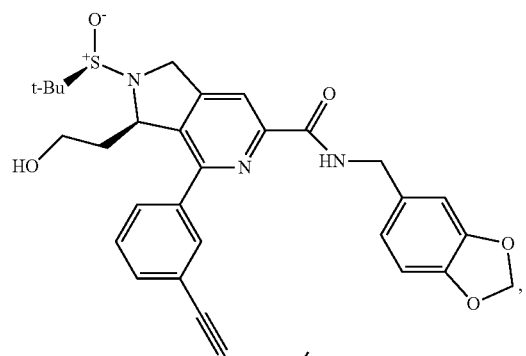

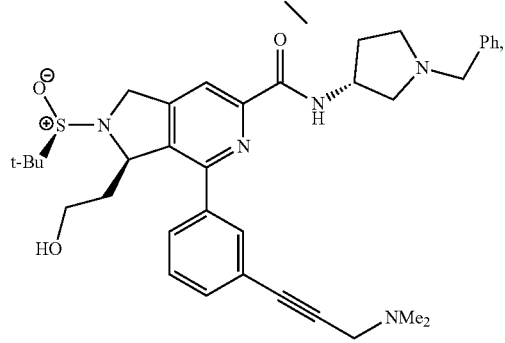

-continued

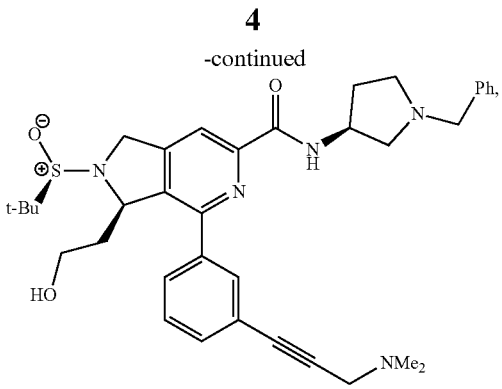

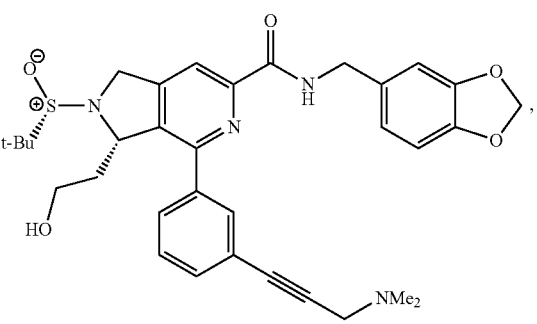

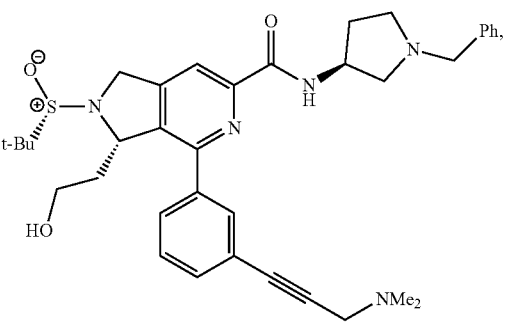

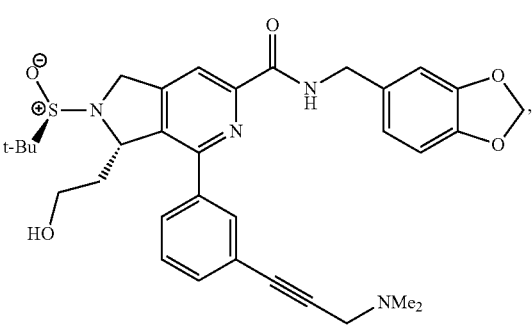

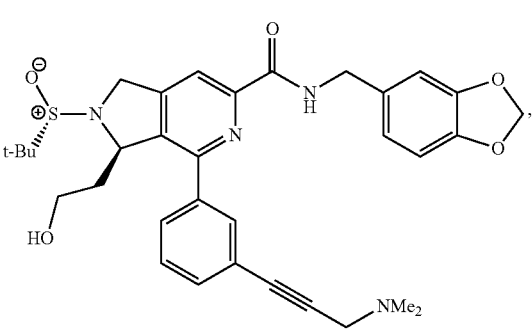

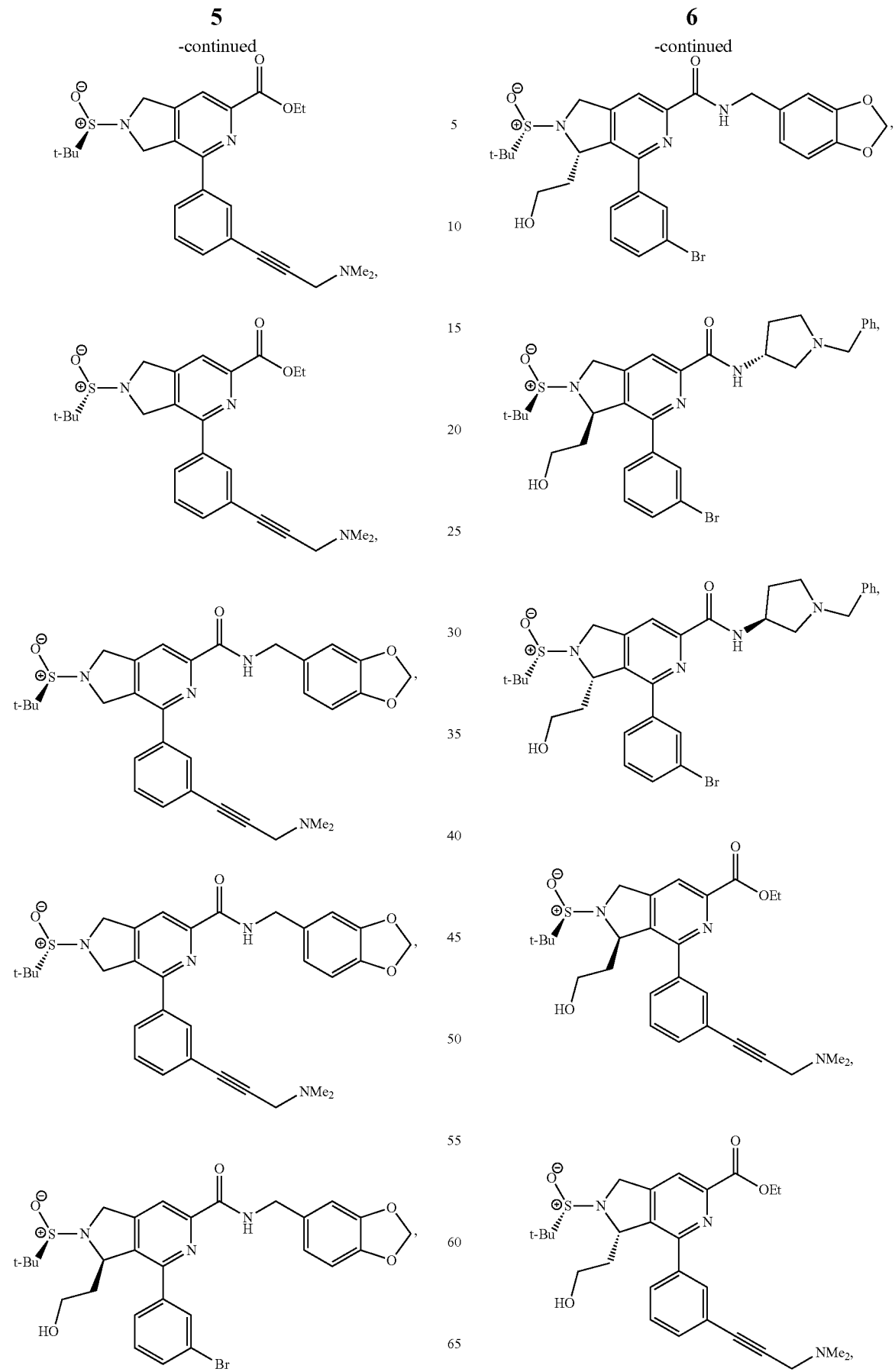

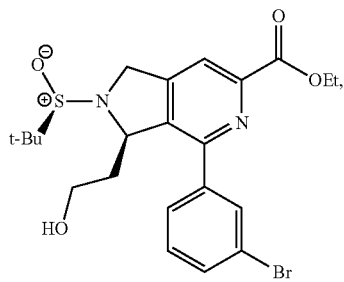
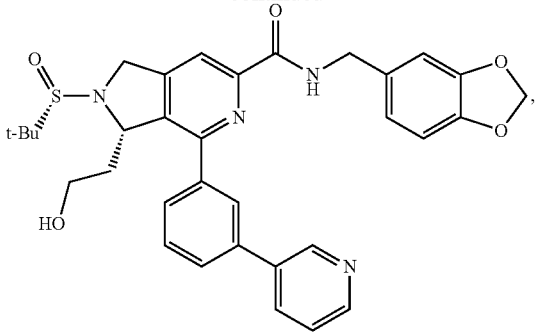
and pharmaceutically acceptable salts, solvates, hydrates, polymorphs, co-crystals, tautomers, stereoisomers, isotopically labeled derivatives, and prodrugs thereof.
Other exemplary compounds of Formula (I') and (I) include, but are not limited to:
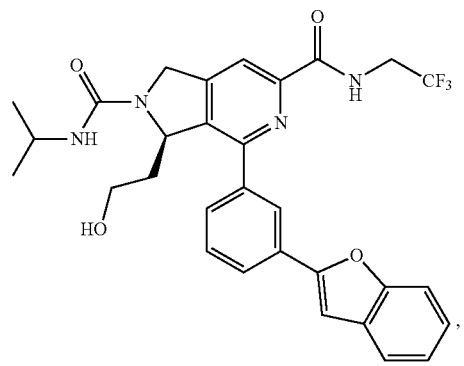
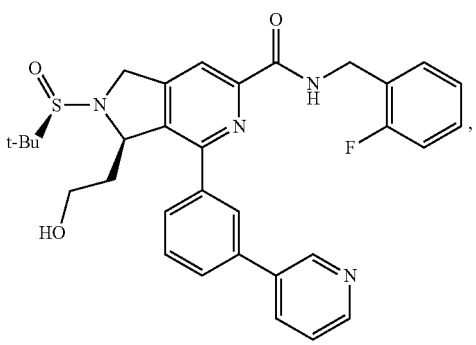
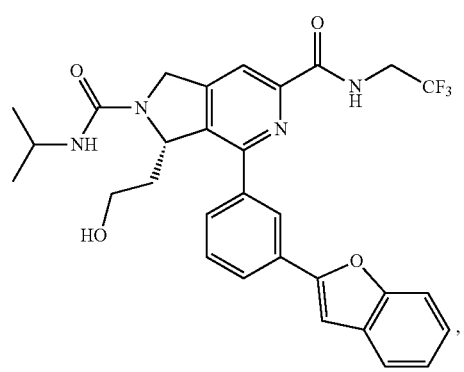
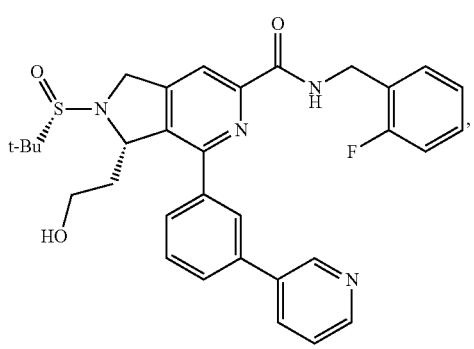
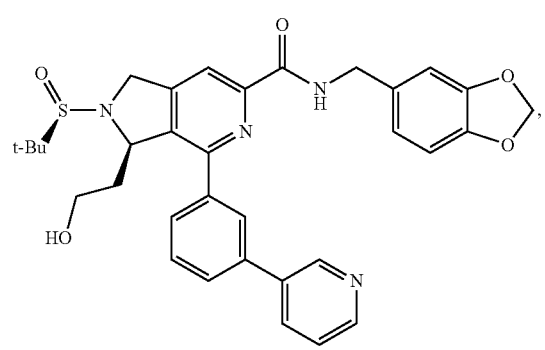
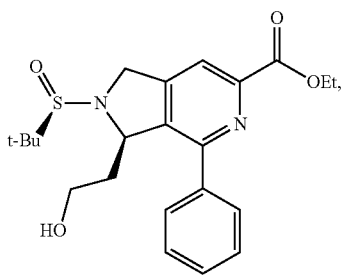
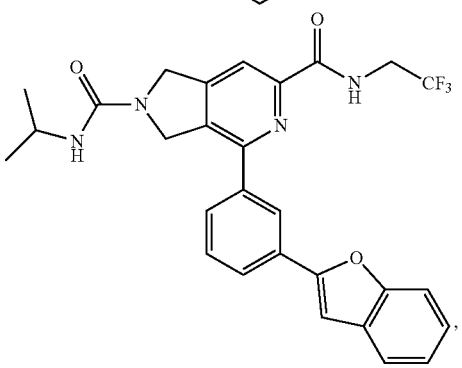

-continued
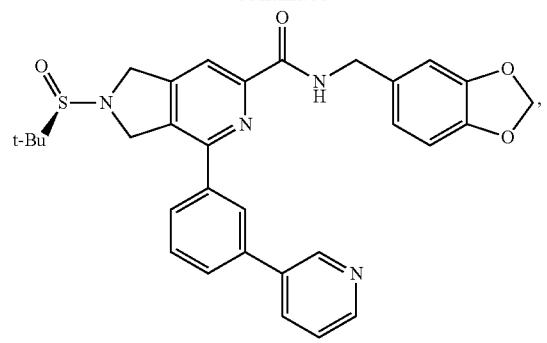
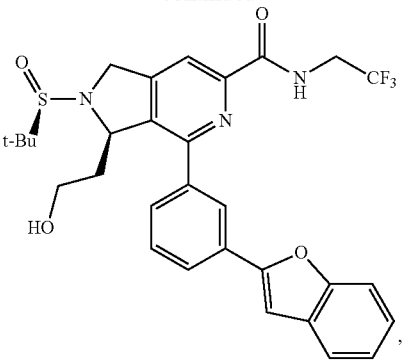
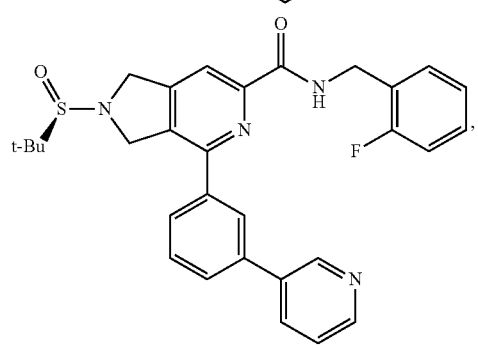
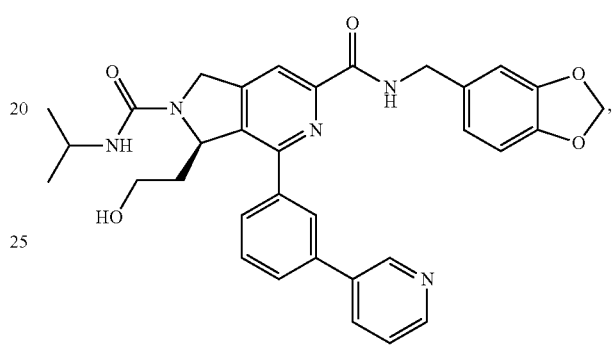
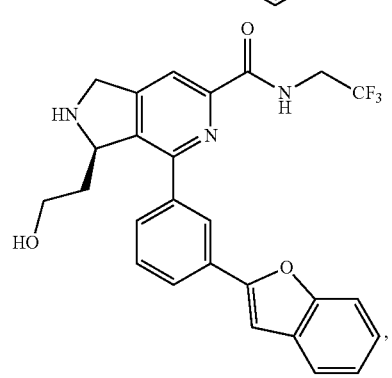
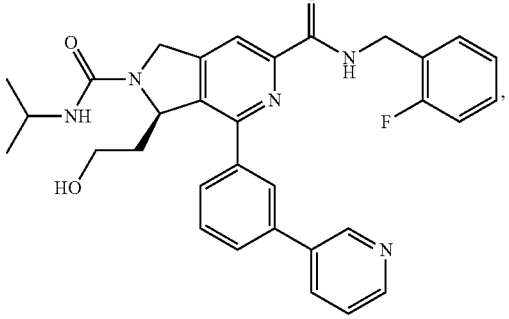
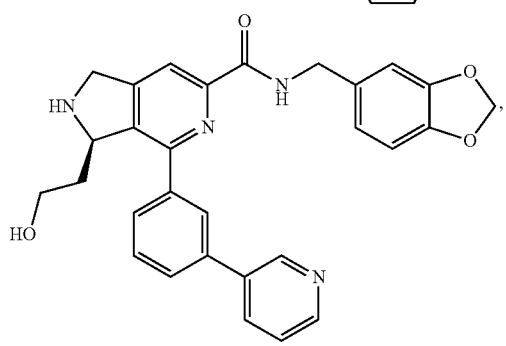
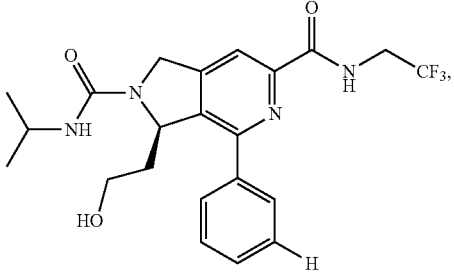
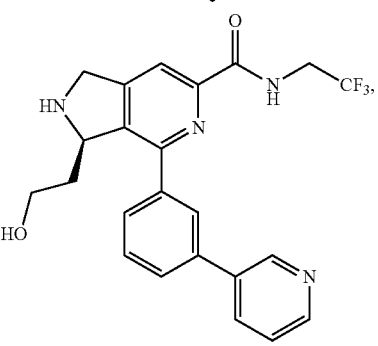
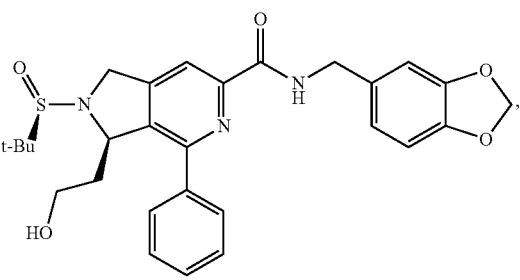

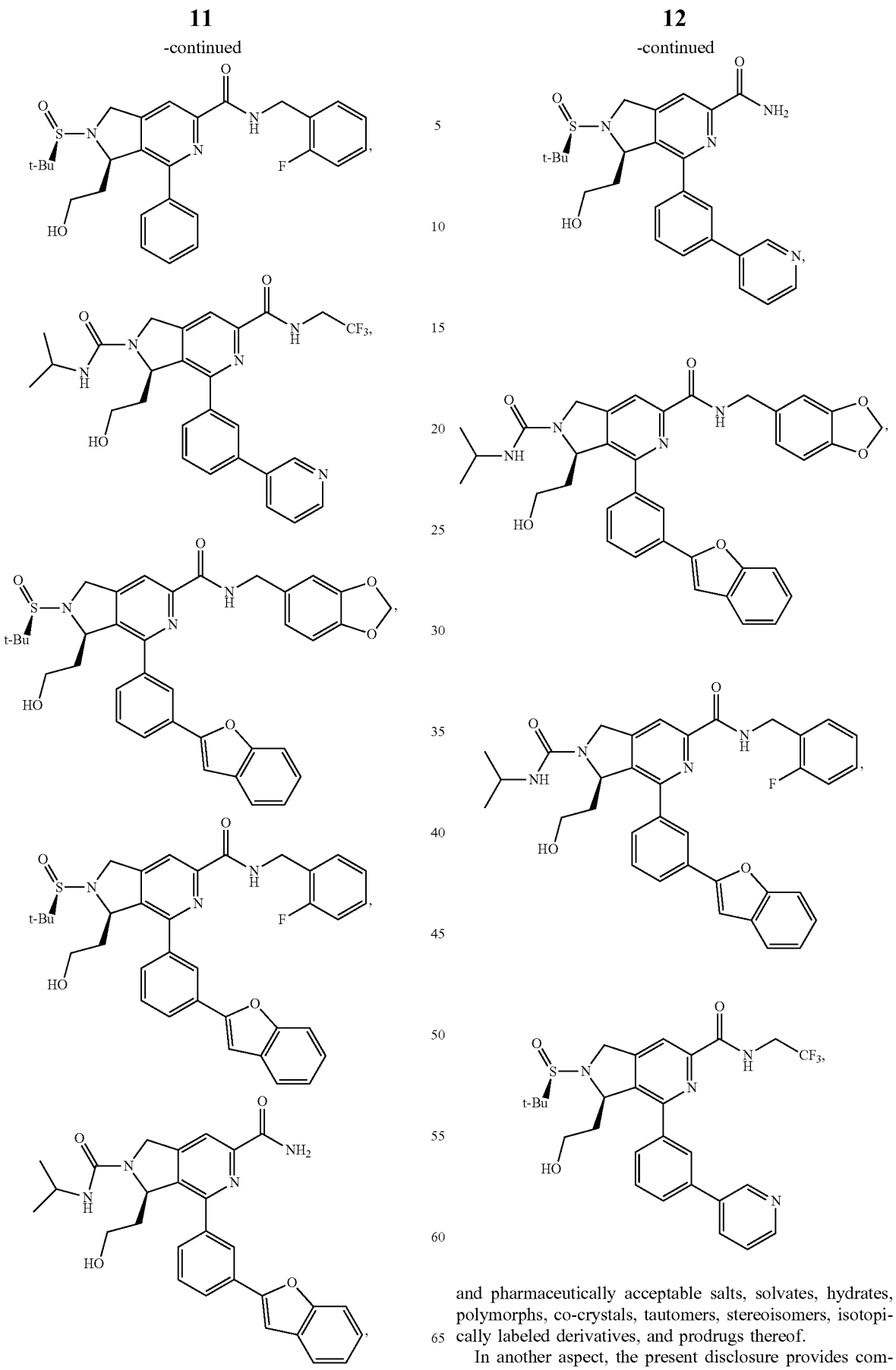
and pharmaceutically acceptable salts, solvates, hydrates, polymorphs, co-crystals, tautomers, stereoisomers, isotopically labeled derivatives, and prodrugs thereof.
In another aspect, the present disclosure provides compounds of Formula (II):

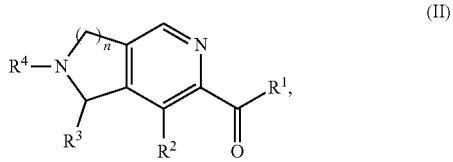

(II)

and pharmaceutically acceptable salts, solvates, hydrates, polymorphs, co-crystals, tautomers, stereoisomers, isotopically labeled derivatives, and prodrugs thereof, wherein n, $R^1$, $R^2$, $R^3$, and $R^4$ are as defined herein.

In another aspect, the present disclosure provides compounds of Formula (III):

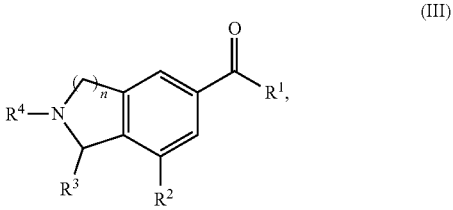

(III)

and pharmaceutically acceptable salts, solvates, hydrates, polymorphs, co-crystals, tautomers, stereoisomers, isotopically labeled derivatives, and prodrugs thereof, wherein n, $R^1$, $R^2$, $R^3$, and $R^4$ are as defined herein.

In another aspect, described herein are pharmaceutical compositions including a compound described herein, and optionally a pharmaceutically acceptable excipient. In certain embodiments, a pharmaceutical composition described herein includes an effective amount (e.g., therapeutically effective amount or prophylactically effective amount) of a compound described herein. The pharmaceutical compositions may be anti-trypanosomal and/or anti-plasmodial compounds. The compounds may be useful in treating parasitic infections, particularly protozoan infections, and also bacterial infections in a subject in need thereof, treating parasitic infections in a subject in need thereof, treating trypanosomal infections (e.g., *Trypanosoma cruzi* (*T. cruzi*) infections) in a subject in need thereof, treating plasmodial infections (e.g., malaria) in a subject in need thereof, treating an infectious disease in a subject in need thereof (e.g., Chagas disease, sleeping sickness, and/or malaria), preventing an infectious disease in a subject at risk of developing an infectious disease, preventing a protozoan infection in a subject at risk of developing a protozoan infection, preventing a trypanosomal infection in a subject at risk of developing a trypanosomal infection (e.g., *T. cruzi* or *Trypanosoma brucei* infections), preventing a plasmodial infection in a subject at risk of developing a protozoan infection, treating infectious disease in a subject in need thereof, preventing a protozoan infection in a subject at risk of developing a protozoan infection (e.g., trypanosomal infections from *T. cruzi* or *Trypanosoma brucei* and plasmodial infections), preventing diseases in a subject at risk of developing an infectious disease (e.g., Chagas disease, malaria, and sleeping sickness), preventing infectious diseases in a subject in need thereof, and as research tools (e.g., for studying trypanosomal infections (e.g., studying *T. cruzi* infections) and plasmodial infections in a subject, biological sample, tissue, or cell).

The diseases being treated and/or prevented using the compounds and compositions described here are typically infectious diseases. In certain embodiments, the disease is a parasitic disease. In certain embodiments, the disease is a protozoan infectious disease. In certain embodiments, the disease is a trypanosomal infectious disease. In certain embodiments, the disease is a *Leishmania* infectious disease. In certain embodiments, a disease is a *Trypanosoma cruzi* (*T. cruzi*) infection. In certain embodiments, the disease is a plasmodial infection. In certain embodiments, the disease is Chagas disease. In certain embodiments, the disease is sleeping sickness. In certain embodiments, the disease is leishmaniasis. In certain embodiments, the disease is malaria.

The pharmaceutical compositions described herein are useful in treating and/or preventing protozoan infections in a subject in need thereof, and/or treating and/or preventing trypanosomal infections (e.g., *Trypanosoma cruzi* (*T. cruzi*) or *Trypanosoma brucei* infections) in a subject in need thereof. The pharmaceutical compositions described herein are useful in treating protozoan infections in a subject in need thereof and/or preventing protozoan infections in a subject at risk of developing a plasmodial infection, and/or treating plasmodial infections in a subject in need thereof and/or preventing plasmodial infections in a subject at risk of developing a plasmodial infection. In certain embodiments, the pharmaceutical compositions described herein are useful in treating and/or preventing diseases (e.g., parasitic infections, protozoan infections, malaria, or Chagas disease), and treating and/or preventing infectious diseases or infections in a subject, biological sample, tissue, or cell. In certain embodiments, the subject being treated with a compound of Formula (I'), Formula (I), Formula (II), or Formula (III) is a human. In certain embodiments, the subject is a non-human animal.

In another aspect, described herein are kits including a container with a compound or pharmaceutical composition described herein. A kit described herein may include a single dose or multiple doses of the compound or pharmaceutical composition. The described kits may be useful in treating parasitic infections, particularly protozoan infections, and bacterial infections in a subject in need thereof, treating trypanosomal infections (e.g., *Trypanosoma cruzi* (*T. cruzi*) infections) and plasmodial infections (e.g., malaria) in a subject in need thereof, treating an infectious disease in a subject in need thereof (e.g., Chagas disease, sleeping sickness, and malaria), preventing an infectious disease in a subject at risk of developing an infectious disease, preventing a protozoan infection in a subject at risk of developing an infectious disease, preventing a trypanosomal infection (e.g., *T. cruzi* or *Trypanosoma brucei* infections) in a subject at risk of developing a trypanosomal infection, preventing a plasmodial infection in a subject at risk of developing a plasmodial infection, preventing a protozoan infection in a subject at risk of developing a protozoan infection (e.g., trypanosomal infections from *T. cruzi* or *Trypanosoma brucei* and/or plasmodial infections), preventing diseases in a subject in need thereof (e.g., Chagas disease, malaria, and sleeping sickness), preventing infectious diseases in a subject at risk of developing an infectious disease, and as research tools (e.g., for studying trypanosomal infections (e.g., studying *T. cruzi* infections) and plasmodial infections in a subject, biological sample, tissue, or cell). In certain embodiments, a kit described herein further includes instructions for using the compound or pharmaceutical composition included in the kit.

Another aspect of the present disclosure relates to methods of treating and/or preventing a disease in a subject in need thereof, the methods comprising administering to the subject an effective amount of a compound or pharmaceutical composition described herein.

In another aspect, the present disclosure provides compounds and pharmaceutical compositions described herein for use in a method of the disclosure (e.g., treating and/or preventing a protozoan infection, treating a subject with Chagas disease and/or malaria, or preventing Chagas disease, sleeping sickness, and/or malaria).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and subrange within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

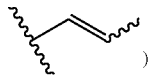
)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3}$-cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C (=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_3$10 carbocyclyl, 3-14 membered heterocyclyl, $C_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocylyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —SC(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein X$^-$ is a counterion;

each instance of R$^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$+X, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, F$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, BPh$_4$$^-$, Al(OC(CF$_3$)$_3$)$_4$$^-$, and a carborane anion (e.g., CB$_{11}$H$_{12}$$^-$ or (HCB$_{11}$Me$_5$Br$_6$)$^-$). Exemplary counterions which may be multivalent include CO$_3$$^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$R, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)$OR^{aa}$, —C(=N$R^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3^+X^-$, —P($OR^{cc}$)$_2$, —P($OR^{cc}$)$_3^+X^-$, —P(=O)($R^{aa}$)$_2$, —P(=O)($OR^{cc}$)$_2$, and —P(=O)(N($R^{bb}$)$_2$)$_2$, wherein $X^-$, $R^{aa}$, $R^{bb}$ and $R^{cc}$ are as defined herein. In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, o-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary sulfur atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)$OR^{aa}$, —C(=N$R^{bb}$)N($R^{bb}$)$_2$, —S(=O)$R^{aa}$, —$SO_2R^{aa}$, —$Si(R^{aa})_3$, —$P(R^{cc})_2$, —$P(R^{cc})_3{}^+X^-$, —$P(OR^{cc})_2$, —$P(OR^{cc})_3{}^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. In certain embodiments, the sulfur atom substituent present on a sulfur atom is a sulfur protecting group (also referred to as a thiol protecting group). Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

The term "leaving group" is given its ordinary meaning in the art of synthetic organic chemistry and refers to an atom or a group capable of being displaced by a nucleophile. See, for example, Smith, *March Advanced Organic Chemistry* 6th ed. (501-502). Examples of suitable leaving groups include, but are not limited to, halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is an activated substituted hydroxyl group (e.g., —$OC(=O)SR^{aa}$, —$OC(=O)R^{aa}$, —$OCO_2R^{aa}$, —$OC(=O)N(R^{bb})_2$, —$OC(=NR^{bb})R^{aa}$, —$OC(=NR^{bb})OR^{aa}$, —$OC(=NR^{bb})N(R^{bb})_2$, —$OS(=O)R^{aa}$, —$OSO_2R^{aa}$, —$OP(R^{cc})_2$, —$OP(R^{cc})_3$, —$OP(=O)_2R^{aa}$, —$OP(=O)(R^{aa})_2$, —$OP(=O)(OR^{cc})_2$, —$OP(=O)_2N(R^{bb})_2$, and —$OP(=O)(NR^{bb})_2$, wherein $R^{aa}$, $R^{bb}$, and $R^{cc}$ are as defined herein). In some cases, the leaving group is a sulfonic acid ester, such as toluenesulfonate (tosylate, —OTs), methanesulfonate (mesylate, —OMs), p-bromobenzenesulfonyloxy (brosylate, —OBs), —$OS(=O)_2(CF_2)_3CF_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other non-limiting examples of leaving groups are water, ammonia, alcohols, ether moieties, thioether moieties, zinc halides, magnesium moieties, diazonium salts, and copper moieties.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4} \text{ alkyl})_4{}^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5$H_2O$)), and polyhydrates (x is a number greater than 1, e.g., dihydrates (R.2$H_2O$) and hexahydrates (R.6$H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The term "inhibition", "inhibiting", "inhibit," or "inhibitor" refer to the ability of a compound to reduce the growth or reproduction of a parasite (e.g., a protozoan (e.g., *T. cruzi*) or a *plasmodium*) or of bacteria.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease (e.g., protozoan infections or Chagas disease).

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay or prevent recurrence.

The term "prevent" refers to a prophylactic treatment of a subject who does not currently have a disease and did not previously have a disease but is at risk of developing the disease or who previously had a disease, or does not currently have the disease, but is at risk of recurrence of the disease. In certain embodiments, the subject is at a higher risk of developing the disease or at a higher risk of recurrence of the disease than an average healthy member of a population.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent. In certain embodiments, a therapeutically effective amount is effective for treating a disease. In certain embodiments, a therapeutically effective amount is effective for treating an infectious disease. In certain embodiments, a therapeutically effective amount is effective for treating Chagas disease. In certain embodiments, a therapeutically effective amount is effective for treating sleeping sickness. In certain embodiments, a therapeutically effective amount is effective for treating malaria. In certain embodiments, a therapeutically effective amount is effective for treating a parasitic infection. In certain embodiments, a therapeutically effective amount is effective for treating a protozoan infection. In certain embodiments, a therapeutically effective amount is effective for treating a trypanosomal infection. In certain embodiments, a therapeutically effective amount is effective for treating a *T. cruzi* infection. In certain embodiments, a therapeutically effective amount is effective for treating a *Trypanosoma brucei* infection. In certain embodiments, a therapeutically effective amount is effective for treating a plasmodial infection. In certain embodiments, a therapeutically effective amount is effective for treating a *Plasmodium falciparum* infection In certain embodiments, a therapeutically effective amount is effective for treating a *Plasmodium vivax* infection. In certain embodiments, a therapeutically effective amount is effective for treating a *Plasmodium ovale* infection. In certain embodiments, a therapeutically effective amount is effective for treating a *Plasmodium malariae* infection. In certain embodiments, a therapeutically effective amount is effective for treating a *Plasmodium knowlesi* infection.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is effective for preventing a parasitic infection. In certain embodiments, a prophylactically effective amount is effective for preventing a protozoan infection. In certain embodiments, a prophylactically effective amount is effective for preventing a trypanosomal infection. In certain embodiments, a prophylactically effective amount is effective for preventing a *T. cruzi* infection. In certain embodiments, a prophylactically effective amount is effective for preventing a *Trypanosoma brucei* infection. In certain embodiments, a prophylactically effective amount is effective for treating a plasmodial infection. In certain embodiments, a prophylactically effective amount is effective for treating a *Plasmodium falciparum* infection In certain embodiments, a prophylactically effective amount is effective for treating a *Plasmodium vivax* infection. In certain embodiments, a prophylactically effective amount is effective for treating a *Plasmodium ovale* infection. In certain embodiments, a prophylactically effective amount is effective for treating a *Plasmodium malariae* infection. In certain embodiments, a prophylactically effective amount is effective for treating a *Plasmodium knowlesi* infection. In certain embodiments, a prophylactically effective amount is effective for preventing a disease (e.g., Chagas disease, sleeping sickness, and/or malaria). In certain embodiments, a prophylactically effective amount is effective for preventing an infectious disease.

An "infection" or "infectious disease" refers to an infection with a microorganism, such as a parasite, protozoa, fungus, bacteria, or virus. In certain embodiments, the infection is an infection with a protozoan parasite, i.e., a protozoan infection. In certain embodiments, the infection is an infection with a *Plasmodium falciparum, Plasmodium vivax, Plasmodium ovale, Plasmodium malariae*, or *Plasmodium knowlesi*. Various infections include, but are not limited to, skin infections, GI infections, urinary tract infections, genito-urinary infections, sepsis, blood infections, and systemic infections.

A "parasite" refers to an organism that lives on or in a host organism, may infect the host organism and obtains its food from or at the expense of its host. Exemplary parasites include protozoan parasites, helminth parasites (e.g., flatworms), and ectoparasites (e.g., ticks or fleas). Exemplary protozoan parasites include Sarcodina amoeba (e.g., *Entamoeba*); Mastigophora flagellates, (e.g., *Giardia, Leishmani*); Ciliophora ciliates, (e.g., *Balantidium*); and Sporozoa (e.g., *Plasmodium* and *Cryptosporidium*). Exemplary protozoan parasites include, but are not limited to, *Leishmania, Cryptosporidium* spp., *Giardia intestinalis, Trichomonas, Cyclospora cayetanensis*, and *Toxoplasma gondii*.

A "trypanosome" refers to a protozoan parasite, which may infect host organisms, such as birds and mammals. In certain embodiments, a trypanosome is *Trypanosoma cruzi*. In certain embodiments, a trypanosome is *Trypanosoma brucei*. Exemplary trypanosomal parasites include, but are not limited to, *Trypanosoma brucei gambiense, Trypanosoma brucei rhodesiense*, and *Trypanosoma cruzi*.

A "*plasmodium*" refers to a protozoan parasite, which may infect host organisms, such as reptiles, birds, and mammals. In certain embodiments, a *plasmodium* is *Plasmodium falciparum*. In certain embodiments, a *plasmodium* is *Plasmodium vivax*. In certain embodiments, a *plasmodium* is *Plasmodium ovale*. In certain embodiments, a *plasmodium* is *Plasmodium malariae*. In certain embodiments, a *plasmodium* is *Plasmodium knowlesi*.

BRIEF DESCRIPTION OF THE DRAWINGS

FIG. 5A-5D show that this is not seen with treatment with compounds Tan003—O08 or Tan002—O12.

DETAILED DESCRIPTION OF CERTAIN EMBODIMENTS OF THE INVENTION

Figure 1:
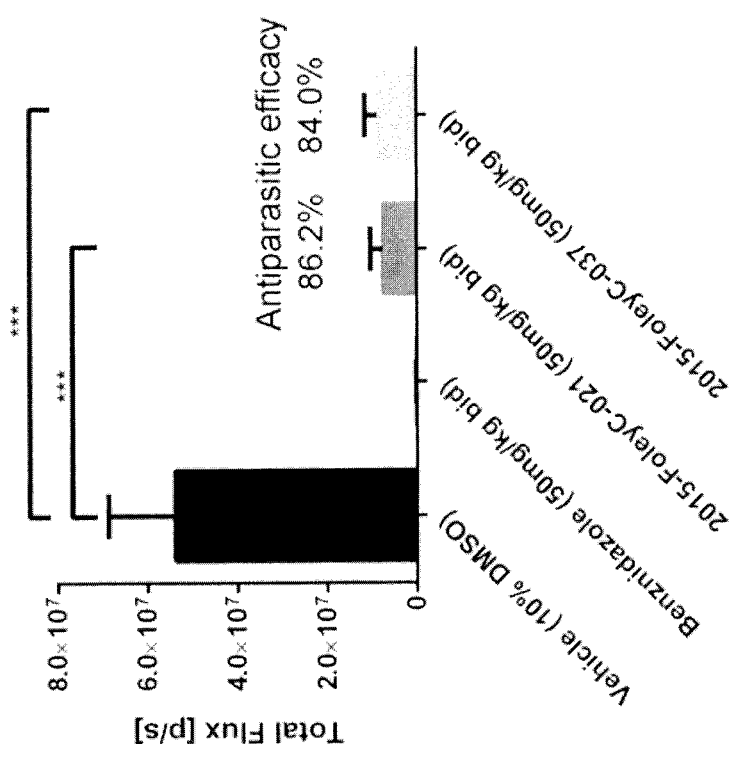
FIG. 1 shows exemplary results of compounds 21 and 37 in an initial in vivo efficacy assay for *T. cruzi* infection in a mouse model. The efficacy of compounds 21 (2015-FoleyC-021) and 37 (2015-FoleyC-037) in *T. cruzi* parasite reduction was measured as a luminescence reading, using an In Vivo Imaging System (IVIS) for *T. cruzi* parasites expressing luciferase after treatment with compounds 21 and 37 for four consecutive days, with 2 doses per day (bid) at 12 hours between the doses.

The present disclosure provides, in one aspect, compounds of Formula (I'), Formula (I), Formula (II), Formula (III), and pharmaceutically acceptable salts, solvates, hydrates, polymorphs, co-crystals, tautomers, stereoisomers, isotopically labeled derivatives, and prodrugs thereof. The compounds may be useful in treating and/or preventing parasitic infections, particularly protozoan infections and also bacterial infections in a subject in need thereof, treating and/or preventing trypanosomal infections (e.g., *Trypanosoma cruzi* (*T. cruzi*) or *Trypanosoma brucei* infections) and treating plasmodial infections (e.g., malaria) in a subject in need thereof. The compounds may be useful in treating and/or preventing an infectious disease in a subject in need thereof (e.g., Chagas disease, malaria, and/or sleeping sickness), and treating and/or preventing an infectious disease in a subject in need thereof, treating and/or preventing an parasitic disease in a subject in need thereof, treating and/or preventing a protozoan infection in need thereof, treating and/or preventing a trypanosomal infection in a subject in need thereof, treating a plasmodial infection (e.g., *T. cruzi* or *Trypanosoma brucei* infections) in a subject in need thereof, preventing a plasmodial infection (e.g., *T. cruzi* or *Trypanosoma brucei* infections) in a subject at risk of developing a plasmodial infection, treating a protozoan infection in a subject in need thereof, and preventing a protozoan infection in a subject at risk of developing a protozoan infection (e.g., trypanosomal infection from *T. cruzi* or *Trypanosoma brucei*, plasmodial infections). The compounds described herein may be anti-parasitic compounds, particularly anti-trypanosomal and/or anti-plasmodial compounds. The compounds may be useful as research tools (e.g., for studying trypanosomal infections (e.g., studying *T. cruzi* infections) and plasmodial infections in a subject, biological sample, tissue, or cell). Also provided are pharmaceutical compositions, kits, methods, and uses including a compound described herein.

Compounds

One aspect of the present disclosure provides the compounds described herein. The compounds may be useful in treating infectious disease, particularly in treating parasitic disease. The compounds may be useful in treating parasitic infections, particularly protozoan infections in a subject in need thereof, and also treating bacterial infections. The compounds may be useful in treating protozoan infections, particularly treating trypanosomal infections (e.g., *Trypanosoma cruzi* (*T. cruzi*) infections) and/or plasmodial infections in a subject in need thereof, treating diseases in a subject in need thereof (e.g., Chagas disease and/or, malaria), treating infectious diseases in a subject in need thereof, particularly parasitic diseases, preventing protozoan infections in a subject at risk of developing a protozoan infection, preventing trypanosomal infections (e.g., *T. cruzi* or *Trypanosoma brucei* infections) in a subject at risk of developing a trypanosomal infection, preventing protozoan infections in a subject at risk of developing a protozoan infection (e.g., trypanosomal infections from *T. cruzi* or *Trypanosoma brucei* and/or plasmodial infections), preventing diseases in a subject in need thereof (e.g., Chagas disease, malaria, or sleeping sickness), preventing infectious diseases in a subject at risk of developing an infectious disease, particularly parasitic diseases, and/or as research tools (e.g., for studying trypanosomal infections (e.g., studying *T. cruzi* infections) and/or plasmodial infections in a subject, biological sample, tissue, or cell). The compounds described herein may be anti-trypanosomal and/or anti-plasmodial compounds. In certain embodiments, a compound described herein is a compound of Formula (I'), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (I), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (II), or a pharmaceutically acceptable salt, solvate, hydrate, polymorph, co-crystal, tautomer, stereoisomer, isotopically labeled derivative, or prodrug thereof. In certain embodiments, a compound described herein is a compound of Formula (III), or a pharmaceutically acceptable salt, solvate, hydrate, polymorph, co-crystal, tautomer, stereoisomer, isotopically labeled derivative, or prodrug thereof.

Compounds of Formula (I')

In certain embodiments, the compound of Formula (I') is of the formula:

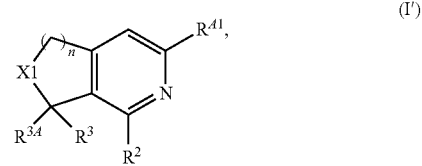

(I')

or a pharmaceutically acceptable salt, solvate, hydrate, polymorph, co-crystal, tautomer, stereoisomer, isotopically labeled derivative, or prodrug thereof, wherein:

n is 1, 2, or 3;

X1 is —CR$^4$—, —NR$^4$—, —O—, or —S—;

R$^{41}$ is hydrogen, halogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR, —N(R$^4$)$_2$, —SR, —CN, —SCN, or —NO$_2$;

R is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or oxygen protecting group;

R$^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

R³ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

R$^{3A}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

R⁴ is halogen, hydrogen, substituted or unsubstituted acyl, substituted or unsubstituted alkyl, substituted or unsubstituted imine, substituted or unsubstituted thiocarbonyl group, substituted or unsubstituted aryl, substituted or unsubstituted heteroaryl,

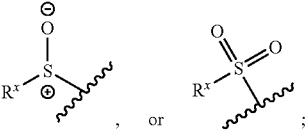
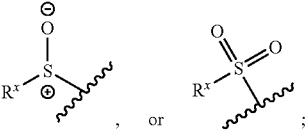
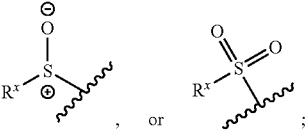
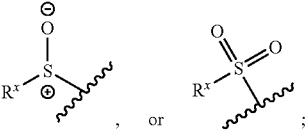
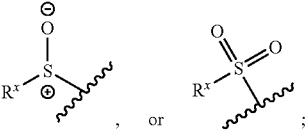

R$^X$ is hydrogen, substituted or unsubstituted alkyl, substituted or unsubstituted carbocyclyl, substituted or unsubstituted heterocyclyl, substituted or unsubstituted aryl, or substituted or unsubstituted heteroaryl; and each instance of R$^A$ is independently hydrogen, substituted or unsubstituted acyl, substituted or unsubstituted alkyl, substituted or unsubstituted carbocyclyl, substituted or unsubstituted heterocyclyl, substituted or unsubstituted aryl, substituted or unsubstituted heteroaryl, nitrogen protecting group, or optionally two R$^A$ are taken together with the intervening atoms to form substituted or unsubstituted heterocyclyl or substituted or unsubstituted heteroaryl.

In certain embodiments, the compound of Formula (I') is of the formula:

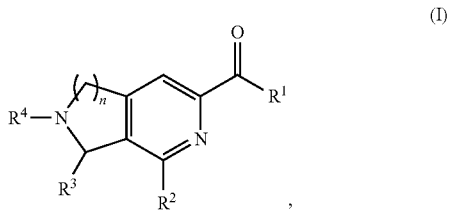

(I)

or a pharmaceutically acceptable salt, solvate, hydrate, polymorph, co-crystal, tautomer, stereoisomer, isotopically labeled derivative, or prodrug thereof, wherein:

n is 1, 2, or 3;

R¹ is hydrogen, substituted or unsubstituted alkyl, substituted or unsubstituted aryl, substituted or unsubstituted heteroaryl, —OR, or —N(R$^A$)$_2$;

R is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or oxygen protecting group;

R² is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

R³ is hydrogen, substituted or unsubstituted alkyl, substituted or unsubstituted aryl, or substituted or unsubstituted heteroaryl;

R⁴ is hydrogen, substituted or unsubstituted acyl, substituted or unsubstituted alkyl, substituted or unsubstituted imine, substituted or unsubstituted thiocarbonyl group, substituted or unsubstituted aryl, substituted or unsubstituted heteroaryl,

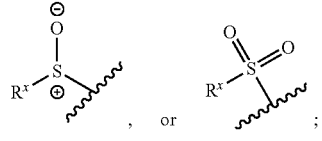
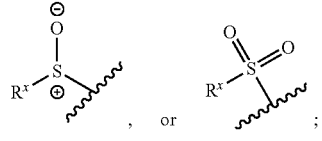
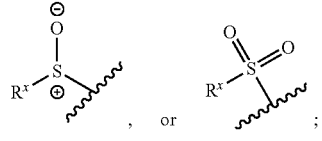
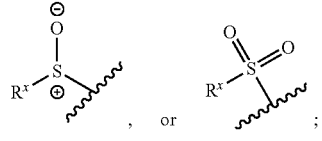
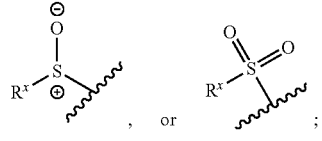

R$^X$ is hydrogen, substituted or unsubstituted alkyl, substituted or unsubstituted carbocyclyl, substituted or unsubstituted heterocyclyl, substituted or unsubstituted aryl, or substituted or unsubstituted heteroaryl; and each instance of R$^A$ is independently hydrogen, substituted or unsubstituted alkyl, substituted or unsubstituted carbocyclyl, substituted or unsubstituted heterocyclyl, substituted or unsubstituted aryl, substituted or unsubstituted heteroaryl, nitrogen protecting group, or optionally two R$^A$ are taken together with the intervening atoms to form substituted or unsubstituted heterocyclyl or substituted or unsubstituted heteroaryl.

Formula (I') includes substituent R$^{41}$. In certain embodiments, R$^{41}$ is hydrogen. In certain embodiments, R$^{41}$ is R$^{41}$ is halogen (e.g., F, Cl, Br, or I). In certain embodiments, R$^{41}$ is substituted or unsubstituted alkyl (e.g., substituted or unsubstituted C$_{1-6}$ alkyl). In certain embodiments, R$^{41}$ is substituted or unsubstituted methyl. In certain embodiments, R$^{41}$ is substituted or unsubstituted ethyl. In certain embodiments, R$^{41}$ is of the formula: —(CH$_2$)$_{x1}$R$^1$, wherein: x1 is 0, 1, 2, 3, 4, 5, or 6; and R¹ is hydrogen, substituted or unsubstituted alkyl, substituted or unsubstituted aryl, substituted or unsubstituted heteroaryl, —OR, or —N(R$^A$)$_2$. In certain embodiments, x1 is 0. In certain embodiments, x1 is 1. In certain embodiments, x1 is 2. In certain embodiments, x1 is 3. In certain embodiments, x1 is 4. In certain embodiments, x1 is 5. In certain embodiments, x1 is 6. In certain embodiments, R$^{41}$ is of the formula: —(CH$_2$)R$^1$, and R¹ is substituted or unsubstituted alkyl, substituted or unsubstituted aryl, substituted or unsubstituted heteroaryl, —OR, or —N(R$^A$)$_2$. In certain embodiments, R$^{41}$ is substituted or unsubstituted acyl. In certain embodiments, R$^{41}$ is of the formula: —C(=O)R$^1$, In certain embodiments, R$^{41}$ is substituted or unsubstituted alkenyl (e.g., substituted or unsubstituted C$_{2-6}$ alkenyl). In certain embodiments, R$^{41}$ is substituted or unsubstituted alkynyl (e.g., substituted or unsubstituted C$_{2-6}$ alkynyl). In certain embodiments, R$^{41}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R$^{41}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R$^{41}$ is substituted or unsubstituted aryl (e.g., substituted or unsubstituted, 6- to 10-membered aryl). In certain embodiments, R$^{41}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^{A1}$ is —OR, and R is substituted or unsubstituted $C_{1-6}$ alkyl (e.g., —OMe or —OEt). In certain embodiments, $R^{A1}$ is —N($R^A$)$_2$ (e.g., —NMe$_2$). In certain embodiments, at least one instance of $R^A$ is hydrogen. In certain embodiments, $R^1$ is —NH$_2$. In certain embodiments, $R^{A1}$ is —SR, —CN, —SCN, or —NO$_2$. In certain embodiments, $R^{A1}$ is —SR. In certain embodiments, $R^{A1}$ is —CN. In certain embodiments, $R^{A1}$ is —SCN. In certain embodiments, $R^{A1}$ is —NO$_2$.

Formula (I') and Formula (I) include substituent $R^1$. In certain embodiments, $R^1$ is substituted or unsubstituted alkyl (e.g., substituted or unsubstituted $C_{1-6}$ alkyl). In certain embodiments, $R^1$ is methyl. In certain embodiments, $R^1$ is ethyl. In certain embodiments, $R^1$ is substituted or unsubstituted aryl (e.g., substituted or unsubstituted, 6- to 10-membered aryl). In certain embodiments, $R^1$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^1$ is —OR, and R is substituted or unsubstituted $C_{1-6}$ alkyl (e.g., —OMe or —OEt). In certain embodiments, $R^1$ is of the formula: —NH(CH$_2$)$_a R^a$, wherein: a is 1, 2, 3, 4, 5, or 6; $R^a$ is substituted or unsubstituted alkyl, substituted or unsubstituted carbocyclyl, substituted or unsubstituted heterocyclyl, substituted or unsubstituted aryl, substituted or unsubstituted heteroaryl, —OR$^{a2}$, —N(R$^{a1}$)$_2$, or —SR$^{a2}$; each instance of $R^{a1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or a nitrogen protecting group if attached to a nitrogen atom; and $R^{a2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group if attached to an oxygen atom, or a sulfur protecting group if attached to a sulfur atom. In certain embodiments, a is 1. In certain embodiments, a is 2. In certain embodiments, a is 3. In certain embodiments, a is 4. In certain embodiments, a is 5. In certain embodiments, a is 6. In certain embodiments, $R^a$ is substituted or unsubstituted $C_{1-6}$ alkyl. In certain embodiments, $R^1$ is —N($R^A$)$_2$ (e.g., —NMe$_2$). In certain embodiments, at least one instance of $R^A$ is hydrogen. In certain embodiments, R is —NH$_2$. In certain embodiments, at least one instance of $R^A$ is substituted or unsubstituted acyl (e.g., —C(=O)Me). In certain embodiments, at least one instance of $R^A$ is substituted or unsubstituted alkyl (e.g., $C_{1-6}$ substituted or unsubstituted alkyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^A$ is a nitrogen protecting group if attached to a nitrogen atom. In certain embodiments, two $R^A$ are taken together with the intervening atoms to form substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two $R^A$ are taken together with the intervening atoms to form substituted or unsubstituted heterocyclyl or substituted or unsubstituted heteroaryl (e.g., morpholine or pyridine). In certain embodiments, $R^1$ is

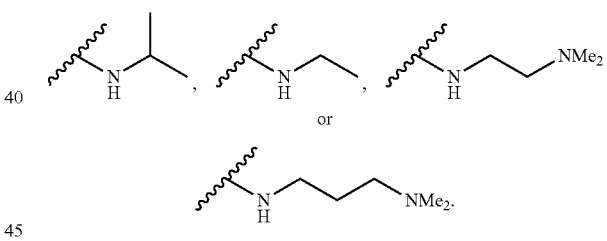

In certain embodiments, $R^a$ is —CF$_3$. In certain embodiments, $R^1$ is

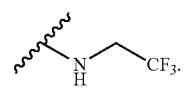

In certain embodiments, $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^1$ is

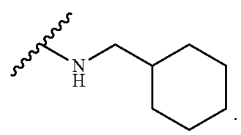 [SMILES: *NCC1CCCCC1]

In certain embodiments, $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is

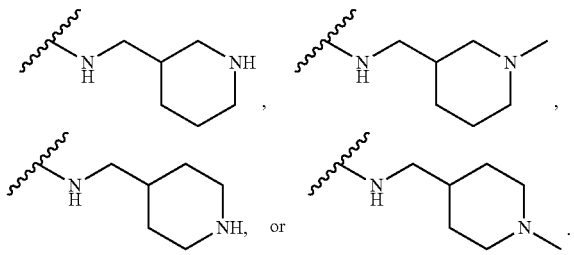

In certain embodiments, $R^a$ is substituted or unsubstituted aryl (e.g., substituted or unsubstituted, 6- to 10-membered aryl). In certain embodiments, $R^a$ is substituted or unsubstituted benzyl. In certain embodiments, $R^a$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^1$ is

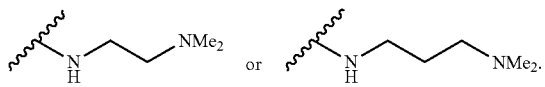

In certain embodiments, $R^a$ is —$OR^{a2}$ (e.g., —OH, —O (substituted or unsubstituted $C_{1-6}$ alkyl) (e.g., —OMe, —OCF$_3$, —OEt, —OPr, —OBu, or —OBn), or —O (substituted or unsubstituted phenyl) (e.g., —OPh)). In certain embodiments, $R^a$ is —$N(R^{a1})_2$ (e.g., —NH$_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^a$ is —NMe$_2$. In certain embodiments, $R^1$ is

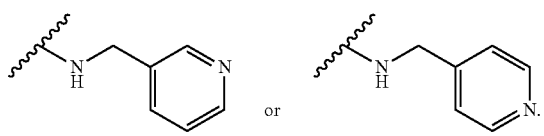 [SMILES: *NCc1cccnc1 ; *NCc1ccncc1]

In certain embodiments, $R^{a2}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^{a2}$ is a sulfur protecting group. In certain embodiments, $R^a$ is —SR (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)).

In certain embodiments, $R^1$ is of the formula:

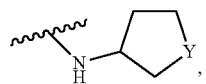

wherein Y is —$CR^E$—, —O— or —$NR^F$—; $R^E$ is independently hydrogen or substituted or unsubstituted $C_{1-6}$ alkyl; and $R^F$ is independently hydrogen or substituted or unsubstituted $C_{1-6}$ alkyl. In certain embodiments, Y is —$CR^E$— (e.g., —CH— or —CMe-). In certain embodiments, Y is —O—. In certain embodiments, Y is —$NR^F$— (e.g., —NH— or —NMe-). In certain embodiments, $R^E$ is hydrogen. In certain embodiments, $R^E$ is substituted or unsubstituted $C_{1-6}$ alkyl. In certain embodiments, $R^F$ is hydrogen. In certain embodiments, $R^F$ is substituted or unsubstituted $C_{1-6}$ alkyl. In certain embodiments, $R^1$ is:

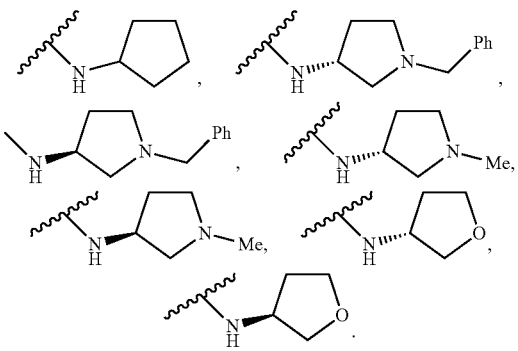

In certain embodiments, $R^1$ is of the formula:

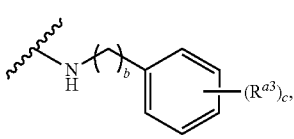

wherein b is 0, 1, 2, 3, 4, 5, or 6; c is 0, 1, 2, 3, 4, or 5; $R^{a3}$ is independently substituted or unsubstituted alkyl, halogen, —$OR^{a4}$, —$N_3$, —$N(R^{a4})_2$, —$SR^{a4}$, —CN, —SCN, —$SO_2R^{a4}$, —C(=O)$R^{a4}$, —C(=O)O$R^{a4}$, —C(=O)N($R^{a4}$)$_2$, —NO$_2$, or two instances of $R^{a3}$ are taken together with the intervening atoms to form substituted or unsubstituted heterocyclyl or substituted or unsubstituted heteroaryl; and $R^{a4}$ is independently hydrogen, or substituted or unsubstituted $C_{1-6}$ alkyl. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, c is 0. In certain embodiments, c is 1. In certain embodiments, c is 2. In certain embodiments, c is 3. In certain embodiments, c is 4. In certain embodiments, c is 5. In certain embodiments, at least one instance of $R^{a3}$ is substituted or unsubstituted $C_{1-6}$ alkyl. In certain embodiments, at least one instance of $R^{a3}$ is —CF$_3$. In certain embodiments, at least one instance of $R^{a3}$ is halogen (e.g., F, Cl, Br, or I). In certain embodiments, at least one instance of $R^{a3}$ is —$OR^{a4}$ (e.g., —OH, —O (substituted or unsubstituted $C_{1-6}$ alkyl) (e.g., —OMe, —OCF$_3$, —OEt, —OPr, or —OBu). In certain embodiments, at least one instance of $R^{a3}$ is —N$_3$. In certain embodiments, at least one instance of $R^{a3}$ is —$N(R^{a4})_2$ (e.g., —NMe$_2$). In certain embodiments, at least one instance of $R^{a3}$ is —$SR^{a4}$ (e.g., —SH, —S(substituted or unsubstituted $C_{1-6}$ alkyl) (e.g., —SMe, —SEt, —SPr, or —SBu). In certain embodiments, at least one instance of $R^{a3}$ is —CN. In certain embodiments, at least one instance of $R^{a3}$ is —SCN. In certain embodiments, at least one instance of $R^{a3}$ is —SO$_2$R$^{a4}$. In certain embodiments, at least one instance of $R^{a3}$ is —C(=O)R$^{a4}$. In certain embodiments, at least one instance of $R^{a3}$ is —C(=O)OR$^{a4}$ (e.g., —C(=O)OH, —C(=O)O (substituted or unsubstituted alkyl) (e.g., —C(=O)OMe). In certain embodiments, at least one instance of $R^{a3}$ is —C(=O)N(R$^{a4}$)$_2$. In certain embodiments, at least one instance of $R^{a3}$ is —NO$_2$. In certain embodiments, two instances of $R^{a3}$ are taken together with the intervening atoms to form substituted or unsubstituted heterocyclyl or substituted or unsubstituted heteroaryl. In certain embodiments, $R^1$ is:

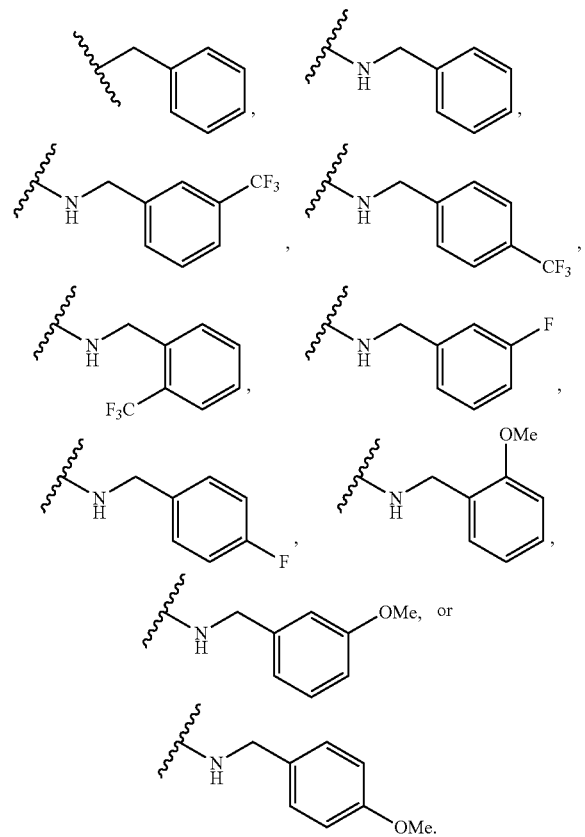

In certain embodiments, $R^1$ is:

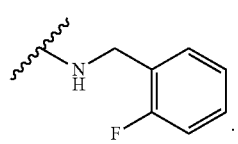 [SMILES: *NCc1ccccc1F]

In certain embodiments, $R^1$ is of the formula:

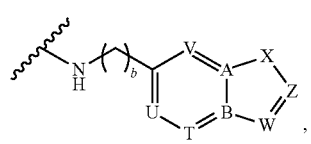

wherein: b is 0, 1, 2, 3, 4, 5, or 6; T is —CH— or —N—, as valency permits; U is —CH— or —N—, as valency permits; V is —CH— or —N—, as valency permits; W is —CH—, —C(R$^Z$)$_2$—, —O—, —NR$^A$—, or —S—, as valency permits; X is —CH—, —C(R$^Z$)$_2$—, —O—, —NR$^A$—, or —S—, as valency permits; Z is —CH—, —C(R$^Z$)$_2$—, —O—, —NR$^A$—, —N—, or —S—, as valency permits; A is —N—, as valency permits; B is —N—, as valency permits; $R^A$ is independently hydrogen or substituted or unsubstituted C$_{1-6}$ alkyl; and $R^Z$ is independently hydrogen or substituted or unsubstituted C$_{1-6}$ alkyl. In certain embodiments, T is —CH— or —N—, as valency permits. In certain embodiments, T is —CH—. In certain embodiments, T is —N—. In certain embodiments, U is —CH— or —N—, as valency permits. In certain embodiments, U is —CH—. In certain embodiments, U is —N—. In certain embodiments, V is —CH— or —N—, as valency permits. In certain embodiments, V is —CH—. In certain embodiments, V is —N—. In certain embodiments, W is —CH—, —C(R$^Z$)$_2$—, —O—, —NR$^A$—, or —S—, as valency permits. In certain embodiments, W is —CH—. In certain embodiments, W is —C(R$^Z$)$_2$— (e.g., —CH$_2$—). In certain embodiments, W is —O—. In certain embodiments, W is —NR$^A$— (e.g., —NH— or —NMe-). In certain embodiments, W is —S—. In certain embodiments, X is —CH—, —O—, —NR$^A$—, or —S—, as valency permits. In certain embodiments, X is —CH—. In certain embodiments, X is —S—. In certain embodiments, X is —NR$^A$— (e.g., —NH— or —NMe-). In certain embodiments, X is —S—. In certain embodiments, Z is —CH—, —C(R$^Z$)$_2$—, —O—, —NR$^A$—, —N—, or —S—, as valency permits. In certain embodiments, Z is —CH—. In certain embodiments, Z is —C(R$^Z$)$_2$— (e.g., —CH$_2$—). In certain embodiments, Z is —O—. In certain embodiments, Z is —NR$^A$— (e.g., —NH— or —NMe-). In certain embodiments, Z is —N—. In certain embodiments, Z is —S—. In certain embodiments, A is —N—, as valency permits. In certain embodiments, A is —N—. In certain embodiments, A is —C—. In certain embodiments, B is —N—, as valency permits. In certain embodiments, B is —N—. In certain embodiments, B is —C—. In certain embodiments, $R^A$ is hydrogen. In certain embodiments, $R^A$ is substituted or unsubstituted C$_{1-6}$ alkyl. In certain embodiments, $R^Z$ is hydrogen. In certain embodiments, $R^Z$ is substituted or unsubstituted C$_{1-6}$ alkyl. In certain embodiments, $R^1$ is

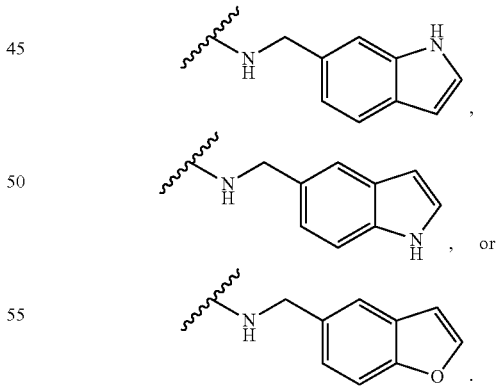

In certain embodiments, $R^1$ is

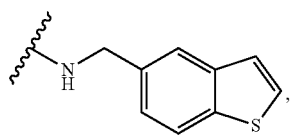

-continued

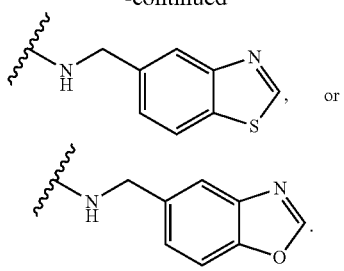

In certain embodiments, $R^1$ is

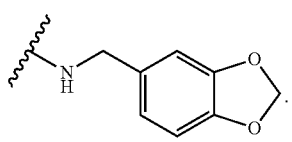 [SMILES: *NCc1ccc2c(c1)OCO2]

Formula (I') and Formula (I) include substituent $R^2$. In certain embodiments, $R^2$ is substituted or unsubstituted alkyl (e.g., $C_{1-6}$ alkyl). In certain embodiments, $R^2$ is of the formula: $-(CH_2)_e R^B$, wherein: e is 1, 2, 3, 4, 5, or 6; $R^B$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{b4}$, $-N(R^{b5})_2$, or $-SR^{b4}$; $R^{b4}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group when attached to an oxygen atom, or sulfur protecting group when attached to a sulfur atom; and each instance of $R^{b5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, nitrogen protecting group when attached to a nitrogen atom, or two instances of $R^{b5}$ are taken together with the intervening atoms to form a substituted or unsubstituted, heterocyclic ring. In certain embodiments, e is 1. In certain embodiments, e is 2. In certain embodiments, e is 3. In certain embodiments, e is 4. In certain embodiments, e is 5. In certain embodiments, e is 6. In certain embodiments, $R^B$ is substituted or unsubstituted $C_{1-6}$ alkyl. In certain embodiments, $R^2$ is

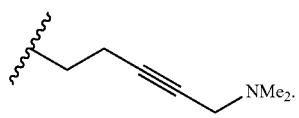 [SMILES: *CCC#CCN(C)C]

In certain embodiments, $R^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^B$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^B$ is substituted or unsubstituted aryl (e.g., substituted or unsubstituted, 6- to 10-membered aryl). In certain embodiments, $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^B$ is $-OR^{b4}$ (e.g., $-OH$, $-O$ (substituted or unsubstituted $C_{1-6}$ alkyl) (e.g., $-OMe$, $-OCF_3$, $-OEt$, $-OPr$, $-OBu$, or $-OBn$), or $-O$ (substituted or unsubstituted phenyl) (e.g., $-OPh$)). In certain embodiments, $R^B$ is $-N(R^{b5})_2$ (e.g., $-NH_2$, $-NH$ (substituted or unsubstituted $C_{1-6}$ alkyl) (e.g., $-NHMe$), or $-NMe_2$). In certain embodiments, $R^B$ is $-SR^{b4}$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)).

In certain embodiments, $R^2$ is of the formula:

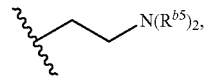

wherein: each instance of $R^{b5}$ is independently hydrogen, substituted or unsubstituted acyl, substituted or unsubstituted alkyl, substituted or unsubstituted alkenyl, or substituted or unsubstituted alkynyl, or two instances of $R^{b5}$ are taken together with the intervening atoms to form a substituted or unsubstituted, heterocyclic ring. In certain embodiments, at least one instance of $R^{b5}$ is hydrogen. In certain embodiments, at least one instance of $R^{b5}$ is substituted or unsubstituted acyl. In certain embodiments, at least one instance of $R^{b5}$ is substituted or unsubstituted alkenyl (e.g., substituted or unsubstituted $C_{2-6}$ alkenyl). In certain embodiments, at least one instance of $R^{b5}$ is substituted or unsubstituted alkynyl (e.g., substituted or unsubstituted $C_{2-6}$ alkynyl). In certain embodiments, at least one instance of $R^{b5}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{b5}$ are taken together with the intervening atoms to form a substituted or unsubstituted, heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, two instances of $R^{b5}$ are taken together with the intervening atoms to form:

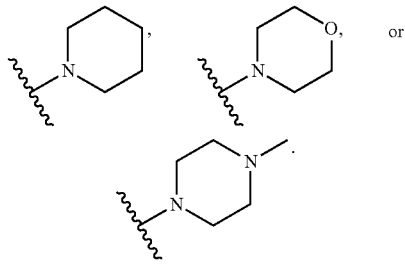

In certain embodiments, R² is

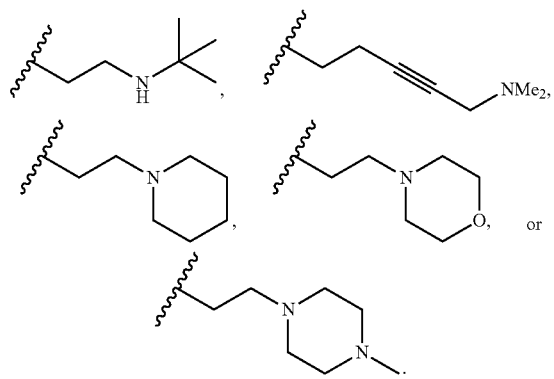

In certain embodiments, R is substituted or unsubstituted alkenyl (e.g., substituted or unsubstituted $C_{2-6}$ alkenyl). In certain embodiments, R² is substituted or unsubstituted alkynyl (e.g., substituted or unsubstituted $C_{2-6}$ alkynyl). In certain embodiments, R² is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R² is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R² is substituted or unsubstituted aryl (e.g., substituted or unsubstituted, 6- to 10-membered aryl). In certain embodiments, R² is substituted benzyl. In certain embodiments, R² is unsubstituted benzyl. In certain embodiments, R² is substituted phenyl. In certain embodiments, R² is unsubstituted phenyl. In certain embodiments, R² is of the formula:

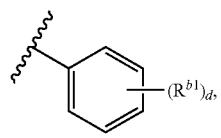

wherein: d is 0, 1, 2, 3, 4, or 5; each instance of $R^{b1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{b2}$, —$N_3$, —$N(R^{b3})_2$, —$SR^{b2}$, —CN, —SCN, —$SO_2R^{b2}$, —C(=O)$R^{b2}$, —C(=O)O$R^{b2}$, —C(=O)N$(R^{b3})_2$, or —$NO_2$; and $R^{b2}$ is hydrogen, or substituted or unsubstituted $C_{1-6}$ alkyl; and
each instance of $R^{b3}$ is independently hydrogen, or substituted or unsubstituted $C_{1-6}$ alkyl.

In certain embodiments, d is 0. In certain embodiments, d is 1. In certain embodiments, R² is

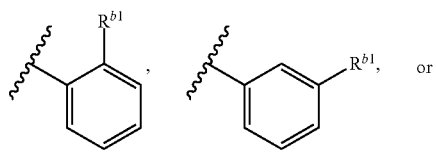

-continued

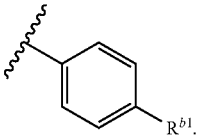

In certain embodiments, d is 2. In certain embodiments, d is 3. In certain embodiments, d is 4. In certain embodiments, d is 5. In certain embodiments, at least one instance of $R^{b1}$ is halogen (e.g., F, Cl, Br, or I). In certain embodiments, at least one instance of $R^{b1}$ is substituted or unsubstituted $C_{1-6}$ alkyl. In certain embodiments, at least one instance of $R^{b1}$ is substituted or unsubstituted alkenyl (e.g., substituted or unsubstituted $C_{2-6}$ alkenyl). In certain embodiments, at least one instance of $R^{b1}$ is substituted or unsubstituted alkynyl (e.g., substituted or unsubstituted $C_{2-6}$ alkynyl). In certain embodiments, at least one instance of $R^{b1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{b1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{b1}$ is substituted or unsubstituted aryl (e.g., substituted or unsubstituted, 6- to 10-membered aryl). In certain embodiments, at least one instance of $R^{b1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{b1}$ is pyridinyl. In certain embodiments, at least one instance of $R^{b1}$ is of the formula:

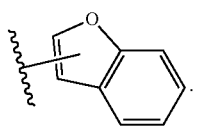

In certain embodiments, at least one instance of $R^{b1}$ is of the formula:

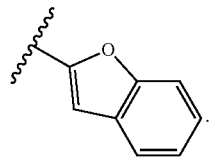 [SMILES: *c1cc2ccccc2o1]

In certain embodiments, at least one instance of $R^{b1}$ is —$OR^{b2}$ (e.g., —OH, —O (substituted or unsubstituted $C_{1-6}$ alkyl) (e.g., —OMe, —OCF₃, —OEt, —OPr, —OBu, or —OBn), or —O (substituted or unsubstituted phenyl) (e.g., —OPh)). In certain embodiments, at least one instance of $R^{b1}$ is —$N_3$. In certain embodiments, at least one instance of $R^{b1}$ is —$N(R^{b3})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{b1}$ is —$SR^{b2}$ (e.g., —SH, —S(substituted or unsubstituted $C_{1-6}$ alkyl) (e.g., —SMe, —SEt, —SPr, or —SBu)). In certain embodiments, at least one instance of $R^{b1}$ is —CN. In certain embodiments, at least one instance of $R^{b1}$ is —SCN. In certain embodiments, at least one instance of $R^{b1}$ is —SO$_2R^{b2}$. In certain embodiments, at least one instance of $R^{b1}$ is —C(=O)$R^{b2}$, —C(=O)O$R^{b2}$, or —C(=O)N($R^{b3}$)$_2$. In certain embodiments, at least one instance of $R^{b1}$ is —NO$_2$. In certain embodiments, $R^2$ is

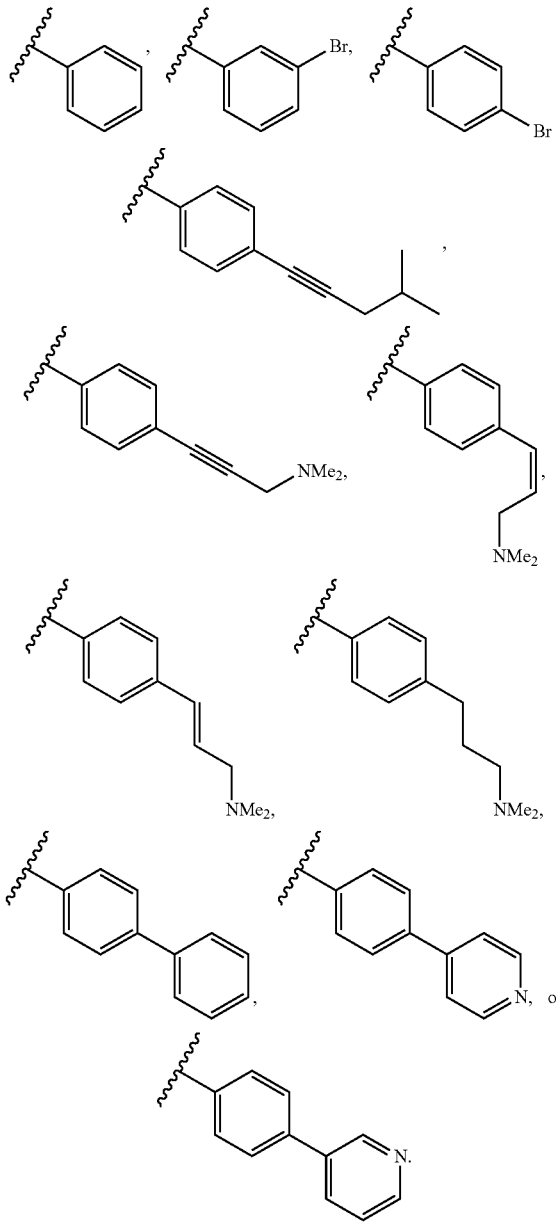

In certain embodiments, $R^2$ is

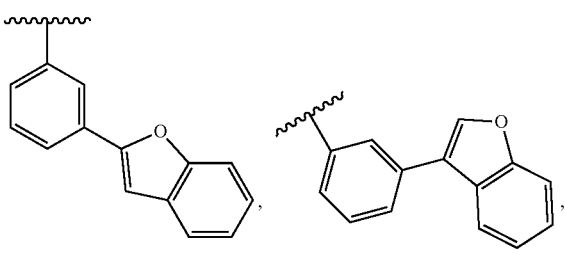

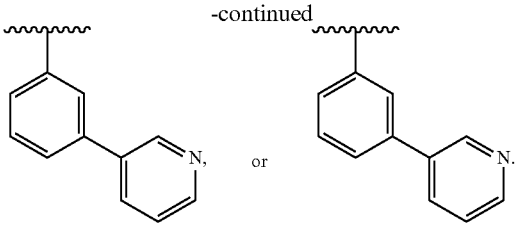

In certain embodiments, $R^2$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl. In certain embodiments, $R^2$ is substituted or unsubstituted pyridinyl.

Formula (I') and Formula (I) also include substituent $R^3$. In certain embodiments, $R^3$ is hydrogen. In certain embodiments, $R^3$ is halogen (e.g., F, Cl, Br, or I). In certain embodiments, $R^3$ is substituted or unsubstituted alkyl (e.g., substituted or unsubstituted C$_{1-6}$ alkyl). In certain embodiments, $R^3$ is of the formula:

wherein f is 1, 2, 3, 4, 5, or 6; $R^C$ is independently substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^{d1}$, —N($R^{c2}$)$_2$, —N$R^{c2}$C(=O)$R^{c1}$, or —S$R^{c1}$; $R^{c1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or oxygen protecting group; and each instance of $R^{c2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or two $R^{c2}$ are taken together with the intervening atoms to form substituted or unsubstituted heterocyclyl or substituted or unsubstituted heteroaryl. In certain embodiments, f is 1. In certain embodiments, f is 2. In certain embodiments, f is 3. In certain embodiments, f is 4. In certain embodiments, f is 5. In certain embodiments, f is 6. In certain embodiments, $R^C$ is substituted or unsubstituted acyl (e.g., acetyl). In certain embodiments, $R^C$ is substituted or unsubstituted C$_{1-6}$ alkyl. In certain embodiments, $R^C$ is substituted or unsubstituted alkenyl (e.g., substituted or unsubstituted C$_{2-6}$ alkenyl). In certain embodiments, $R^C$ is substituted or unsubstituted alkynyl (e.g., substituted or unsubstituted C$_{2-6}$ alkynyl). In certain embodiments, $R^C$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^C$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^C$ is —$OR^{c1}$ (e.g., —OH, —O (substituted or unsubstituted $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, $R^{c1}$ is an oxygen protecting group (e.g., t-butyloxycarbonyl (BOC or Boc), methoxylmethyl (MOM) or methylthiomethyl (MTM)). In certain embodiments, $R^C$ is —$N(R^{c2})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{c2}$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)) when attached to a nitrogen atom. In certain embodiments, when $R^C$ is —$N(R^{c2})_2$, one instance of $R^{c2}$ is substituted or unsubstituted $C_{1-6}$ alkyl, and the other instance of $R^{c2}$ is hydrogen. In certain embodiments, two $R^{c2}$ are taken together with the intervening atoms to form substituted or unsubstituted heterocyclyl or substituted or unsubstituted heteroaryl (e.g., piperidine or pyridine). In certain embodiments, $R^C$ is —$NR^{c2}C(=O)R^{d1}$ (e.g., —NHC(=O)(substituted or unsubstituted $C_{1-6}$ alkyl) (e.g., —NHC(=O)Me, —NHC(=O)Ph, or —NHC(=O)(substituted phenyl)). In certain embodiments, when $R^C$ is —$N(R^{c2})C(=O)R^{c1}$, $R^{c1}$ is substituted or unsubstituted $C_{1-6}$ alkyl, and $R^{c2}$ is substituted or unsubstituted $C_{1-6}$ alkyl. In certain embodiments, when $R^C$ is —$N(R^{c2})C(=O)R^{c1}$, $R^{c1}$ is substituted or unsubstituted $C_{1-6}$ alkyl, and $R^{c2}$ is hydrogen. In certain embodiments, $R^C$ is —$SR^{c1}$ (e.g., —SH, —S(substituted or unsubstituted $C_{1-6}$ alkyl) (e.g., —SMe, —SEt, —SPr, —SBu, or —SBn), or —S (substituted or unsubstituted phenyl) (e.g., —SPh)). In certain embodiments, $R^3$ is:

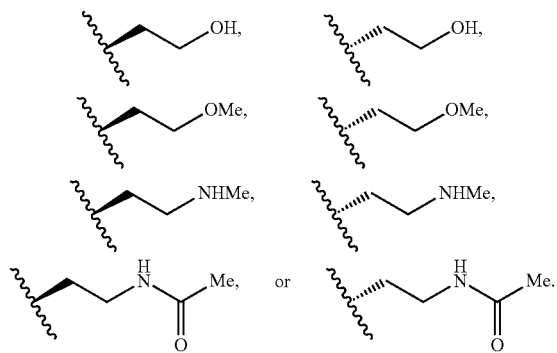

In certain embodiments, $R^3$ is substituted or unsubstituted alkenyl (e.g., substituted or unsubstituted $C_{2-6}$ alkenyl). In certain embodiments, $R^3$ is substituted or unsubstituted alkynyl (e.g., substituted or unsubstituted $C_{2-6}$ alkynyl). In certain embodiments, $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^3$ is substituted or unsubstituted aryl (e.g., substituted or unsubstituted, 6- to 10-membered aryl). In certain embodiments, $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (I') includes substituent $R^{3A}$. In certain embodiments, $R^{3A}$ is hydrogen. In certain embodiments, $R^{3A}$ is halogen (e.g., F, Cl, Br, or I). In certain embodiments, $R^{3A}$ is substituted or unsubstituted alkyl (e.g., substituted or unsubstituted $C_{1-6}$ alkyl). In certain embodiments, $R^{3A}$ is of the formula:

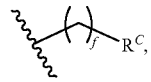

wherein f is 1, 2, 3, 4, 5 or 6; $R^C$ is independently substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{c1}$, —$N(R^{c2})_2$, —$NR^{c2}C(=O)R^{c1}$, or —$SR^{c1}$; $R^{c1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or oxygen protecting group; and each instance of $R^{c2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or two $R^{c2}$ are taken together with the intervening atoms to form substituted or unsubstituted heterocyclyl or substituted or unsubstituted heteroaryl. In certain embodiments, f is 1. In certain embodiments, f is 2. In certain embodiments, f is 3. In certain embodiments, f is 4. In certain embodiments, f is 5. In certain embodiments, f is 6. In certain embodiments, $R^C$ is substituted or unsubstituted acyl (e.g., acetyl). In certain embodiments, $R^C$ is substituted or unsubstituted $C_{1-6}$ alkyl. In certain embodiments, $R^C$ is substituted or unsubstituted alkenyl (e.g., substituted or unsubstituted $C_{2-6}$ alkenyl). In certain embodiments, $R^C$ is substituted or unsubstituted alkynyl (e.g., substituted or unsubstituted $C_{2-6}$ alkynyl). In certain embodiments, $R^C$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^C$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^C$ is —$OR^{c1}$ (e.g., —OH, —O (substituted or unsubstituted $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, $R^{c1}$ is an oxygen protecting group (e.g., t-butyloxycarbonyl (BOC or Boc), methoxylmethyl (MOM) or methylthiomethyl (MTM)). In certain embodiments, $R^C$ is —$N(R^{c2})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^{c2}$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)) when attached to a nitrogen atom. In certain embodiments, when $R^C$ is —$N(R^{c2})_2$, one instance of $R^{c2}$ is substituted or unsubstituted $C_{1-6}$ alkyl, and the other instance of $R^{c2}$ is hydrogen. In certain embodiments, two $R^{c2}$ are taken together with the intervening atoms to form substituted or unsubstituted heterocyclyl or substituted or unsubstituted heteroaryl (e.g., piperidine or pyridine). In certain embodiments, $R^C$ is —$NR^{c2}C(=O)R^{c1}$ (e.g., —NHC(=O)(substituted or unsubstituted $C_{1-6}$ alkyl) (e.g., —NHC(=O)Me), —NHC(=O)Ph, or —NHC(=O) (substituted phenyl)). In certain embodiments, when $R^C$ is —$N(R^{c2})C(=O)R^{c1}$, $R^{c1}$ is substituted or unsubstituted $C_{1-6}$ alkyl, and $R^{c2}$ is substituted or unsubstituted $C_{1-6}$ alkyl. In certain embodiments, when $R^C$ is —$N(R^{c2})C(=O)R^{c1}$, $R^{c1}$ is substituted or unsubstituted $C_{1-6}$ alkyl, and $R^{c2}$ is hydrogen. In certain embodiments, $R^C$ is —$SR^{c1}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^{3A}$ is:

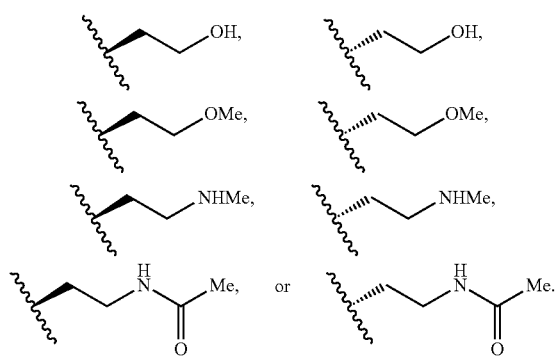

In certain embodiments, $R^{3A}$ is substituted or unsubstituted alkenyl (e.g., substituted or unsubstituted $C_{2-6}$ alkenyl). In certain embodiments, $R^{3A}$ is substituted or unsubstituted alkynyl (e.g., substituted or unsubstituted $C_{2-6}$ alkynyl). In certain embodiments, $R^{3A}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^{3A}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^{3A}$ is substituted or unsubstituted aryl (e.g., substituted or unsubstituted, 6- to 10-membered aryl). In certain embodiments, $R^{3A}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (I') includes substituent X1. In certain embodiments, X1 is —$CR^4$—. In certain embodiments, X1 is —$NR^4$—. In certain embodiments, X1 is —O—. In certain embodiments, X1 is —S—.

Formula (I') and Formula (I) also include substituent $R^4$. In certain embodiments, $R^4$ is hydrogen. In certain embodiments, $R^4$ is halogen (e.g., F, Cl, Br, or I). In certain embodiments, $R^4$ is substituted or unsubstituted acyl. In certain embodiments, $R^4$ is of the formula: —$C(=O)R^D$, and $R^D$ is hydrogen or substituted or unsubstituted $C_{1-6}$ alkyl. In certain embodiments, $R^4$ is of the formula: —$C(=O)OR^D$, and $R^D$ is hydrogen or substituted or unsubstituted $C_{1-6}$ alkyl. In certain embodiments, $R^4$ is

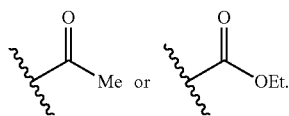

In certain embodiments, $R^4$ is of the formula: —$C(=NR^Y)$ $R^D$, wherein $R^Y$ is hydrogen, substituted or unsubstituted $C_{1-6}$ alkyl, or nitrogen protecting group; and $R^D$ is hydrogen or substituted or unsubstituted $C_{1-6}$ alkyl. In certain embodiments, $R^4$ is —C(=NH)Me. In certain embodiments, $R^4$ is of the formula: —$C(=NR^Y)OR^D$, wherein $R^Y$ is hydrogen, substituted or unsubstituted $C_{1-6}$ alkyl, or nitrogen protecting group; and $R^D$ is hydrogen or substituted or unsubstituted $C_{1-6}$ alkyl. In certain embodiments, $R^4$ is —C(=NH)OMe. In certain embodiments, $R^4$ is of the formula: —$C(=O)N(R^{d1})_2$, and each instance of $R^{d1}$ is independently hydrogen or substituted or unsubstituted $C_{1-6}$ alkyl. In certain embodiments, $R^4$ is

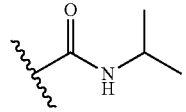

In certain embodiments, $R^4$ is of the formula: —$C(=O)N(R^{d1})_2$, and each instance of $R^{d1}$ is independently hydrogen or substituted or unsubstituted $C_{1-6}$ alkyl, nitrogen protecting group, or two instances of $R^{d1}$ are taken together with the intervening atoms to form a substituted or unsubstituted, heterocyclic ring. In certain embodiments, each instance of $R^{d1}$ is independently a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{d1}$ are taken together with the intervening atoms to form a substituted or unsubstituted, heterocyclic ring (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^4$ is substituted or unsubstituted alkyl (e.g., substituted or unsubstituted $C_{1-6}$ alkyl). In certain embodiments, $R^4$ is substituted or unsubstituted aryl (e.g., substituted or unsubstituted, 6- to 10-membered aryl). In certain embodiments, $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^4$ is

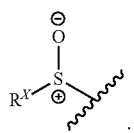

In certain embodiments, $R^X$ is substituted or unsubstituted $C_{1-6}$ alkyl. In certain embodiments, $R^4$ is

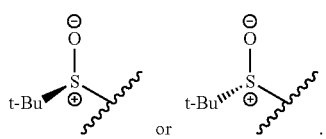

In certain embodiments, $R^4$ is

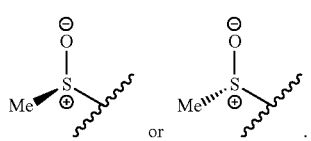

In certain embodiments, $R^4$ is

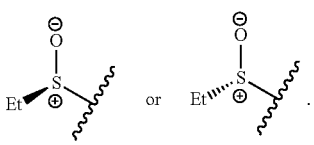 [SMILES: *[S@+]([O-])CC ; *[S@@+]([O-])CC]

In certain embodiments, $R^4$ is

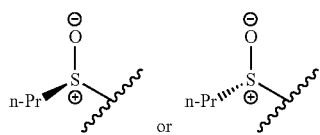

In certain embodiments, $R^4$ is

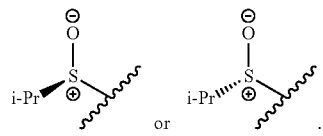

In certain embodiments, $R^4$ is

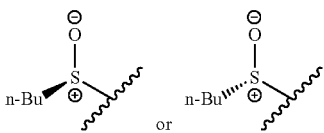

In certain embodiments, $R^4$ is

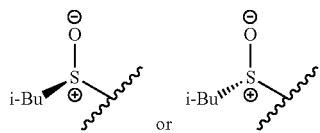

In certain embodiments, $R^4$ is

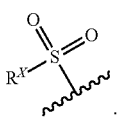

In certain embodiments, $R^X$ is substituted or unsubstituted $C_{1-6}$ alkyl. In certain embodiments, $R^4$

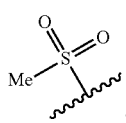

In certain embodiments, $R^4$ is

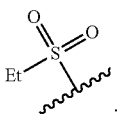

In certain embodiments, R¹ is

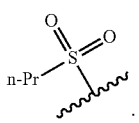

In certain embodiments, R⁴ is

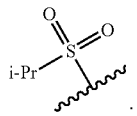

In certain embodiments, R⁴ is

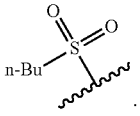

In certain embodiments, R⁴ is

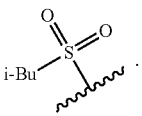

In certain embodiments, R⁴ is

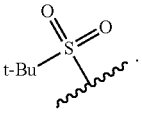

In certain embodiments, n is 1. In certain embodiments, n is 2. In certain embodiments, n is 3.

In certain embodiments, the compound of Formula (I') is of the formula:

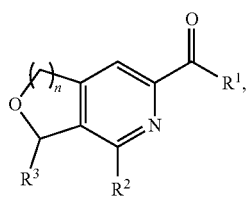

(I'-A)

or a pharmaceutically acceptable salt, solvate, hydrate, polymorph, co-crystal, tautomer, stereoisomer, isotopically labeled derivative, or prodrug thereof, wherein n, R¹, R², and R³ are as described herein.

In certain embodiments, the compound of Formula (I') is of the formula:

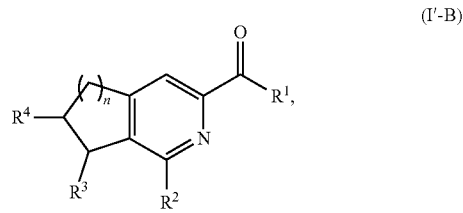

(I'-B)

or a pharmaceutically acceptable salt, solvate, hydrate, polymorph, co-crystal, tautomer, stereoisomer, isotopically labeled derivative, or prodrug thereof, wherein n, R¹, R², R³, and R⁴ are as described herein.

In certain embodiments, the compound of Formula (I') is of the formula:

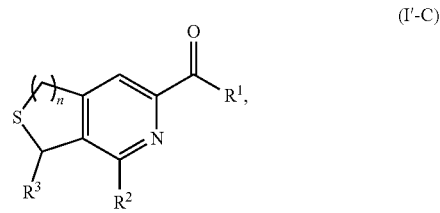

(I'-C)

or a pharmaceutically acceptable salt, solvate, hydrate, polymorph, co-crystal, tautomer, stereoisomer, isotopically labeled derivative, or prodrug thereof, wherein n, R¹, R², R³, and R⁴ are as described herein.

In certain embodiments, the compound of Formula (I') is of one of the following formulae:

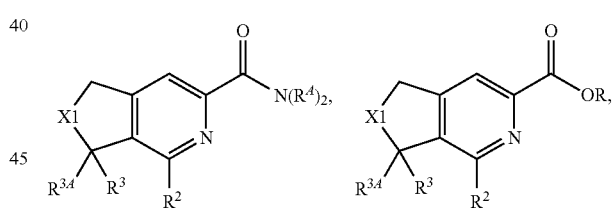

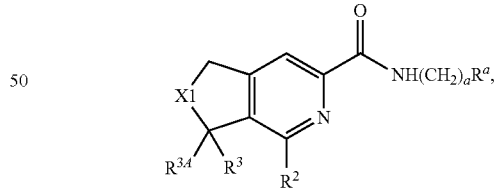

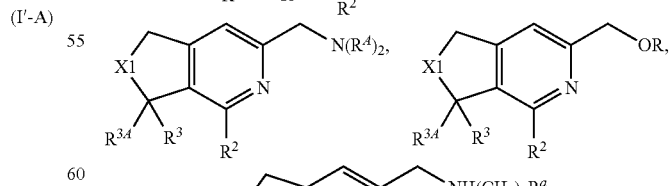

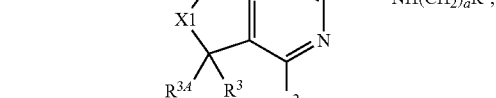

or a pharmaceutically acceptable salt thereof.

In certain embodiments, the compound of Formula (I') is of one of the following formulae:
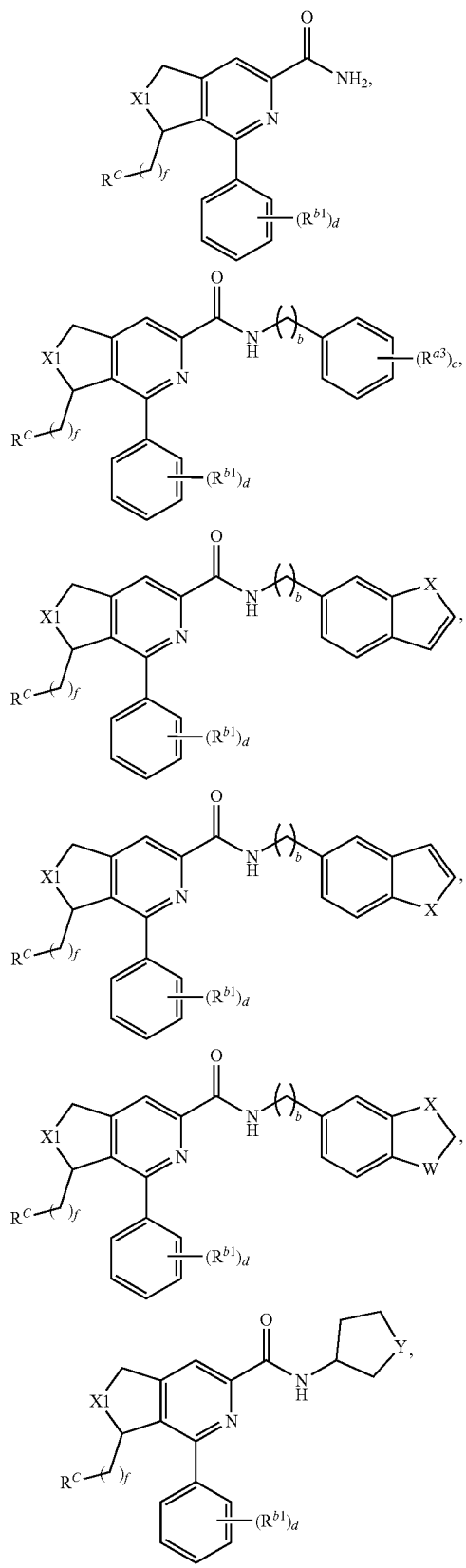
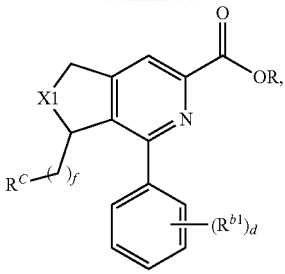
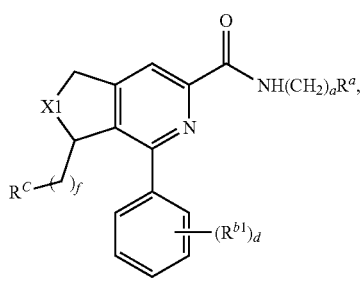
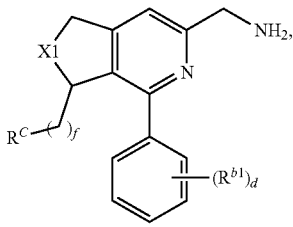
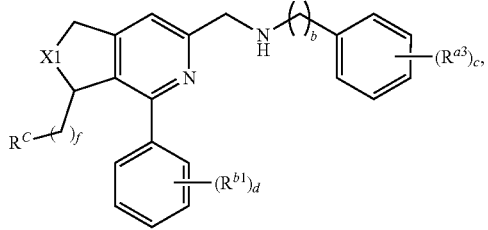
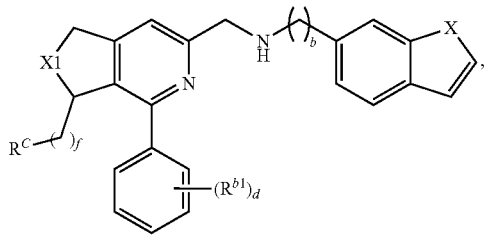
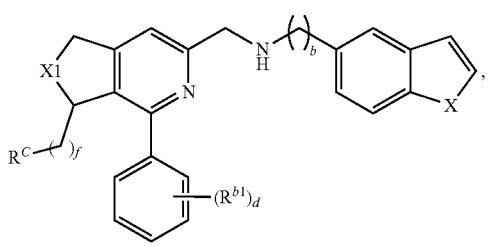

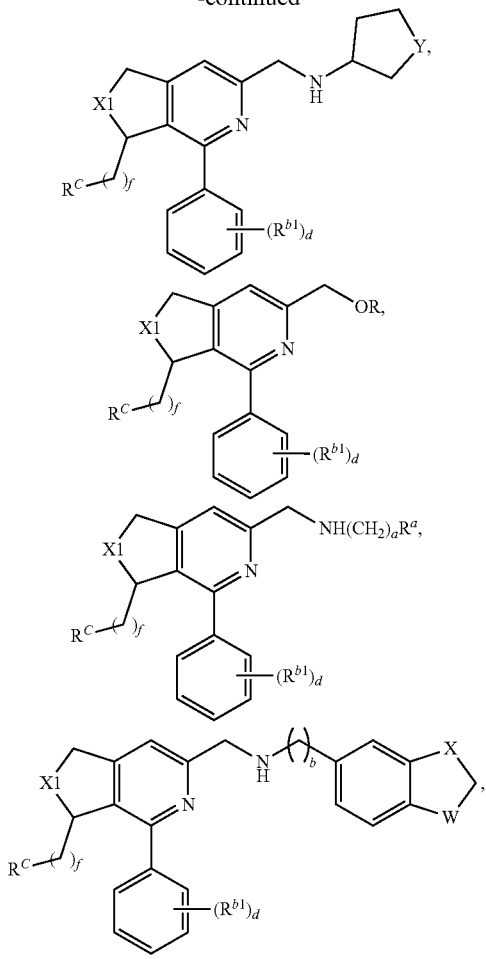
or a pharmaceutically acceptable salt thereof.
In certain embodiments, the compound of Formula (I') is of one of the following formulae:
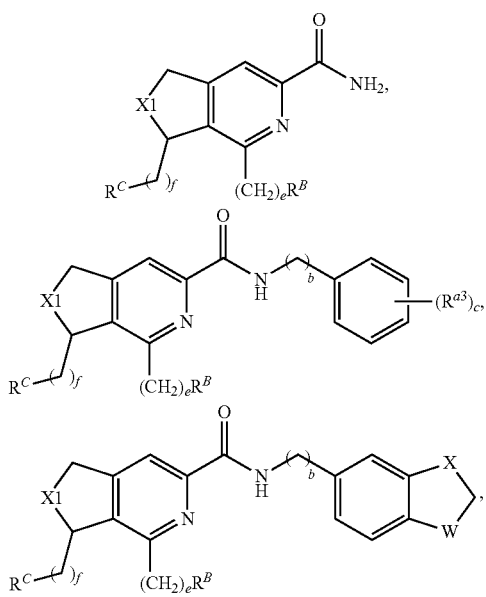

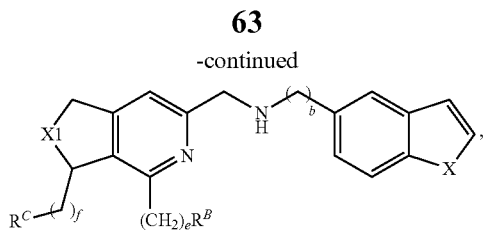
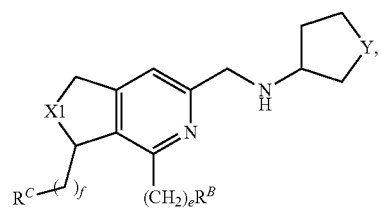
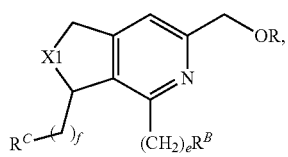
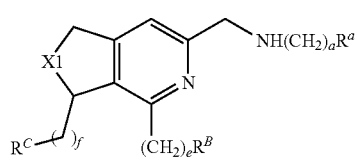
or a pharmaceutically acceptable salt thereof.
In certain embodiments, the compound of Formula (I') is of one of the following formulae:
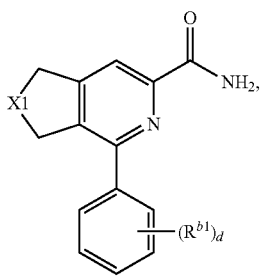
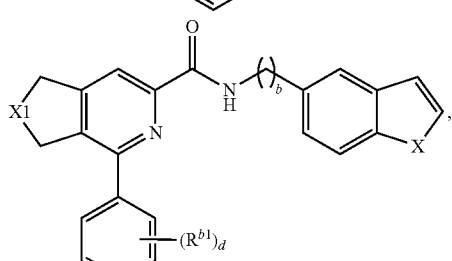
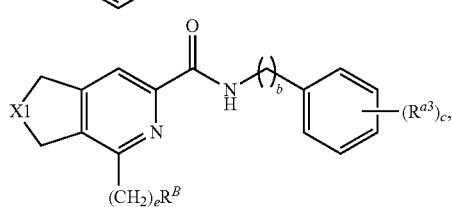
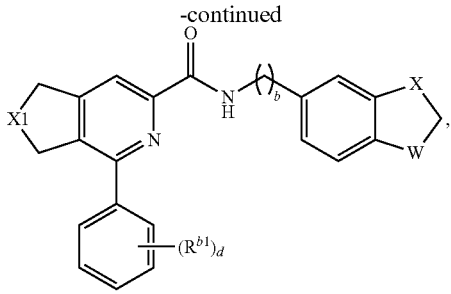
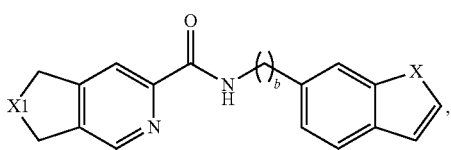
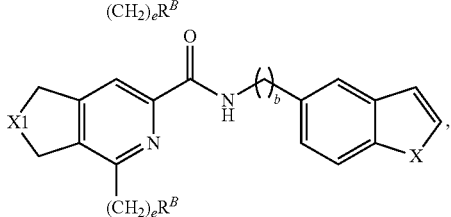
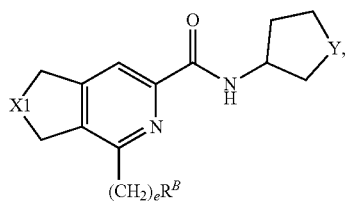
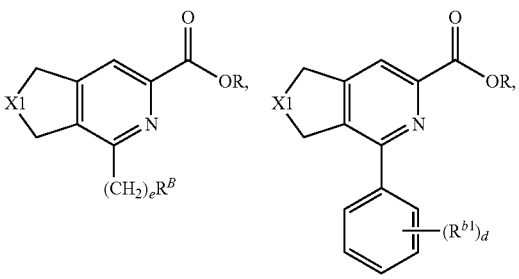
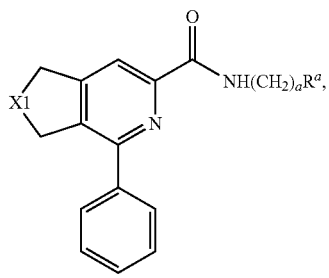

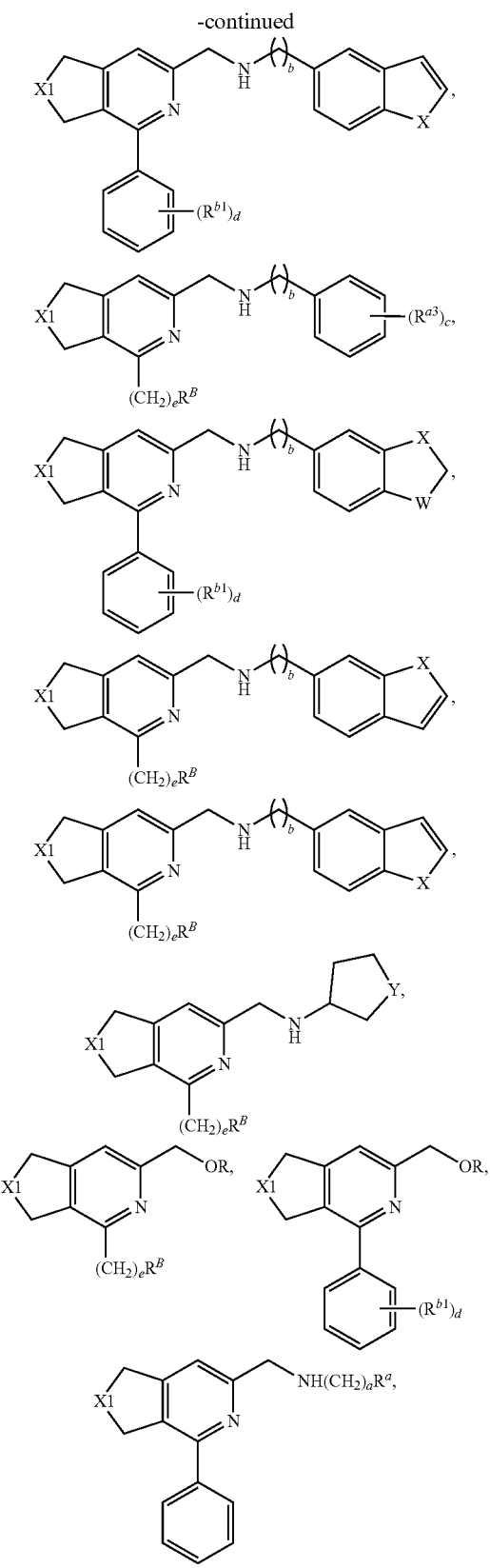
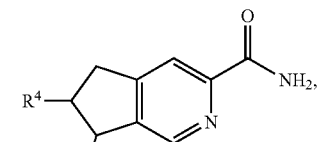
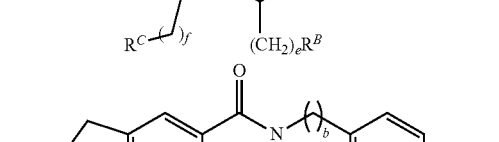
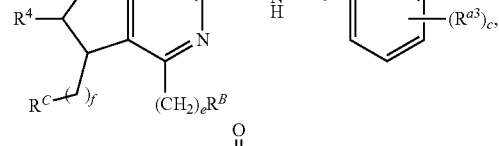
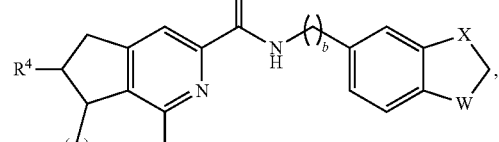
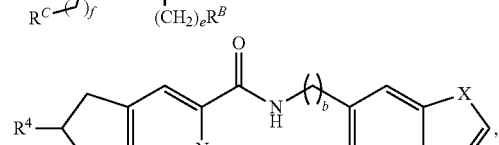
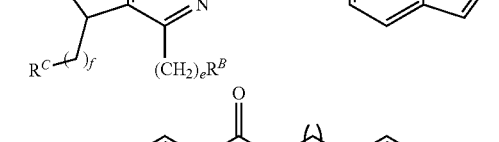
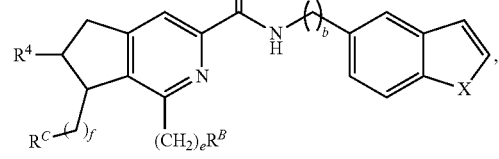
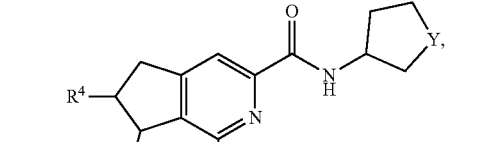
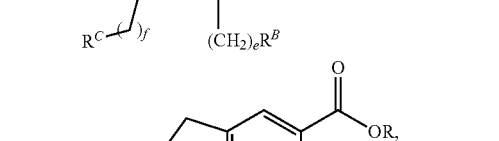
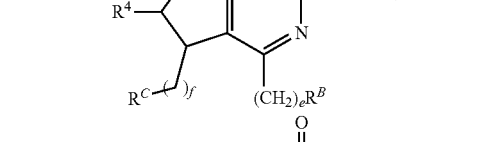
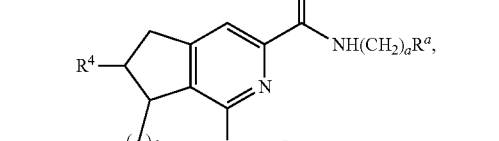
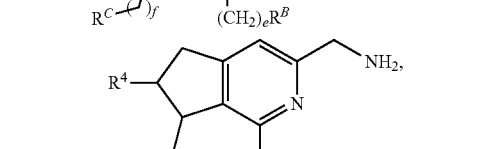
or a pharmaceutically acceptable salt thereof.
In certain embodiments, the compound of Formula (I') is of one of the following formulae:

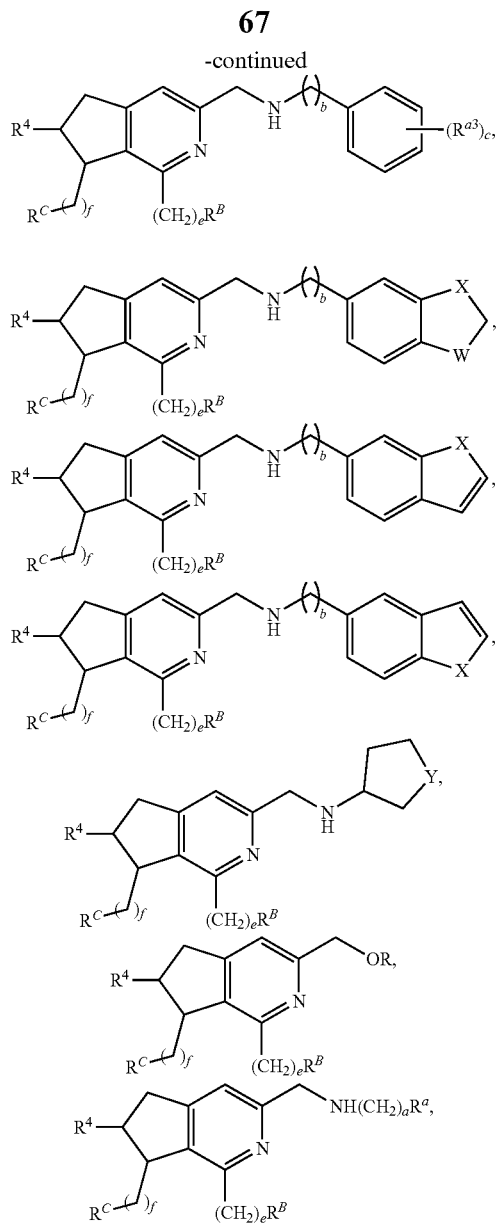
or a pharmaceutically acceptable salt thereof.
In certain embodiments, the compound of Formula (I') is of one of the following formulae:
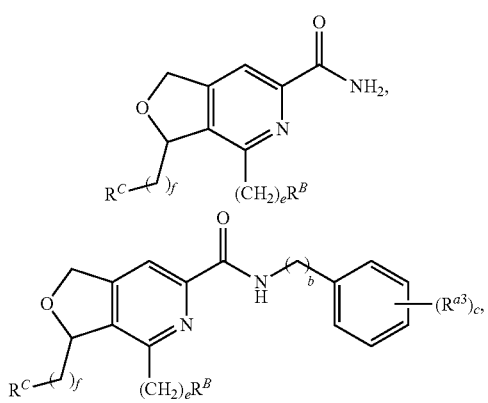
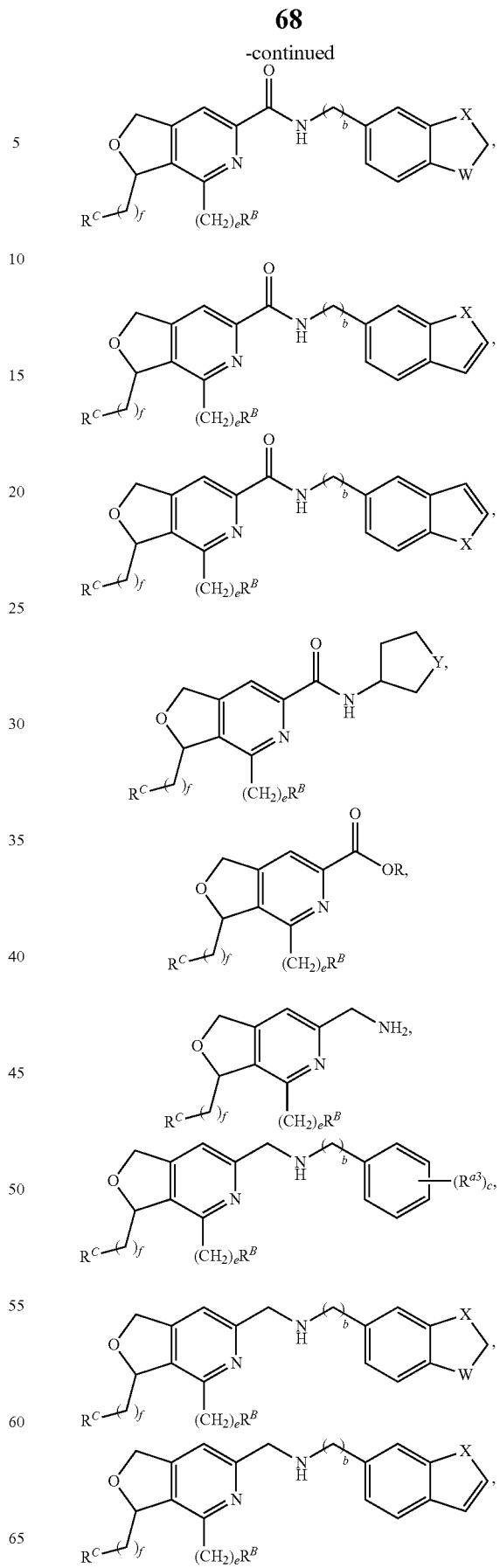

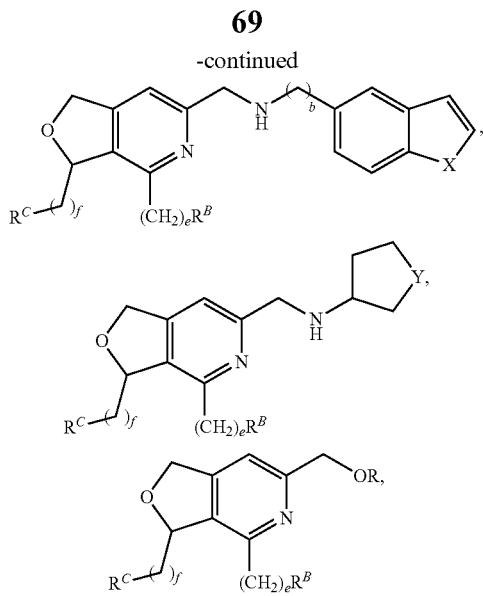
or a pharmaceutically acceptable salt thereof.
In certain embodiments, the compound of Formula (I') is of one of the following formulae:
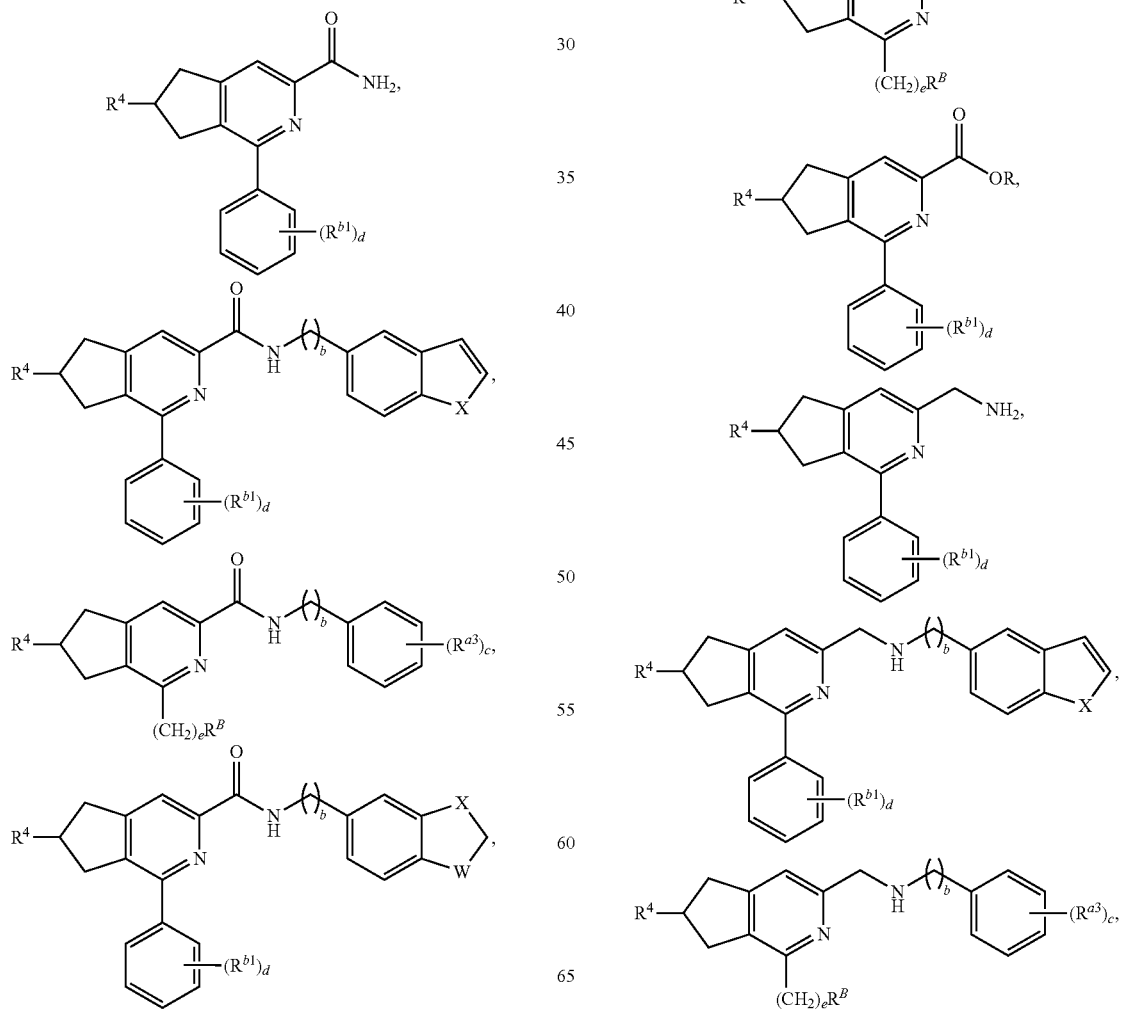

-continued
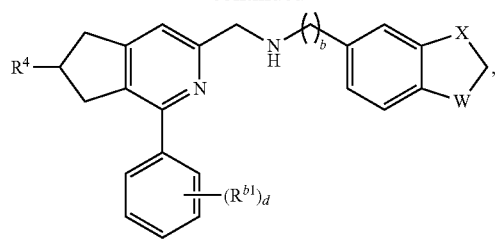
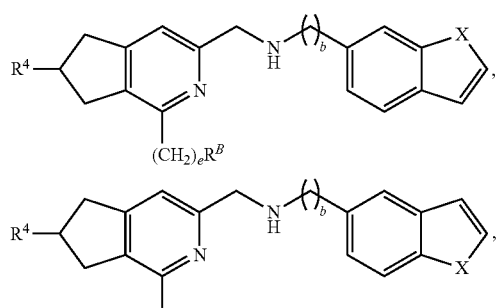
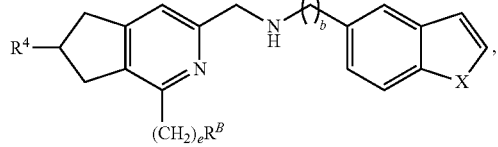
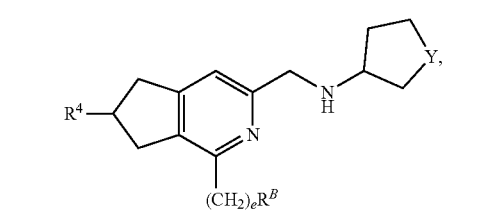
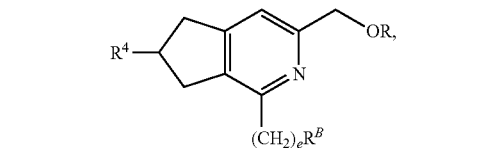
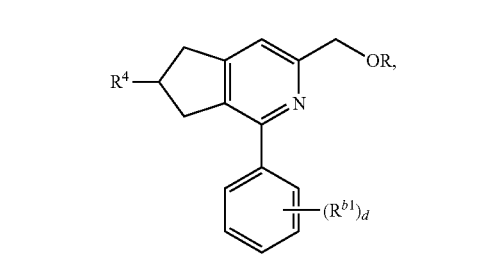
or a pharmaceutically acceptable salt thereof.
In certain embodiments, the compound of Formula (I') is of one of the following formulae:
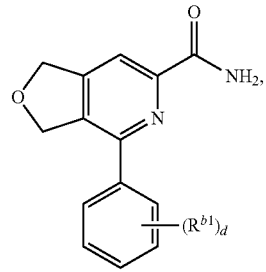
-continued
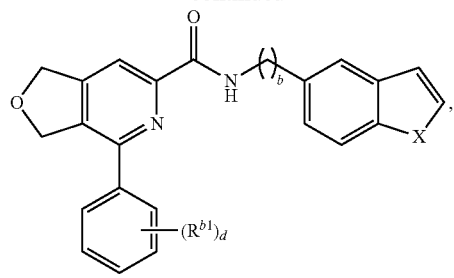
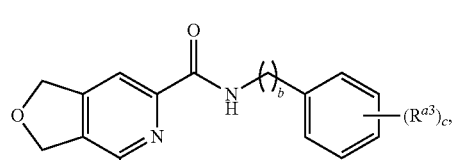
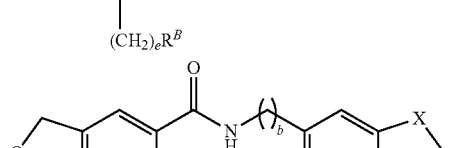
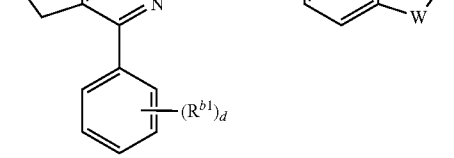
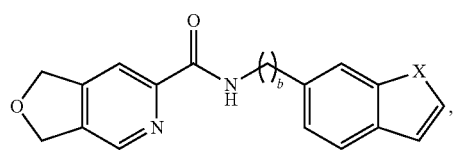
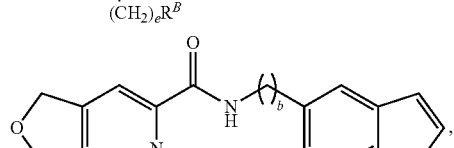
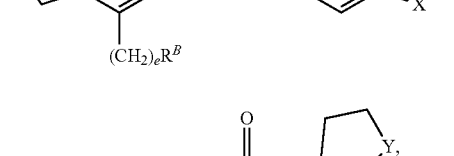
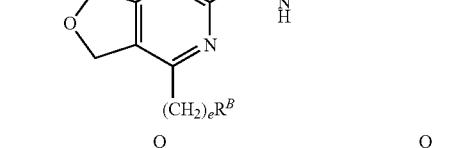
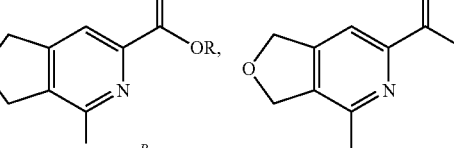
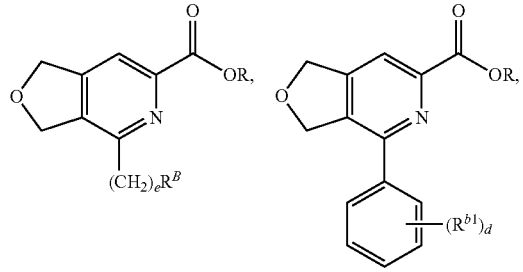

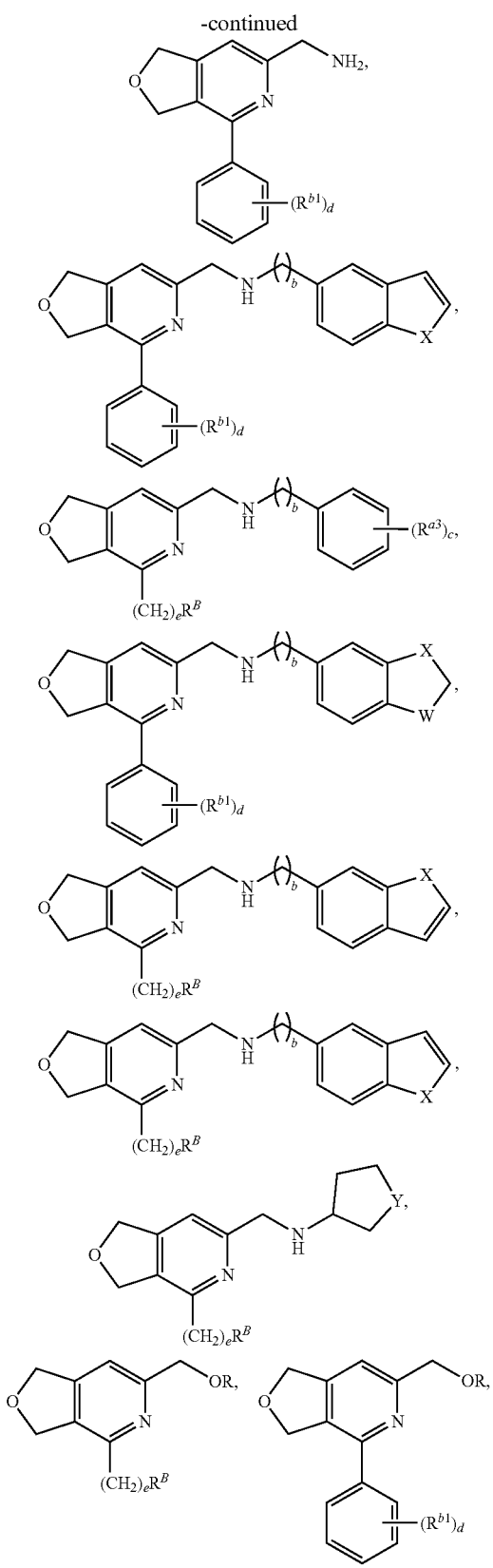
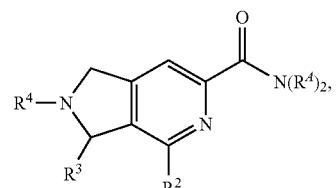
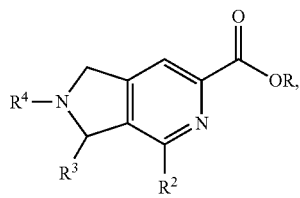
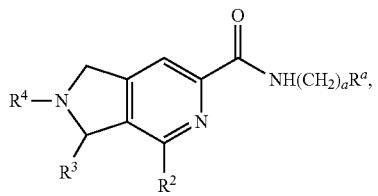
or a pharmaceutically acceptable salt thereof.
In certain embodiments, the compound of Formula (I) is of one of the following formulae:
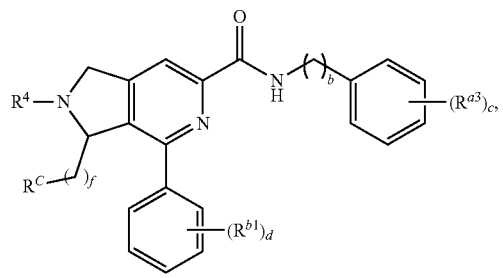
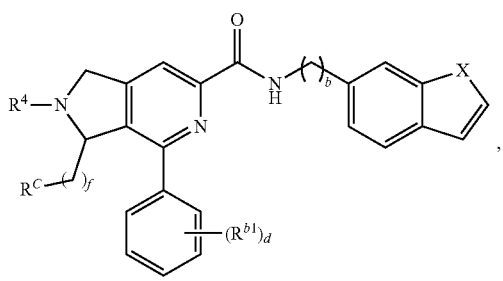
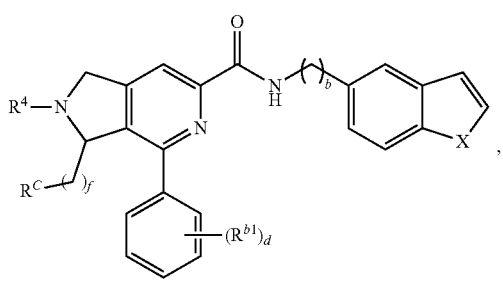
or a pharmaceutically acceptable salt thereof.
In certain embodiments, the compound of Formula (I) is of one of the following formulae:

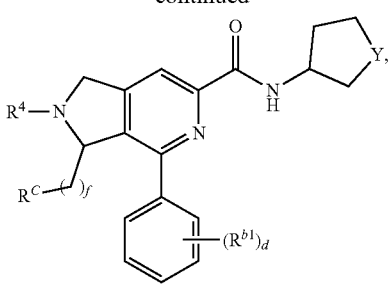

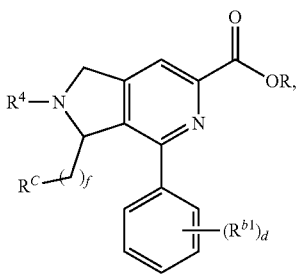

or a pharmaceutically acceptable salt thereof.

In certain embodiments, the compound of Formula (I) is of one of the following formulae:

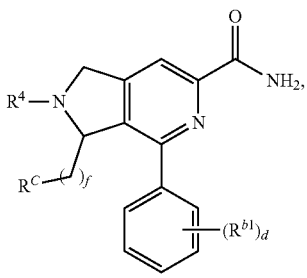

or a pharmaceutically acceptable salt thereof.

In certain embodiments, the compound of Formula (I) is of one of the following formulae:

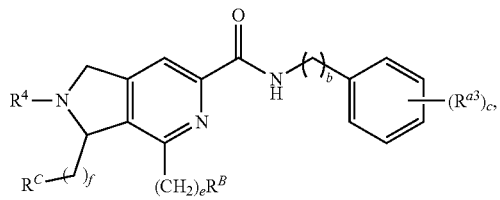

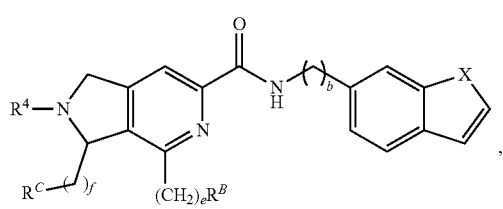

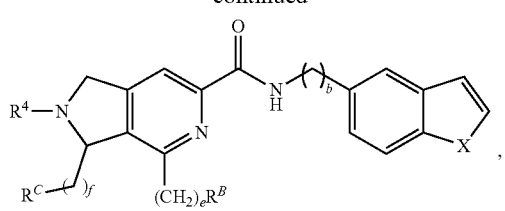

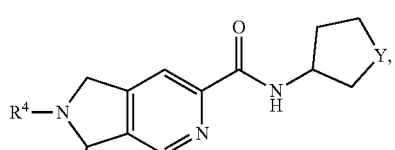

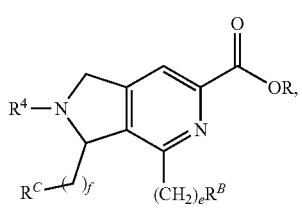

or a pharmaceutically acceptable salt thereof.

In certain embodiments, the compound of Formula (I) is of one of the following formulae:

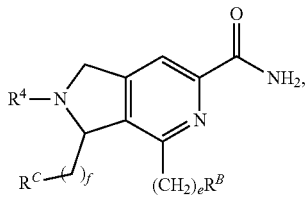

or a pharmaceutically acceptable salt thereof.

In certain embodiments, the compound of Formula (I) is of one of the following formulae:

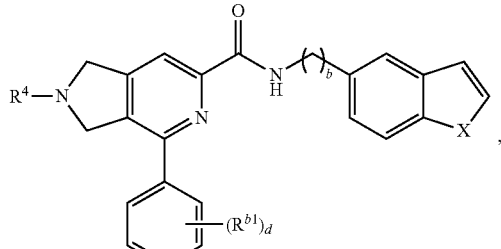

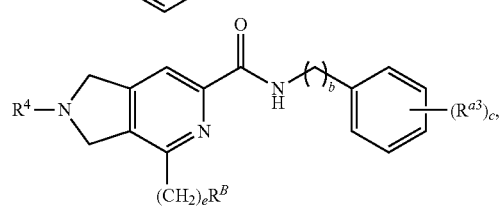

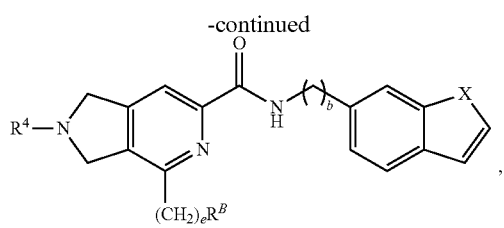
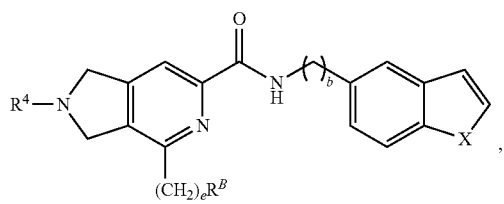
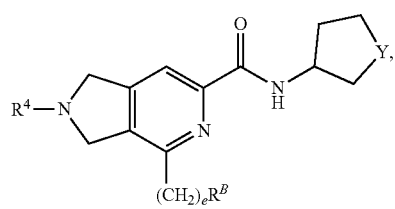
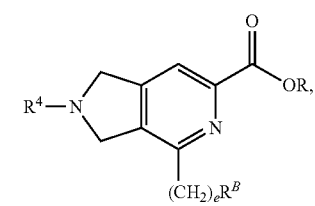
or a pharmaceutically acceptable salt thereof.
In certain embodiments, the compound of Formula (I) is of one of the following formulae:
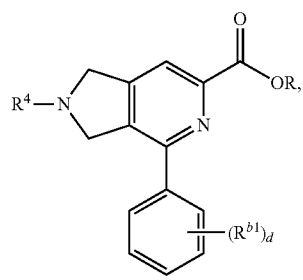
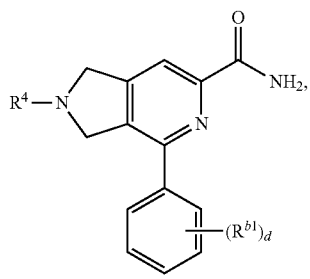
or a pharmaceutically acceptable salt thereof.
In certain embodiments, the compound of Formula (I') or (I) is of the formula:
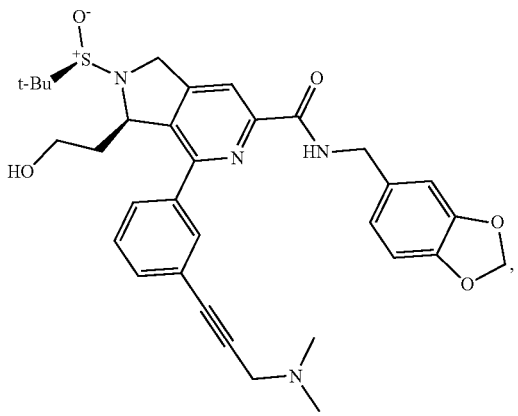
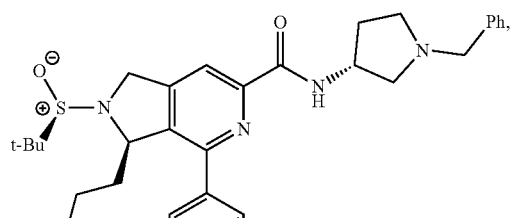
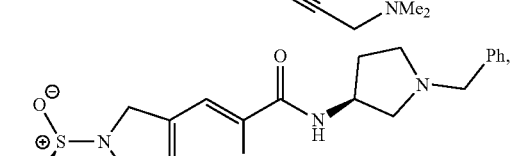
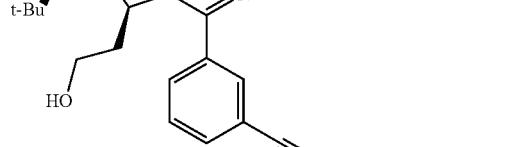
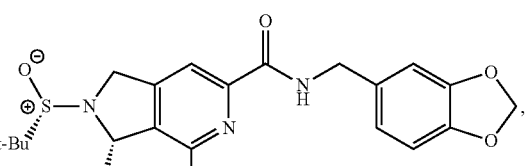
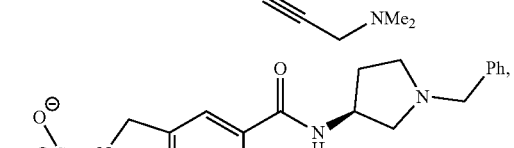
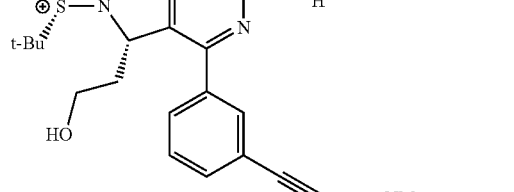

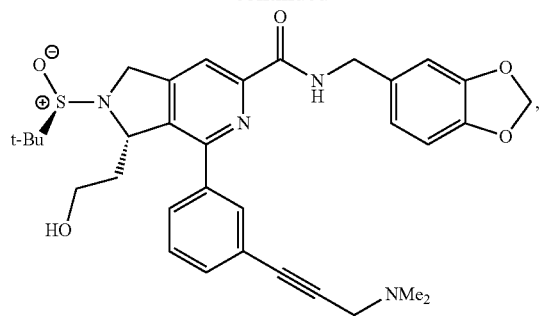
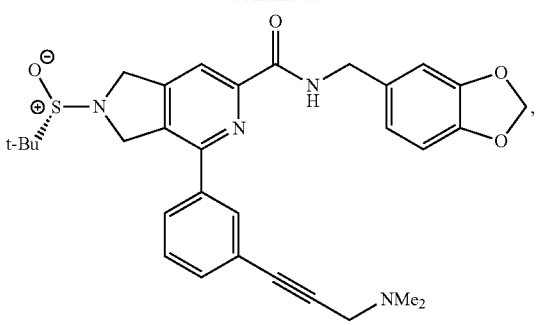
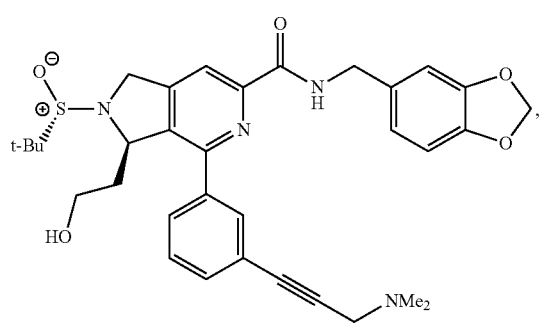
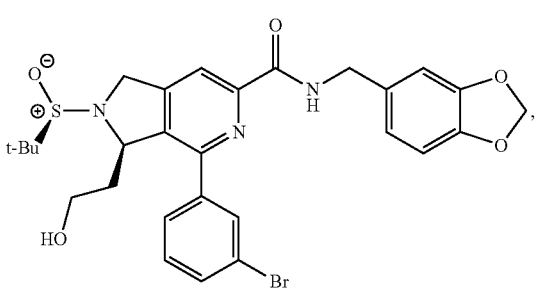
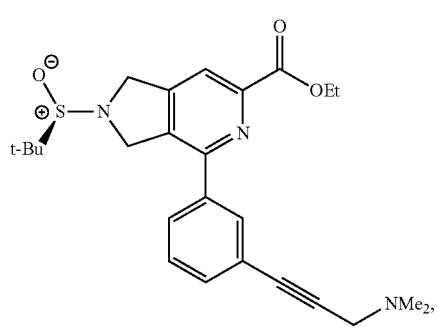
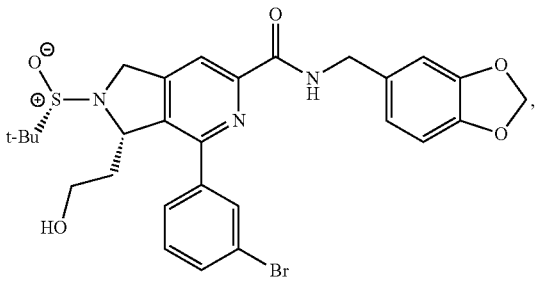
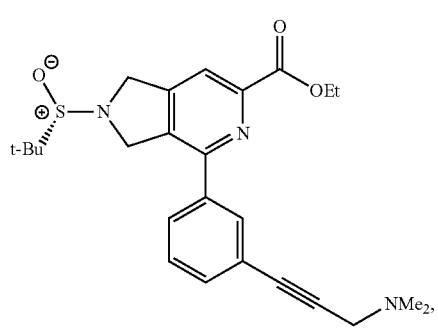
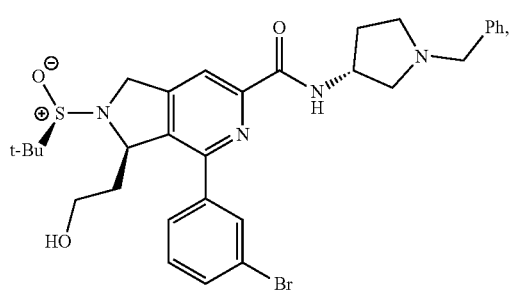
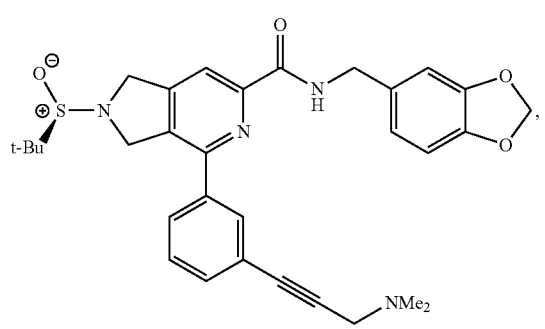
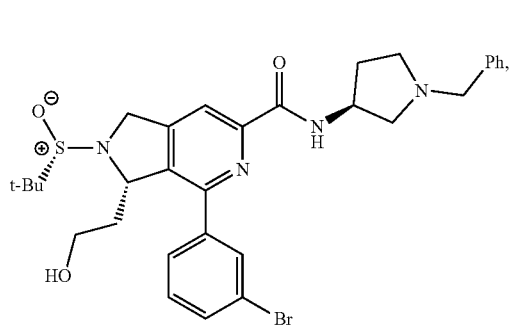

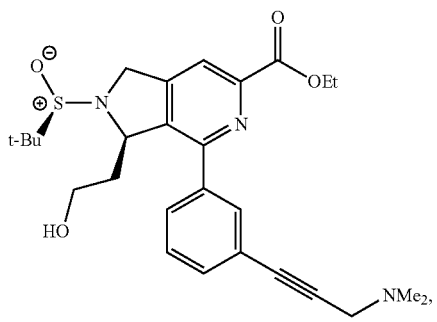
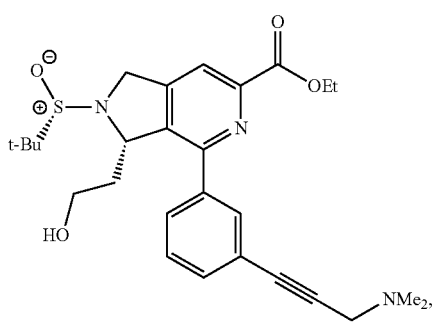
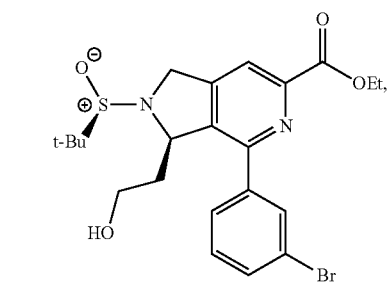
or a pharmaceutically acceptable salt thereof.
In certain embodiments, the compound of Formula (I') or (I) is of the formula:
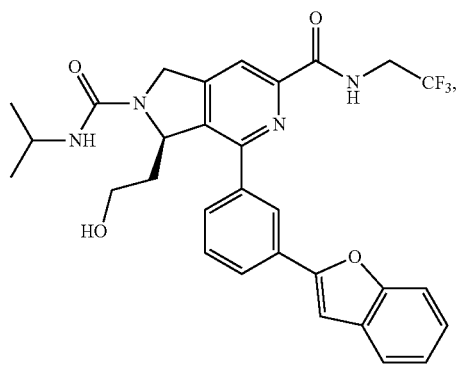
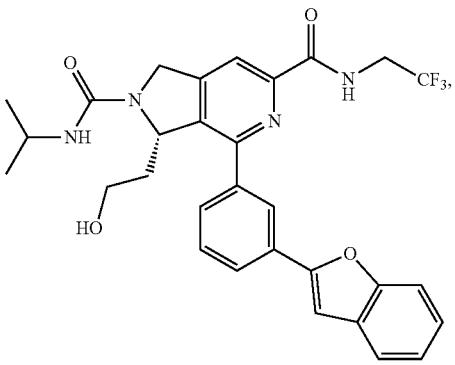
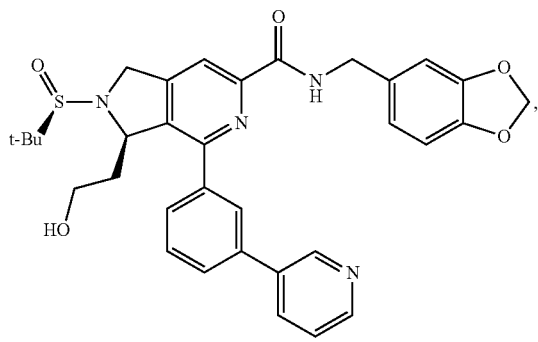
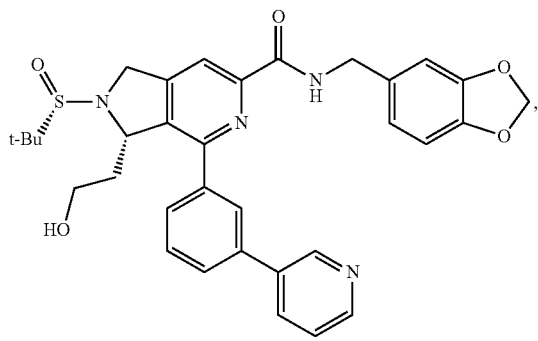
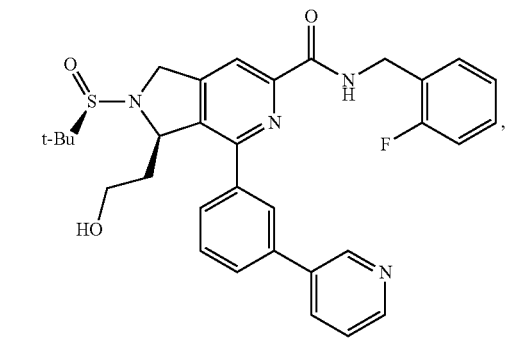
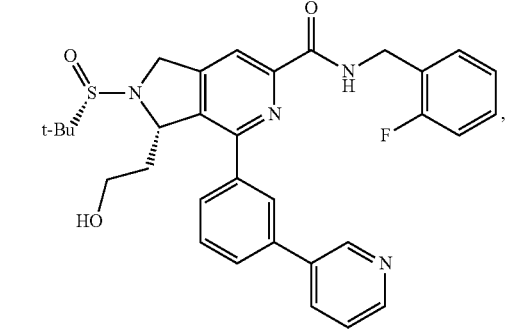

83
-continued
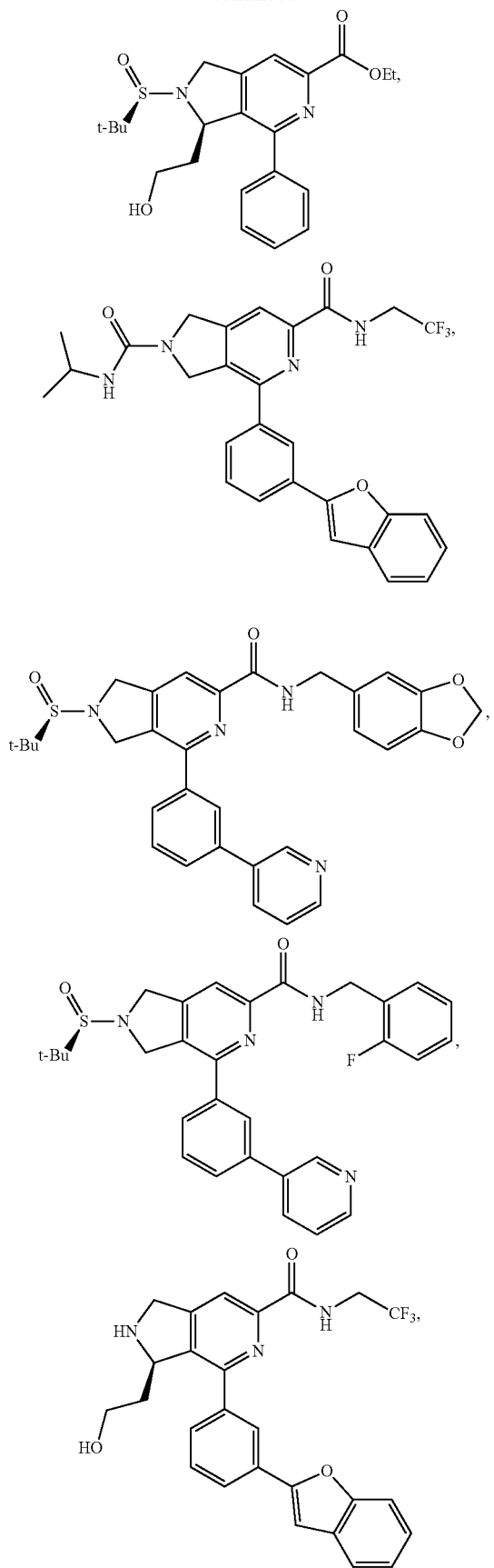
84
-continued
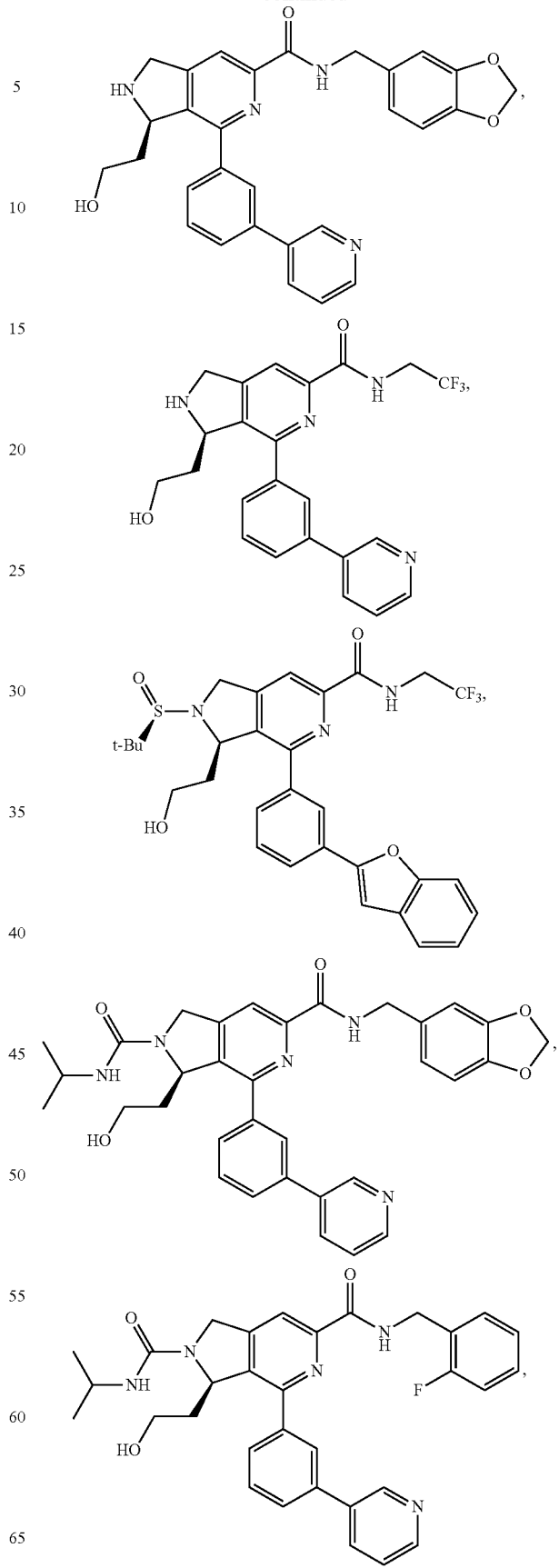

85
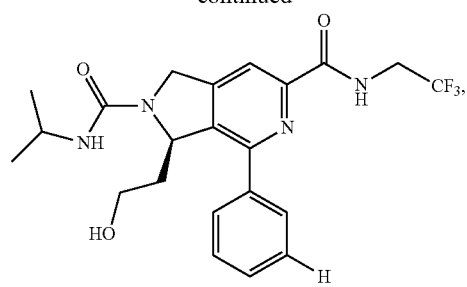
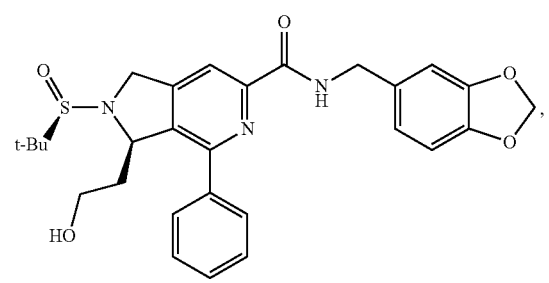
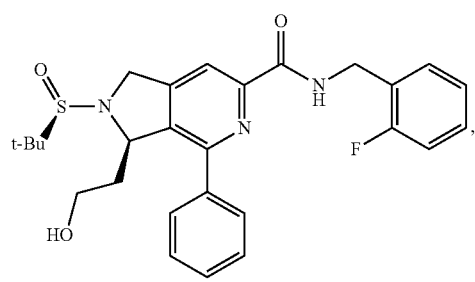
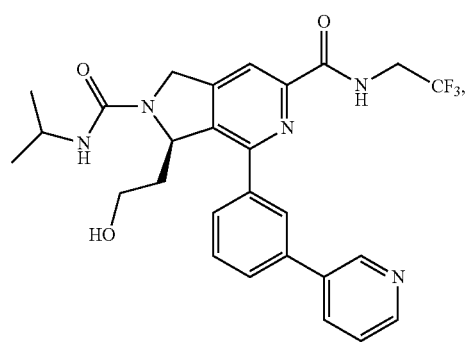
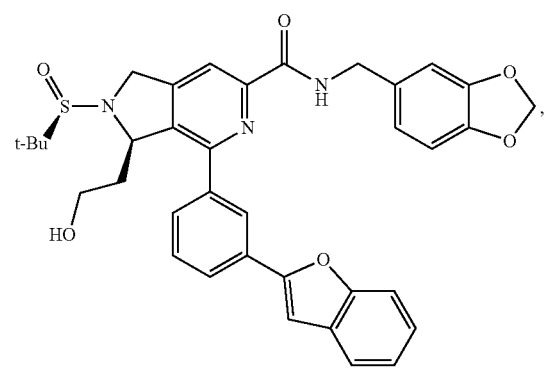
86
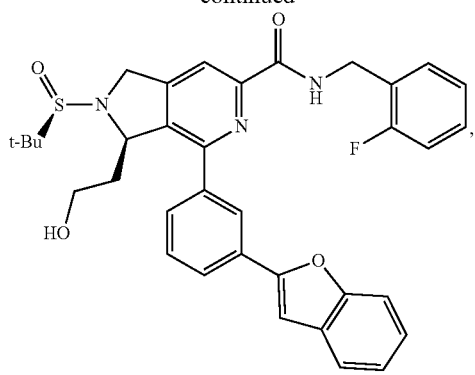
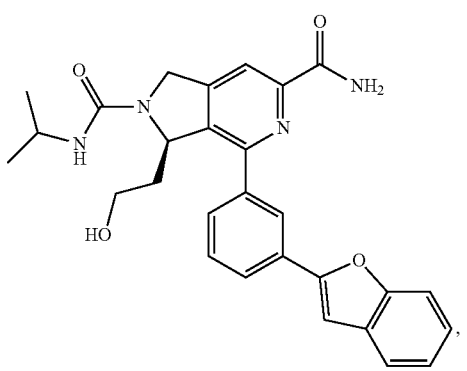
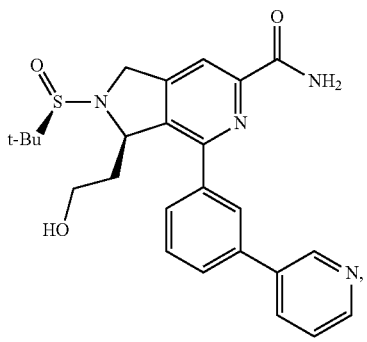
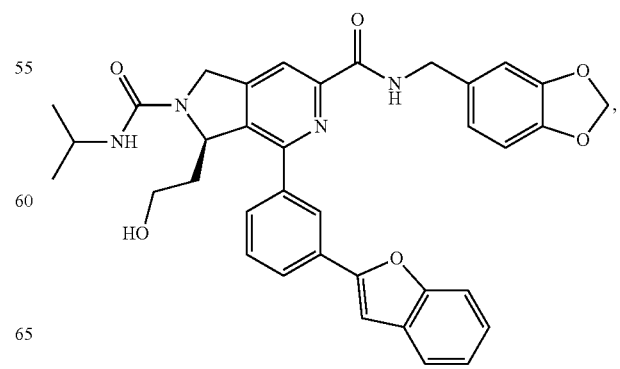

-continued

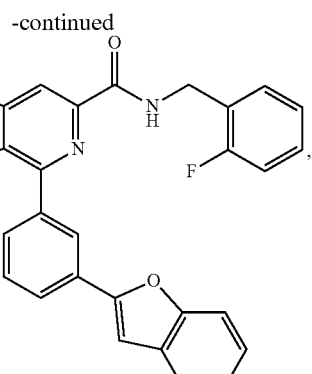

,

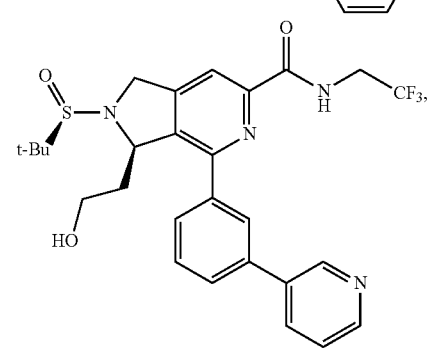

or a pharmaceutically acceptable salt thereof.

Compounds of Formula (II)

In certain embodiments, the compound of Formula (II) is of the formula:

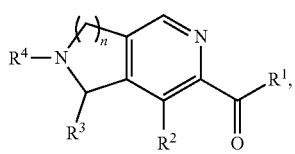

(II)

or a pharmaceutically acceptable salt thereof, wherein:

n is 1, 2, or 3;

$R^1$ is hydrogen, substituted or unsubstituted alkyl, substituted or unsubstituted aryl, substituted or unsubstituted heteroaryl, —OR, or —N($R^A$)$_2$;

R is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or oxygen protecting group;

$R^2$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^3$ is hydrogen, substituted or unsubstituted alkyl, substituted or unsubstituted aryl, or substituted or unsubstituted heteroaryl;

$R^4$ is hydrogen, substituted or unsubstituted acyl, substituted or unsubstituted alkyl, substituted or unsubstituted imine, substituted or unsubstituted thiocarbonyl group, substituted or unsubstituted aryl, substituted or unsubstituted heteroaryl,

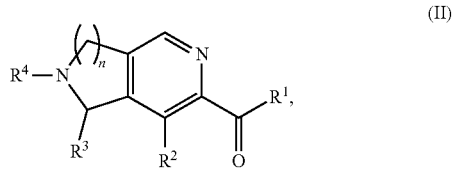

, or

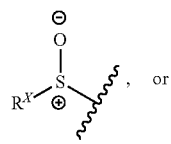

$R^X$ is hydrogen, substituted or unsubstituted alkyl, substituted or unsubstituted carbocyclyl, substituted or unsubstituted heterocyclyl, substituted or unsubstituted aryl, or substituted or unsubstituted heteroaryl; and each instance of $R^A$ is independently hydrogen, substituted or unsubstituted alkyl, substituted or unsubstituted carbocyclyl, substituted or unsubstituted heterocyclyl, substituted or unsubstituted aryl, substituted or unsubstituted heteroaryl, nitrogen protecting group, or optionally two $R^A$ are taken together with the intervening atoms to form substituted or unsubstituted heterocyclyl or substituted or unsubstituted heteroaryl.

In certain embodiments, the compound of Formula (II) is of the formula:

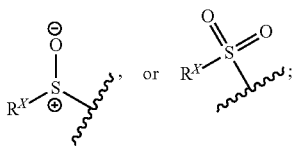

(II)

or a pharmaceutically acceptable salt, solvate, hydrate, polymorph, co-crystal, tautomer, stereoisomer, isotopically labeled derivative, or prodrug thereof, wherein:

n is 1, 2, or 3;

$R^1$ is hydrogen, substituted or unsubstituted alkyl, substituted or unsubstituted aryl, substituted or unsubstituted heteroaryl, —OR, or —N($R^A$)$_2$;

R is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or oxygen protecting group;

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^4$ is hydrogen, halogen, substituted or unsubstituted acyl, substituted or unsubstituted alkyl, substituted or unsubstituted imine, substituted or unsubstituted thiocarbonyl group, substituted or unsubstituted aryl, substituted or unsubstituted heteroaryl, $R^X$ is hydrogen, substituted or unsubstituted alkyl, substituted or unsubstituted carbocyclyl, substituted or unsubstituted heterocyclyl, substituted or unsubstituted aryl, or substituted or unsubstituted heteroaryl; and each instance of $R^A$ is independently hydrogen, substituted or unsubstituted alkyl, substituted or unsubstituted carbocyclyl, substituted or unsubstituted heterocyclyl, substituted or unsubstituted aryl, substituted or unsubstituted heteroaryl, nitrogen protecting group, or optionally two $R^A$ are taken together with the intervening atoms to form substituted or unsubstituted heterocyclyl or substituted or unsubstituted heteroaryl.

Formula (II) includes substituent $R^1$. In certain embodiments, $R^1$ is substituted or unsubstituted alkyl (e.g., substituted or unsubstituted $C_{1-6}$ alkyl). In certain embodiments, $R^1$ is methyl. In certain embodiments, $R^1$ is ethyl. In certain embodiments, $R^1$ is substituted or unsubstituted aryl (e.g., substituted or unsubstituted, 6- to 10-membered aryl). In certain embodiments, $R^1$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^1$ is —OR, and R is substituted or unsubstituted $C_{1-6}$ alkyl (e.g., —OMe or —OEt). In certain embodiments, $R^1$ is of the formula: —NH(CH$_2$)$_a$R$^a$, wherein: a is 1, 2, 3, 4, 5, or 6; $R^a$ is substituted or unsubstituted alkyl, substituted or unsubstituted carbocyclyl, substituted or unsubstituted heterocyclyl, substituted or unsubstituted aryl, substituted or unsubstituted heteroaryl, —OR$^{a2}$, —N(R$^{a1}$)$_2$, or —SR$^{a2}$; each instance of R$^{a1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or a nitrogen protecting group if attached to a nitrogen atom; and R$^{a2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group if attached to an oxygen atom, or a sulfur protecting group if attached to a sulfur atom. In certain embodiments, a is 1. In certain embodiments, a is 2. In certain embodiments, a is 3. In certain embodiments, a is 4. In certain embodiments, a is 5. In certain embodiments, a is 6. In certain embodiments, $R^a$ is substituted or unsubstituted $C_{1-6}$ alkyl. In certain embodiments, $R^1$ is —N(R$^A$)$_2$ (e.g., —NMe$_2$). In certain embodiments, at least one instance of $R^A$ is hydrogen. In certain embodiments, R is —NH$_2$. In certain embodiments, at least one instance of $R^A$ is substituted or unsubstituted alkyl (e.g., C$_{1-6}$ substituted or unsubstituted alkyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^A$ is a nitrogen protecting group if attached to a nitrogen atom. In certain embodiments, two $R^A$ are taken together with the intervening atoms to form substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two $R^A$ are taken together with the intervening atoms to form substituted or unsubstituted heterocyclyl or substituted or unsubstituted heteroaryl (e.g., morpholine or pyridine). In certain embodiments, $R^1$ is

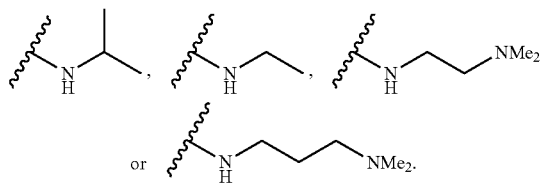

In certain embodiments, $R^a$ is —CF$_3$. In certain embodiments, $R^1$ is

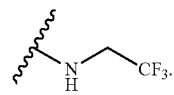

In certain embodiments, $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^1$ is

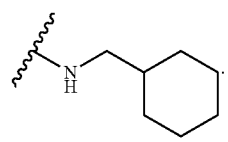 [SMILES: *NCC1CCCCC1]

In certain embodiments, $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is

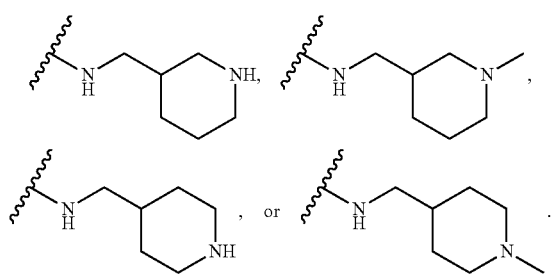

In certain embodiments, $R^a$ is substituted or unsubstituted aryl (e.g., substituted or unsubstituted, 6- to 10-membered aryl). In certain embodiments, $R^a$ is substituted or unsubstituted benzyl. In certain embodiments, $R^a$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^1$ is

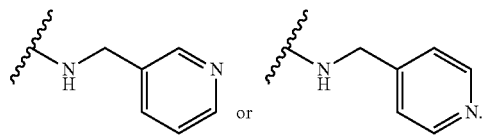 [SMILES: *NCc1cccnc1 ; *NCc1ccncc1]

In certain embodiments, $R^a$ is —$OR^{a2}$ (e.g., —OH, —O (substituted or unsubstituted $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, $R^a$ is —$N(R^{a1})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, $R^a$ is —$NMe_2$. In certain embodiments, $R^1$ is

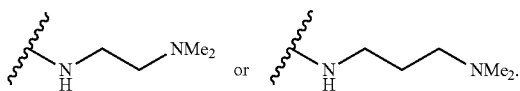 [SMILES: *NCCN(C)C ; *NCCCN(C)C]

In certain embodiments, $R^{a2}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^{a2}$ is a sulfur protecting group. In certain embodiments, $R^a$ is —$SR^{a2}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)).

In certain embodiments, $R^1$ is of the formula:

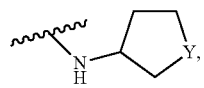

wherein Y is —$CR^E$—, —O— or —$NR^F$—; $R^E$ is independently hydrogen or substituted or unsubstituted $C_{1-6}$ alkyl; and $R^F$ is independently hydrogen or substituted or unsubstituted $C_{1-6}$ alkyl. In certain embodiments, Y is —$CR^E$— (e.g., —CH— or —CMe-). In certain embodiments, Y is —O—. In certain embodiments, Y is —$NR^F$— (e.g., —NH— or —NMe-). In certain embodiments, $R^E$ is hydrogen. In certain embodiments, R is substituted or unsubstituted $C_{1-6}$ alkyl. In certain embodiments, $R^F$ is hydrogen. In certain embodiments, $R^F$ is substituted or unsubstituted $C_{1-6}$ alkyl. In certain embodiments, $R^1$ is:

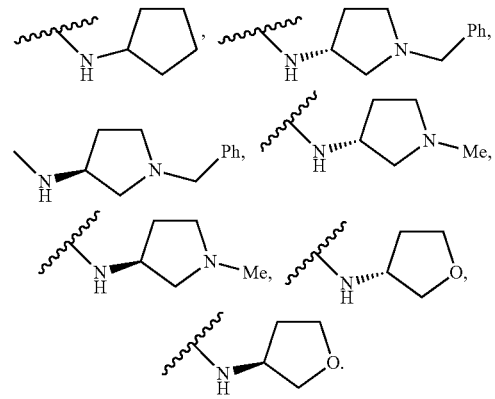

In certain embodiments, $R^1$ is of the formula:

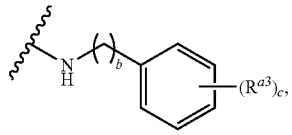

wherein b is 0, 1, 2, 3, 4, 5, or 6; c is 0, 1, 2, 3, 4, or 5; $R^{a3}$ is independently substituted or unsubstituted alkyl, halogen, —$OR^{a4}$, —$N_3$, —$N(R^{a4})_2$, —$SR^{a4}$, —CN, —SCN, —$SO_2R^{a4}$, —C(=O)$R^{a4}$, —C(=O)$OR^{a4}$, —C(=O)N$(R^{a4})_2$, —$NO_2$, or two instances of $R^{a3}$ are taken together with the intervening atoms to form substituted or unsubstituted heterocyclyl or substituted or unsubstituted heteroaryl; and $R^{a4}$ is independently hydrogen, or substituted or unsubstituted $C_{1-6}$ alkyl. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, c is 0. In certain embodiments, c is 1. In certain embodiments, c is 2. In certain embodiments, c is 3. In certain embodiments, c is 4. In certain embodiments, c is 5. In certain embodiments, at least one instance of $R^a$ is substituted or unsubstituted $C_{1-6}$ alkyl. In certain embodiments, at least one instance of $R^{a3}$ is —$CF_3$. In certain embodiments, at least one instance of $R^{a3}$ is halogen (e.g., F, Cl, Br, or I). In certain embodiments, at least one instance of $R^{a3}$ is —$OR^{a4}$ (e.g., —OH, —O (substituted or unsubstituted $C_{1-6}$ alkyl) (e.g., —OMe, —$OCF_3$, —OEt, —OPr, or —OBu). In certain embodiments, at least one instance of $R^{a3}$ is —$N_3$. In certain embodiments, at least one instance of $R^a$ is —$N(R^{a4})_2$ (e.g., —$NMe_2$). In certain embodiments, at least one instance of $R^{a3}$ is —$SR^{a4}$ (e.g., —SH, —S(substituted or unsubstituted $C_{1-6}$ alkyl) (e.g., —SMe, —SEt, —SPr, or —SBu). In certain embodiments, at least one instance of $R^{a3}$ is —CN. In certain embodiments, at least one instance of $R^{a3}$ is —SCN. In certain embodiments, at least one instance of $R^{a3}$ is —$SO_2R^{a4}$. In certain embodiments, at least one instance of $R^{a3}$ is —C(=O)$R^{a4}$. In certain embodiments, at least one instance of $R^{a3}$ is —C(=O)OR$^{a4}$ (e.g., —C(=O)OH, —C(=O)O (substituted or unsubstituted alkyl) (e.g., —C(=O)OMe). In certain embodiments, at least one instance of R$^{a3}$ is —C(=O)N(R$^{a4}$)$_2$. In certain embodiments, at least one instance of R$^{a3}$ is —NO$_2$. In certain embodiments, two instances of R$^{a3}$ are taken together with the intervening atoms to form substituted or unsubstituted heterocyclyl or substituted or unsubstituted heteroaryl. In certain embodiments, R$^1$ is:

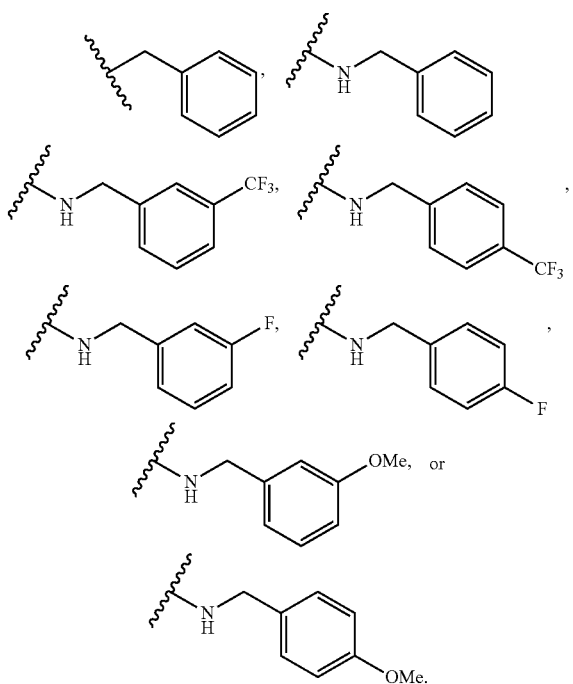

In certain embodiments, R$^1$ is:

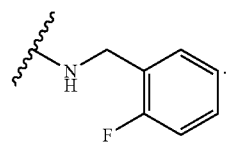

In certain embodiments, R$^1$ is of the formula:

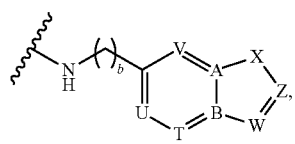

wherein: b is 0, 1, 2, 3, 4, 5, or 6; T is —CH— or —N—, as valency permits; U is —CH— or —N—, as valency permits; V is —CH— or —N—, as valency permits; W is —CH—, —C(R$^Z$)$_2$—, —O—, —NR$^A$—, or —S—, as valency permits; X is —CH—, —C(R$^Z$)$_2$—, —O—, —NR$^A$—, or —S—, as valency permits; Z is —CH—, —C(R$^Z$)$_2$—, —O—, —NR$^A$—, —N—, or —S—, as valency permits; A is —N—, as valency permits; B is —N—, as valency permits; R$^A$ is independently hydrogen or substituted or unsubstituted C$_{1-6}$ alkyl; and R$^Z$ is independently hydrogen or substituted or unsubstituted C$_{1-6}$ alkyl. In certain embodiments, T is —CH— or —N—, as valency permits. In certain embodiments, T is —CH—. In certain embodiments, T is —N—. In certain embodiments, U is —CH— or —N—, as valency permits. In certain embodiments, U is —CH—. In certain embodiments, U is —N—. In certain embodiments, V is —CH— or —N—, as valency permits. In certain embodiments, V is —CH—. In certain embodiments, V is —N—. In certain embodiments, W is —CH—, —C(R$^Z$)$_2$—, —O—, —NR$^A$—, or —S—, as valency permits. In certain embodiments, W is —CH—. In certain embodiments, W is —C(R$^Z$)$_2$— (e.g., —CH$_2$—). In certain embodiments, W is —O—. In certain embodiments, W is —NR$^A$— (e.g., —NH— or —NMe-). In certain embodiments, W is —S—. In certain embodiments, X is —CH—, —O—, —NR$^A$—, or —S—, as valency permits. In certain embodiments, X is —CH—. In certain embodiments, X is —O—. In certain embodiments, X is —NR$^A$— (e.g., —NH— or —NMe-). In certain embodiments, X is —S—. In certain embodiments, Z is —CH—, —C(R$^Z$)$_2$—, —O—, —NR$^A$—, —N—, or —S—, as valency permits. In certain embodiments, Z is —CH—. In certain embodiments, Z is —C(R$^Z$)$_2$— (e.g., —CH$_2$—). In certain embodiments, Z is —O—. In certain embodiments, Z is —NR$^A$— (e.g., —NH— or —NMe-). In certain embodiments, Z is —N—. In certain embodiments, Z is —S—. In certain embodiments, A is —N—, as valency permits. In certain embodiments, A is —N—. In certain embodiments, B is —N—, as valency permits. In certain embodiments, B is —N—. In certain embodiments, R$^A$ is hydrogen. In certain embodiments, R$^A$ is substituted or unsubstituted C$_{1-6}$ alkyl. In certain embodiments, R$^Z$ is hydrogen. In certain embodiments, R$^Z$ is substituted or unsubstituted C$_{1-6}$ alkyl. In certain embodiments, R$^1$ is

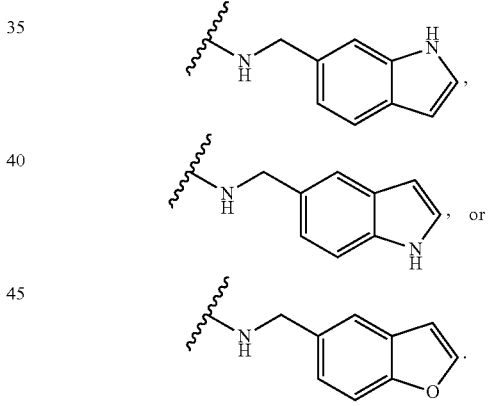

In certain embodiments, R$^1$ is

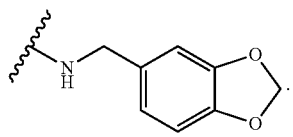 [SMILES: *NCc1ccc2c(c1)OCO2]

Formula (II) includes substituent R$^2$. In certain embodiments, R is halogen (e.g., F, Cl, Br, or I). In certain embodiments, R$^2$ is alkyl (e.g., substituted or unsubstituted C$_{1-6}$ alkyl). In certain embodiments, R$^2$ is of the formula: —(CH$_2$)$_e$R$^B$, wherein: e is 1, 2, 3, 4, 5, or 6; R$^B$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR^{b4}, —N(R^{b5})_2, or —SR^{b4}; R^{b4} is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group when attached to an oxygen atom, or sulfur protecting group when attached to a sulfur atom; and each instance of R^{b5} is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, nitrogen protecting group when attached to a nitrogen atom, or two instances of R^{b5} are taken together with the intervening atoms to form a substituted or unsubstituted, heterocyclic ring. In certain embodiments, e is 1. In certain embodiments, e is 2. In certain embodiments, e is 3. In certain embodiments, e is 4. In certain embodiments, e is 5. In certain embodiments, e is 6. In certain embodiments, R^B is substituted or unsubstituted C_{1-6} alkyl. In certain embodiments, R is

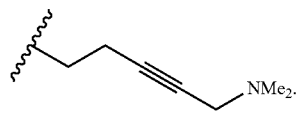 [SMILES: *CCC#CCN(C)C]

In certain embodiments, R^B is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R^B is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R^B is substituted or unsubstituted aryl (e.g., substituted or unsubstituted, 6- to 10-membered aryl). In certain embodiments, R^B is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; substituted or unsubstituted, 9- to 10-membered, bicyclic heteroaryl, wherein one, two, three, or four atoms in the heteroaryl ring system are independently nitrogen, oxygen, or sulfur). In certain embodiments, R^B is —OR^{b4} (e.g., —OH, —O (substituted or unsubstituted C_{1-6} alkyl) (e.g., —OMe, —OCF_3, —OEt, —OPr, —OBu, or —OBn), or —O (substituted or unsubstituted phenyl) (e.g., —OPh)). In certain embodiments, R^B is —N(R^{b5})_2 (e.g., —NH_2, —NH (substituted or unsubstituted C_{1-6} alkyl) (e.g., —NHMe), or —NMe_2). In certain embodiments, R^B is —SR^{b4} (e.g., —SH, —S(substituted or unsubstituted C_{1-6} alkyl) (e.g., —SMe, —SEt, —SPr, —SBu, or —SBn), or —S(substituted or unsubstituted phenyl) (e.g., —SPh)).

In certain embodiments, R^2 is of the formula:

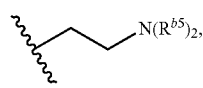

wherein: each instance of R^{b5} is independently hydrogen, substituted or unsubstituted acyl, substituted or unsubstituted alkyl, substituted or unsubstituted alkenyl, or substituted or unsubstituted alkynyl, or two instances of R^{b5} are taken together with the intervening atoms to form a substituted or unsubstituted, heterocyclic ring. In certain embodiments, at least one instance of R^{b5} is hydrogen. In certain embodiments, at least one instance of R^{b5} is substituted or unsubstituted acyl. In certain embodiments, at least one instance of R^{b5} is substituted or unsubstituted alkenyl (e.g., substituted or unsubstituted C_{2-6} alkenyl). In certain embodiments, at least one instance of R^{b5} is substituted or unsubstituted alkynyl (e.g., substituted or unsubstituted C_{2-6} alkynyl). In certain embodiments, at least one instance of R^{b5} is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of R^{b5} are taken together with the intervening atoms to form a substituted or unsubstituted, heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, two instances of R^{b5} are taken together with the intervening atoms to form:

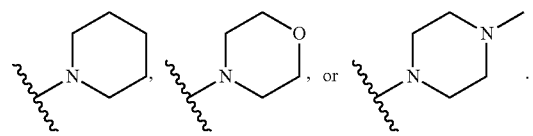

In certain embodiments, R^2 is

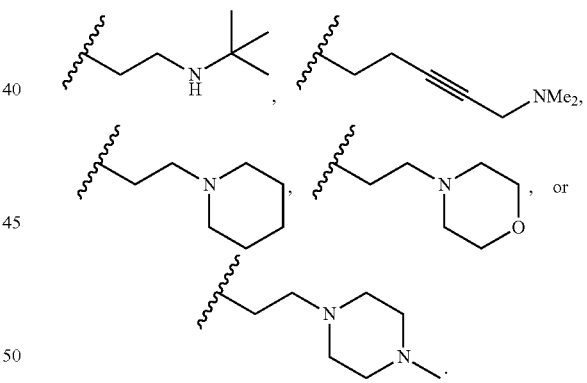

In certain embodiments, R^2 is substituted or unsubstituted alkenyl (e.g., substituted or unsubstituted C_{2-6} alkenyl). In certain embodiments, R^2 is substituted or unsubstituted alkynyl (e.g., substituted or unsubstituted C_{2-6} alkynyl). In certain embodiments, R^2 is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, R^2 is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, R^2 is substituted or unsubstituted aryl (e.g., substituted or unsubstituted, 6- to 10-membered aryl). In certain embodiments, R^2 is substituted benzyl. In certain embodiments, R² is unsubstituted benzyl. In certain embodiments, R² is substituted phenyl. In certain embodiments, R² is unsubstituted phenyl. In certain embodiments, R² is of the formula:

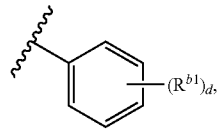

wherein: d is 0, 1, 2, 3, 4, or 5; each instance of $R^{b1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{b2}$, —$N_3$, —$N(R^{b3})_2$, —$SR^{b2}$, —CN, —SCN, —$SO_2R^{b2}$, —C(=O)$R^{b2}$, —C(=O)$OR^{b2}$, —C(=O)N$(R^{b3})_2$, or —$NO_2$; and $R^{b2}$ is hydrogen, or substituted or unsubstituted $C_{1-6}$ alkyl; and
each instance of $R^{b3}$ is independently hydrogen, or substituted or unsubstituted $C_{1-6}$ alkyl.

In certain embodiments, d is 0. In certain embodiments, d is 1. In certain embodiments, R² is

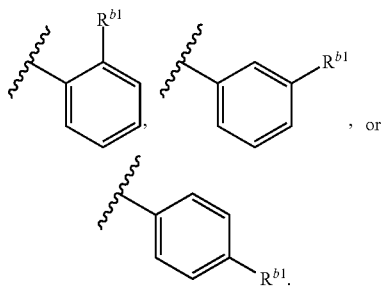

In certain embodiments, d is 2. In certain embodiments, d is 3. In certain embodiments, d is 4. In certain embodiments, d is 5. In certain embodiments, at least one instance of $R^{b1}$ is halogen (e.g., F, Cl, Br, or I). In certain embodiments, at least one instance of $R^{b1}$ is substituted or unsubstituted $C_{1-6}$ alkyl. In certain embodiments, at least one instance of $R^{b1}$ is substituted or unsubstituted alkenyl (e.g., substituted or unsubstituted $C_{2-6}$ alkenyl). In certain embodiments, at least one instance of $R^{b1}$ is substituted or unsubstituted alkynyl (e.g., substituted or unsubstituted $C_{2-6}$ alkynyl). In certain embodiments, at least one instance of $R^{b1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{b1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{b1}$ is substituted or unsubstituted aryl (e.g., substituted or unsubstituted, 6- to 10-membered aryl). In certain embodiments, at least one instance of $R^{b1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{b1}$ is pyridinyl. In certain embodiments, at least one instance of $R^{b1}$ is pyrimidinyl. In certain embodiments, at least one instance of $R^{b1}$ is pyrazinyl. In certain embodiments, at least one instance of $R^{b1}$ is indolyl. In certain embodiments, at least one instance of $R^{b1}$ is of the formula:

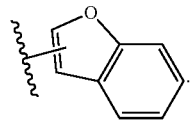

In certain embodiments, at least one instance of $R^{b1}$ is of the formula:

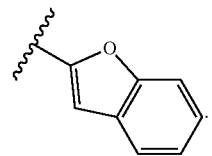 [SMILES: *c1cc2ccccc2o1]

In certain embodiments, at least one instance of $R^{b1}$ is —$OR^{b2}$ (e.g., —OH, —O (substituted or unsubstituted $C_{1-6}$ alkyl) (e.g., —OMe, —OCF₃, —OEt, —OPr, —OBu, or —OBn), or —O (substituted or unsubstituted phenyl) (e.g., —OPh)). In certain embodiments, at least one instance of $R^{b1}$ is —$N_3$. In certain embodiments, at least one instance of $R^{b1}$ is —$N(R^{b3})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —$NMe_2$)). In certain embodiments, at least one instance of $R^{b1}$ is —$SR^{b2}$ (e.g., —SH, —S(substituted or unsubstituted $C_{1-6}$ alkyl) (e.g., —SMe, —SEt, —SPr, or —SBu)). In certain embodiments, at least one instance of $R^{b1}$ is —CN. In certain embodiments, at least one instance of $R^{b1}$ is —SCN. In certain embodiments, at least one instance of $R^{b1}$ is —$SO_2R^{b2}$. In certain embodiments, at least one instance of $R^{b1}$ is —C(=O)$R^{b2}$, —C(=O)$OR^{b2}$, or —C(=O)$N(R^{b3})_2$. In certain embodiments, at least one instance of $R^{b1}$ is —$NO_2$. In certain embodiments, R² is

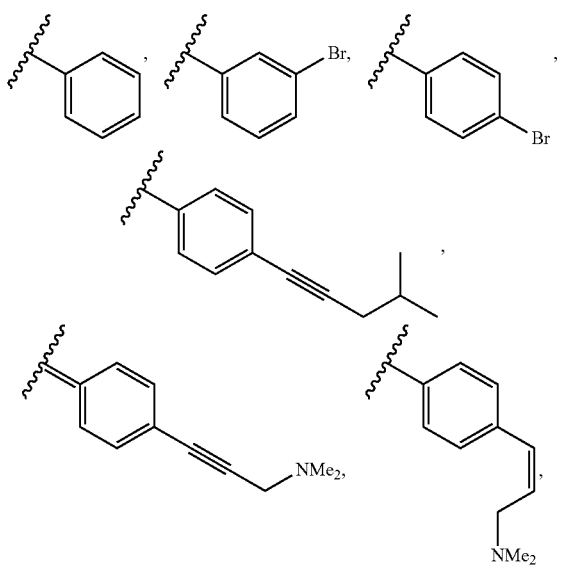

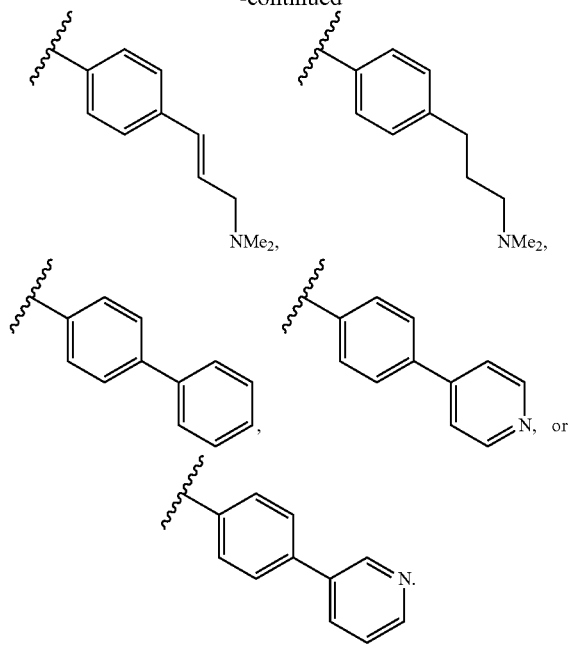

In certain embodiments, R² is

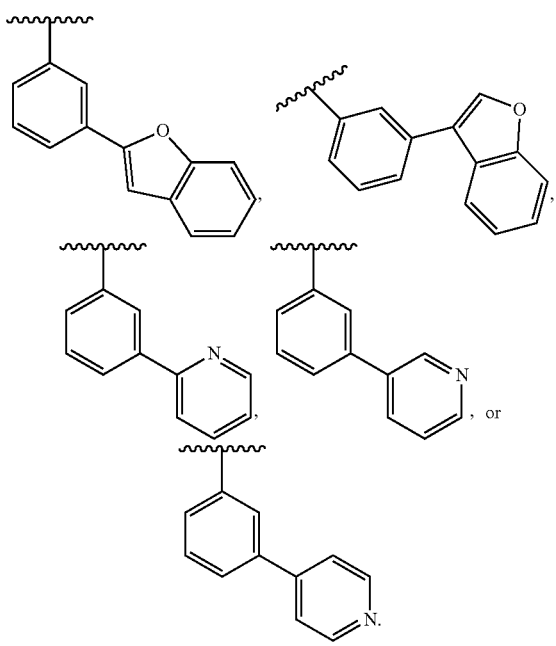

In certain embodiments, R² is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl. In certain embodiments, R² is substituted or unsubstituted pyridinyl.

Formula (II) also includes substituent R³. In certain embodiments, R³ is halogen (e.g., F, Cl, Br, or I). In certain embodiments, R³ is hydrogen. In certain embodiments, R³ is substituted or unsubstituted alkyl (e.g., substituted or unsubstituted $C_{1-6}$ alkyl). In certain embodiments, R³ is of the formula:

wherein f is 1, 2, 3, 4, 5, or 6; $R^C$ is independently substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{c1}$, —$N(R^2)_2$, —$NR^{c2}C(=O)R^{c1}$, or —$SR^{c1}$; $R^{c1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or oxygen protecting group; and each instance of $R^{c2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or two $R^{c2}$ are taken together with the intervening atoms to form substituted or unsubstituted heterocyclyl or substituted or unsubstituted heteroaryl. In certain embodiments, f is 1. In certain embodiments, f is 2. In certain embodiments, f is 3. In certain embodiments, f is 4. In certain embodiments, f is 5. In certain embodiments, f is 6. In certain embodiments, $R^C$ is substituted or unsubstituted acyl (e.g., acetyl). In certain embodiments, $R^C$ is substituted or unsubstituted $C_{1-6}$ alkyl. In certain embodiments, $R^C$ is substituted or unsubstituted alkenyl (e.g., substituted or unsubstituted $C_{2-6}$ alkenyl). In certain embodiments, $R^C$ is substituted or unsubstituted alkynyl (e.g., substituted or unsubstituted $C_{2-6}$ alkynyl). In certain embodiments, $R^C$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^C$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^C$ is —$OR^{c1}$ (e.g., —OH, —O (substituted or unsubstituted $C_{1-6}$ alkyl) (e.g., —OMe, —$OCF_3$, —OEt, —OPr, —OBu, or —OBn), or —O (substituted or unsubstituted phenyl) (e.g., —OPh)). In certain embodiments, $R^{c1}$ is an oxygen protecting group (e.g., t-butyloxycarbonyl (BOC or Boc), methoxylmethyl (MOM) or methylthiomethyl (MTM)). In certain embodiments, $R^C$ is —$N(R^{c2})_2$ (e.g., —$NH_2$, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe$_2$)). In certain embodiments, $R^{c2}$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)) when attached to a nitrogen atom. In certain embodiments, when $R^C$ is —N($R^{c2}$)$_2$, one instance of $R^{c2}$ is substituted or unsubstituted $C_{1-6}$ alkyl, and the other instance of $R^{c2}$ is hydrogen. In certain embodiments, two $R^{c2}$ are taken together with the intervening atoms to form substituted or unsubstituted heterocyclyl or substituted or unsubstituted heteroaryl (e.g., piperidine or pyridine). In certain embodiments, $R^C$ is —NR$^{c2}$C(=O)R$^{c1}$ (e.g., —NHC(=O)(substituted or unsubstituted $C_{1-6}$ alkyl) (e.g., —NHC(=O)Me), —NHC(=O)Ph, or —NHC(=O)(substituted phenyl)). In certain embodiments, when $R^C$ is —N($R^{c2}$)C(=O)R$^{c1}$, $R^{c1}$ is substituted or unsubstituted $C_{1-6}$ alkyl, and $R^{c2}$ is substituted or unsubstituted $C_{1-6}$ alkyl. In certain embodiments, when $R^C$ is —N($R^{c2}$)C(=O)R$^{c1}$, $R^{c1}$ is substituted or unsubstituted $C_{1-6}$ alkyl, and $R^{c2}$ is hydrogen. In certain embodiments, $R^C$ is —SR$^{c1}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)). In certain embodiments, $R^3$ is:

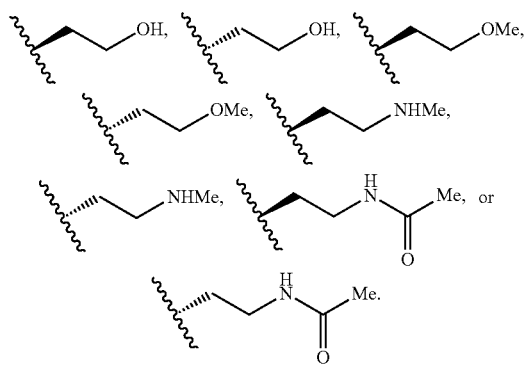

In certain embodiments, $R^3$ is substituted or unsubstituted alkenyl (e.g., substituted or unsubstituted $C_{2-6}$ alkenyl). In certain embodiments, $R^3$ is substituted or unsubstituted alkynyl (e.g., substituted or unsubstituted $C_{2-6}$ alkynyl). In certain embodiments, $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^3$ is substituted or unsubstituted aryl (e.g., substituted or unsubstituted, 6- to 10-membered aryl). In certain embodiments, $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (II) also includes substituent $R^4$. In certain embodiments, $R^4$ is halogen (e.g., F, Cl, Br, or I). In certain embodiments, $R^4$ is hydrogen. In certain embodiments, $R^4$ is substituted or unsubstituted acyl. In certain embodiments, $R^4$ is of the formula: —C(=O)R$^D$, and $R^D$ is hydrogen or substituted or unsubstituted $C_{1-6}$ alkyl. In certain embodiments, $R^4$ is of the formula: —C(=O)OR$^D$, and $R^D$ is hydrogen or substituted or unsubstituted $C_{1-6}$ alkyl. In certain embodiments, $R^4$ is

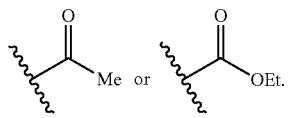

In certain embodiments, $R^4$ is of the formula: —C(=NR$^Y$)R$^D$, wherein $R^Y$ is hydrogen, substituted or unsubstituted $C_{1-6}$ alkyl, or nitrogen protecting group; and $R^D$ is hydrogen or substituted or unsubstituted $C_{1-6}$ alkyl. In certain embodiments, $R^4$ is —C(=NH)Me. In certain embodiments, $R^4$ is of the formula: —C(=NR$^Y$)OR$^D$, wherein $R^Y$ is hydrogen, substituted or unsubstituted $C_{1-6}$ alkyl, or nitrogen protecting group; and $R^D$ is hydrogen or substituted or unsubstituted $C_{1-6}$ alkyl. In certain embodiments, $R^4$ is —C(=NH)OMe. In certain embodiments, $R^4$ is of the formula: —C(=O)N(R$^{d1}$)$_2$, and each instance of $R^{d1}$ is independently hydrogen or substituted or unsubstituted $C_{1-6}$ alkyl. In certain embodiments, $R^4$ is

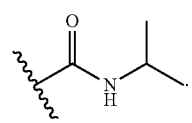 [SMILES: *C(=O)NC(C)C]

In certain embodiments, $R^4$ is substituted or unsubstituted alkyl (e.g., substituted or unsubstituted $C_{1-6}$ alkyl). In certain embodiments, $R^4$ is substituted or unsubstituted aryl (e.g., substituted or unsubstituted, 6- to 10-membered aryl). In certain embodiments, $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^4$ is

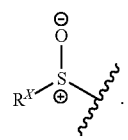

In certain embodiments, Rx is substituted or unsubstituted $C_{1-6}$ alkyl. In certain embodiments, $R^4$ is

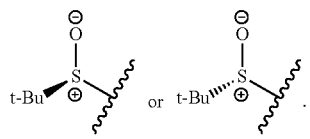 [SMILES: *[S@+]([O-])C(C)(C)C ; *[S@@+]([O-])C(C)(C)C]

In certain embodiments, R[4] is

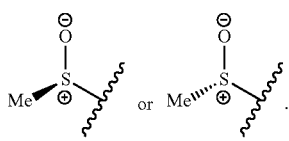

In certain embodiments, R[4] is

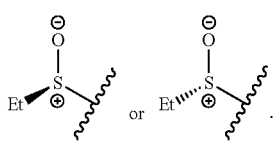

In certain embodiments, R[4] is

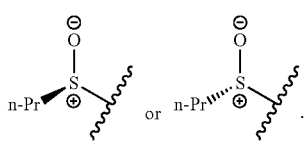

In certain embodiments, R[4] is

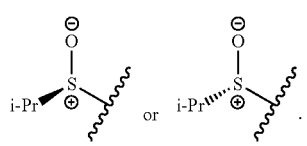 [SMILES: *[S@+]([O-])C(C)C ; *[S@@+]([O-])C(C)C]

In certain embodiments, R[4] is

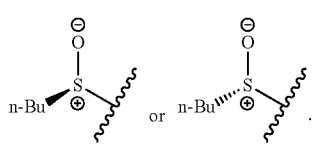

In certain embodiments, R[4] is

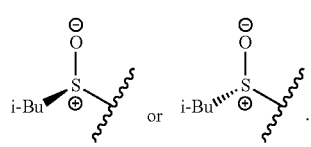

In certain embodiments, R[4] is

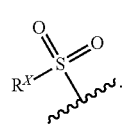

In certain embodiments, R[X] is substituted or unsubstituted $C_{1-6}$ alkyl. In certain embodiments, R[4] is

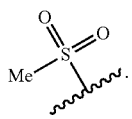

In certain embodiments, R[4] is

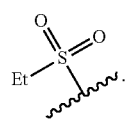

In certain embodiments, R[4] is

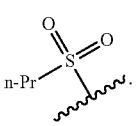

In certain embodiments, R[4] is

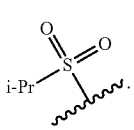

In certain embodiments, R[4] is

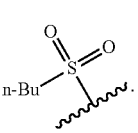

In certain embodiments, R[4] is

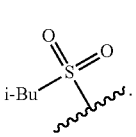

In certain embodiments, R[4] is

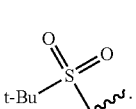

In certain embodiments, n is 1. In certain embodiments, n is 2. In certain embodiments, n is 3.

Compounds of Formula (III)

In certain embodiments, the compound of Formula (III) is of the formula:

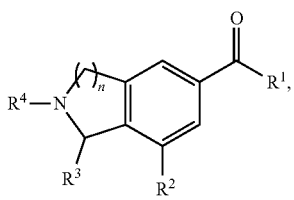

(III)

or a pharmaceutically acceptable salt, solvate, hydrate, polymorph, co-crystal, tautomer, stereoisomer, isotopically labeled derivative, or prodrug thereof, wherein:

n is 1, 2, or 3;

$R^1$ is hydrogen, substituted or unsubstituted alkyl, substituted or unsubstituted aryl, substituted or unsubstituted heteroaryl, —OR, or —N(R$^4$)$_2$;

R is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or oxygen protecting group;

$R^2$ is halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^4$ is hydrogen, halogen, substituted or unsubstituted acyl, substituted or unsubstituted alkyl, substituted or unsubstituted imine, substituted or unsubstituted thiocarbonyl group, substituted or unsubstituted aryl, substituted or unsubstituted heteroaryl,

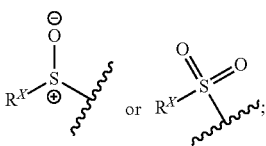

$R^X$ is hydrogen, substituted or unsubstituted alkyl, substituted or unsubstituted carbocyclyl, substituted or unsubstituted heterocyclyl, substituted or unsubstituted aryl, or substituted or unsubstituted heteroaryl; and each instance of $R^A$ is independently hydrogen, substituted or unsubstituted acyl, substituted or unsubstituted alkyl, substituted or unsubstituted carbocyclyl, substituted or unsubstituted heterocyclyl, substituted or unsubstituted aryl, substituted or unsubstituted heteroaryl, nitrogen protecting group, or optionally two $R^A$ are taken together with the intervening atoms to form substituted or unsubstituted heterocyclyl or substituted or unsubstituted heteroaryl.

Formula (III) includes substituent $R^1$. In certain embodiments, $R^1$ is substituted or unsubstituted alkyl (e.g., substituted or unsubstituted $C_{1-6}$ alkyl). In certain embodiments, $R^1$ is methyl. In certain embodiments, $R^1$ is ethyl. In certain embodiments, $R^1$ is substituted or unsubstituted aryl (e.g., substituted or unsubstituted, 6- to 10-membered aryl). In certain embodiments, $R^1$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^1$ is —OR, and R is substituted or unsubstituted $C_{1-6}$ alkyl (e.g., —OMe or —OEt). In certain embodiments, $R^1$ is of the formula: —NH(CH$_2$)$_a$R$^a$, wherein: a is 1, 2, 3, 4, 5, or 6; $R^a$ is substituted or unsubstituted alkyl, substituted or unsubstituted carbocyclyl, substituted or unsubstituted heterocyclyl, substituted or unsubstituted aryl, substituted or unsubstituted heteroaryl, —OR$^{a2}$, —N(R$^{a1}$)$_2$, or —SR$^{a2}$; each instance of $R^{a1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or a nitrogen protecting group if attached to a nitrogen atom; and $R^{a2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, an oxygen protecting group if attached to an oxygen atom, or a sulfur protecting group if attached to a sulfur atom. In certain embodiments, a is 1. In certain embodiments, a is 2. In certain embodiments, a is 3. In certain embodiments, a is 4. In certain embodiments, a is 5. In certain embodiments, a is 6. In certain embodiments, $R^a$ is substituted or unsubstituted $C_{1-6}$ alkyl. In certain embodiments, $R^1$ is —N(R$^4$)$_2$ (e.g., —NMe$_2$). In certain embodiments, at least one instance of $R^A$ is hydrogen. In certain embodiments, R is —NH$_2$. In certain embodiments, at least one instance of $R^A$ is substituted or unsubstituted alkyl (e.g., $C_{1-6}$ substituted or unsubstituted alkyl). In certain embodiments, at least one instance of $R^A$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^A$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^A$ is substituted or unsubstituted aryl (e.g., substituted or unsubstituted, 6- to 10-membered aryl). In certain embodiments, at least one instance of $R^A$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^A$ is a nitrogen protecting group if attached to a nitrogen atom. In certain embodiments, two $R^A$ are taken together with the intervening atoms to form substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur) or substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, two $R^A$ are taken together with the intervening atoms to form substituted or unsubstituted heterocyclyl or substituted or unsubstituted heteroaryl (e.g., morpholine or pyridine). In certain embodiments, $R^1$ is

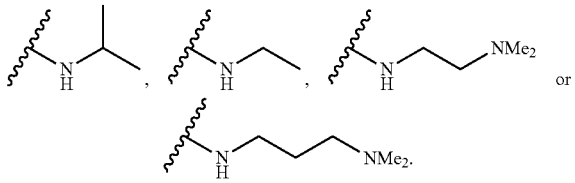

In certain embodiments, $R^a$ is —CF$_3$. In certain embodiments, $R^1$ is

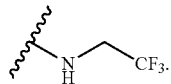

In certain embodiments, $R^a$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^1$ is

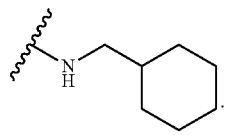 [SMILES: *NCC1CCCCC1]

In certain embodiments, $R^a$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^1$ is

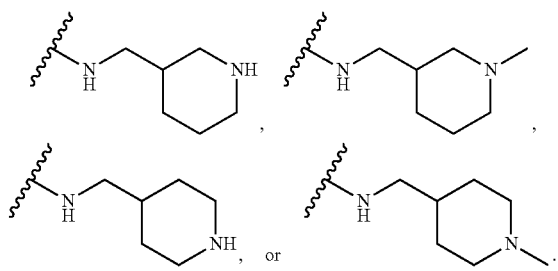

In certain embodiments, $R^a$ is substituted or unsubstituted aryl (e.g., substituted or unsubstituted, 6- to 10-membered aryl). In certain embodiments, $R^a$ is substituted or unsubstituted benzyl. In certain embodiments, $R^a$ is substituted or unsubstituted, 5- to 6-membered, monocyclic heteroaryl, wherein one, two, three, or four atoms in the heteroaryl ring system are independently nitrogen, oxygen, or sulfur. In certain embodiments, $R^1$ is

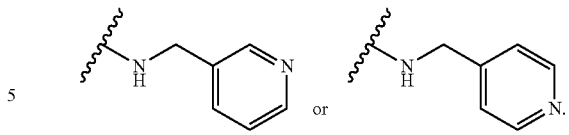

In certain embodiments, $R^a$ is —OR$^{a2}$ (e.g., —OH, —O (substituted or unsubstituted C$_{1-6}$ alkyl) (e.g., —OMe, —OCF$_3$, —OEt, —OPr, —OBu, or —OBn), or —O (substituted or unsubstituted phenyl) (e.g., —OPh)). In certain embodiments, $R^a$ is —N(R$^{a1}$)$_2$ (e.g., —NH$_2$, —NH (substituted or unsubstituted C$_{1-6}$ alkyl) (e.g., —NHMe), or —N(substituted or unsubstituted C$_{1-6}$ alkyl)-(substituted or unsubstituted C$_{1-6}$ alkyl) (e.g., —NMe$_2$)). In certain embodiments, $R^a$ is —NMe$_2$. In certain embodiments, $R^1$ is

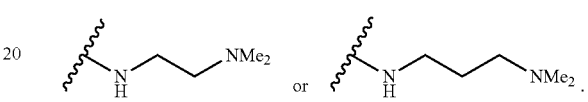

In certain embodiments, $R^{a2}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, $R^{a2}$ is a sulfur protecting group. In certain embodiments, $R^a$ is —SR$^{a2}$ (e.g., —SH, —S(substituted or unsubstituted C$_{1-6}$ alkyl) (e.g., —SMe, —SEt, —SPr, —SBu, or —SBn), or —S(substituted or unsubstituted phenyl) (e.g., —SPh)).

In certain embodiments, $R^1$ is of the formula:

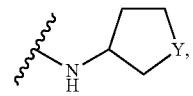

wherein Y is —CR$^E$—, —O— or —NR$^F$—; $R^E$ is independently hydrogen or substituted or unsubstituted C$_{1-6}$ alkyl; and $R^F$ is independently hydrogen or substituted or unsubstituted C$_{1-6}$ alkyl. In certain embodiments, Y is —CR$^E$— (e.g., —CH— or —CMe-). In certain embodiments, Y is —O—. In certain embodiments, Y is —NR$^F$— (e.g., —NH— or —NMe-). In certain embodiments, $R^E$ is hydrogen. In certain embodiments, $R^E$ is substituted or unsubstituted C$_{1-6}$ alkyl. In certain embodiments, $R^F$ is hydrogen. In certain embodiments, $R^F$ is substituted or unsubstituted C$_{1-6}$ alkyl. In certain embodiments, $R^1$ is:

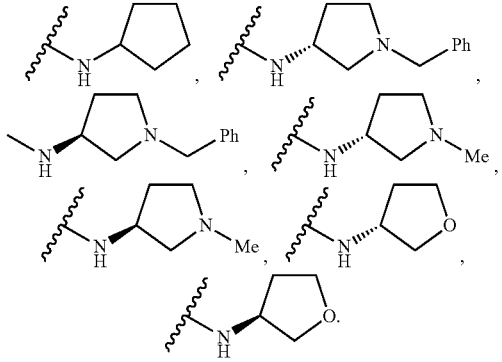

In certain embodiments, R¹ is of the formula:

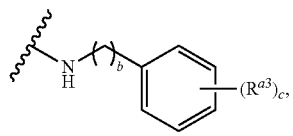

wherein b is 0, 1, 2, 3, 4, 5, or 6; c is 0, 1, 2, 3, 4, or 5; $R^{a3}$ is independently substituted or unsubstituted alkyl, halogen, —$OR^{a4}$, —$N_3$, —$N(R^{a4})_2$, —$SR^{a4}$, —CN, —SCN, —$SO_2R^{a4}$, —C(=O)$R^{a4}$, —C(=O)$OR^{a4}$, —C(=O)N$(R^{a4})_2$, —$NO_2$, or two instances of $R^{a3}$ are taken together with the intervening atoms to form substituted or unsubstituted heterocyclyl or substituted or unsubstituted heteroaryl; and $R^{a4}$ is independently hydrogen, or substituted or unsubstituted $C_{1-6}$ alkyl. In certain embodiments, b is 0. In certain embodiments, b is 1. In certain embodiments, b is 2. In certain embodiments, b is 3. In certain embodiments, b is 4. In certain embodiments, b is 5. In certain embodiments, b is 6. In certain embodiments, c is 0. In certain embodiments, c is 1. In certain embodiments, c is 2. In certain embodiments, c is 3. In certain embodiments, c is 4. In certain embodiments, c is 5. In certain embodiments, at least one instance of $R^{a3}$ is substituted or unsubstituted $C_{1-6}$ alkyl. In certain embodiments, at least one instance of $R^{a3}$ is —$CF_3$. In certain embodiments, at least one instance of $R^{a3}$ is halogen (e.g., F, Cl, Br, or I). In certain embodiments, at least one instance of $R^{a3}$ is —$OR^{a4}$ (e.g., —OH, —O (substituted or unsubstituted $C_{1-6}$ alkyl) (e.g., —OMe, —$OCF_3$, —OEt, —OPr, or —OBu). In certain embodiments, at least one instance of $R^{a3}$ is —$N_3$. In certain embodiments, at least one instance of $R^{a3}$ is —$N(R^{a4})_2$ (e.g., —$NMe_2$). In certain embodiments, at least one instance of $R^{a3}$ is —$SR^{a4}$ (e.g., —SH, —S(substituted or unsubstituted $C_{1-6}$ alkyl) (e.g., —SMe, —SEt, —SPr, or —SBu). In certain embodiments, at least one instance of $R^{a3}$ is —CN. In certain embodiments, at least one instance of $R^{a3}$ is —SCN. In certain embodiments, at least one instance of $R^{a3}$ is —$SO_2R^{a4}$. In certain embodiments, at least one instance of $R^{a3}$ is —C(=O)$R^{a4}$. In certain embodiments, at least one instance of $R^{a3}$ is —C(=O)$OR^{a4}$ (e.g., —C(=O)OH, —C(=O)O (substituted or unsubstituted alkyl) (e.g., —C(=O)OMe). In certain embodiments, at least one instance of $R^{a3}$ is —C(=O)N$(R^{a4})_2$. In certain embodiments, at least one instance of $R^{a3}$ is —$NO_2$. In certain embodiments, two instances of $R^{a3}$ are taken together with the intervening atoms to form substituted or unsubstituted heterocyclyl or substituted or unsubstituted heteroaryl. In certain embodiments, R¹ is:

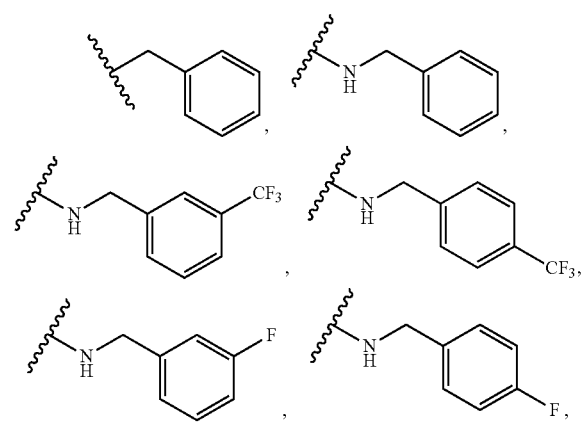

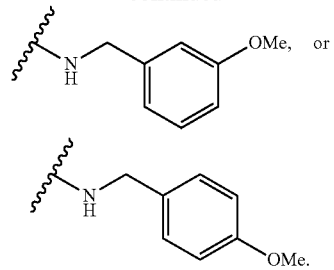

In certain embodiments, R¹ is:

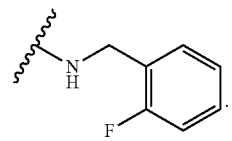

In certain embodiments, R¹ is of the formula:

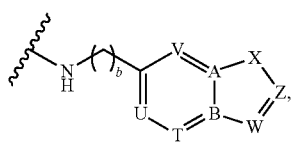

wherein: b is 0, 1, 2, 3, 4, 5, or 6; T is —CH— or —N—, as valency permits; U is —CH— or —N—, as valency permits; V is —CH— or —N—, as valency permits; W is —CH—, —C($R^Z$)$_2$—, —O—, —$NR^A$—, or —S—, as valency permits; X is —CH—, —C($R^Z$)$_2$—, —O—, —$NR^A$—, or —S—, as valency permits; Z is —CH—, —C($R^Z$)$_2$—, —O—, —$NR^A$—, —N—, or —S—, as valency permits; A is —N—, as valency permits; B is —N—, as valency permits; $R^A$ is independently hydrogen or substituted or unsubstituted $C_{1-6}$ alkyl; and $R^Z$ is independently hydrogen or substituted or unsubstituted $C_{1-6}$ alkyl. In certain embodiments, T is —CH— or —N—, as valency permits. In certain embodiments, T is —CH—. In certain embodiments, T is —N—. In certain embodiments, U is —CH— or —N—, as valency permits. In certain embodiments, U is —CH—. In certain embodiments, U is —N—. In certain embodiments, V is —CH— or —N—, as valency permits. In certain embodiments, V is —CH—. In certain embodiments, V is —N—. In certain embodiments, W is —CH—, —C($R^Z$)$_2$—, —O—, —$NR^A$—, or —S—, as valency permits. In certain embodiments, W is —CH—. In certain embodiments, W is —C($R^Z$)$_2$— (e.g., —$CH_2$—). In certain embodiments, W is —O—. In certain embodiments, W is —$NR^A$— (e.g., —NH— or —NMe-). In certain embodiments, W is —S—. In certain embodiments, X is —CH—, —O—, —$NR^A$—, or —S—, as valency permits. In certain embodiments, X is —CH—. In certain embodiments, X is —O—. In certain embodiments, X is —$NR^A$— (e.g., —NH— or —NMe-). In certain embodiments, X is —S—. In certain embodiments, Z is —CH—, —C($R^Z$)$_2$—, —O—, —$NR^A$—, —N—, or —S—, as valency permits. In certain embodiments, Z is —CH—. In certain embodiments, Z is —C($R^Z$)$_2$— (e.g., —$CH_2$—). In certain embodiments, Z is —O—. In certain embodiments, Z is —$NR^A$— (e.g., —NH— or —NMe-). In certain embodiments, Z is —N—.

In certain embodiments, Z is —S—. In certain embodiments, A is —N—, as valency permits. In certain embodiments, A is —N—. In certain embodiments, B is —N—, as valency permits. In certain embodiments, B is —N—. In certain embodiments, $R^A$ is hydrogen. In certain embodiments, $R^A$ is substituted or unsubstituted $C_{1-6}$ alkyl. In certain embodiments, $R^Z$ is hydrogen. In certain embodiments, $R^Z$ is substituted or unsubstituted $C_{1-6}$ alkyl. In certain embodiments, $R^1$ is

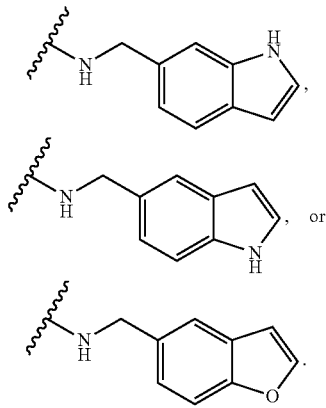

In certain embodiments, $R^1$ is

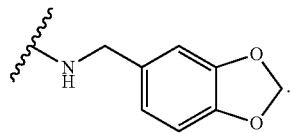 [SMILES: *NCc1ccc2c(c1)OCO2]

Formula (III) includes substituent $R^2$. In certain embodiments, $R^2$ is halogen (e.g., F, Cl, Br, or I). In certain embodiments, $R^2$ is alkyl (e.g., substituted or unsubstituted $C_{1-6}$ alkyl). In certain embodiments, $R^2$ is of the formula: —$(CH_2)_e R^B$, wherein: e is 1, 2, 3, 4, 5, or 6; $R^B$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{b4}$, —$N(R^{b5})_2$, or —$SR^{b4}$; $R^{b4}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, oxygen protecting group when attached to an oxygen atom, or sulfur protecting group when attached to a sulfur atom; and each instance of $R^{b5}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, nitrogen protecting group when attached to a nitrogen atom, or two instances of $R^{b5}$ are taken together with the intervening atoms to form a substituted or unsubstituted, heterocyclic ring. In certain embodiments, e is 1. In certain embodiments, e is 2. In certain embodiments, e is 3. In certain embodiments, e is 4. In certain embodiments, e is 5. In certain embodiments, e is 6. In certain embodiments, $R^B$ is substituted or unsubstituted $C_{1-6}$ alkyl. In certain embodiments, $R^2$ is

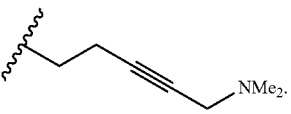 [SMILES: *CCC#CCN(C)C]

In certain embodiments, $R^B$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^B$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^B$ is substituted or unsubstituted aryl (e.g., substituted or unsubstituted, 6- to 10-membered aryl). In certain embodiments, $R^B$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^B$ is —$OR^{b4}$ (e.g., —OH, —O (substituted or unsubstituted $C_{1-6}$ alkyl) (e.g., —OMe, —OCF$_3$, —OEt, —OPr, —OBu, or —OBn), or —O (substituted or unsubstituted phenyl) (e.g., —OPh)). In certain embodiments, $R^B$ is —$N(R^{b5})_2$ (e.g., —NH$_2$, —NH (substituted or unsubstituted $C_{1-6}$ alkyl) (e.g., —NHMe), or —NMe$_2$). In certain embodiments, $R^B$ is —$SR^{b4}$ (e.g., —SH, —S(substituted or unsubstituted $C_{1-6}$ alkyl) (e.g., —SMe, —SEt, —SPr, —SBu, or —SBn), or —S(substituted or unsubstituted phenyl) (e.g., —SPh)).

In certain embodiments, $R^2$ is of the formula:

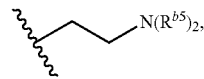

wherein: each instance of $R^{b5}$ is independently hydrogen, substituted or unsubstituted acyl, substituted or unsubstituted alkyl, substituted or unsubstituted alkenyl, or substituted or unsubstituted alkynyl, or two instances of $R^{b5}$ are taken together with the intervening atoms to form a substituted or unsubstituted, heterocyclic ring. In certain embodiments, at least one instance of $R^{b5}$ is hydrogen. In certain embodiments, at least one instance of $R^{b5}$ is substituted or unsubstituted acyl. In certain embodiments, at least one instance of $R^{b5}$ is substituted or unsubstituted alkenyl (e.g., substituted or unsubstituted $C_{2-6}$ alkenyl). In certain embodiments, at least one instance of $R^{b5}$ is substituted or unsubstituted alkynyl (e.g., substituted or unsubstituted $C_{2-6}$ alkynyl). In certain embodiments, at least one instance of $R^{b5}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, two instances of $R^{b5}$ are taken together with the intervening atoms to form a substituted or unsubstituted, heterocyclic ring (e.g., substituted or unsubstituted, 3- to 7-membered, monocyclic heterocyclyl comprising zero, one, or two double bonds in the heterocyclic ring system, wherein one, two, or three atoms in the heterocyclic ring system are independently nitrogen, oxygen, or sulfur). In certain embodiments, two instances of $R^{b5}$ are taken together with the intervening atoms to form:

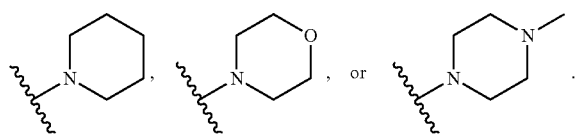

In certain embodiments, $R^2$ is

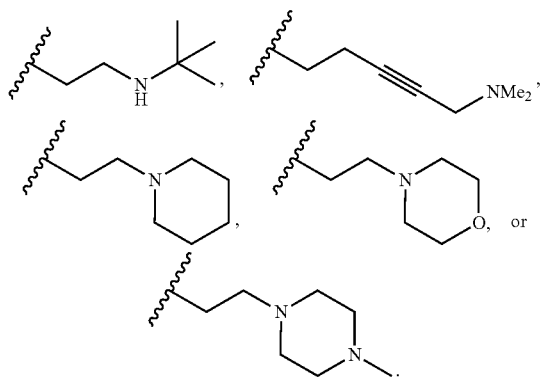

In certain embodiments, $R^2$ is substituted or unsubstituted alkenyl (e.g., substituted or unsubstituted $C_{2-6}$ alkenyl). In certain embodiments, $R^2$ is substituted or unsubstituted alkynyl (e.g., substituted or unsubstituted $C_{2-6}$ alkynyl). In certain embodiments, $R^2$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^2$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^2$ is substituted or unsubstituted aryl (e.g., substituted or unsubstituted, 6- to 10-membered aryl). In certain embodiments, $R^2$ is substituted benzyl. In certain embodiments, $R^2$ is unsubstituted benzyl. In certain embodiments, $R^2$ is substituted phenyl. In certain embodiments, $R^2$ is unsubstituted phenyl. In certain embodiments, $R^2$ is of the formula:

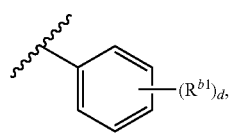

wherein: d is 0, 1, 2, 3, 4, or 5; each instance of $R^{b1}$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{b2}$, $-N_3$, $-N(R^{b3})_2$, $-SR^{b2}$, $-CN$, $-SCN$, $-SO_2R^{b2}$, $-C(=O)R^{b2}$, $-C(=O)OR^{b2}$, $-C(=O)N(R^{b3})_2$, or $-NO_2$; and $R^{b2}$ is hydrogen, or substituted or unsubstituted $C_{1-6}$ alkyl; and
each instance of $R^{b3}$ is independently hydrogen, or substituted or unsubstituted $C_{1-6}$ alkyl.

In certain embodiments, d is 0. In certain embodiments, d is 1. In certain embodiments, $R^2$ is

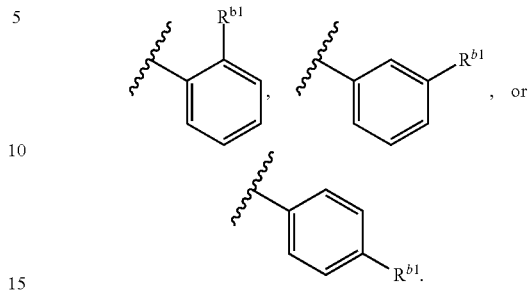

In certain embodiments, d is 2. In certain embodiments, d is 3. In certain embodiments, d is 4. In certain embodiments, d is 5. In certain embodiments, at least one instance of $R^{b1}$ is halogen (e.g., F, Cl, Br, or I). In certain embodiments, at least one instance of $R^{b1}$ is substituted or unsubstituted $C_{1-6}$ alkyl. In certain embodiments, at least one instance of $R^{b1}$ is substituted or unsubstituted alkenyl (e.g., substituted or unsubstituted $C_{2-6}$ alkenyl). In certain embodiments, at least one instance of $R^{b1}$ is substituted or unsubstituted alkynyl (e.g., substituted or unsubstituted $C_{2-6}$ alkynyl). In certain embodiments, at least one instance of $R^{b1}$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, at least one instance of $R^{b1}$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, at least one instance of $R^{b1}$ is substituted or unsubstituted aryl (e.g., substituted or unsubstituted, 6- to 10-membered aryl). In certain embodiments, at least one instance of $R^{b1}$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, at least one instance of $R^{b1}$ is pyridinyl. In certain embodiments, at least one instance of $R^{b1}$ is of the formula:

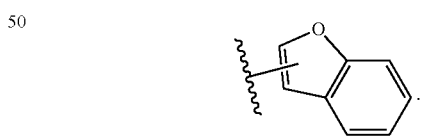

In certain embodiments, at least one instance of $R^{b1}$ is of the formula:

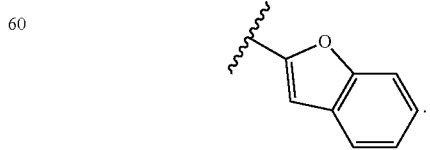

In certain embodiments, at least one instance of $R^{b1}$ is $-OR^{b2}$ (e.g., $-OH$, $-O$ (substituted or unsubstituted $C_{1-6}$ alkyl) (e.g., —OMe, —OCF₃, —OEt, —OPr, —OBu, or —OBn), or —O (substituted or unsubstituted phenyl) (e.g., —OPh)). In certain embodiments, at least one instance of $R^{b1}$ is —N₃. In certain embodiments, at least one instance of $R^{b1}$ is —N($R^{b3}$)₂ (e.g., —NH₂, —NH (substituted or unsubstituted $C_{1-6}$ alkyl) (e.g., —NHMe), or —N(substituted or unsubstituted $C_{1-6}$ alkyl)-(substituted or unsubstituted $C_{1-6}$ alkyl) (e.g., —NMe₂)). In certain embodiments, at least one instance of $R^{b1}$ is —S$R^{b2}$ (e.g., —SH, —S(substituted or unsubstituted $C_{1-6}$ alkyl) (e.g., —SMe, —SEt, —SPr, or —SBu)). In certain embodiments, at least one instance of $R^{b1}$ is —CN. In certain embodiments, at least one instance of $R^{b1}$ is —SCN. In certain embodiments, at least one instance of $R^{b1}$ is —SO₂$R^{b2}$. In certain embodiments, at least one instance of $R^{b1}$ is —C(=O)$R^{b2}$, —C(=O)O$R^{b2}$, or —C(=O)N($R^{b3}$)₂. In certain embodiments, at least one instance of $R^{b1}$ is —NO₂. In certain embodiments, $R^2$ is

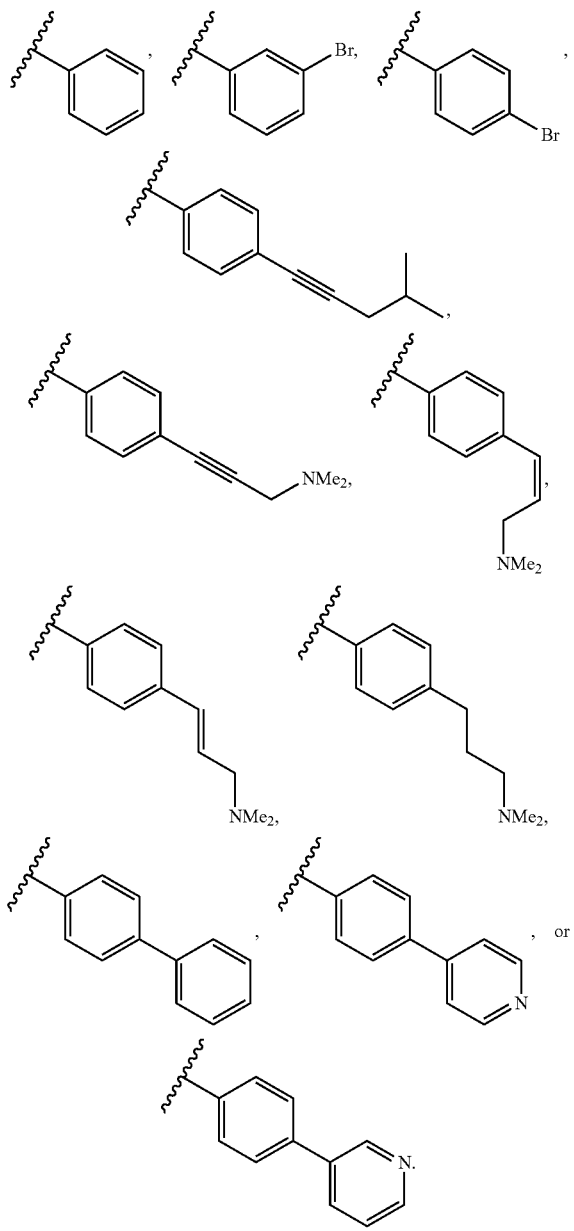

In certain embodiments, $R^2$ is

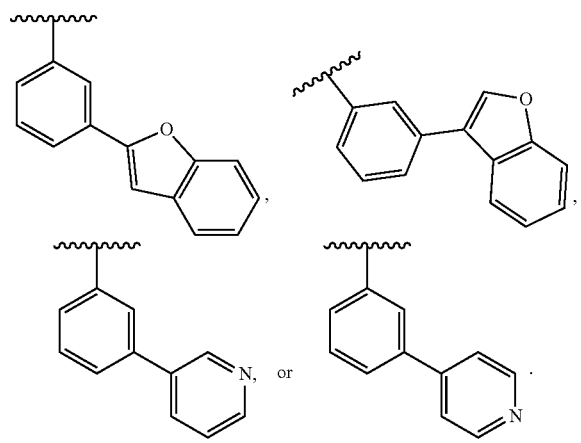

In certain embodiments, $R^2$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl. In certain embodiments, $R^2$ is substituted or unsubstituted pyridinyl.

Formula (III) also includes substituent $R^3$. In certain embodiments, $R^3$ is hydrogen. halogen (e.g., F, Cl, Br, or I). In certain embodiments, $R^3$ is substituted or unsubstituted alkyl (e.g., substituted or unsubstituted $C_{1-6}$ alkyl). In certain embodiments, $R^3$ is of the formula:

wherein f is 1, 2, 3, 4, 5, or 6; $R^C$ is independently substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —O$R^c$, —N($R^{c2}$)₂, —N$R^{c2}$C(=O)$R^{c1}$, or —S$R^{c1}$; $R^{c1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or oxygen protecting group; and each instance of $R^{c2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, nitrogen protecting group, or two $R^{c2}$ are taken together with the intervening atoms to form substituted or unsubstituted heterocyclyl or substituted or unsubstituted heteroaryl. In certain embodiments, f is 1. In certain embodiments, f is 2. In certain embodiments, f is 3. In certain embodiments, f is 4. In certain embodiments, f is 5. In certain embodiments, f is 6. In certain embodiments, $R^C$ is substituted or unsubstituted acyl (e.g., acetyl). In certain embodiments, $R^C$ is substituted or unsubstituted $C_{1-6}$ alkyl. In certain embodiments, $R^C$ is substituted or unsubstituted alkenyl (e.g., substituted or unsubstituted $C_{2-6}$ alkenyl). In certain embodiments, $R^C$ is substituted or unsubstituted alkynyl (e.g., substituted or unsubstituted $C_{2-6}$ alkynyl). In certain embodiments, $R^C$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^C$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^C$ is substituted or unsubstituted aryl (e.g., substituted or unsubstituted, 6- to 10-membered aryl). In certain embodiments, $R^C$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^C$ is $-OR^{c1}$ (e.g., $-OH$, $-O$ (substituted or unsubstituted $C_{1-6}$ alkyl) (e.g., $-OMe$, $-OCF_3$, $-OEt$, $-OPr$, $-OBu$, or $-OBn$), or $-O$ (substituted or unsubstituted phenyl) (e.g., $-OPh$)). In certain embodiments, $R^{c1}$ is an oxygen protecting group (e.g., t-butyloxycarbonyl (BOC or Boc), methoxylmethyl (MOM) or methylthiomethyl (MTM)). In certain embodiments, $R^C$ is $-N(R^{c2})_2$ (e.g., $-NH_2$, $-NH$ (substituted or unsubstituted $C_{1-6}$ alkyl) (e.g., $-NHMe$), or $-N$(substituted or unsubstituted $C_{1-6}$ alkyl)-(substituted or unsubstituted $C_{1-6}$ alkyl) (e.g., $-NMe_2$)). In certain embodiments, $R^{c2}$ is an nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)) when attached to a nitrogen atom. In certain embodiments, when $R^C$ is $-N(R^{c2})_2$, one instance of $R^{c2}$ is substituted or unsubstituted $C_{1-6}$ alkyl, and the other instance of $R^{c2}$ is hydrogen. In certain embodiments, two $R^{c2}$ are taken together with the intervening atoms to form substituted or unsubstituted heterocyclyl or substituted or unsubstituted heteroaryl (e.g., piperidine or pyridine). In certain embodiments, $R^C$ is $-NR^{c2}C(=O)R^{c1}$ (e.g., $-NHC(=O)$(substituted or unsubstituted $C_{1-6}$ alkyl) (e.g., $-NHC(=O)Me$), $-NHC(=O)Ph$, or $-NHC(=O)$(substituted phenyl)). In certain embodiments, when $R^C$ is $-N(R^{c2})C(=O)R^{c1}$, $R^{c1}$ is substituted or unsubstituted $C_{1-6}$ alkyl, and $R^{c2}$ is substituted or unsubstituted $C_{1-6}$ alkyl. In certain embodiments, when $R^C$ is $-N(R^{c2})C(=O)R^{c1}$, $R^{c1}$ is substituted or unsubstituted $C_{1-6}$ alkyl, and $R^{c2}$ is hydrogen. In certain embodiments, $R^C$ is $-SR^{c1}$ (e.g., $-SH$, $-S$(substituted or unsubstituted $C_{1-6}$ alkyl) (e.g., $-SMe$, $-SEt$, $-SPr$, $-SBu$, or $-SBn$), or $-S$(substituted or unsubstituted phenyl) (e.g., $-SPh$)). In certain embodiments, $R^3$ is:

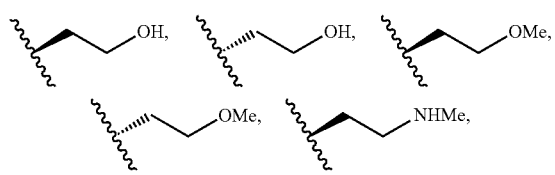

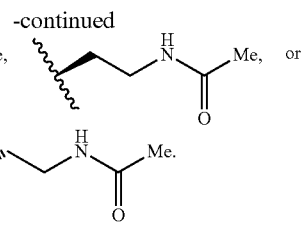

In certain embodiments, $R^3$ is substituted or unsubstituted alkenyl (e.g., substituted or unsubstituted $C_{2-6}$ alkenyl). In certain embodiments, $R^3$ is substituted or unsubstituted alkynyl (e.g., substituted or unsubstituted $C_{2-6}$ alkynyl). In certain embodiments, $R^3$ is substituted or unsubstituted carbocyclyl (e.g., substituted or unsubstituted, 3- to 7-membered, monocyclic carbocyclyl comprising zero, one, or two double bonds in the carbocyclic ring system). In certain embodiments, $R^3$ is substituted or unsubstituted heterocyclyl (e.g., substituted or unsubstituted, 5- to 10-membered monocyclic or bicyclic heterocyclic ring, wherein one or two atoms in the heterocyclic ring are independently nitrogen, oxygen, or sulfur). In certain embodiments, $R^3$ is substituted or unsubstituted aryl (e.g., substituted or unsubstituted, 6- to 10-membered aryl). In certain embodiments, $R^3$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur).

Formula (III) also includes substituent $R^4$. In certain embodiments, $R^4$ is hydrogen. In certain embodiments, $R^4$ is halogen (e.g., F, Cl, Br, or I). In certain embodiments, $R^4$ is substituted or unsubstituted acyl. In certain embodiments, $R^4$ is of the formula: $-C(=O)R^D$, and $R^D$ is hydrogen or substituted or unsubstituted $C_{1-6}$ alkyl. In certain embodiments, $R^4$ is of the formula: $-C(=O)OR^D$, and $R^D$ is hydrogen or substituted or unsubstituted $C_{1-6}$ alkyl. In certain embodiments, $R^4$ is

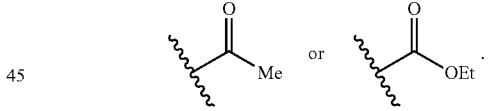

In certain embodiments, $R^4$ is of the formula: $-C(=NR^Y)R^D$, wherein $R^Y$ is hydrogen, substituted or unsubstituted $C_{1-6}$ alkyl, or nitrogen protecting group; and $R^D$ is hydrogen or substituted or unsubstituted $C_{1-6}$ alkyl. In certain embodiments, $R^4$ is $-C(=NH)Me$. In certain embodiments, $R^4$ is of the formula: $-C(=NR^Y)OR^D$, wherein $R^Y$ is hydrogen, substituted or unsubstituted $C_{1-6}$ alkyl, or nitrogen protecting group; and $R^D$ is hydrogen or substituted or unsubstituted $C_{1-6}$ alkyl. In certain embodiments, $R^4$ is $-C(=NH)OMe$. In certain embodiments, $R^4$ is of the formula: $-C(=O)N(R^{d1})_2$, and each instance of $R^{d1}$ is independently hydrogen or substituted or unsubstituted $C_{1-6}$ alkyl. In certain embodiments, $R^4$ is

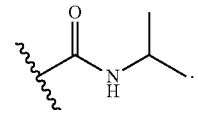 [SMILES: *C(=O)NC(C)C]

In certain embodiments, $R^4$ is substituted or unsubstituted alkyl (e.g., substituted or unsubstituted $C_{1-6}$ alkyl). In certain embodiments, $R^4$ is substituted or unsubstituted aryl (e.g., substituted or unsubstituted, 6- to 10-membered aryl). In certain embodiments, $R^4$ is substituted or unsubstituted heteroaryl (e.g., substituted or unsubstituted, 5- to 6-membered, monocyclic heteroaryl, wherein one, two, three, or four atoms in the heteroaryl ring system are independently nitrogen, oxygen, or sulfur; or substituted or unsubstituted, 9- to 10-membered, bicyclic heteroaryl, wherein one, two, three, or four atoms in the heteroaryl ring system are independently nitrogen, oxygen, or sulfur). In certain embodiments, $R^4$ is

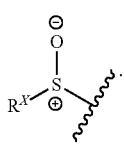

In certain embodiments, Rx is substituted or unsubstituted $C_{1-6}$ alkyl. In certain embodiments, $R^4$ is

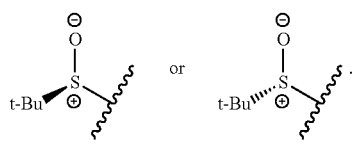 [SMILES: *[S@+]([O-])C(C)(C)C ; *[S@@+]([O-])C(C)(C)C]

In certain embodiments, $R^4$ is

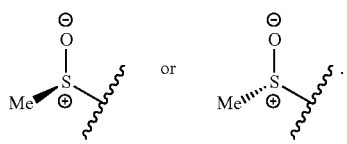

In certain embodiments, $R^4$ is

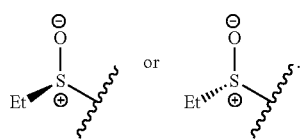 [SMILES: *[S@+]([O-])CC ; *[S@@+]([O-])CC]

In certain embodiments, $R^4$ is

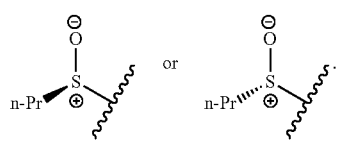

In certain embodiments, $R^4$ is

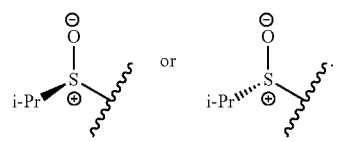 [SMILES: *[S@+]([O-])C(C)C ; *[S@@+]([O-])C(C)C]

In certain embodiments, $R^4$ is

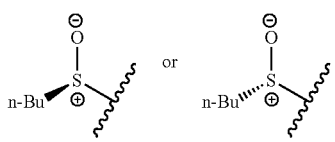

In certain embodiments, $R^4$ is

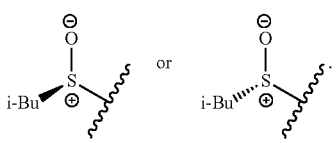

In certain embodiments, $R^4$ is

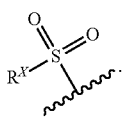

In certain embodiments, $R^X$ is substituted or unsubstituted $C_{1-6}$ alkyl. In certain embodiments, $R^4$ is

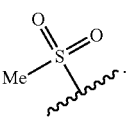

In certain embodiments, $R^4$ is

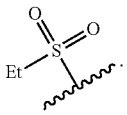

In certain embodiments, $R^4$ is

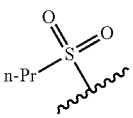

In certain embodiments, $R^4$ is

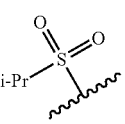

In certain embodiments, $R^4$ is

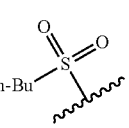

In certain embodiments, R⁴ is

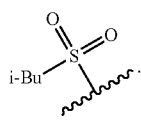

In certain embodiments, R⁴ is

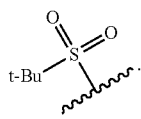

In certain embodiments, n is 1. In certain embodiments, n is 2. In certain embodiments, n is 3.

The compounds described herein may be useful in treating infectious disease, particularly parasitic diseases. The compounds described herein may be useful in treating parasitic infections. The compounds described herein may be anti-parasitic compounds, particularly anti-trypanosomal and/or anti-plasmodial compounds. The compounds described herein may be useful in treating protozoan infections. The compounds described herein may be useful in treating bacterial infections. The compounds described herein may be useful in treating trypanosomal infections (e.g. *T. cruzi* infections). The compounds described herein may be useful in treating plasmodial infections. The compounds described herein may be anti-trypanosomal compounds. The compounds described herein may be anti-plasmodial compounds. The compounds may be useful in treating protozoan infections in a subject in need thereof and/or preventing protozoan infections in a subject at risk of developing a protozoan infection, treating trypanosomal infections in a subject in need thereof and/or preventing trypanosomal infections (e.g., *Trypanosoma cruzi* (*T. cruzi*) or *Trypanosoma brucei* infections) in a subject at risk of developing a trypanosomal infection, treating plasmodial infections in a subject in need thereof and/or preventing plasmodial infection in a subject at risk of developing a plasmodial infection, and treating parasitic disease in a subject in need thereof and/or preventing parasitic diseases in a subject at risk of developing a parasitic disease. The compounds may be useful in treating infectious disease in a subject in need thereof and/or preventing an infectious disease in a subject at risk of developing an infectious disease (e.g., Chagas disease, malaria, and/or sleeping sickness), and/or as research tools (e.g., for studying trypanosomal infections (e.g., studying *T. cruzi* infections) and/or plasmodial infections in a subject, biological sample, tissue, or cell).

Pharmaceutical Compositions, Kits, and Administration

The present disclosure also provides pharmaceutical compositions comprising a compound described herein and optionally a pharmaceutically acceptable excipient.

The pharmaceutical compositions described herein may be useful in treating infectious disease, particularly parasitic diseases. The pharmaceutical compositions described herein may be useful in treating parasitic infections. The pharmaceutical compositions described herein may be pharmaceutical compositions with anti-parasitic compounds, particularly pharmaceutical compositions with anti-trypanosomal and/or anti-plasmodial pharmaceutical compounds. The pharmaceutical compositions described herein may be useful in treating bacterial infections. The pharmaceutical compositions described herein may be useful in treating and/or preventing protozoan infections. The pharmaceutical compositions described herein may be useful in treating trypanosomal infections in a subject in need thereof and/or preventing trypanosomal infections (e.g. *T. cruzi* infections) in a subject at risk of developing a trypanosomal infection. The pharmaceutical compositions described herein may be useful in treating plasmodial infections in a subject in need thereof and/or preventing plasmodial infections in a subject at risk of developing a plasmodial infection. The compounds described herein may be anti-trypanosomal and/or anti-plasmodial compounds. The pharmaceutical compositions may be useful in treating protozoan infections in a subject in need thereof and/or preventing protozoan infections (e.g., trypanosomal infections from *T. cruzi* or *Trypanosoma brucei* and/or plasmodial infections) in a subject at risk of developing a protozoan infection, treating trypanosomal infections in a subject in need thereof and/or preventing trypanosomal infections (e.g., *Trypanosoma cruzi* (*T. cruzi*) or *Trypanosoma brucei* infections) in a subject at risk of developing a trypanosomal infection, and/or plasmodial infections in a subject at risk of developing a plasmodial infection, treating infectious disease in a subject in need thereof and/or preventing an infectious disease in a subject at risk of developing an infectious disease (e.g., Chagas disease, sleeping sickness, and malaria), particularly treating parasitic diseases in a subject in need thereof, and as research tools (e.g., for studying trypanosomal infections (e.g., studying *T. cruzi* infections) and/or plasmodial infections in a subject, biological sample, tissue, or cell). The pharmaceutical compositions may be useful as pharmaceutical compositions with anti-trypanosomal and/or anti-plasmodial compounds.

In certain embodiments, the subject being treated with a compound of Formula (I'), Formula (I), Formula (II), or Formula (III) is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, a therapeutically effective amount is effective for treating a disease. In certain embodiments, a therapeutically effective amount is effective for treating an infectious disease (e.g., Chagas disease and/or, sleeping sickness, malaria). In certain embodiments, a therapeutically effective amount is effective for treating an parasitic disease. In certain embodiments, a therapeutically effective amount is effective for treating an parasitic infection. In certain embodiments, a therapeutically effective amount is effective for treating a bacterial infection. In certain embodiments, a therapeutically effective amount is effective for treating a protozoan infection. In certain embodiments, a therapeutically effective amount is effective for treating a trypanosomal and/or plasmodial infection. In certain embodiments, a therapeutically effective amount is effective for treating a *T. cruzi* infection. In certain embodiments, a therapeutically effective amount is effective for treating a plasmodial infection. In certain embodiments, a prophylactically effective amount is effective for preventing a disease. In certain embodiments, a prophylactically effective amount is effective for preventing an infectious disease (e.g., Chagas disease and/or malaria). In certain embodiments, a prophylactically effective amount is effective for preventing a parasitic disease. In certain embodiments, a prophylactically effective amount is effective for preventing a parasitic infection. In certain embodiments, a prophylactically effective amount is effective for preventing a protozoan infection. In certain embodiments, a prophylactically effective amount is effective for preventing a trypanosomal and/or plasmodial infection. In certain embodiments, a prophylactically effective amount is effective for preventing a *T. cruzi* infection. In certain embodiments, a prophylactically effective amount is effective for preventing a plasmodial infection.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating and/or preventing protozoan infections in a subject in need thereof, treating and/or preventing trypanosomal infections (e.g., *Trypanosoma cruzi* (*T. cruzi*) or *Trypanosoma brucei* infections) and/or plasmodial infections in a subject in need thereof, treating and/or preventing diseases (e.g., Chagas disease, malaria, and/or sleeping sickness), and treating and/or preventing infectious diseases in a subject, biological sample, tissue, or cell. The compounds or compositions can also be administered in combination with additional pharmaceutical agents that improve bioavailability, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-parasitic agents, anti-bacterial agents, anti-viral agents, cardiovascular agents, pain-relieving agents, and a combination thereof. In certain embodiments, the additional pharmaceutical agent is an anti-parasitic agent. In certain embodiments, the additional pharmaceutical agent is an anti-trypsanosomal agent. In certain embodiments, the additional pharmaceutical agent is an anti-plasmodial agent. In certain embodiments, the additional pharmaceutical agent is a pharmaceutical agent useful for treating and/or preventing a disease (e.g., infectious disease, parasitic infection, protozoan infection, trypanosomal infection, plasmodial infection, Chagas disease, malaria, or sleeping sickness).

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. The kits described herein may be useful in treating protozoan infections in a subject in need thereof, treating trypanosomal infections (e.g., *Trypanosoma cruzi* (*T. cruzi*) infections) and/or treating plasmodial infections in a subject in need thereof, treating diseases in a subject in need thereof (e.g., Chagas disease and/or malaria), treating infectious diseases in a subject in need thereof, preventing protozoan infections, preventing trypanosomal infections (e.g., *T. cruzi* or *Trypanosoma brucei* infections) and/or plasmodial infections in a subject at risk of developing a protozoan or plamsodial infection, preventing protozoan infections in a subject at risk of developing a protozoan infection (e.g., trypanosomal infections from *T. cruzi* or *Trypanosoma brucei* and/or plasmodial infections), preventing infectious diseases in a subject at risk of developing an infectious disease, and/or preventing diseases in a subject in need thereof (e.g., Chagas disease, malaria, and/or sleeping sickness). The kits described herein may also be useful as research tools (e.g., for studying trypanosomal infections (e.g., studying *T. cruzi* and/or plasmodial infections) in a subject, biological sample, tissue, or cell).

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., Chagas disease and/or malaria) in a subject in need thereof. In certain embodiments, the kits and instructions provide for preventing an infectious disease (e.g., Chagas disease and/or malaria) in a subject at risk of developing an infectious disease. In certain embodiments, the kits and instructions provide for modulating (e.g., inhibiting) the activity of *T. cruzi* and/or plasmodial activity in a subject, biological sample, tissue, or cell. A kit described herein may include one or more additional pharmaceutical agents described herein as a separate composition.

Methods of Treatment and Uses

The protozoan parasite *T. cruzi* is associated with a number of diseases (e.g., Chagas disease). The protozoan parasite *plasmodium* is associated with a number of diseases (e.g., malaria). The compounds described herein may be capable of treating and/or preventing protozoan infections in a subject in need thereof, treating and/or preventing trypanosomal infections (e.g., *Trypanosoma cruzi* (*T. cruzi*) or *Trypanosoma brucei* infections) and/or plasmodial infections in a subject in need thereof. The compounds described herein may be capable of treating and/or preventing bacterial infections in a subject in need thereof. The compounds described herein may be capable of treating and/or preventing diseases in a subject in need thereof (e.g., Chagas disease, malaria, and/or sleeping sickness).

The present disclosure thus provides methods of treating and/or preventing protozoan infections in a subject in need thereof, the methods comprising administering to the subject an effective amount (e.g., therapeutically effective amount) of a compound or pharmaceutical composition described herein. Another aspect of the present disclosure relates to treating and/or preventing trypanosomal infections (e.g., *Trypanosoma cruzi* (*T. cruzi*) or *Trypanosoma brucei* infections) and/or plasmodial infections in a subject in need thereof, the methods comprising administering to the subject an effective amount (e.g., therapeutically effective amount) of a compound or pharmaceutical composition described herein. Another aspect of the present disclosure relates to treating and/or preventing diseases in a subject in need thereof (e.g., Chagas disease, malaria, and/or sleeping sickness), the methods comprising administering to the subject an effective amount (e.g., therapeutically effective amount) of a compound or pharmaceutical composition described herein. Another aspect of the present disclosure relates to treating and/or preventing infectious diseases in a subject in need thereof, the methods comprising administering to the subject an effective amount (e.g., therapeutically effective amount) of a compound or pharmaceutical composition described herein.

The present disclosure provides methods of treating and/or preventing protozoan infections in a subject in need thereof, the methods comprising killing or inhibiting the growth of protozoan parasites. Another aspect of the present disclosure relates to treating and/or preventing trypanosomal and/or plasmodial infections in a subject in need thereof, the methods comprising killing or inhibiting the growth of protozoan parasites. Another aspect of the present disclosure relates to treating and/or preventing diseases in a subject in need thereof, the methods comprising killing or inhibiting the growth of protozoan parasites. Another aspect of the present disclosure relates to treating and/or preventing diseases in a subject in need thereof (e.g., Chagas disease, malaria, and/or sleeping sickness), the methods comprising killing or inhibiting the growth of protozoan parasites. The present disclosure provides methods of treating and/or preventing infectious diseases, the methods comprising killing or inhibiting the growth of protozoan parasites. In certain embodiments, the method comprises killing protozoan parasites. In certain embodiments, the method comprises inhibiting the growth of protozoan parasites. In certain embodiments, the $IC_{50}$ is below 5.0 µM. In certain embodiments, the $IC_{50}$ is below 1.0 µM. In certain embodiments, the $IC_{50}$ is below 0.5 µM. In certain embodiments, the $IC_{50}$ is below 0.1 µM. In certain embodiments, the $IC_{50}$ is below 0.05 µM.

In certain embodiments, a disease being treated and/or prevented is an infectious disease. In certain embodiments, a disease being treated and/or prevented is an parasitic disease. In certain embodiments, a disease described herein is a protozoan infectious disease. In certain embodiments, the disease is a plasmodial infectious disease. In certain embodiments, the disease is a trypanosomal infectious disease. In certain embodiments, the disease is a *Leishmania* infectious disease. In certain embodiments, a disease is a *Trypanosoma cruzi* (*T. cruzi*) infection. In certain embodiments, the disease is Chagas disease. In certain embodiments, the disease is sleeping sickness. In certain embodiments, the disease is leishmaniasis. In certain embodiments, the disease is malaria.

In still another aspect, the present disclosure provides the pharmaceutical compositions described herein for use in a method described herein (e.g., a method of treating and/or preventing protozoan infections in a subject in need thereof, a method of treating and/or preventing trypanosomal infections (e.g., *Trypanosoma cruzi* (*T. cruzi*) or *Trypanosoma brucei* infections) and/or plasmodial infections in a subject in need thereof, a method of treating and/or preventing diseases in a subject in need thereof (e.g., Chagas disease, malaria, and/or sleeping sickness), and a method of treating and/or preventing infectious diseases in a subject in need thereof.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Preparation and Characterization of the Compounds Described Herein

Preparation of the Compounds

The compounds provided herein can be prepared from readily available starting materials using methods known in the art, such as the methods described in Mauger et al., *Eur. Pat. Appl.*, 1746097, 24 Jan. 2007, and the methods described in Nitsche et al., *Journal of Medicinal Chemistry*, 56(21), 8389-8403; 2013, and Bauer et al., *Organic Letters*, 12(9), 2084-2087; 2010 and Moura-Letts et al., *Proceedings of the National Academy of Science USA*, 108(17), 6745-6750; 2011. Where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Materials and Methods

Reagents were obtained from Aldrich Chemical (www.sigma-aldrich.com) or Acros Organics (www.fishersci.com) and used without further purification. Optima or HPLC grade solvents were obtained from Fisher Scientific (www.fishersci.com), degassed with Ar, and purified on a solvent drying system. Reactions were performed in flame-dried glassware under positive Ar pressure with magnetic stirring. TLC was performed on 0.25 mm E. Merck silica gel 60 F254 plates and visualized under UV light (254 nm) or by staining with potassium permanganate (KMnO4), cerium ammonium molybdenate (CAM), or iodine (I2). Silica flash chromatography was performed on E. Merck 230-400 mesh silica gel 60. Optical rotations were recorded on a JASCO model P-1020 digital polarimeter. IR spectra were recorded on a Bruker Optics Tensor 27 FTIR spectrometer with Pike technologies MIRacle ATR (attenuated total reflectance, ZnSe crystal) accessory and peaks reported in $cm^{-1}$. NMR spectra were recorded on a Bruker Avance III 500 instrument or Bruker Avance III 600 instrument at 24° C. in CDCl3 unless otherwise indicated. Spectra were processed using Bruker TopSpin or Mnova (www.mestrelab.com/software/mnova-nmr), and chemical shifts are expressed in ppm relative to TMS (1H, 0 ppm) or residual solvent signals: CDCl3 ($^{13}$C, 77.0 ppm); coupling constants are expressed in Hz. Mass spectra were obtained at the MSKCC Analytical Core Facility on a Waters Acuity SQD LC-MS by electrospray (ESI) ionization or atmospheric pressure chemical ionization (AP-CI).

General Preparation of Exemplary Compounds

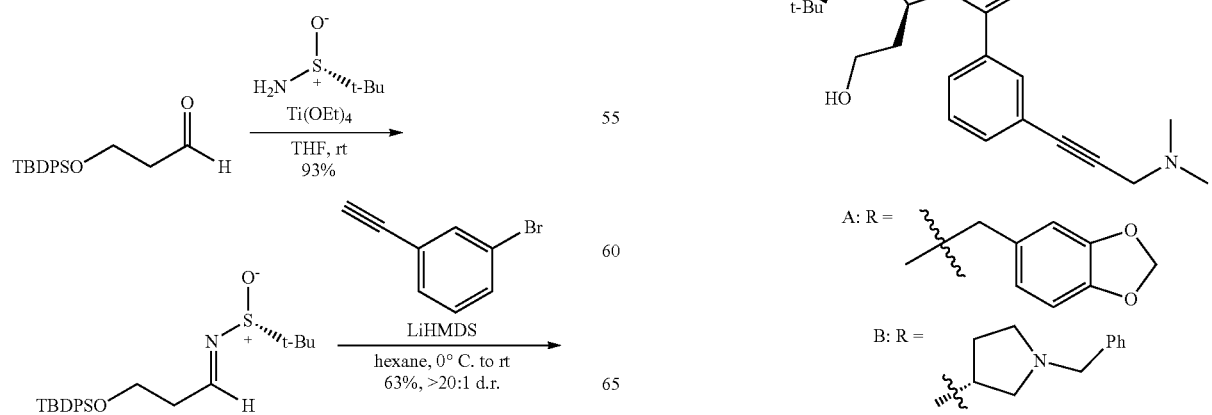

137
Synthesis of Anti Analogues
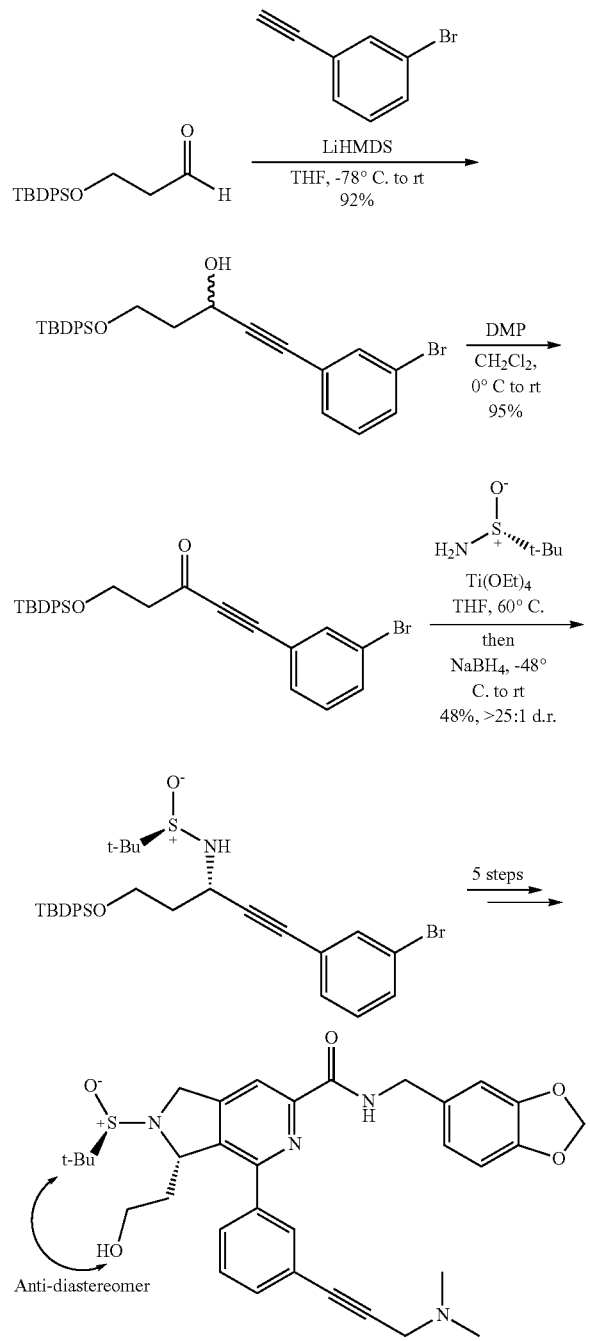
Synthesis of Deshydroxyethyl Analogues
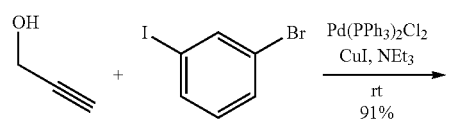
138
-continued
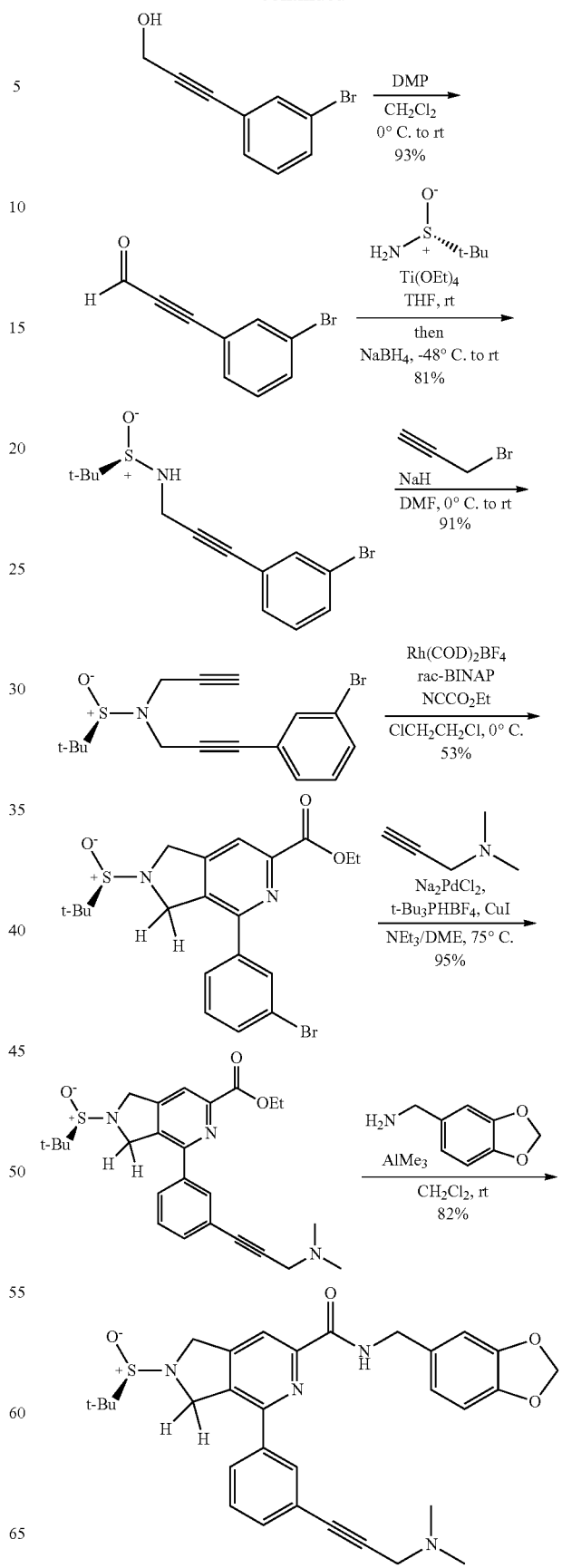

Synthesis of Syn Analogues

Example 1. Preparation of Compound 21

(R)—N—((R)-1-(3-Bromophenyl)-5-((tert-butyldiphenylsilyl)oxy)pent-1-yn-3-yl)-2-methyl-propane-2-sulfinamide

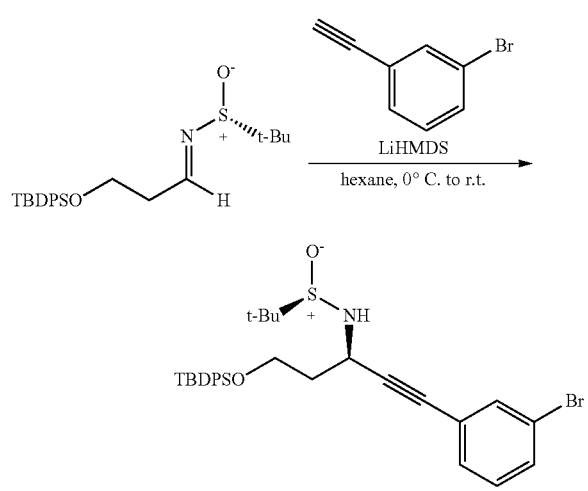

In a 100 mL roundbottom flask, LiHMDS (1.0 M in THF, 3.0 mL, 3.0 mmol, 1.1 equiv) was dissolved in 22 mL anhyd hexanes and cooled to 0° C. 1-bromo-3-ethynylbenzene (415 μL, 3.3 mmol, 1.2 equiv) was added and the reaction removed from the cold bath and stirred for 15 min. The reaction was recooled to 0° C., and (R,E)-N-(3-((tert-butyldiphenylsilyl)oxy)propylidene)-2-methylpropane-2-sulfinamide (1.15 g, 2.77 mmol, 1.0 equiv) was transferred via cannula into the reaction in 5.5 mL anhyd hexanes. The reaction was allowed to warm to room temperature with stirring for 12 h. Equal volumes of saturated aqueous NH$_4$Cl and Et$_2$O (20 mL each) were added to the reaction mixture. The layers were separated and the aq layer extracted with Et$_2$O (3×20 mL) then EtOAc (1×20 mL). The combined organic extracts were washed with brine (1×20 mL), dried (Na$_2$SO$_4$), filtered, and concentrated by rotary evaporation. 1H NMR analysis of the crude sample indicated the product was produced in >20:1 d.r. Purification by silica flash chromatography (2:1 hexanes/EtOAc) yielded the N-propargyl sulfinamide as a sticky brown foam (1.05 g, 63%). TLC: R$_f$ 0.47 (40% EtOAc/hexanes). [α]$_D^{20}$: −10.4° (c 0.55, CHCl$_3$). IR (ATR): 2958, 2931, 2858, 1590, 1556, 1473, 1428, 1111, 1073, 762, 703. $^1$H-NMR (600 MHz): δ 7.67 (ddd, J=8.1, 2.7, 1.4 Hz, 4H), 7.52 (t, J=1.7 Hz, 1H), 7.44 (ddd, J=8.0, 2.0, 1.0 Hz, 1H), 7.43-7.39 (m, 2H), 7.39-7.33 (m, 4H), 7.32 (dt, J=7.7, 1.3 Hz, 1H), 7.16 (t, J=7.9 Hz, 1H), 4.59 (q, J=6.9 Hz, 1H), 3.91 (ddd, J=10.5, 6.6, 5.1 Hz, 1H), 3.86 (ddd, J=10.5, 6.4, 5.1 Hz, 1H), 3.61 (d, J=7.4 Hz, 1H), 2.11-1.96 (m, 2H), 1.21 (s, 9H), 1.06 (s, 9H). $^{13}$C-NMR (151 MHz): δ 135.5, 134.4, 133.3, 133.3, 131.5, 130.4, 129.7, 129.6, 127.7, 127.7, 124.6, 122.0, 90.2, 83.6, 60.3, 56.3, 45.6, 39.5, 26.8, 22.5, 19.2. HRMS m/z calcd for C$_{31}$H$_{38}$NO$_2$NaSiSBr ([M+Na]$^+$) 618.1474; found 618.1462.

(R)—N—((R)-1-(3-Bromophenyl)-5-((tert-butyldiphenylsilyl)oxy)pent-1-yn-3-yl)-2-methyl-N-(prop-2-yn-1-yl)propane-2-sulfinamide

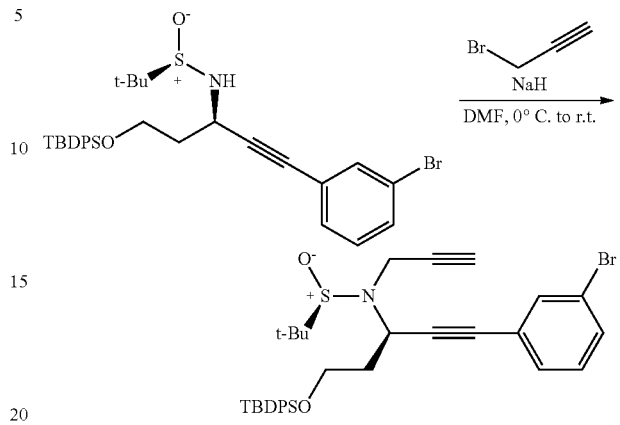

In a 100 mL roundbottom flask, (R)—N—((R)-1-(3-Bromophenyl)-5-((tert-butyldiphenylsilyl)oxy)pent-1-yn-3-yl)-2-methyl-propane-2-sulfinamide (5.18 g, 8.68 mmol, 1.0 equiv) was dissolved in 43 mL DMF and cooled to 0° C. Sodium hydride (60% dispersion in mineral oil, 416 mg, 10.4 mmol, 1.2 equiv) was added, followed by propargyl bromide (80% in toluene, 1.4 mL, 13.0 mmol, 1.5 equiv) and the mixture was stirred at 0° C. for 40 min, then allowed to warm to room temperature and stirred for 2 h. The reaction was quenched by the addition of 50 mL saturated aqueous NH$_4$Cl, then diluted with 50 mL of Et$_2$O. The organic layer was washed with water (3×50 mL), then the combined aqueous layers extracted with Et$_2$O (2×50 mL). The combined organic extracts were washed with brine (1×50 mL), dried (MgSO$_4$), filtered, and concentrated by rotary evaporation. Purification by silica flash chromatography (10%→30% EtOAc/hexanes) yielded the diyne as a sticky brown foam (5.14 g, 93%). TLC: R$_f$ 0.60 (30% EtOAc/hexanes). [α]$_d^{21}$: +22.8° (c 1.0, CHCl$_3$). IR (ATR): 3306, 2959, 2932, 2858, 1590, 1557, 1473, 1428, 1362, 1111, 1083, 761, 704. $^1$H-NMR (600 MHz): δ 7.70-7.63 (m, 4H), 7.51 (t, J=1.7 Hz, 1H), 7.47-7.41 (m, 2H), 7.41-7.36 (m, 3H), 7.36-7.31 (m, 2H), 7.30 (dt, J=7.7, 1.3 Hz, 1H), 7.16 (t, J=7.9 Hz, 1H), 4.76 (dd, J=9.1, 6.2 Hz, 1H), 4.18 (dd, J=19.1, 2.6 Hz, 1H), 3.91 (dt, J=10.2, 5.0 Hz, 1H), 3.84 (ddd, J=10.5, 8.5, 4.0 Hz, 1H), 3.50 (dd, J=19.1, 2.4 Hz, 1H), 2.27 (dddd, J=13.4, 8.5, 6.2, 4.8 Hz, 1H), 2.15 (t, J=2.5 Hz, 1H), 2.13-2.06 (m, 1H), 1.26 (s, 9H), 1.06 (s, 9H). $^{13}$C-NMR (151 MHz): δ 135.6, 135.5, 134.5, 133.5, 133.4, 131.6, 130.4, 129.7, 129.7, 129.6, 127.7, 127.7, 124.4, 122.0, 88.1, 84.6, 81.8, 77.0, 71.4, 60.1, 58.6, 37.6, 26.8, 22.9, 19.2, 14.2. HRMS m/z calcd for C$_{34}$H$_{40}$NO$_2$NaSiSBr ([M+Na]$^+$) 656.1630; found 656.1633.

Ethyl (R)-4-(3-bromophenyl)-3-(2-((tert-butyldiphenylsilyl)oxy)ethyl)-2-((R)-tert-butyl-sulfinyl)-2,3-dihydro-1H-pyrrolo[3,4-c]pyridine-6-carboxylate

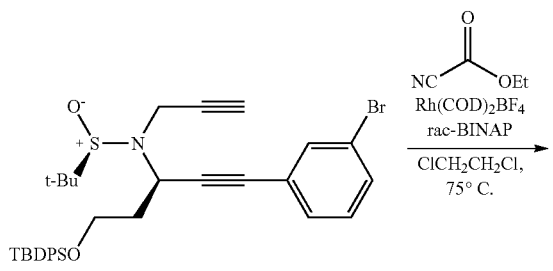

-continued

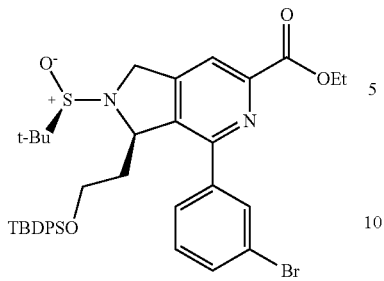

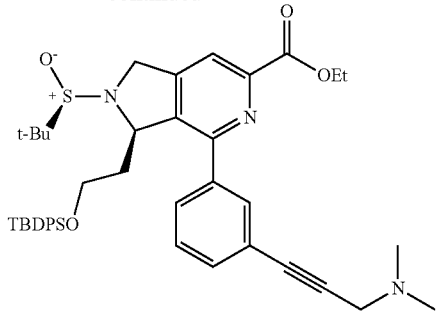

In a 500 mL roundbottom flask, Rh(COD)$_2$BF$_4$ (493 mg, 1.21 mmol, 15 mol %) and rac-BINAP (1.01 g, 1.62 mmol, 20 mol %) were dissolved in 260 mL of degassed 1,2-dichloroethane. Ethyl cyanoformate (4.0 mL, 40.5 mmol, 5.0 equiv) was added, followed by a solution of (R)—N—((R)-1-(3-Bromophenyl)-5-((tert-butyldiphenylsilyl)oxy) pent-1-yn-3-yl)-2-methyl-N-(prop-2-yn-1-yl)propane-2-sulfinamide (5.14 g, 8.10 mmol, 1.0 equiv) in 10 mL of 1,2-dichloroethane. The mixture was heated to 75° C. (oil bath, ext temp) for 4 h, then cooled to room temperature and concentrated by rotary evaporation. Purification by silica flash chromatography (25→45% EtOAc/hexanes) yielded the pyrrolopyridinecarboxylate as an orange foam (5.08 g, 85%). TLC: R$_f$0.14 (30% EtOAc/hexanes). [α]$_D^{19}$: +30.7° (c 1.0, CHCl$_3$). IR (ATR): 3071, 3050, 3050, 2932, 2858, 1742, 1717, 1576, 1227 1108, 1075, 741, 703. $^1$H-NMR (600 MHz): δ 7.96 (s, 1H), 7.92 (t, J=1.8 Hz, 1H), 7.60 (dt, J=7.7, 1.2 Hz, 1H), 7.53 (ddd, J=8.0, 2.0, 1.0 Hz, 1H), 7.50-7.45 (m, 2H), 7.45-7.39 (m, 4H), 7.36-7.30 (m, 4H), 7.11 (t, J=7.8 Hz, 1H), 5.74 (dt, J=8.1, 2.6 Hz, 3H), 5.17 (d, J=15.9 Hz, 1H), 4.52 (dq, J=10.9, 7.1 Hz, 1H), 4.44 (dq, J=10.9, 7.1 Hz, 1H), 4.00 (ddd, J=15.8, 2.0, 1.0 Hz, 1H), 3.67 (ddd, J=10.4, 8.9, 4.9 Hz, 1H), 3.46 (ddd, J=10.4, 6.1, 4.2 Hz, 1H), 1.73 (dddd, J=14.6, 9.1, 6.2, 3.2 Hz, 1H), 1.53-1.47 (m, 1H), 1.44 (t, J=7.1 Hz, 3H), 1.22 (s, 9H), 0.98 (s, 9H). $^{13}$C-NMR (151 MHz): δ 164.9, 152.1, 151.5, 147.7, 140.5, 139.3, 135.5, 135.4, 133.4, 133.2, 132.1, 131.9, 130.2, 129.7, 129.7, 127.7, 127.6, 126.7, 123.2, 118.5, 68.5, 62.0, 59.3, 58.6, 45.7, 37.7, 26.8, 23.7, 19.1, 14.3. HRMS m/z calcd for C$_{38}$H$_{46}$N$_2$O$_4$SiSBr ([M+H]$^+$) 733.2131; found 733.2120.

Ethyl (R)-3-(2-((tert-butyldiphenylsilyl)oxy)ethyl)-2-((R)-tert-butylsulfinyl)-4-(3-(3-(di-methylamino) prop-1-yn-1-yl)phenyl)-2,3-dihydro-1H-pyrrolo[3,4-c]pyridine-6-carboxylate In a 100 mL roundbottom flask, Ethyl (R)-4-(3-bromophenyl)-3-(2-((tert-butyldiphenylsilyl)oxy)ethyl)-2-((R)-tert-butyl-sulfinyl)-2,3-dihydro-1H-pyrrolo[3,4-c]pyridine-6-carboxylate (556 mg, 0.758 mmol, 1.0 equiv), Na$_2$PdCl$_4$ (22 mg, 0.0758 mmol, 10 mol %), t-Bu$_3$PHBF$_4$ (33 mg, 0.114 mmol, 15 mol %), and CuI (29 mg, 0.152 mmol, 20 mol %) were dissolved in 4.7 mL of degassed 1,2-dimethoxyethane and 14.1 mL of degassed i-Pr$_2$NH. N,N-dimethylprop-2-yn-1-amine (408 μL, 3.79 mmol, 5.0 equiv) was added, then the mixture heated to 75° C. (oil bath, ext temp) for 24 h. The reaction was cooled to room temperature and diluted with EtOAc, then filtered through Celite and concentrated by rotary evaporation. Purification by silica flash chromatography (4% MeOH/CH$_2$Cl$_2$) yielded Ethyl (R)-3-(2-((tert-butyldiphenylsilyl)oxy)ethyl)-2-((R)-tert-butylsulfinyl)-4-(3-(3-(di¬methyl-amino)prop-1-yn-1-yl)phenyl)-2,3-dihydro-1H-pyrrolo[3,4-c]pyridine-6-carboxylate as a dark orange foam (496 mg, 89%). TLC: R$_f$0.25 (5% MeOH/CH$_2$Cl$_2$). [α]$_D^{19}$: +29.0° (c 1.0, CHCl$_3$). IR (ATR): 3071, 3050, 2956, 2859, 2777, 1741, 1718, 1577, 1472, 1256, 1219, 1107, 1076, 742, 703. $^1$H-NMR (600 MHz): δ 7.94 (s, 1H), 7.83 (s, 1H), 7.60 (dt, J=7.8, 1.4 Hz, 1H), 7.48 (ddd, J=8.0, 6.3, 1.4 Hz, 3H), 7.43-7.37 (m, 4H), 7.33 (td, J=7.2, 1.5 Hz, 4H), 7.23 (t, J=7.8 Hz, 1H), 5.73 (dt, J=7.8, 2.5 Hz, 1H), 5.16 (d, J=15.7 Hz, 1H), 4.51 (dq, J=10.9, 7.1 Hz, 1H), 4.44 (dq, J=10.9, 7.1 Hz, 1H), 3.98 (d, J=14.9 Hz, 0H), 3.64 (ddd, J=10.3, 8.7, 5.1 Hz, 1H), 3.50 (s, 2H), 3.44 (ddd, J=10.5, 6.3, 4.4 Hz, 1H), 2.38 (s, 6H), 1.74 (dddd, J=14.6, 9.2, 6.3, 3.2 Hz, 1H), 1.52-1.45 (m, 1H), 1.43 (t, J=7.1 Hz, 3H), 1.21 (s, 9H), 0.97 (s, 9H). $^{13}$C-NMR (151 MHz): δ 165.0, 153.0, 151.2, 147.6, 139.2, 138.8, 135.5, 135.4, 133.3, 133.2, 132.3, 132.0, 129.7, 129.6, 128.7, 127.7, 127.6, 127.6, 124.0, 118.3, 85.3, 85.0, 68.6, 61.9, 59.4, 58.5, 48.6, 45.7, 44.3, 37.5, 26.8, 23.7, 19.0, 14.3. HRMS m/z calcd for C$_{43}$H$_{54}$N$_3$O$_4$SSi ([M+H]$^+$) 736.3604; found 736.3615.

(R)—N-(Benzo[d][1,3]dioxol-5-ylmethyl)-3-(2-((tert-butyldiphenylsilyl)oxy)ethyl)-2-((R)-tert-butylsulfinyl)-4-(3-(3-(dimethylamino)prop-1-yn-1-yl) phenyl)-2,3-dihydro-1H-pyrrolo[3,4-c]pyridine-6-carboxamide

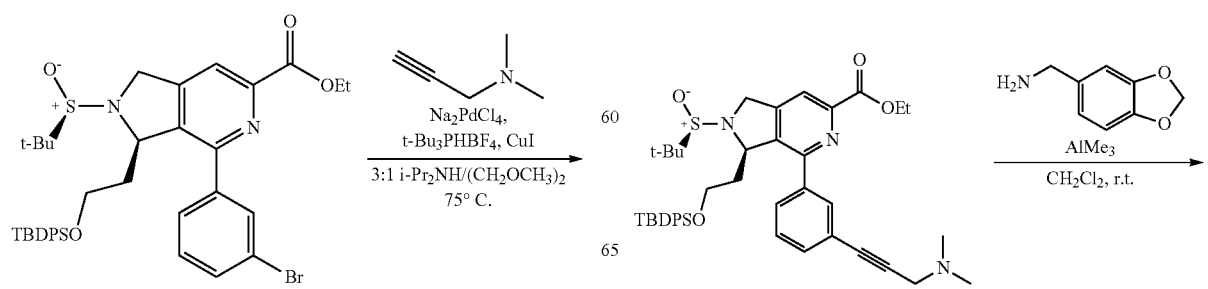

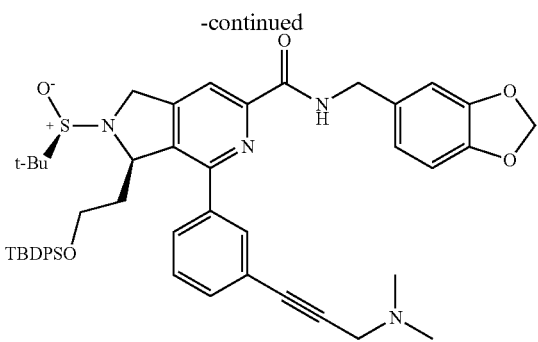

To a 10 mL roundbottom flask containing ethyl (R)-3-(2-((tert-butyldiphenylsilyl)oxy)ethyl)-2-((R)-tert-butylsulfinyl)-4-(3-(3-(di¬methyl-amino)prop-1-yn-1-yl)phenyl)-2,3-dihydro-1H-pyrrolo[3,4-c]pyridine-6-carboxylate (247 mg, 0.336 mmol, 1.0 equiv, azeotroped 3× with toluene) at room temperature was slowly added a pre-stirred (>2 h) stock solution of dimethylaluminum piperonylamide (0.2 M solution in CH$_2$Cl$_2$/toluene, 3.36 mL, 0.671 mmol, 2.0 equiv). The mixture was stirred at room temperature for 17 h, then carefully quenched by dropwise addition of 0.5 mL MeOH followed by dilution with 5 mL of CH$_2$Cl$_2$ and careful addition of 5 mL saturated aqueous NaHCO$_3$. The aqueous layer was extracted with EtOAc (3×5 mL), then the combined organic layers were dried (Na$_2$SO$_4$), filtered, and concentrated by rotary evaporation. Purification by silica flash chromatography (70% EtOAc/hexanes→100% EtOAc) yielded (R)—N-(Benzo[d][1,3]dioxol-5-ylmethyl)-3-(2-((tert-butyldiphenylsilyl)oxy)ethyl)-2-((R)-tert-butylsulfinyl)-4-(3-(3-(dimethylamino)prop-1-yn-1-yl)phenyl)-2,3-dihydro-1H-pyrrolo¬[3,4 c]¬¬-pyridine-6-carboxamide as a light orange foam (203 mg, 72%). TLC: R$_f$0.50 (10% MeOH/CH$_2$Cl$_2$). [α]$_D^{20}$: +22.1° (c 1.0, CHCl$_3$). IR (ATR): 3388, 3052, 2978, 2945, 2912, 2873, 2779, 1670, 1574, 1526, 1490, 1445, 1253, 1040, 929, 737. $^1$H-NMR (600 MHz): δ 8.33 (t, J=6.3 Hz, 1H), 8.10 (s, 1H), 7.73 (t, J=1.7 Hz, 1H), 7.59 (dt, J=7.8, 1.4 Hz, 1H), 7.53 (dt, J=7.7, 1.3 Hz, 1H), 7.47-7.40 (m, 1H), 6.86 (d, J=1.7 Hz, 1H), 6.82 (dd, J=7.9, 1.7 Hz, 1H), 6.76 (d, J=7.9 Hz, 1H), 5.93 (q, J=1.4 Hz, 2H), 5.66 (dt, J=5.9, 2.6 Hz, 1H), 5.20 (d, J=15.7 Hz, 1H), 4.64-4.49 (m, 2H), 4.14 (d, J=14.5 Hz, 1H), 3.54 (ddd, J=10.8, 7.7, 6.1 Hz, 1H), 3.41 (ddd, J=11.2, 6.7, 5.1 Hz, 1H), 2.38 (s, 6H), 1.78-1.67 (m, 1H), 1.63-1.59 (m, 2H), 1.31 (s, 9H). $^{13}$C-NMR (151 MHz): δ 163.8, 151.8, 151.4, 149.4, 147.9, 146.9, 138.6, 137.4, 132.4, 132.1, 131.4, 128.8, 127.8, 123.9, 121.0, 115.8, 108.4, 108.3, 101.0, 85.8, 84.5, 68.6, 58.5, 58.4, 48.6, 46.0, 44.4, 43.2, 37.5, 23.8. HRMS m/z calcd for C$_{33}$H$_{39}$N$_4$O$_5$S ([M+H]$^+$) 603.2641; found 603.2643.

Preparation of Dimethylaluminum Piperonylamide Stock Solution

To a 10 mL roundbottom flask containing piperonylamine (125 µL, 1.0 mmol, 1.0 equiv) in 9.5 mL of CH2Cl2 was slowly added trimethylaluminum solution (2 M in toluene, 0.5 mL, 1.0 mmol, 1.0 equiv) at rt. The mixture was stirred for >2 h before use. Solution can be stored at −20° C. for at least 1 month.

(R)—N-(Benzo[d][1,3]dioxol-5-ylmethyl)-2-((R)-tert-butylsulfinyl)-4-(3-(3-(dimethyl-amino)prop-1-yn-1-yl)phenyl)-3-(2-hydroxyethyl)-2,3-dihydro-1H-pyrrolo[3,4-c]pyridine-6-carboxamide (Compound 21)

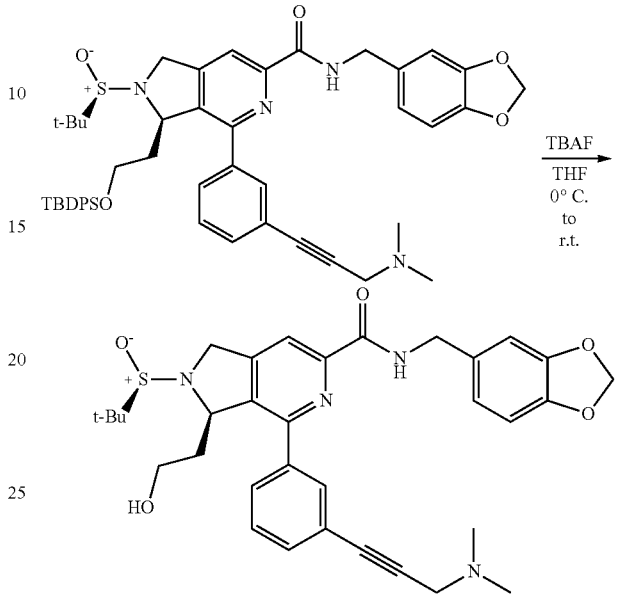

In a 10 mL roundbottom flask, (R)—N-(Benzo[d][1,3]dioxol-5-ylmethyl)-3-(2-((tert-butyldiphenylsilyl)oxy)ethyl)-2-((R)-tert-butylsulfinyl)-4-(3-(dimethylamino)prop-1-yn-1-yl)phenyl)-2,3-dihydro-1H-pyrrolo¬[3,4c]¬¬-pyridine-6-carboxamide (190 mg, 0.226 mmol, 1.0 equiv) was dissolved in 2.3 mL of THF and cooled to 0° C. n-Bu$_4$NF solution (1.0 M in THF, 339 µL, 0.339 mmol, 1.5 equiv) was added dropwise and the mixture was stirred at 0° C. for 1 hour, then allowed to warm to room temperature over 4.5 h. The reaction mixture was diluted with 3 mL EtOAc and 3 mL saturated aqueous NaHCO$_3$, then the aqueous layer was extracted with EtOAc (3×3 mL). The combined organic extracts were washed with brine (1×3 mL), dried (Na$_2$SO$_4$), filtered, and concentrated by rotary evaporation. Purification by silica flash chromatography (10% MeOH/EtOAc) yielded pyrrolopyridinecarboxamide compound 21 as a light yellow foam (98 mg, 72%).

Preparation of Compound 79

Preparation of enantiomer 79 is analogous to the synthesis of compound 21.

Example 2. Preparation of Compound 37

(R)—N—((R)-1-Benzylpyrrolidin-3-yl)-3-(2-((tert-butyldiphenylsilyl)oxy)ethyl)-2-((R)-tert-butylsulfinyl)-4-(3-(3-(dimethylamino)prop-1-yn-1-yl)phenyl)-2,3-dihydro-1H-pyrrolo[3,4-c]pyridine-6-carboxamide

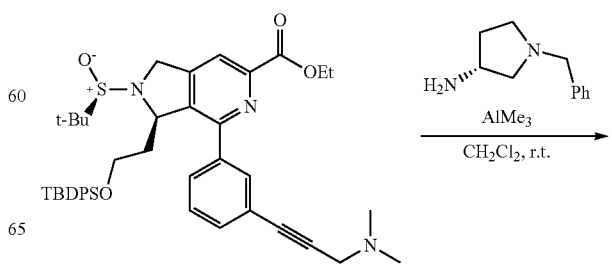

-continued

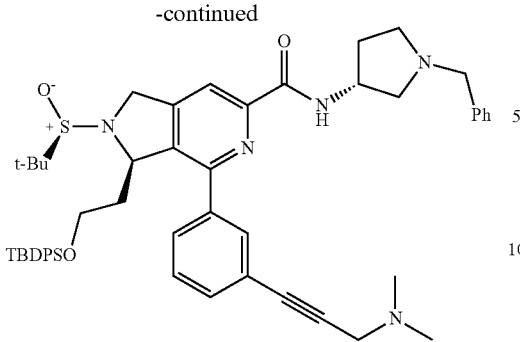

To a 10 mL roundbottom flask containing ethyl (R)-3-(2-((tert-butyldiphenylsilyl)oxy)ethyl)-2-((R)-tert-butylsulfinyl)-4-(3-(3-(di¬methyl-amino)prop-1-yn-1-yl)phenyl)-2,3-dihydro-1H-pyrrolo[3,4-c]pyridine-6-carboxylate (247 mg, 0.336 mmol, 1.0 equiv, azeotroped 3× with toluene) at room temperature was slowly added a pre-stirred (>2 h) stock solution of dimethylaluminum (R)-1-benzylpyrrolidin-3-amide (0.2 M solution in $CH_2Cl_2$/toluene, 3.36 mL, 0.671 mmol, 2.0 equiv). The mixture was stirred at room temperature for 22 h, then carefully quenched by dropwise addition of 0.5 mL MeOH followed by dilution with 5 mL of $CH_2Cl_2$ and careful addition of 5 mL saturated aqueous $NaHCO_3$. The aqueous layer was extracted with EtOAc (3×5 mL), then the combined organic layers were dried ($Na_2SO_4$), filtered, and concentrated by rotary evaporation. Purification by silica flash chromatography (100% $CH_2Cl_2$→10% MeOH/$CH_2Cl_2$) yielded (R)—N—((R)-1-Benzylpyrrolidin-3-yl)-3-(2-((tert-butyldiphenylsilyl)oxy)ethyl)-2-((R)-tert-butylsulfinyl)-4-(3-(dimethylamino)prop-1-yn-1-yl)phenyl)-2,3-dihydro-1H-pyrrolo[3,4-c]pyridine-6-carboxamide as a yellow foam (218 mg, 75%). TLC: $R_f$ 0.19 (5% MeOH/$CH_2Cl_2$). $[α]_D^{20}$: +25.5° (c 1.0, $CHCl_3$). IR (ATR): 3384, 3068, 2955, 2858, 2783, 1674, 1574, 1519, 1472, 1454, 1428, 1111, 1076, 755, 702. $^1$H-NMR (600 MHz): δ 8.25 (d, J=8.5 Hz, 1H), 8.01 (s, 1H), 7.76 (s, 1H), 7.58 (d, J=7.8 Hz, 1H), 7.55 (d, J=7.8 Hz, 1H), 7.46 (d, J=6.8 Hz, 2H), 7.43-7.28 (m, 13H), 7.23 (t, J=7.2 Hz, 1H), 5.71 (d, J=6.8 Hz, 1H), 5.14 (d, J=15.8 Hz, 1H), 4.73-4.58 (m, 1H), 3.96 (d, J=15.4 Hz, 1H), 3.70 (d, J=12.9 Hz, 1H), 3.66-3.55 (m, 2H), 3.48 (s, 2H), 3.43 (dt, J=10.5, 5.5 Hz, 1H), 2.87 (td, J=8.7, 4.4 Hz, 1H), 2.75 (dd, J=9.6, 6.6 Hz, 1H), 2.67 (dd, J=9.7, 3.5 Hz, 1H), 2.44-2.39 (m, 1H), 2.38 (s, 6H), 2.36-2.31 (m, 1H), 1.82-1.67 (m, 2H), 1.54-1.42 (m, 1H), 1.21 (s, 9H), 0.95 (s, 9H). $^{13}$C-NMR (151 MHz): δ 163.2, 151.6, 151.3, 149.3, 138.9, 138.9, 138.3, 135.5, 135.4, 133.3, 133.2, 132.3, 131.5, 129.6, 129.6, 128.8, 128.7, 128.3, 127.8, 127.6, 127.6, 127.0, 124.0, 115.5, 85.7, 84.8, 68.4, 60.5, 60.0, 59.4, 58.5, 52.8, 48.6, 48.6, 45.9, 44.4, 37.7, 32.3, 26.8, 23.8, 19.0. HRMS m/z calcd for $C_{52}H_{64}N_5O_3SSi$ ([M+H]$^+$) 866.4499; found 866.4496.

Preparation of dimethylaluminum (R)-1-benzylpyrrolidin-3-amide Stock Solution

To a 10 mL roundbottom flask containing (R)-1-benzylpyrrolidin-3-amine (173 μL, 1.0 mmol, 1.0 equiv) in 9.5 mL of CH2Cl2 was slowly added trimethylaluminum solution (2 M in toluene, 0.5 mL, 1.0 mmol, 1.0 equiv) at room temperature. The mixture was stirred for >2 h before use. Solution can be stored at −20° C. for at least 1 month.

(R)—N—((R)-1-Benzylpyrrolidin-3-yl)-2-((R)-tert-butylsulfinyl)-4-(3-(3-(dimethylamino)prop-1-yn-1-yl)phenyl)-3-(2-hydroxyethyl)-2,3-dihydro-1H-pyrrolo[3,4-c]pyridine-6-carboxamide (Compound 37)

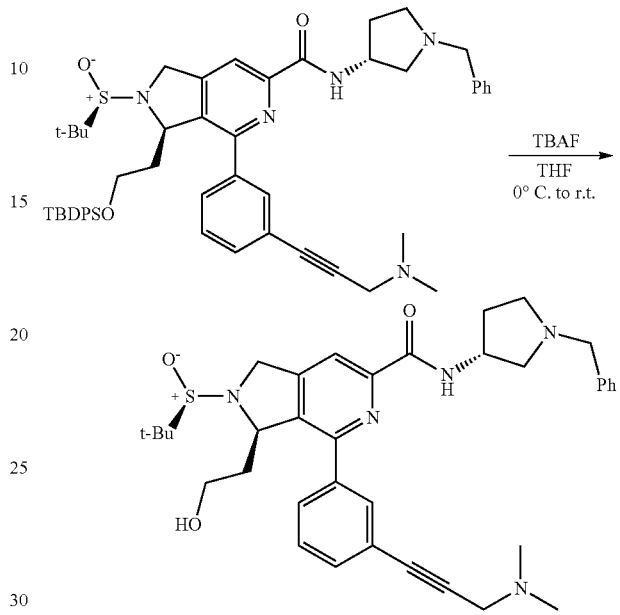

In a 10 mL roundbottom flask, (R)—N—((R)-1-Benzylpyrrolidin-3-yl)-3-(2-((tert-butyldiphenylsilyl)oxy)ethyl)-2-((R)-tert-butylsulfinyl)-4-(3-(dimethylamino)prop-1-yn-1-yl)phenyl)-2,3-dihydro-1H-pyrrolo[3,4-c]pyridine-6-carboxamide (205 mg, 0.237 mmol, 1.0 equiv) was dissolved in 2.4 mL of THF and cooled to 0° C. n-Bu$_4$NF solution (1.0 M in THF, 355 μL, 0.355 mmol, 1.5 equiv) was added dropwise and the mixture was stirred at 0° C. for 1 hour, then allowed to warm to room temperature over 4.5 h. The reaction mixture was diluted with 3 mL EtOAc and 3 mL saturated aqueous NaHCO$_3$, then the aqueous layer was extracted with EtOAc (3×3 mL). The combined organic extracts were washed with brine (1×3 mL), dried (Na$_2$SO$_4$), filtered, and concentrated by rotary evaporation. Purification by silica flash chromatography (10% MeOH/EtOAc) yielded pyrrolopyridinecarboxamide 37 as a light yellow foam (102 mg, 68%). TLC: $R_f$ 0.44 (10% MeOH/$CH_2Cl_2$). $[α]_D^{20}$: +10.7° (c 1.0, $CHCl_3$). IR (ATR): 3378, 2951, 2974, 2869, 2822, 2785, 1669, 1573, 1522, 1455, 1265, 1070, 751, 701. $^1$H-NMR (600 MHz): δ 8.29 (d, J=8.6 Hz, 1H), 8.04 (s, 1H), 7.78 (s, 1H), 7.66 (d, J=7.8 Hz, 1H), 7.57 (d, J=7.8 Hz, 1H), 7.48 (t, J=7.7 Hz, 1H), 7.37-7.30 (m, 4H), 7.25-7.23 (m, 1H), 5.72-5.60 (m, 1H), 5.19 (d, J=15.7 Hz, 1H), 4.74-4.58 (m, 1H), 4.12 (d, J=15.6 Hz, 1H), 3.70 (d, J=12.9 Hz, 1H), 3.62 (d, J=12.9 Hz, 1H), 3.54 (dt, J=10.8, 6.9 Hz, 1H), 3.49 (s, 2H), 3.41 (dt, J=11.0, 5.2 Hz, 1H), 2.89 (td, J=8.7, 4.1 Hz, 1H), 2.74 (dd, J=9.7, 6.6 Hz, 1H), 2.70 (dd, J=9.8, 3.4 Hz, 1H), 2.44-2.40 (m, 1H), 2.39 (s, 6H), 2.38-2.31 (m, 1H), 1.81-1.68 (m, 2H), 1.64-1.56 (m, 1H), 1.30 (s, 9H). $^{13}$C-NMR (151 MHz): δ 163.2, 151.6, 151.3, 149.5, 138.7, 137.2, 132.5, 131.4, 128.8, 128.7, 128.3, 128.3, 128.0, 127.1, 123.9, 115.6, 85.6, 84.7, 68.6, 60.4, 59.9, 58.5, 58.4, 52.7, 48.6, 48.5, 46.0, 44.3, 37.6, 32.3, 23.8. HRMS m/z calcd for $C_{36}H_{46}N_5O_3S$ ([M+H]$^+$) 628.3321; found 628.3331.

Preparation of Compound 88

Preparation of enantiomer 88 is analogous to the synthesis of compound 37.

Example 3. Preparation of Compound 89

(R)—N—((S)-1-Benzylpyrrolidin-3-yl)-3-(2-((tert-butyldiphenylsilyl)oxy)ethyl)-2-((R)-tert-butylsulfinyl)-4-(3-(3-(dimethylamino)prop-1-yn-1-yl)phenyl)-2,3-dihydro-1H-pyrrolo[3,4-c]pyridine-6-carboxamide

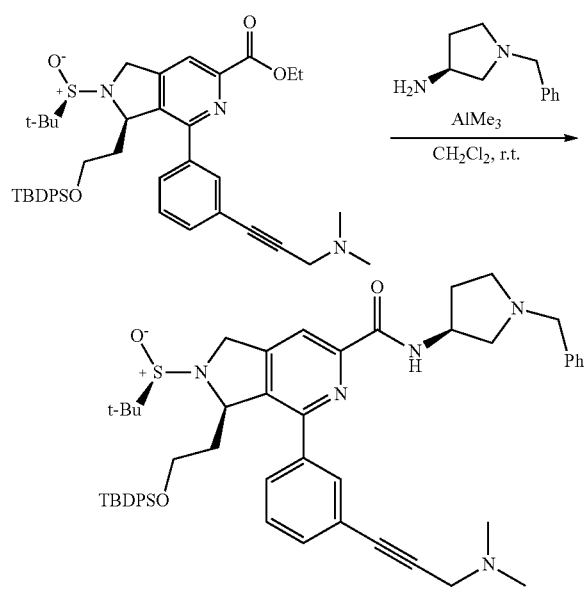

To a 10 mL roundbottom flask containing Ethyl (R)-3-(2-((tert-butyldiphenylsilyl)oxy)ethyl)-2-((R)-tert-butylsulfinyl)-4-(3-(di¬methyl-amino)prop-1-yn-1-yl)phenyl)-2,3-dihydro-1H-pyrrolo[3,4-c]pyridine-6-carboxylate (333 mg, 0.452 mmol, 1.0 equiv, azeotroped 3× with toluene) at room temperature was slowly added a pre-stirred (>2 h) stock solution of dimethylaluminum (S)-1-benzylpyrrolidin-3-amide (0.2 M solution in $CH_2Cl_2$/toluene, 4.5 mL, 0.905 mmol, 2.0 equiv). The mixture was stirred at room temperature for 12 h, then carefully quenched by dropwise addition of 0.5 mL MeOH followed by dilution with 5 mL of $CH_2Cl_2$ and careful addition of 5 mL saturated aqueous $NaHCO_3$. The aqueous layer was extracted with EtOAc (3×5 mL), then the combined organic layers were dried ($Na_2SO_4$), filtered, and concentrated by rotary evaporation. Purification by silica flash chromatography (100% $CH_2Cl_2$→10% MeOH/$CH_2Cl_2$) yielded (R)—N—((S)-1-Benzylpyrrolidin-3-yl)-3-(2-((tert-butyldiphenylsilyl)oxy)ethyl)-2-((R)-tert-butylsulfinyl)-4-(3-(3-(dimethylamino)prop-1-yn-1-yl)phenyl)-2,3-dihydro-1H-pyrrolo[3,4-c]pyridine-6-carboxamide as a sticky yellow foam (338 mg, 86%). TLC: $R_f$ 0.45 (10% MeOH/$CH_2Cl_2$). $[\alpha]_D^{19}$: +92.03° (c 1.0, $CHCl_3$). IR (ATR): 3387, 2954, 2859, 2786, 1673, 1575, 1520, 1109, 1076, 758, 703. $^1$H-NMR (600 MHz): δ 8.23 (d, J=8.2 Hz, 1H), 8.01 (s, 1H), 7.76 (s, 1H), 7.59 (d, J=7.8 Hz, 1H), 7.54 (d, J=7.8 Hz, 1H), 7.46 (d, J=7.9 Hz, 2H), 7.44-7.36 (m, 4H), 7.36-7.29 (m, 7H), 7.28-7.27 (m, 1H), 7.26-7.23 (m, 1H), 7.21 (t, J=7.2 Hz, 1H), 5.71 (d, J=6.9 Hz, 1H), 5.14 (d, J=15.8 Hz, 1H), 4.70-4.58 (m, 1H), 3.97 (d, J=15.0 Hz, 1H), 3.70-3.55 (m, 3H), 3.50 (s, 2H), 3.43 (dt, J=10.5, 5.8 Hz, 1H), 2.87 (td, J=8.5, 7.9, 4.2 Hz, 1H), 2.76 (dd, J=9.8, 6.8 Hz, 1H), 2.63 (dd, J=9.8, 3.7 Hz, 1H), 2.50-2.31 (m, 8H), 1.87-1.77 (m, 1H), 1.77-1.68 (m, 1H), 1.56-1.45 (m, 1H), 1.21 (s, 9H), 0.96 (s, 9H). $^{13}$C-NMR (151 MHz): δ 163.3, 151.6, 151.3, 149.2, 138.9, 138.7, 138.2, 135.4, 135.4, 133.3, 133.2, 132.2, 131.6, 129.6, 129.6, 128.8, 128.7, 128.2, 127.7, 127.6, 127.6, 127.0, 123.9, 115.4, 85.5, 84.9, 68.4, 60.2, 60.0, 59.3, 58.5, 52.7, 48.7, 48.6, 45.8, 44.3, 37.7, 32.5, 26.8, 23.8, 19.0. HRMS m/z calcd for $C_{52}H_{64}N_5O_3SSi$ ($[M+H]^+$) 866.4499; found 866.4534.

Preparation of Dimethylaluminum (S)-1-benzylpyrrolidin-3-amide Stock Solution To a 10 mL roundbottom flask containing (S)-1-benzylpyrrolidin-3-amine (173 µL, 1.0 mmol, 1.0 equiv) in 9.5 mL of CH2Cl2 was slowly added trimethylaluminum solution (2 M in toluene, 0.5 mL, 1.0 mmol, 1.0 equiv) at rt. The mixture was stirred for >2 h before use. Solution can be stored at −20° C. for at least 1 month.

(R)—N—((S)-1-benzylpyrrolidin-3-yl)-2-((R)-tert-butylsulfinyl)-4-(3-(3-(dimethylamino)prop-1-yn-1-yl)phenyl)-3-(2-hydroxyethyl)-2,3-dihydro-1H-pyrrolo[3,4-c]pyridine-6-carboxamide (Compound 89)

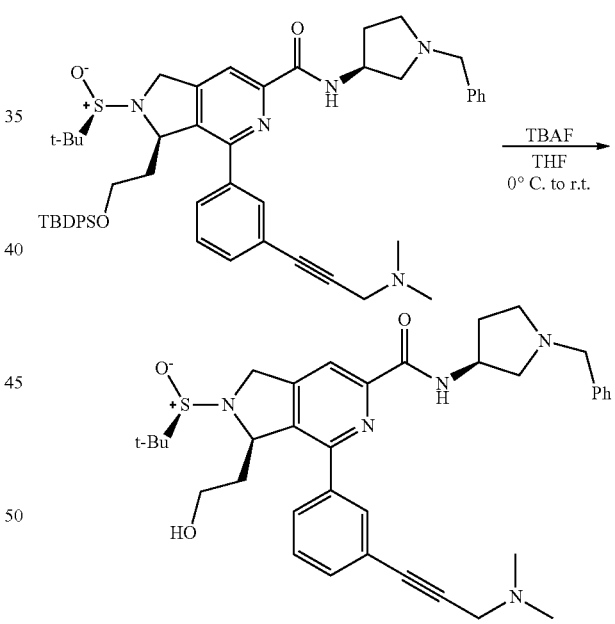

In a 10 mL roundbottom flask, (R)—N—((S)-1-Benzylpyrrolidin-3-yl)-3-(2-((tert-butyldiphenylsilyl)oxy)ethyl)-2-((R)-tert-butylsulfinyl)-4-(3-(3-(dimethylamino)prop-1-yn-1-yl)phenyl)-2,3-dihydro-1H-pyrrolo[3,4-c]pyridine-6-carboxamide (312 mg, 0.360 mmol, 1.0 equiv) was dissolved in 2.3 mL of THF and cooled to 0° C. n-Bu$_4$NF solution (1.0 M in THF, 540 µL, 0.540 mmol, 1.5 equiv) was added dropwise and the mixture was stirred at 0° C. for 1 hour, then allowed to warm to room temperature over 5 h. The reaction mixture was diluted with 3 mL EtOAc and 3 mL saturated aqueous $NaHCO_3$, then the aqueous layer was extracted with EtOAc (3×3 mL). The combined organic extracts were washed with brine (1×3 mL), dried (Na$_2$SO$_4$), filtered, and concentrated by rotary evaporation. Purification by silica flash chromatography (10% MeOH/EtOAc) yielded compound 89 as a light yellow foam (150 mg, 66%). TLC: R$_f$ 0.19 (10% MeOH/CH$_2$Cl$_2$). [α]$_D^{20}$: +77.9° (c 1.0, CHCl$_3$). IR (ATR): 3376, 3063, 2950, 2869, 2789, 1667, 1574, 1523, 1454, 1361, 1068, 757. $^1$H-NMR (600 MHz): δ 8.24 (d, J=8.3 Hz, 1H), 8.04 (s, 1H), 7.77 (s, 1H), 7.65 (d, J=7.7 Hz, 1H), 7.56 (d, J=7.7 Hz, 1H), 7.47 (t, J=7.7 Hz, 1H), 7.33-7.29 (m, 2H), 7.25-7.18 (m, 2H), 5.69-5.63 (m, 1H), 5.18 (d, J=15.7 Hz, 1H), 4.68-4.57 (m, 2H), 4.12 (d, J=15.6 Hz, 1H), 3.68-3.58 (m, 2H), 3.54 (dt, J=10.8, 6.9 Hz, 1H), 3.49 (s, 2H), 3.41 (dt, J=11.2, 5.9 Hz, 1H), 2.91-2.84 (m, 1H), 2.74 (dd, J=9.6, 6.9 Hz, 1H), 2.64 (dd, J=10.8, 2.7 Hz, 1H), 2.47-2.33 (m, 8H), 1.85-1.76 (m, 1H), 1.77-1.70 (m, 1H), 1.65-1.56 (m, 1H), 1.30 (s, 9H). $^{13}$C-NMR (151 MHz): δ 163.3, 151.6, 151.2, 149.4, 138.7, 138.3, 137.2, 132.4, 131.4, 128.8, 128.8, 128.3, 128.0, 127.1, 123.8, 115.5, 85.2, 84.9, 68.6, 60.1, 59.9, 58.5, 58.4, 52.7, 48.6, 48.3, 46.0, 44.0, 37.6, 32.4, 23.8. HRMS m/z calcd for C$_{36}$H$_{46}$N$_5$O$_3$S ([M+H]$^+$) 628.3321; found 628.3323.

Example 4. Preparation of Compound 51

Ethyl (R)-4-(3-bromophenyl)-2-((R)-tert-butylsulfinyl)-3-(2-hydroxyethyl)-2,3-dihydro-1H-pyrrolo[3,4-c]pyridine-6-carboxylate (Compound 51)

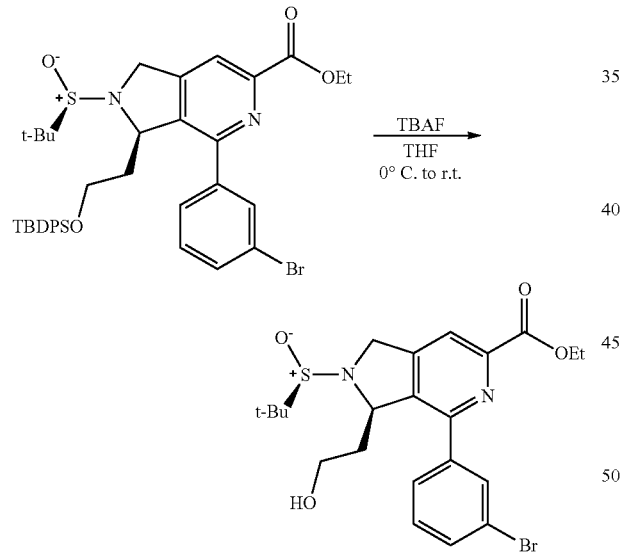

In a small vial, ethyl (R)-4-(3-bromophenyl)-3-(2-((tert-butyldiphenylsilyl)oxy)ethyl)-2-((R)-tert-butyl-sulfinyl)-2,3-dihydro-1H-pyrrolo[3,4-c]pyridine-6-carboxylate (19 mg, 0.0255 mmol, 1.0 equiv) was dissolved in 0.25 mL of THF and cooled to 0° C. n-Bu$_4$NF solution (1.0 M in THF, 33 µL, 0.331 mmol, 1.5 equiv) was added dropwise and the mixture was stirred at 0° C. for 15 min, then allowed to warm to room temperature. After 3 h, the reaction mixture was diluted with 1 mL EtOAc and 1 mL saturated aqueous NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (3% MeOH/EtOAc) yielded compound 51 as a light yellow foam (9 mg, 72%). TLC: R$_f$ 0.47 (10% MeOH/CH$_2$Cl$_2$). $^1$H-NMR (600 MHz): δ 7.99 (s, 1H), 7.91 (t, J=1.8 Hz, 1H), 7.67 (ddd, J=7.7, 1.7, 1.0 Hz, 1H), 7.58 (ddd, J=8.1, 2.0, 1.0 Hz, 1H), 7.35 (t, J=7.9 Hz, 1H), 5.67 (ddd, J=6.8, 3.4, 2.0 Hz, 1H), 5.21 (dd, J=15.6, 1.0 Hz, 1H), 4.51 (dq, J=10.8, 7.1 Hz, 1H), 4.45 (dq, J=10.9, 7.1 Hz, 1H), 4.13 (ddd, J=15.7, 2.2, 1.0 Hz, 1H), 3.57 (ddt, J=11.3, 7.9, 5.8 Hz, 1H), 3.52-3.41 (m, 1H), 1.79-1.68 (m, 1H), 1.68-1.58 (m, 1H), 1.44 (t, J=7.1 Hz, 3H), 1.31 (s, 9H), 1.07 (t, J=5.4 Hz, 1H). $^{13}$C-NMR (151 MHz): δ 164.9, 152.2, 151.4, 147.9, 140.4, 138.2, 132.3, 131.6, 130.2, 127.0, 123.1, 118.5, 68.7, 62.1, 58.5, 58.5, 45.8, 37.5, 23.8, 14.3. LRMS (ESI+) m/z calcd for C$_{22}$H$_{27}$BrN$_2$O$_4$S ([M+H]$^+$) 495.09; found 494.9.

Example 5. Preparation of Compound 90

Ethyl (R)-2-((R)-tert-butylsulfinyl)-4-(3-(3-(dimethylamino)prop-1-yn-1-yl)phenyl)-3-(2-hydroxyethyl)-2,3-dihydro-1H-pyrrolo[3,4-c]pyridine-6-carboxylate (Compound 90)

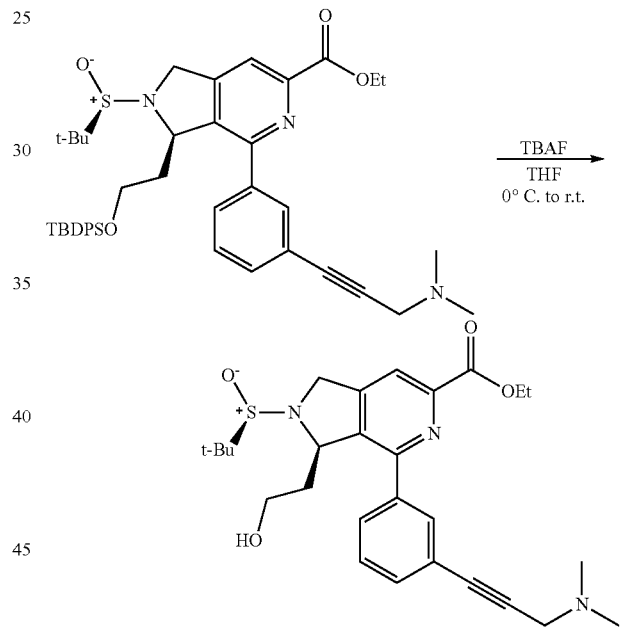

In a small vial, ethyl (R)-3-(2-((tert-butyldiphenylsilyl)oxy)ethyl)-2-((R)-tert-butylsulfinyl)-4-(3-(3-(di¬methylamino)prop-1-yn-1-yl)phenyl)-2,3-dihydro-1H-pyrrolo[3,4-c]pyridine-6-carboxylate (22 mg, 0.0299 mmol, 1.0 equiv) was dissolved in 0.30 mL of THF and cooled to 0° C. n-Bu$_4$NF solution (1.0 M in THF, 45 µL, 0.448 mmol, 1.5 equiv) was added dropwise and the mixture was stirred at 0° C. for 1 h, then allowed to warm to room temperature over 4 h. The reaction mixture was diluted with 1 mL EtOAc and 1 mL saturated aqueous NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (5% MeOH/EtOAc) yielded pyrrolopyridinecarboxylate 90 as a light yellow foam (13 mg, 65%). TLC: R$_f$ 0.32 (10% MeOH/CH$_2$Cl$_2$). $^1$H-NMR (600 MHz): δ 7.98 (s, 1H), 7.81 (t, J=1.7 Hz, 1H), 7.67 (dt, J=7.8, 1.5 Hz, 1H), 7.51 (dt, J=7.7, 1.4 Hz, 1H), 7.42 (t, J=7.7 Hz, 1H), 5.67 (ddd, J=6.0, 3.3, 2.0 Hz, 1H), 5.20 (d, J=16.4 Hz, 1H), 4.51 (dq, J=10.9, 7.1 Hz, 1H), 4.44 (dq, J=10.8, 7.1 Hz, 1H), 4.13 (ddd, J=15.6, 2.1, 1.0 Hz, 1H), 3.53 (ddd, J=10.8, 7.7, 6.1 Hz, 1H), 3.49 (s, 2H), 3.42 (ddd, J=10.8, 6.7, 5.1 Hz, 1H), 2.38 (s, 6H), 1.76-1.69 (m, 1H), 1.64-1.56 (m, 1H), 1.44 (t, J=7.1 Hz, 3H), 1.30 (s, 9H). $^{13}$C-NMR (151 MHz): δ 165.0, 153.0, 151.2, 147.9, 138.6, 138.1, 132.4, 131.7, 128.7, 128.1, 123.9, 118.3, 85.3, 84.9, 68.8, 62.0, 58.5, 58.4, 48.5, 45.8, 44.2, 37.5, 23.7, 14.3. HRMS m/z calcd for $C_{27}H_{36}N_3O_4S$ ([M+H]$^+$) 498.2427; found 498.2446.

Preparation of Compound 91

Preparation of enantiomer 91 is analogous to the synthesis of compound 90.

Example 6. Preparation of Compound 77

(R)—N-(Benzo[d][1,3]dioxol-5-ylmethyl)-4-(3-bromophenyl)-3-(2-((tert-butyldiphenyl-silyl)oxy)ethyl)-2-((R)-tert-butylsulfinyl)-2,3-dihydro-1H-pyrrolo[3,4-c]pyridine-6-carboxamide

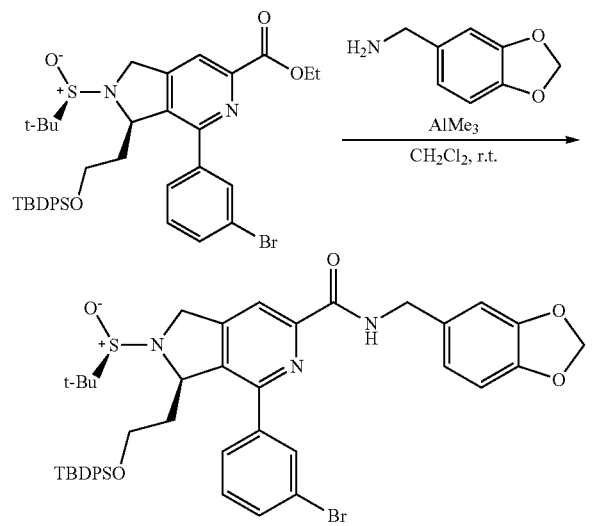

To a vial containing ethyl (R)-4-(3-bromophenyl)-3-(2-((tert-butyldiphenylsilyl)oxy)ethyl)-2-((R)-tert-butyl-sulfinyl)-2,3-dihydro-1H-pyrrolo[3,4-c]pyridine-6-carboxylate (22 mg, 0.0301 mmol, 1.0 equiv, azeotroped 3× with toluene) at room temperature was slowly added a pre-stirred (>2 h) stock solution of dimethylaluminum piperonylamide³ (0.2 M solution in CH$_2$Cl$_2$/toluene, 0.30 mL, 0.0602 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (40% EtOAc/hexanes) yielded (R)—N-(Benzo[d][1,3]dioxol-5-ylmethyl)-4-(3-bromophenyl)-3-(2-((tert-butyldi¬phenyl-silyl)oxy)ethyl)-2-((R)-tert-butylsulfinyl)-2,3-dihydro-1H-pyrrolo[3,4-c]pyridine-6-carboxamide as a sticky orange foam (18 mg, 72%). TLC: R$_f$ 0.26 (50% EtOAc/hexanes). [α]$_D^{20}$: +61.2° (c 1.0, CHCl$_3$). IR (ATR): 3392, 2956, 2932, 2859, 1674, 1574, 1525, 1490, 1444, 1253, 1189, 1108, 1074, 1043, 933, 760, 704. $^1$H-NMR (600 MHz): δ 8.29 (t, J=6.3 Hz, 1H), 8.08 (s, 1H), 7.79 (t, J=1.8 Hz, 1H), 7.58-7.52 (m, 2H), 7.48-7.44 (m, 2H), 7.44-7.36 (m, 4H), 7.36-7.29 (m, 4H), 7.12 (t, J=7.9 Hz, 1H), 6.86 (d, J=1.7 Hz, 1H), 6.83 (dd, J=8.0, 1.7 Hz, 1H), 6.77 (d, J=7.9 Hz, 1H), 5.93 (s, 1H), 5.71 (dt, J=7.8, 2.6 Hz, 1H), 5.16 (d, J=15.8 Hz, 1H), 4.65-4.52 (m, 2H), 4.00 (ddd, J=15.8, 2.0, 1.0 Hz, 1H), 3.66 (ddd, J=10.4, 8.6, 4.9 Hz, 1H), 3.45 (ddd, J=10.5, 6.0, 4.5 Hz, 1H), 1.79-1.66 (m, 1H), 1.54-1.44 (m, 1H), 1.22 (s, 9H), 0.96 (s, 9H). $^{13}$C-NMR (151 MHz): δ 163.7, 152.0, 150.5, 149.2, 147.9, 146.9, 140.5, 138.6, 135.5, 135.4, 133.4, 133.2, 132.2, 132.1, 131.6, 130.3, 129.7, 129.7, 127.7, 127.6, 126.6, 123.0, 121.0, 115.9, 108.4, 108.3, 101.0, 68.4, 59.3, 58.6, 45.9, 43.2, 37.8, 26.8, 23.8, 19.1. HRMS m/z calcd for $C_{44}H_{49}BrN_3O_5SSi$ ([M+H]$^+$) 838.2346; found 838.2344.

(R)—N-(Benzo[d][1,3]dioxol-5-ylmethyl)-4-(3-bromophenyl)-2-((R)-tert-butylsulfinyl)-3-(2-hydroxyethyl)-2,3-dihydro-1H-pyrrolo[3,4-c]pyridine-6-carboxamide (Compound 77)

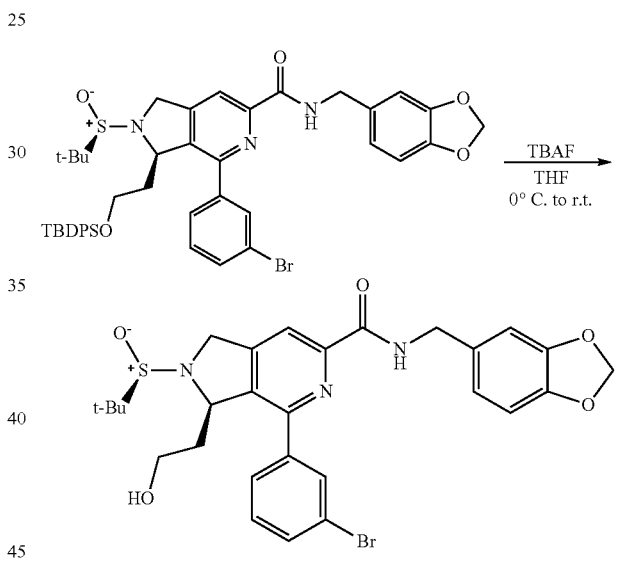

In a small vial, (R)—N-(Benzo[d][1,3]dioxol-5-ylmethyl)-4-(3-bromophenyl)-3-(2-((tert-butyldi¬phenyl-silyl)oxy)ethyl)-2-((R)-tert-butylsulfinyl)-2,3-dihydro-1H-pyrrolo[3,4-c]pyridine-6-carboxamide (18 mg, 0.0215 mmol, 1.0 equiv) was dissolved in 0.21 mL of THF and cooled to 0° C. n-Bu$_4$NF solution (1.0 M in THF, 28 μL, 0.279 mmol, 1.5 equiv) was added dropwise and the mixture was stirred at 0° C. for 1 h, then allowed to warm to room temperature over 5 h. The reaction mixture was diluted with 1 mL EtOAc and 1 mL saturated aqueous NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (75% EtOAc/hexanes) yielded pyrrolopyridinecarboxamide 77 as a light yellow foam (7 mg, 58%). TLC: R$_f$ 0.56 (10% MeOH/CH$_2$Cl$_2$). [α]$_D^{19}$: +37.8° (c 0.74, CHCl$_3$). IR (ATR): 3391, 2957, 2924, 1666, 1572, 1527, 1491, 1444, 1252, 1041, 932, 758. $^1$H-NMR (600 MHz): δ 8.30 (t, J=6.3 Hz, 1H), 8.11 (s, 1H), 7.82 (t, J=1.9 Hz, 1H), 7.63-7.54 (m, 2H), 7.36 (t, J=7.8 Hz, 1H), 6.85 (d, J=1.7 Hz, 1H), 6.82 (dd, J=7.9, 1.6 Hz, 1H), 6.77 (d, J=7.9 Hz, 1H), 5.99-5.91 (m, 2H), 5.65 (dt, J=5.9, 2.6 Hz, 1H), 5.20 (d, J=15.6 Hz, 1H), 4.64-4.52 (m, 1H), 4.14 (d, J=15.6 Hz, 1H), 3.66-3.53 (m, 1H), 3.51-3.36 (m, 1H), 1.72 (dddd, J=14.5, 7.9, 6.6, 3.3 Hz, 1H), 1.63-1.58 (m, 2H), 1.31 (s, 9H). $^{13}$C-NMR (151 MHz): δ 163.7, 152.0, 150.6, 149.4, 147.9, 146.9, 140.3, 137.6, 132.3, 132.1, 131.4, 130.3, 126.8, 123.0, 121.0, 116.0, 108.4, 108.3, 101.0, 68.6, 58.5, 58.5, 46.0, 43.3, 37.6, 23.8. HRMS m/z calcd for $C_{28}H_{31}BrN_3O_5S$ ([M+H]$^+$) 600.1168; found 600.1152.

Preparation of Compound 78

Preparation of enantiomer 78 is analogous to the synthesis of compound 77.

Example 7. Preparation of Compound 86 (R)—N—((R)-1-Benzylpyrrolidin-3-yl)-4-(3-bromophenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxamide

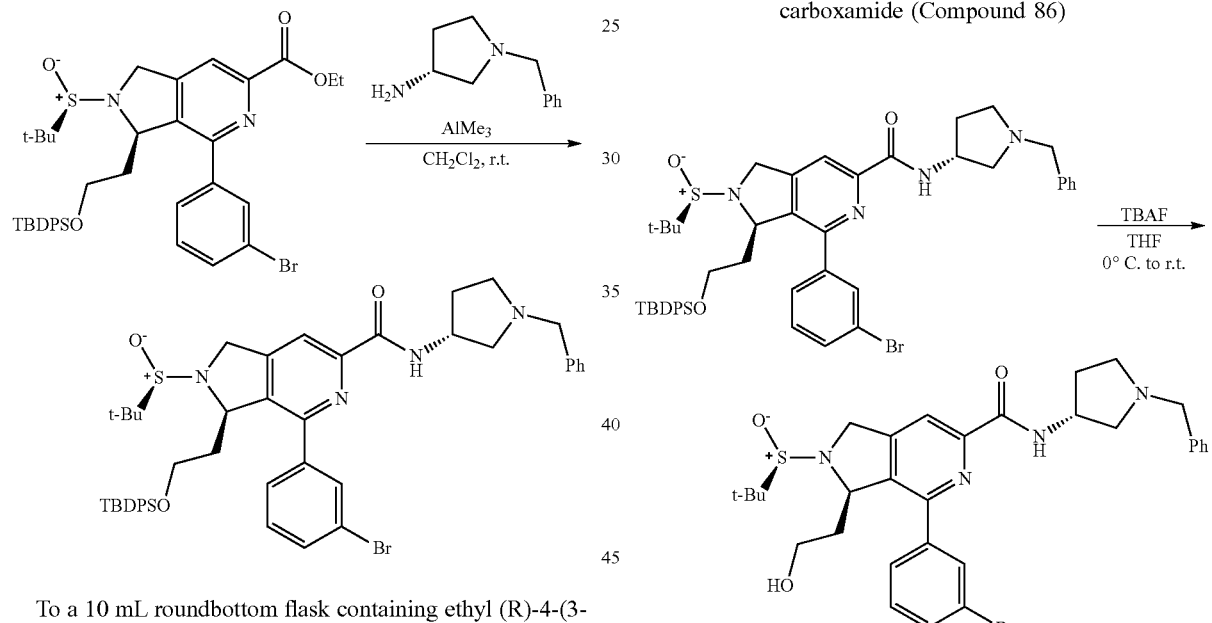

To a 10 mL roundbottom flask containing ethyl (R)-4-(3-bromophenyl)-3-(2-((tert-butyldiphenylsilyl)oxy)ethyl)-2-((R)-tert-butyl-sulfinyl)-2,3-dihydro-1H-pyrrolo[3,4-c]pyridine-6-carboxylate (24 mg, 0.0330 mmol, 1.0 equiv, azeotroped 3× with toluene) at room temperature was slowly added a pre-stirred (>2 h) stock solution of dimethylaluminum (R)-1-benzylpyrrolidin-3-amide$^4$ (0.2 M solution in CH$_2$Cl$_2$/toluene, 0.33 mL, 0.0660 mmol, 2.0 equiv). The mixture was stirred at room temperature for 20 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (1×5 mL), then the combined organic layers were dried (Na$_2$SO$_4$), filtered, and concentrated by rotary evaporation. Purification by silica flash chromatography (4% MeOH/CH$_2$Cl$_2$) yielded (R)—N—((R)-1-Benzylpyrrolidin-3-yl)-4-(3-bromophenyl)-3-(2-((tert-butyl¬diphenyl-silyl)oxy)ethyl)-2-((R)-tert-butylsulfinyl)-2,3-dihydro-1H-pyrrolo[3,4-c]pyridine-6-carboxamide as a sticky orange foam (25 mg, 89%). TLC: R$_f$ 0.68 (10% MeOH/CH$_2$Cl$_2$). [α]$_D^{19}$: +40.4° (c 1.0, CHCl$_3$). IR (ATR): 3388, 3069, 2956, 2859, 2797, 1672, 1573, 1520, 1474, 1428, 1217, 1108, 1074, 942, 757, 702. $^1$H-NMR (600 MHz): δ 8.24 (d, J=8.7 Hz, 1H), 8.03 (s, 1H), 7.87 (t, J=1.8 Hz, 1H), 7.65-7.56 (m, 2H), 7.48-7.44 (m, 2H), 7.44-7.41 (m, 2H), 7.41-7.37 (m, 2H), 7.37-7.28 (m, 8H), 7.25-7.20 (m, 1H), 7.17 (t, J=7.8 Hz, 1H), 5.72 (ddd, J=8.0, 3.2, 1.8 Hz, 1H), 5.15 (d, J=16.3 Hz, 1H), 4.74-4.59 (m, 1H), 3.97 (d, J=15.7 Hz, 0H), 3.70 (d, J=12.9 Hz, 1H), 3.66 (ddd, J=10.1, 8.5, 4.8 Hz, 1H), 3.62 (d, J=12.9 Hz, 1H), 3.45 (ddd, J=10.4, 6.0, 4.4 Hz, 1H), 2.90 (td, J=8.3, 7.5, 3.5 Hz, 1H), 2.73 (dd, J=9.8, 6.3 Hz, 1H), 2.70 (dd, J=9.8, 3.6 Hz, 1H), 2.51-2.27 (m, 2H), 1.83-1.66 (m, 2H), 1.57-1.43 (m, 1H), 1.21 (s, 9H), 0.97 (s, 9H). $^{13}$C-NMR (151 MHz): δ 163.1, 151.9, 150.4, 149.3, 140.6, 138.8, 138.4, 135.5, 135.4, 133.4, 133.1, 132.1, 131.6, 130.3, 129.7, 129.7, 128.7, 128.3, 127.6, 127.6, 127.0, 126.7, 123.0, 115.7, 68.4, 60.5, 60.0, 59.3, 58.5, 52.7, 48.6, 45.8, 37.8, 32.3, 26.8, 23.8, 19.1. HRMS m/z calcd for $C_{47}H_{56}BrN_4O_3SSi$ ([M+H]$^+$) 863.3026; found 863.3022.

(R)—N—((R)-1-Benzylpyrrolidin-3-yl)-4-(3-bromophenyl)-2-((R)-tert-butylsulfinyl)-3-(2-hydroxyethyl)-2,3-dihydro-1H-pyrrolo[3,4-c]pyridine-6-carboxamide (Compound 86)

In a small vial, (R)—N—((R)-1-Benzylpyrrolidin-3-yl)-4-(3-bromophenyl)-3-(2-((tert-butyl¬diphenyl-silyl)oxy)ethyl)-2-((R)-tert-butylsulfinyl)-2,3-dihydro-1H-pyrrolo[3,4-c]pyridine-6-carboxamide (25 mg, 0.0293 mmol, 1.0 equiv) was dissolved in 0.29 mL of THF and cooled to 0° C. n-Bu$_4$NF solution (1.0 M in THF, 44 µL, 0.439 mmol, 1.5 equiv) was added dropwise and the mixture was stirred at 0° C. for 1 h, then allowed to warm to room temperature over 4 h. The reaction mixture was diluted with 1 mL EtOAc and 1 mL saturated aqueous NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (3% MeOH/EtOAc) yielded pyrrolopyridinecarboxylamide 86 as a light yellow foam (14 mg, 76%). TLC: R$_f$ 0.50 (10% MeOH/CH$_2$Cl$_2$). [α]$_D^{19}$: +19.6° (c 1.0, CHCl$_3$). IR (ATR): 3381, 2956, 2802, 1667, 1573, 1524, 1453, 1238, 1070, 923, 758, 670. $^1$H-NMR (600

MHz): δ 8.27 (d, J=8.6 Hz, 1H), 8.05 (s, 1H), 7.88 (t, J=1.8 Hz, 1H), 7.66 (d, J=7.7 Hz, 1H), 7.63 (d, J=8.0 Hz, 1H), 7.40 (t, J=7.9 Hz, 1H), 7.37-7.29 (m, 4H), 7.26-7.24 (m, 1H), 5.71-5.61 (m, 1H), 5.18 (d, J=15.8 Hz, 1H), 4.74-4.50 (m, 1H), 4.12 (d, J=14.6 Hz, 1H), 3.71 (d, J=12.8 Hz, 1H), 3.63 (d, J=12.9 Hz, 1H), 3.56 (ddd, J=10.7, 7.8, 6.0 Hz, 1H), 3.43 (ddd, J=11.1, 6.6, 5.0 Hz, 1H), 2.91 (td, J=8.5, 7.9, 3.5 Hz, 1H), 2.76-2.65 (m, 2H), 2.45-2.26 (m, 2H), 1.84-1.66 (m, 2H), 1.66-1.54 (m, 1H), 1.30 (s, 9H). $^{13}$C-NMR (151 MHz): δ 163.0, 151.9, 150.4, 149.5, 140.4, 138.6, 137.4, 132.3, 131.4, 130.3, 128.8, 128.3, 127.1, 126.9, 123.0, 115.8, 68.6, 60.4, 59.9, 58.4, 58.4, 52.7, 48.6, 45.9, 37.6, 32.3, 23.8. HRMS m/z calcd for $C_{31}H_{38}BrN_4O_3S$ ([M+H]$^+$) 625.1848; found 625.1872.

Preparation of Compound 87

Preparation of enantiomer 87 is analogous to the synthesis of compound 86.

Synthesis of Anti Analogues

Example 8. Preparation of Compound 85

1-(3-Bromophenyl)-5-((tert-butyldiphenylsilyl)oxy)pent-1-yn-3-ol

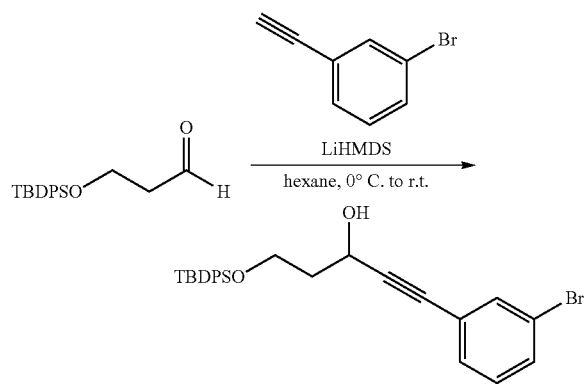

In a 25 mL roundbottom flask, 1-bromo-3-ethynylbenzene (243 μL, 1.94 mmol, 1.1 equiv) was dissolved in 10 mL THF and cooled to −78° C. A solution of LiHMDS (1 M in THF, 1.9 mL, 1.85 mmol, 1.05 equiv) was added dropwise, then the mixture allow to warm to room temperature and stir for 15 min. The reaction was cooled again to −78° C. and a solution of 3-((tert-butyldiphenylsilyl)oxy)propanal (552 mg, 1.77 mmol, 1.0 equiv) in 1.8 mL THF was added by cannula. The reaction was allowed to warm to room temperature and was stirred for 12 hr. 10 mL saturated aqueous NH$_4$Cl was added to quench the reaction, followed by 10 mL Et$_2$O, then the aq layer was extracted with Et$_2$O (3×10 mL). The combined organic extracts were washed with brine (1×10 mL), dried (MgSO$_4$), filtered, and concentrated by rotary evaporation. Purification by silica flash chromatography (10-20% EtOAc/hexanes) yielded the propargyl alcohol as a clear yellow oil (802 mg, 92%). TLC: R$_f$ 0.49 (20% EtOAc/hexanes). $^1$H-NMR (600 MHz): δ 7.76-7.64 (m, 4H), 7.56 (t, J=1.8 Hz, 1H), 7.48-7.32 (m, 8H), 7.18 (t, J=7.9 Hz, 1H), 4.92 (td, J=6.4, 4.3 Hz, 1H), 4.12 (ddd, J=10.5, 8.2, 3.7 Hz, 1H), 3.89 (ddd, J=10.3, 5.9, 4.2 Hz, 1H), 3.49 (d, J=6.4 Hz, 1H), 2.20-2.07 (m, 1H), 2.03-1.96 (m, 1H), 1.06 (s, 9H). $^{13}$C-NMR (151 MHz): δ 135.5, 134.5, 132.7, 131.5, 130.3, 129.9, 129.7, 127.8, 124.7, 122.0, 91.0, 83.5, 62.2, 61.9, 38.5, 26.8, 19.0.

1-(3-Bromophenyl)-5-((tert-butyldiphenylsilyl)oxy)pent-1-yn-3-one

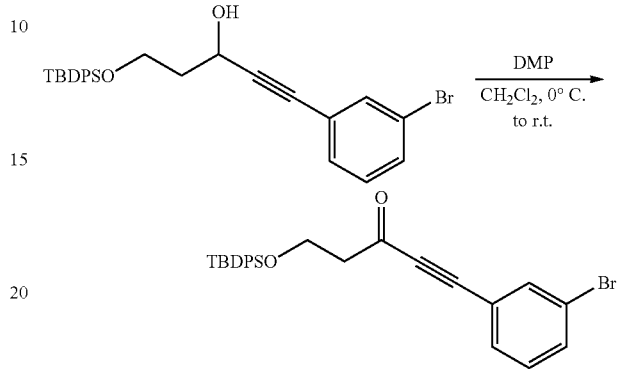

In a 25 mL roundbottom flask, the propargyl alcohol (802 mg, 1.63 mmol, 1.0 equiv) was dissolved in 10.8 mL CH$_2$Cl$_2$ and cooled to 0° C. Dess-Martin periodinane (758 mg, 1.79 mmol, 1.1 equiv) was added and the mixture was stirred at 0° C. for 15 min, then allowed to warm to room temperature. After 5 h, 8 mL sat aq NaHCO$_3$ was added to quench the reaction and the layers separated. The aq layer was extracted with CH$_2$Cl$_2$ (2×8 mL), then the combined organic extracts were washed with brine (1×8 mL), dried (Na$_2$SO$_4$), filtered, and concentrated by rotary evaporation. Purification by silica flash chromatography (10% EtOAc/hexanes) yielded the alkynone as a light yellow oil (763 mg, 95%). TLC: R$_f$ 0.47 (10% EtOAc/hexanes). $^1$H-NMR (600 MHz): δ 7.69-7.64 (m, 5H), 7.59 (ddd, J=8.1, 2.0, 1.1 Hz, 1H), 7.46-7.40 (m, 3H), 7.38-7.34 (m, 4H), 7.28-7.24 (m, 1H), 4.08 (t, J=6.1 Hz, 2H), 2.88 (t, J=6.1 Hz, 2H), 1.03 (s, 9H). $^{13}$C-NMR (151 MHz): δ 186.0, 135.6, 135.5, 133.8, 133.2, 131.5, 130.0, 129.7, 127.7, 122.3, 121.9, 88.7, 88.3, 59.4, 48.3, 26.7, 19.2.

(S)—N—((R)-1-(3-Bromophenyl)-5-((tert-butyldiphenylsilyl)oxy)pent-1-yn-3-yl)-2-methyl-propane-2-sulfinamide

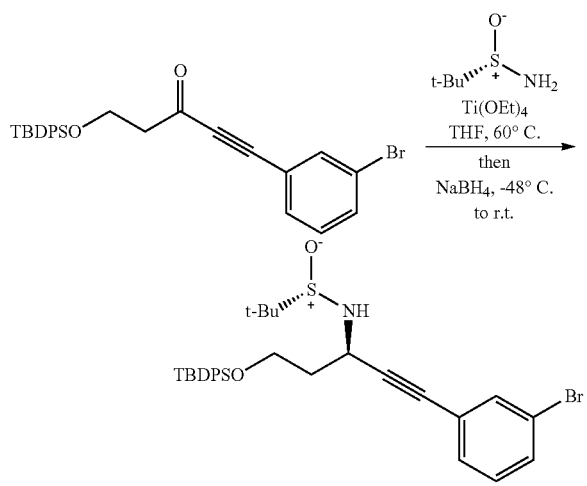

In a 15 mL roundbottom flask, the alkynone (328 mg, 0.667 mmol, 1.0 equiv)] and (S)-2-methylpropane-2-sulfinamide (89 mg, 0.734 mmol, 1.1 equiv) were dissolved in 2.7 mL THF and Ti(OEt)₄ (technical grade, ca. 20% Ti, 699 μL, 3.34 mmol, 5.0 equiv) was added at room temperature. The reaction was heated to 60° C. until full consumption of the alkynone (24 h), then cooled to −48° C. and solid NaBH₄ (101 mg, 2.67 mmol, 4.0 equiv) was added in one portion. The reaction was stirred at −48° C. for 1 h, then allowed to warm to room temperature and stirred for 14 h. The reaction was quenched by the slow addition of 1.5 mL MeOH, then the mixture was poured into vigorously stirring brine (5 mL) and diluted with 10 mL EtOAc. The layers were separated and the aq layer extracted with EtOAc (3×10 mL). The combined organic extracts were dried (Na₂SO₄), filtered, and concentrated by rotary evaporation. Purification by silica flash chromatography (25-45% EtOAc/hexanes) yielded the N-propargyl sulfinamide as a light yellow oil (263 mg, 66%). TLC: R$_f$0.46 (33% EtOAc/hexanes). ¹H-NMR (600 MHz): δ 7.68 (ddd, J=7.9, 3.4, 1.4 Hz, 4H), 7.51 (t, J=1.8 Hz, 1H), 7.47-7.32 (m, 8H), 7.29 (dt, J=7.7, 1.3 Hz, 1H), 7.16 (t, J=7.9 Hz, 1H), 4.66 (dt, J=7.3, 6.0 Hz, 1H), 3.90 (tdd, J=10.6, 9.2, 4.9 Hz, 2H), 3.73 (d, J=5.8 Hz, 1H), 2.25-2.11 (m, 1H), 2.05 (dddd, J=13.4, 7.3, 5.8, 4.4 Hz, 1H), 1.22 (s, 9H), 1.07 (s, 9H). ¹³C NMR (151 MHz): δ 135.6, 135.5, 134.4, 133.2, 133.2, 131.5, 130.3, 129.7, 129.7, 129.7, 127.8, 127.7, 124.7, 122.0, 89.7, 83.6, 60.9, 56.0, 46.6, 39.5, 26.9, 22.5, 19.2.

(S)—N—((R)-1-(3-Bromophenyl)-5-((tert-butyldiphenylsilyl)oxy)pent-1-yn-3-yl)-2-methyl-N-(prop-2-yn-1-yl)propane-2-sulfinamide

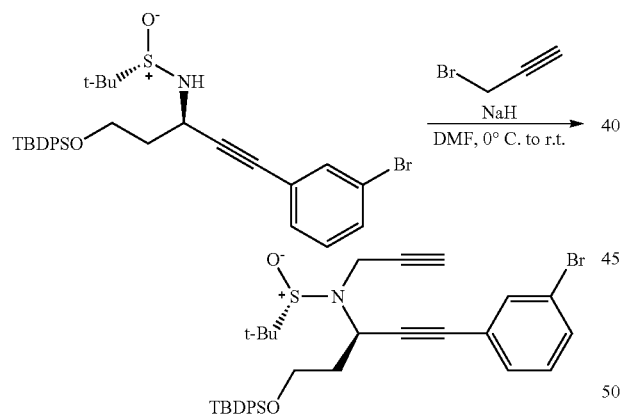

In a 10 mL roundbottom flask, (S)—N—((R)-1-(3-Bromophenyl)-5-((tert-butyldiphenylsilyl)oxy)pent-1-yn-3-yl)-2-methyl-propane-2-sulfinamide (252 mg, 0.422 mmol, 1.0 equiv) was dissolved in 2.1 mL DMF and cooled to 0° C. Sodium hydride (60% dispersion in mineral oil, 20 mg, 0.507 mmol, 1.2 equiv) was added, followed by propargyl bromide (80% in toluene, 68 μL, 0.633 mmol, 1.5 equiv) and the mixture was stirred at 0° C. for 15 min, then allowed to warm to room temperature and stirred for 1.5 h. The reaction was quenched by the addition of 5 mL sat aq NH₄Cl, then diluted with 5 mL of Et₂O. The organic layer was washed with water (3×5 mL), then the combined aq layers extracted with Et₂O (2×5 mL). The combined organic extracts were washed with brine (1×5 mL), dried (MgSO₄), filtered, and concentrated by rotary evaporation. Purification by silica flash chromatography (10%→30% EtOAc/hexanes) yielded (S)—N—((R)-1-(3-Bromophenyl)-5-((tert-butyldiphenylsilyl)oxy)pent-1-yn-3-yl)-2-methyl-N-(prop-2-yn-1-yl)propane-2-sulfinamide as a sticky orange foam (175 mg, 65%). TLC: R$_f$0.68 (40% EtOAc/hexanes). ¹H-NMR (600 MHz): δ 7.73-7.67 (m, 4H), 7.53 (t, J=1.8 Hz, 1H), 7.46-7.31 (m, 8H), 7.15 (t, J=7.9 Hz, 1H), 4.73 (dd, J=10.4, 4.9 Hz, 1H), 4.15 (dd, J=18.4, 2.6 Hz, 1H), 3.93-3.75 (m, 2H), 3.57 (d, J=18.3 Hz, 1H), 2.23 (t, J=2.5 Hz, 1H), 2.17-2.07 (m, 1H), 2.07-1.97 (m, 1H), 1.25 (s, 9H), 1.07 (s, 9H). ¹³C-NMR (151 MHz): δ 135.6, 135.6, 134.5, 133.4, 133.3, 131.4, 130.5, 129.7, 129.7, 129.6, 127.7, 127.7, 124.6, 121.9, 88.5, 84.1, 80.3, 72.3, 60.2, 58.2, 38.4, 26.8, 23.2, 19.2; 2 C not observed.

Ethyl (R)-4-(3-bromophenyl)-3-(2-((tert-butyldiphenylsilyl)oxy)ethyl)-2-((S)-tert-butyl-sulfinyl)-2,3-dihydro-1H-pyrrolo[3,4-c]pyridine-6-carboxylate

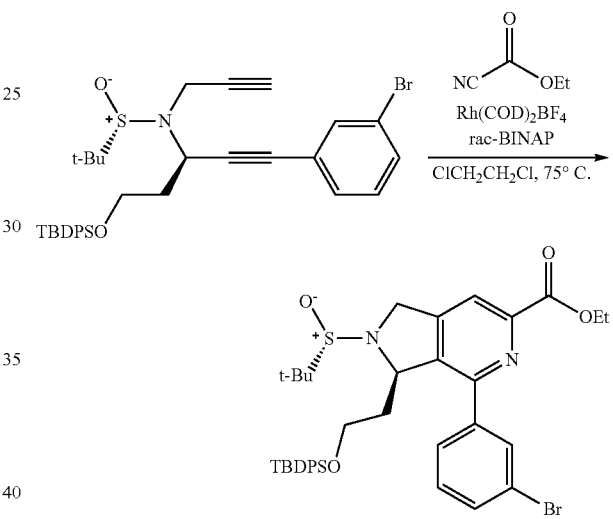

In a vial, Rh(COD)₂BF₄ (13 mg, 0.0328 mmol, 15 mol %) and rac-BINAP (27 mg, 0.0438 mmol, 20 mol %) were dissolved in 6.3 mL of degassed 1,2-dichloroethane. Ethyl cyanoformate (108 μL, 1.09 mmol, 5.0 equiv) was added, followed by a solution of (S)—N—((R)-1-(3-Bromophenyl)-5-((tert-butyldiphenylsilyl)oxy)pent-1-yn-3-yl)-2-methyl-N-(prop-2-yn-1-yl)propane-2-sulfinamide (139 mg, 0.219 mmol, 1.0 equiv) in 1 mL of 1,2-dichloroethane. The vial was sealed with a Teflon-faced screw cap and the mixture was heated to 75° C. (oil bath, ext temp) for 4 h, then cooled to room temperature and concentrated by rotary evaporation. Purification by silica flash chromatography (20→40% EtOAc/hexanes) yielded ethyl (R)-4-(3-bromophenyl)-3-(2-((tert-butyldiphenylsilyl)oxy)ethyl)-2-((S)-tert-butyl-sulfinyl)-2,3-dihydro-1H-pyrrolo[3,4-c]pyridine-6-carboxylate as an orange foam (143 mg, 89%). TLC: R$_f$0.31 (33% EtOAc/hexanes). [α]$_D^{19}$: +41.7° (c 1.0, CHCl₃). IR (ATR): 3072, 3055, 2960, 2859, 1741, 1718, 1573, 1473, 1446, 1428, 1390, 1367, 1332, 1266, 1227, 1106, 1089, 906, 759, 741. ¹H-NMR (600 MHz): δ 7.94 (s, 1H), 7.91 (t, J=1.9 Hz, 1H), 7.67 (dt, J=7.7, 1.3 Hz, 1H), 7.51 (ddd, J=8.0, 2.0, 1.0 Hz, 1H), 7.44-7.36 (m, 6H), 7.35-7.29 (m, 4H), 7.22 (t, J=7.8 Hz, 1H), 5.67 (t, J=5.6 Hz, 1H), 4.68-4.57 (m, 2H), 4.54 (dq, J=10.9, 7.1 Hz, 1H), 4.44 (dq, J=10.8, 7.1 Hz, 1H), 3.47 (dt, J=10.6, 6.5 Hz, 1H), 3.36

(dt, J=10.6, 6.4 Hz, 1H), 1.82-1.66 (m, 2H), 1.45 (t, J=7.1 Hz, 3H), 1.23 (s, 9H), 0.89 (s, 9H). $^{13}$C-NMR (151 MHz): δ 165.0, 152.1, 151.0, 147.5, 141.5, 140.7, 135.4, 135.3, 133.2, 133.2, 132.1, 131.9, 130.3, 129.6, 129.6, 127.6, 126.9, 123.1, 118.1, 62.0, 60.1, 58.0, 57.8, 56.8, 36.5, 26.7, 22.9, 19.0, 14.4.

Ethyl (R)-3-(2-((tert-butyldiphenylsilyl)oxy)ethyl)-2-((S)-tert-butylsulfinyl)-4-(3-(3-(di-methylamino)prop-1-yn-1-yl)phenyl)-2,3-dihydro-1H-pyrrolo[3,4-c]pyridine-6-carboxylate

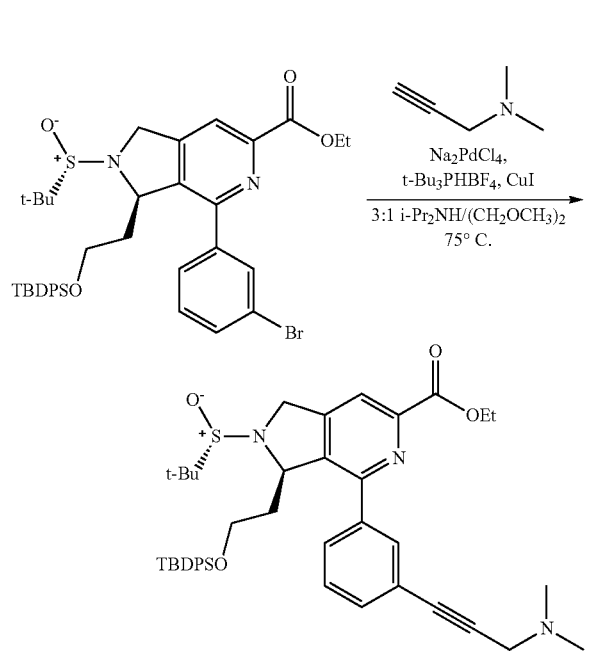

In a vial, ethyl (R)-4-(3-bromophenyl)-3-(2-((tert-butyldiphenylsilyl)oxy)ethyl)-2-((S)-tert-butyl-sulfinyl)-2,3-dihydro-1H-pyrrolo[3,4-c]pyridine-6-carboxylate (51 mg, 0.0695 mmol, 1.0 equiv), Na₂PdCl₄ (2 mg, 0.00695 mmol, 10 mol %), t-Bu₃PHBF₄ (3 mg, 0.0104 mmol, 15 mol %), and CuI (3 mg, 0.0139 mmol, 20 mol %) were dissolved in 0.4 mL of degassed 1,2-dimethoxyethane and 1.3 mL of degassed i-Pr₂NH. N,N-dimethylprop-2-yn-1-amine (37 μL, 0.347 mmol, 5.0 equiv) was added, then the vial was sealed with a Teflon-faced screw cap and the mixture heated to 75° C. (oil bath, ext temp) for 24 h. The reaction was cooled to room temperature and diluted with EtOAc, then filtered through Celite and concentrated by rotary evaporation. Purification by silica flash chromatography (4% MeOH/CH₂Cl₂) yielded ethyl (R)-3-(2-((tert-butyldiphenylsilyl)oxy)ethyl)-2-((S)-tert-butylsulfinyl)-4-(3-(3-(di¬methyl-amino)prop-1-yn-1-yl)phenyl)-2,3-dihydro-1H-pyrrolo[3,4-c]pyridine-6-carboxylate as a dark orange oil (48 mg, 94%). TLC: $R_f$ 0.41 (5% MeOH/CH₂Cl₂). $[\alpha]_D^{21}$: +85.7° (c 1.0, CHCl₃). $^1$H-NMR (500 MHz): δ 7.92 (s, 1H), 7.85 (s, 1H), 7.66 (d, J=7.8 Hz, 1H), 7.46 (d, J=7.7 Hz, 1H), 7.43-7.35 (m, 6H), 7.34-7.28 (m, 5H), 5.69 (t, J=5.3 Hz, 1H), 4.69-4.58 (m, 2H), 4.57-4.49 (m, 1H), 4.49-4.40 (m, 1H), 3.51 (s, 2H), 3.48-3.42 (m, 1H), 3.41-3.28 (m, 1H), 2.38 (s, 6H), 1.83-1.74 (m, 1H), 1.74-1.65 (m, 1H), 1.44 (t, J=7.1 Hz, 3H), 1.23 (s, 9H), 0.88 (s, 9H). $^{13}$C-NMR (126 MHz): δ 165.1, 153.0, 150.7, 147.5, 141.2, 138.9, 135.4, 135.3, 133.3, 132.2, 132.0, 129.6, 128.7, 128.0, 127.6, 124.0, 117.8, 85.1, 77.2, 61.9, 60.1, 58.0, 57.5, 57.0, 48.6, 44.2, 36.4, 26.7, 22.9, 18.9, 14.3. HRMS m/z calcd for $C_{43}H_{54}N_3O_4SSi$ ([M+H]⁺) 736.3604; found 736.3604.

(R)—N-(Benzo[d][1,3]dioxol-5-ylmethyl)-3-(2-((tert-butyldiphenylsilyl)oxy)ethyl)-2-((S)-tert-butylsulfinyl)-4-(3-(3-(dimethylamino)prop-1-yn-1-yl)phenyl)-2,3-dihydro-1H-pyrrolo[3,4-c]pyridine-6-carboxamide

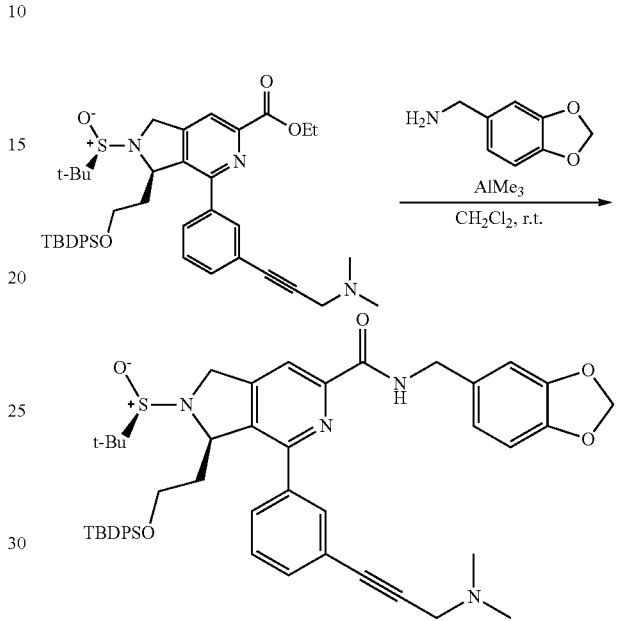

To a vial containing ethyl (R)-3-(2-((tert-butyldiphenyl-silyl)oxy)ethyl)-2-((S)-tert-butylsulfinyl)-4-(3-(3-(di¬methyl-amino)prop-1-yn-1-yl)phenyl)-2,3-dihydro-1H-pyrrolo[3,4-c]pyridine-6-carboxylate (20 mg, 0.0227 mmol, 1.0 equiv, azeotroped 3× with toluene) at room temperature was slowly added a pre-stirred (>2 h) stock solution of dimethylaluminum piperonylamide[3] (0.2 M solution in CH₂Cl₂/toluene, 0.28 mL, 0.0554 mmol, 2.0 equiv). The mixture was stirred at room temperature for 12 h, then carefully quenched by addition of a few drops of MeOH followed by dilution with 1 mL of CH₂Cl₂ and careful addition of 1 mL sat aq NaHCO₃. The aqueous layer was extracted with EtOAc (3×1 mL), then the combined organic layers were dried (Na₂SO₄), filtered, and concentrated by rotary evaporation. Purification by silica flash chromatography (4% MeOH/CH₂Cl₂) yielded (R)—N-(Benzo[d][1,3]dioxol-5-ylmethyl)-3-(2-((tert-butyldiphenylsilyl)oxy)ethyl)-2-((S)-tert-butylsulfinyl)-4-(3-(3-(dimethylamino)prop-1-yn-1-yl)phenyl)-2,3-dihydro-1H-pyrrolo[3,4-c]pyridine-6-carboxamide as a sticky yellow foam (14 mg, 62%). TLC: $R_f$ 0.25 (5% MeOH/CH₂Cl₂). $[\alpha]_D^{20}$: +93.3° (c 1.0, CHCl₃). IR (ATR): 3391, 3070, 2933, 2859, 2777, 1672, 1573, 1523, 1489, 1444, 1361, 1328, 1251, 1090, 1041, 931, 756, 703. $^1$H-NMR (600 MHz): δ 8.36 (t, J=6.3 Hz, 1H), 8.06 (s, 1H), 7.73 (s, 1H), 7.61 (d, J=7.7 Hz, 1H), 7.48 (d, J=7.7 Hz, 1H), 7.42-7.33 (m, 6H), 7.33-7.27 (m, 5H), 6.87 (d, J=1.6 Hz, 1H), 6.83 (dd, J=7.9, 1.7 Hz, 1H), 6.76 (d, J=7.9 Hz, 1H), 5.93 (s, 2H), 5.67 (t, J=5.4 Hz, 1H), 4.69-4.53 (m, 4H), 3.50 (s, 2H), 3.45 (dt, J=10.7, 6.6 Hz, 1H), 3.34 (dt, J=10.7, 6.5 Hz, 1H), 2.38 (s, 6H), 1.83-1.65 (m, 3H), 1.22 (s, 9H), 0.87 (s, 9H). $^{13}$C-NMR (151 MHz): δ 163.9, 151.4, 151.3, 149.0, 147.9, 146.9, 140.8, 138.9, 135.4, 135.3, 133.3, 133.2, 132.3, 132.2, 131.7, 129.6, 129.5, 128.8, 127.9, 127.6, 127.6, 123.9, 121.0, 115.3, 108.4, 108.2, 101.0, 85.5, 84.9, 60.1, 58.0, 56.6, 53.4, 48.6, 44.3, 43.2, 36.6, 26.7, 22.8, 18.9. HRMS m/z calcd for $C_{49}H_{57}N_4O_5SSi$ ([M+H]$^+$) 841.3819; found 841.3840.

(R)—N-(Benzo[d][1,3]dioxol-5-ylmethyl)-2-((S)-tert-butylsulfinyl)-4-(3-(3-(dimethyl-amino)prop-1-yn-1-yl)phenyl)-3-(2-hydroxyethyl)-2,3-dihydro-1H-pyrrolo[3,4-c]pyridine-6-carboxamide (Compound 85)

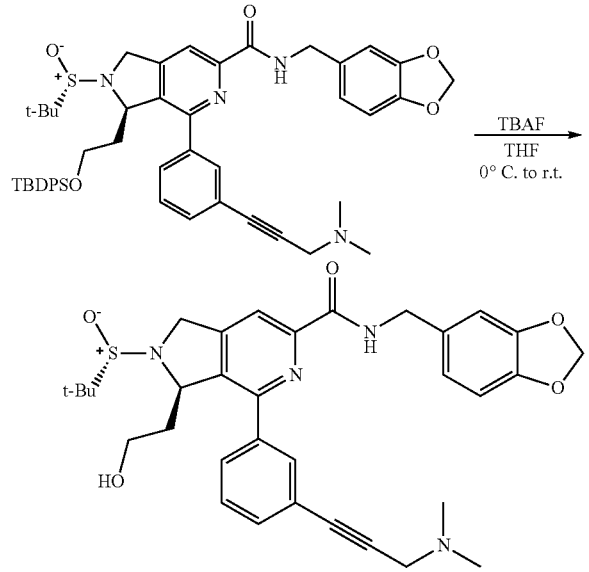

In a small vial, (R)—N-(Benzo[d][1,3]dioxol-5-ylmethyl)-3-(2-((tert-butyldiphenylsilyl)oxy)ethyl)-2-((S)-tert-butylsulfinyl)-4-(3-(3-(dimethylamino)prop-1-yn-1-yl)phenyl)-2,3-dihydro-1H-pyrrolo[3,4-c]pyridine-6-carboxamide (14 mg, 0.0171 mmol, 1.0 equiv) was dissolved in 0.17 mL of THF and cooled to 0° C. n-Bu$_4$NF solution (1.0 M in THF, 22 µL, 0.223 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (10% MeOH/EtOAc) yielded the pyrrolopyridinecarboxamide 85 as a light yellow foam (8 mg, 82%). TLC: R$_f$0.47 (10% MeOH/CH$_2$Cl$_2$). [α]$_D^{19}$: +133.5° (c 0.85, CHCl$_3$). IR (ATR): 3387, 2948, 2781, 1668, 1573, 1526, 1490, 1445, 1362, 1330, 1252, 1041, 929, 759. $^1$H-NMR (600 MHz): δ 8.35 (t, J=6.2 Hz, 1H), 8.12 (s, 1H), 7.76 (s, 1H), 7.64 (d, J=7.7 Hz, 1H), 7.52 (d, J=7.8 Hz, 1H), 7.44 (t, J=7.7 Hz, 1H), 6.85 (d, J=1.4 Hz, 1H), 6.82 (dd, J=8.0, 1.4 Hz, 1H), 6.76 (d, J=7.9 Hz, 1H), 5.93 (q, J=1.5 Hz, 2H), 5.67 (t, J=4.4 Hz, 1H), 4.83 (d, J=15.7 Hz, 1H), 4.66-4.53 (m, 3H), 3.49 (s, 2H), 3.38-3.17 (m, 2H), 2.38 (s, 6H), 2.05-1.93 (m, 1H), 1.70 (dq, J=15.1, 5.6 Hz, 1H), 1.32 (s, 9H). $^{13}$C NMR (151 MHz): δ 163.8, 151.6, 151.1, 149.3, 147.9, 146.9, 138.8, 138.7, 132.4, 132.1, 131.5, 128.9, 127.8, 124.0, 121.0, 115.6, 108.4, 108.3, 101.0, 85.6, 84.7, 59.9, 58.5, 58.2, 54.8, 48.5, 44.2, 43.2, 35.7, 23.3. HRMS m/z calcd for $C_{33}H_{39}N_4O_5S$ ([M+H]$^+$) 603.2641; found 603.2628.

Preparation of Compound 84

Preparation of enantiomer 84 is analogous to the synthesis of compound 85.

Synthesis of Deshydroxyethyl Compounds

Example 9. Preparation of Compound 49

3-(3-Bromophenyl)propiolaldehyde

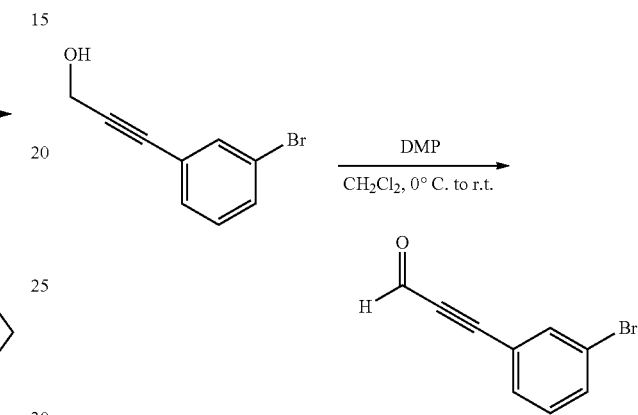

In a 250 mL roundbottom flask, 3-(3-bromophenyl)prop-2-yn-1-ol (1.54 g, 7.30 mmol, 1.0 equiv) was dissolved in 73 mL CH$_2$Cl$_2$. Dess-Martin periodinane (3.40 g, 8.03 mmol, 1.1 equiv) was added at room temperature and the mixture was stirred at 1 h. 50 mL sat aq NaHCO$_3$ was added to quench the reaction and the layers separated. The aq layer was extracted with CH$_2$Cl$_2$ (2×50 mL), then the combined organic extracts were washed with brine (1×8 mL), dried (Na$_2$SO$_4$), filtered, and concentrated by rotary evaporation. Purification by silica flash chromatography (30% EtOAc/hexanes) yielded the propargyl aldehyde as a white solid (1.41 g, 93%). TLC: R$_f$0.79 (33% EtOAc/hexanes). $^1$H-NMR (600 MHz): δ 9.42 (s, 1H), 7.74 (t, J=1.7 Hz, 1H), 7.62 (ddd, J=8.1, 2.0, 1.0 Hz, 1H), 7.53 (dt, J=7.7, 1.2 Hz, 1H), 7.29 (t, J=7.9 Hz, 1H). $^{13}$C-NMR (151 MHz): δ 176.4, 135.6, 134.3, 131.7, 130.1, 122.4, 121.3, 92.6, 88.7.

3-(3-bromophenyl)prop-2-yn-1-ol was prepared according to literature procedure: Nanayakkara, P.; Alper, H. Adv. Synth. Catal. 2006, 348, 545-550.

(R)—N-(3-(3-Bromophenyl)prop-2-yn-1-yl)-2-methylpropane-2-sulfinamide

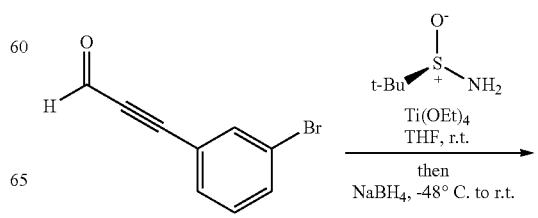

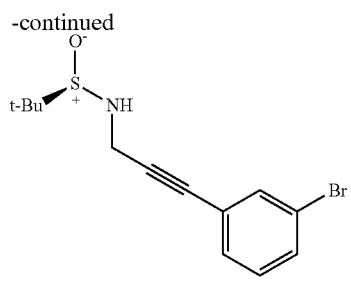

In a 50 mL roundbottom flask, 3-(3-Bromophenyl)propiolaldehyde (688 mg, 3.29 mmol, 1.0 equiv)] and (R)-2-methylpropane-2-sulfinamide (439 mg, 3.62 mmol, 1.1 equiv) were dissolved in 13.2 mL THF and Ti(OEt)$_4$ (technical grade, ca. 20% Ti, 1.7 mL, 8.23 mmol, 2.5 equiv) was added at room temperature. After full consumption of the 3-(3-Bromophenyl)propiolaldehyde (2 h), the reaction was cooled to −48° C. and solid NaBH$_4$ (498 mg, 13.2 mmol, 4.0 equiv) was added in one portion. The reaction was stirred at −48° C. for 30 min, then allowed to warm to room temperature and stirred for 2.5 h. The reaction was quenched by the slow addition of 7 mL MeOH, then the mixture was poured into vigorously stirring brine (7 mL) and diluted with 15 mL EtOAc. The layers were separated and the aq layer extracted with EtOAc (3×15 mL). The combined organic extracts were dried (Na$_2$SO$_4$), filtered, and concentrated by rotary evaporation. Purification by silica flash chromatography (40% EtOAc/hexanes) yielded the N-propargyl sulfinamide as a light yellow oil (836 mg, 81%). TLC: R$_f$0.10 (33% EtOAc/hexanes). $^1$H-NMR (600 MHz): δ 7.58 (t, J=1.8 Hz, 1H), 7.45 (ddd, J=8.1, 2.0, 1.1 Hz, 1H), 7.36 (dt, J=7.8, 1.3 Hz, 1H), 7.17 (t, J=7.9 Hz, 1H), 4.17 (dd, J=17.0, 5.3 Hz, 1H), 4.09 (dd, J=17.0, 6.5 Hz, 1H), 3.47 (t, J=6.0 Hz, 1H), 1.26 (s, 9H). $^{13}$C-NMR (151 MHz): δ 134.4, 131.6, 130.3, 129.7, 124.5, 122.1, 86.8, 83.0, 56.2, 35.4, 22.5.

(R)—N-(3-(3-bromophenyl)prop-2-yn-1-yl)-2-methyl-N-(prop-2-yn-1-yl)propane-2-sulfinamide

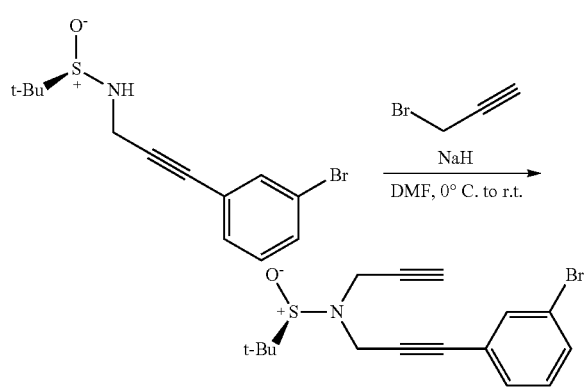

In a 50 mL roundbottom flask, (R)—N-(3-(3-Bromophenyl)prop-2-yn-1-yl)-2-methylpropane-2-sulfinamide (815 mg, 2.59 mmol, 1.0 equiv) was dissolved in 13 mL DMF and cooled to 0° C. Sodium hydride (60% dispersion in mineral oil, 114 mg, 2.85 mmol, 1.1 equiv) was added, followed by propargyl bromide (80% in toluene, 419 μL, 3.89 mmol, 1.5 equiv) and the mixture was stirred at 0° C. for 2 h. The reaction was quenched by the addition of 15 mL sat aq NH$_4$Cl, then diluted with 15 mL of Et$_2$O. The organic layer was washed with water (3×15 mL), then the combined aq layers extracted with Et$_2$O (2×15 mL). The combined organic extracts were washed with brine (1×15 mL), dried (MgSO$_4$), filtered, and concentrated by rotary evaporation. Purification by silica flash chromatography (10%→30% EtOAc/hexanes) yielded the diyne as a viscous yellow oil (831 mg, 91%). TLC: R$_f$0.53 (40% EtOAc/hexanes). $^1$H-NMR (600 MHz): δ 7.58 (t, J=1.8 Hz, 1H), 7.45 (ddd, J=8.1, 2.1, 1.1 Hz, 1H), 7.36 (dt, J=7.7, 1.3 Hz, 1H), 7.18 (t, J=7.9 Hz, 1H), 4.20 (d, J=18.7 Hz, 1H), 4.10-3.96 (m, 2H), 3.81 (dd, J=18.0, 1.9 Hz, 1H), 2.32 (t, J=2.4 Hz, 1H), 1.24 (s, 9H). $^{13}$C-NMR (151 MHz): δ 134.4, 131.6, 130.3, 129.7, 124.5, 122.0, 85.5, 83.4, 78.8, 73.1, 58.8, 25.4, 22.6.

Ethyl (R)-4-(3-bromophenyl)-2-(tert-butylsulfinyl)-2,3-dihydro-1H-pyrrolo[3,4-c]pyridine-6-carboxylate

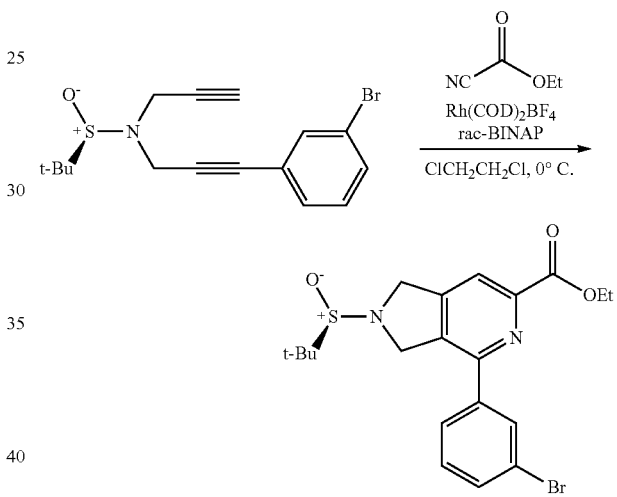

In a 200 mL roundbottom flask, Rh(COD)$_2$BF$_4$ (121 mg, 0.298 mmol, 15 mol %) and rac-BINAP (248 mg, 0.398 mmol, 20 mol %) were dissolved in 60 mL of degassed 1,2-dichloroethane. The mixture was cooled to 0° C., then ethyl cyanoformate (982 μL, 9.95 mmol, 5.0 equiv) was added, followed by a solution of the diyne (701 mg, 1.99 mmol, 1.0 equiv) in 6.3 mL of 1,2-dichloroethane. The mixture was stirred at 0° C. for 14 h, then cooled to room temperature and concentrated by rotary evaporation. Purification by silica flash chromatography (25→45% EtOAc/hexanes) yielded ethyl (R)-4-(3-bromophenyl)-2-(tert-butylsulfinyl)-2,3-dihydro-1H-pyrrolo[3,4-c]pyridine-6-carboxylate as an orange foam (478 mg, 53%). TLC: R$_f$0.43 (50% EtOAc/hexanes). [α]$_D^{19}$: −39.7° (c 1.0, CHCl$_3$). IR (ATR): 3060, 2981, 2865, 1740, 1717, 1575, 1563, 1457, 1390, 1368, 1331, 1305, 1225, 1071, 1021, 747. $^1$H-NMR (600 MHz): δ 7.99 (s, 1H), 7.95 (t, J=1.8 Hz, 1H), 7.67 (d, J=7.8 Hz, 1H), 7.58 (d, J=8.0 Hz, 1H), 7.35 (t, J=7.9 Hz, 1H), 5.06 (d, J=15.3 Hz, 1H), 4.99 (d, J=15.5 Hz, 1H), 4.68 (d, J=15.0 Hz, 1H), 4.54-4.44 (m, 3H), 1.46 (t, J=7.1 Hz, 3H), 1.27 (s, 9H). $^{13}$C-NMR (151 MHz): δ 165.0, 151.7, 150.7, 147.8, 140.3, 135.6, 132.3, 131.4, 130.2, 126.6, 123.0, 118.2, 62.1, 58.2, 23.2, 14.3; 2C not observed.

Ethyl (R)-2-(tert-butylsulfinyl)-4-(3-(3-(dimethylamino)prop-1-yn-1-yl)phenyl)-2,3-dihydro-1H-pyrrolo[3,4-c]pyridine-6-carboxylate (Compound 49)

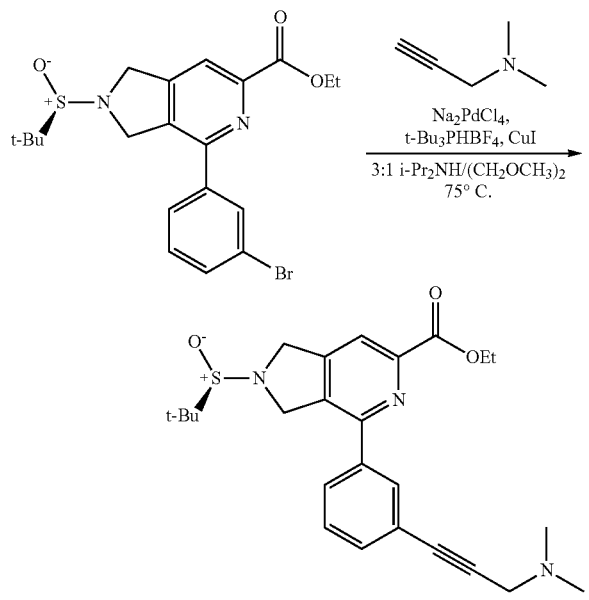

In a vial, pyrrolopyridinecarboxylate (203 mg, 0.450 mmol, 1.0 equiv), $Na_2PdCl_4$ (13 mg, 0.0450 mmol, 10 mol %), $t-Bu_3PHBF_4$ (20 mg, 0.0675 mmol, 15 mol %), and CuI (17 mg, 0.0899 mmol, 20 mol %) were dissolved in 2.8 mL of degassed 1,2-dimethoxyethane and 8.4 mL of degassed $i-Pr_2NH$. N,N-dimethylprop-2-yn-1-amine (242 μL, 2.25 mmol, 5.0 equiv) was added, then the vial was sealed with a Teflon-faced screw cap and the mixture heated to 75° C. (oil bath, ext temp) for 12 h. The reaction was cooled to room temperature and diluted with EtOAc, then filtered through Celite and concentrated by rotary evaporation. Purification by silica flash chromatography (4% $MeOH/CH_2Cl_2$) yielded pyrrolopyridinecarboxylate 49 as a dark orange oil (194 mg, 95%). TLC: $R_f$ 0.17 (70% EtOAc/hexanes). $[α]_D^{19}$: −39.9° (c 1.0, $CHCl_3$). IR (ATR): 2978, 2943, 2908, 2864, 2823, 2777, 1740, 1717, 1575, 1457, 1425, 1392, 1368, 1333, 1301, 1255, 1087, 1069, 1022, 948, 749. $^1$H-NMR (600 MHz): δ 7.98 (s, 1H), 7.83 (s, 1H), 7.71 (d, J=7.8 Hz, 1H), 7.51 (d, J=7.7 Hz, 1H), 7.42 (t, J=7.7 Hz, 1H), 5.06 (d, J=15.2 Hz, 1H), 4.99 (d, J=15.3 Hz, 1H), 4.69 (d, J=15.1 Hz, 1H), 4.55-4.44 (m, 3H), 3.50 (s, 2H), 2.39 (s, 6H), 1.45 (t, J=7.2 Hz, 3H), 1.27 (s, 9H). $^{13}$C-NMR (151 MHz): δ 165.1, 152.5, 150.5, 147.7, 138.5, 135.5, 132.5, 131.4, 128.7, 127.9, 124.0, 118.0, 85.2, 84.9, 62.0, 58.2, 48.6, 44.3, 23.2, 14.3; 2C not observed. LRMS (ESI+) m/z calcd for $C_{25}H_{31}N_3O_3S$ ([M+H]$^+$) 454.21; found 454.0.

Preparation of Compound 50

Preparation of enantiomer 50 is analogous to the synthesis of compound 49.

Example 10. Preparation of Compound 57

(R)—N-(Benzo[d][1,3]dioxol-5-ylmethyl)-2-(tert-butylsulfinyl)-4-(3-(3-(dimethylamino)prop-1-yn-1-yl)phenyl)-2,3-dihydro-1H-pyrrolo[3,4-c]pyridine-6-carboxamide (Compound 57)

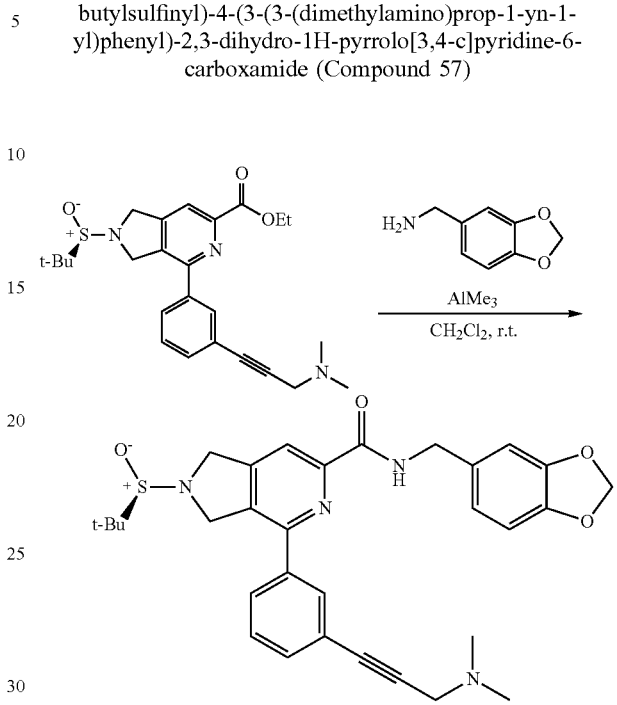

To a vial containing pyrrolopyridinecarboxylate 49 (127 mg, 0.280 mmol, 1.0 equiv, azeotroped 3× with toluene) at room temperature was slowly added a pre-stirred (>2 h) stock solution of dimethylaluminum piperonylamide[3] (0.2 M solution in $CH_2Cl_2$/toluene, 2.8 mL, 0.560 mmol, 2.0 equiv). The mixture was stirred at room temperature for 12 h, then carefully quenched by addition dropwise addition of 0.5 mL of MeOH followed by dilution with 5 mL of $CH_2Cl_2$ and careful addition of 5 mL sat aq $NaHCO_3$. The aqueous layer was extracted with EtOAc (3×5 mL), then the combined organic layers were dried ($Na_2SO_4$), filtered, and concentrated by rotary evaporation. Purification by silica flash chromatography (4% $MeOH/CH_2Cl_2$) yielded pyrrolopyridinecarboxamide 57 as a light yellow foam (128 mg, 82%). TLC: $R_f$ 0.33 (10% $MeOH/CH_2Cl_2$). $[α]_D^{19}$: −33.6° (c 1.0, $CHCl_3$). IR (ATR): 3392, 2976, 2846, 2866, 2823, 2778, 1672, 1574, 1524, 1504, 1490, 1445, 1253, 1066, 1039, 931, 744. $^1$H-NMR (600 MHz): δ 8.37 (t, J=6.3 Hz, 1H), 8.11 (s, 1H), 7.75 (s, 1H), 7.61 (d, J=8.1 Hz, 1H), 7.52 (d, J=7.5 Hz, 1H), 7.43 (t, J=7.7 Hz, 1H), 6.87 (d, J=1.6 Hz, 1H), 6.84 (dd, J=7.9, 1.3 Hz, 1H), 6.77 (d, J=7.9 Hz, 1H), 5.94 (s, 2H), 5.05 (d, J=14.5 Hz, 1H), 4.98 (d, J=15.3 Hz, 1H), 4.65 (d, J=14.8 Hz, 1H), 4.61 (d, J=6.2 Hz, 2H), 4.53 (d, J=15.3 Hz, 1H), 3.48 (s, 2H), 2.38 (s, 6H), 1.26 (s, 9H). $^{13}$C-NMR (151 MHz): δ 163.9, 151.1, 150.9, 149.2, 147.9, 146.9, 138.4, 134.9, 132.5, 132.1, 131.2, 128.7, 127.6, 123.8, 121.0, 115.5, 108.4, 108.3, 101.0, 85.7, 84.6, 58.2, 48.6, 44.4, 43.3, 23.3. LRMS (ESI+) m/z calcd for $C_{31}H_{34}N_4O_4S$ ([M+H]$^+$) 559.23; found 559.2.

Preparation of Compound 58

Preparation of enantiomer 58 is analogous to the synthesis of compound 57.

167

Synthesis of Tan003-M03

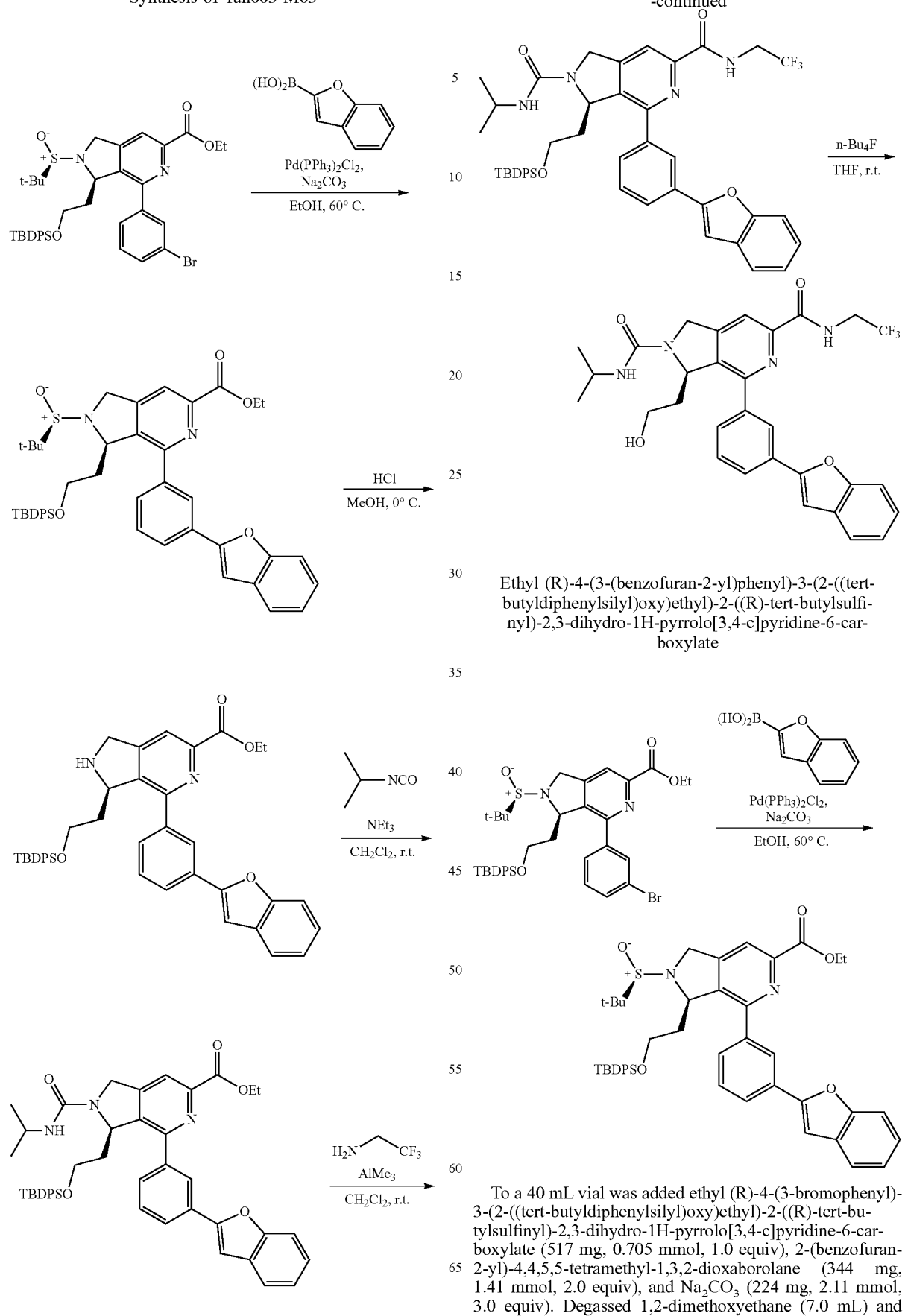

Ethyl (R)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate To a 40 mL vial was added ethyl (R)-4-(3-bromophenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate (517 mg, 0.705 mmol, 1.0 equiv), 2-(benzofuran-2-yl)-4,4,5,5-tetramethyl-1,3,2-dioxaborolane (344 mg, 1.41 mmol, 2.0 equiv), and $Na_2CO_3$ (224 mg, 2.11 mmol, 3.0 equiv). Degassed 1,2-dimethoxyethane (7.0 mL) and degassed deionized water (0.7 mL) were added, and the whole solution purged with argon for ~10 minutes. Bis(triphenylphosphine)palladium dichloride (25 mg, 0.0352 mmol, 0.05 equiv) was quickly added to the reaction, then it was capped with a teflon-lined cap and stirred at 60° C. After 12 hours, the reaction was cooled to room temperature, then diluted with EtOAc and deionized water. The aqueous layer was extracted with EtOAc (3×10 mL), then the combined organic layers were dried ($Na_2SO_4$), filtered, and concentrated by rotary evaporation. Purification by silica flash chromatography (40% EtOAc/hex, then 20% EtOAc/$CH_2Cl_2$) yielded ethyl (R)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate as a white foam (527 mg, 97%).

TLC: $R_f$ 0.28 (40% EtOAc/hexanes). $[\alpha]_D^{20}$: +92.2° (c 1.0, $CHCl_3$). IR (ATR): 3409, 3070, 2958, 2930, 2858, 1740, 1718, 1574, 1473, 1451, 1428, 1258, 1227, 1108, 1077, 940, 752, 703. $^1$H-NMR (600 MHz): δ 8.22 (t, J=1.8 Hz, 1H), 7.98 (s, 1H), 7.92 (d, J=7.8 Hz, 1H), 7.64 (d, J=7.5 Hz, 1H), 7.60 (d, J=7.2 Hz, 1H), 7.54 (d, J=8.1 Hz, 1H), 7.46-7.42 (m, 2H), 7.42-7.37 (m, 3H), 7.37-7.32 (m, 2H), 7.32-7.28 (m, 1H), 7.27 (d, J=6.3 Hz, 3H), 7.25-7.22 (m, 2H), 7.08 (s, 1H), 5.77 (d, J=7.0 Hz, 1H), 5.19 (d, J=15.7 Hz, 1H), 4.53 (dq, J=10.8, 7.1 Hz, 1H), 4.46 (dq, J=10.9, 7.1 Hz, 1H), 4.01 (d, J=14.8 Hz, 1H), 3.69-3.55 (m, 1H), 3.54-3.34 (m, 1H), 1.84-1.72 (m, 1H), 1.58-1.49 (m, 1H), 1.45 (t, J=7.1 Hz, 3H), 1.21 (s, 9H), 0.91 (s, 9H). $^{13}$C-NMR (151 MHz): δ 165.1, 155.3, 154.9, 153.4, 151.2, 147.7, 139.3, 139.2, 135.4, 135.3, 133.3, 133.2, 131.1, 129.6, 129.6, 129.3, 129.1, 128.3, 127.6, 127.5, 125.4, 125.2, 124.4, 122.9, 121.0, 118.3, 111.3, 102.0, 68.7, 61.9, 59.4, 58.5, 45.8, 37.6, 26.7, 23.7, 19.0, 14.3. HRMS m/z calcd for $C_{46}H_{50}N_2O_5SSi$ ([M+Na]$^+$) 793.3107; found 793.3077.

Ethyl (R)-4-(3-(benzofuran-2-yl)phenyl)-3-(2-((tert-butyldiphenylsilyl)oxy)ethyl)-2,3-dihydro-1H-pyrrolo[3,4-c]pyridine-6-carboxylate To a 20 mL vial was added ethyl (R)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate (527 mg, 0.683 mmol, 1.0 equiv). Methanol (6.8 mL) was added and the reaction cooled to 0° C., then HCl (4.0 M in dioxane, 188 μL, 0.752 mmol, 1.1 equiv) was added. After 2 hours, the reaction was quenched by addition of sat. aq. $NaHCO_3$ and then diluted with EtOAc. The aqueous layer was extracted with EtOAc (3×10 mL), then the combined organic layers were dried ($Na_2SO_4$), filtered, and concentrated by rotary evaporation. Purification by silica flash chromatography (50% EtOAc/hexanes) yielded ethyl (R)-4-(3-(benzofuran-2-yl)phenyl)-3-(2-((tert-butyldiphenylsilyl)oxy)ethyl)-2,3-dihydro-1H-pyrrolo[3,4-c]pyridine-6-carboxylate as a light yellow foam (451 mg, 99%).

TLC: $R_f$ 0.48 (70% EtOAc/hexanes). $[\alpha]_D^{20}$: +188.8° (c 1.0, $CHCl_3$). IR (ATR): 3365, 3070, 2931, 2857, 1736, 1718, 1568, 1451, 1428, 1390, 1258, 1108, 798, 702. $^1$H-NMR (600 MHz): δ 8.21 (s, 1H), 8.02 (s, 1H), 7.89 (d, J=7.9 Hz, 1H), 7.64 (d, J=7.7 Hz, 1H), 7.58 (d, J=7.4 Hz, 1H), 7.55-7.49 (m, 5H), 7.44 (t, J=7.7 Hz, 1H), 7.40-7.34 (m, 2H), 7.33-7.27 (m, 5H), 7.23 (t, J=7.4 Hz, 1H), 7.06 (s, 1H), 5.22 (d, J=9.2 Hz, 1H), 4.55 (dq, J=10.9, 7.1 Hz, 1H), 4.47 (dq, J=10.9, 7.1 Hz, 1H), 4.32 (s, 2H), 3.68 (ddd, J=10.5, 8.9, 3.6 Hz, 1H), 3.60 (dt, J=10.1, 4.8 Hz, 1H), 1.81-1.64 (m, 1H), 1.47 (t, J=7.1 Hz, 3H), 1.42-1.29 (m, 1H), 0.97 (s, 9H). $^{13}$C-NMR (151 MHz): δ 165.5, 155.4, 154.9, 153.9, 153.7, 147.2, 142.2, 139.6, 135.4, 135.4, 133.3, 133.2, 130.9, 129.7, 129.6, 129.1, 129.1, 128.4, 127.6, 127.6, 125.2, 125.2, 124.4, 122.9, 121.0, 118.5, 111.2, 101.8, 61.9, 61.5, 61.1, 51.1, 35.5, 26.8, 19.0, 14.4. HRMS m/z calcd for $C_{42}H_{43}N_2O_4Si$ ([M+H]$^+$) 667.2992; found 667.2969.

Ethyl (R)-4-(3-(benzofuran-2-yl)phenyl)-3-(2-((tert-butyldiphenylsilyl)oxy)ethyl)-2-(isopropylcarbamoyl)-2,3-dihydro-1H-pyrrolo[3,4-c]pyridine-6-carboxylate

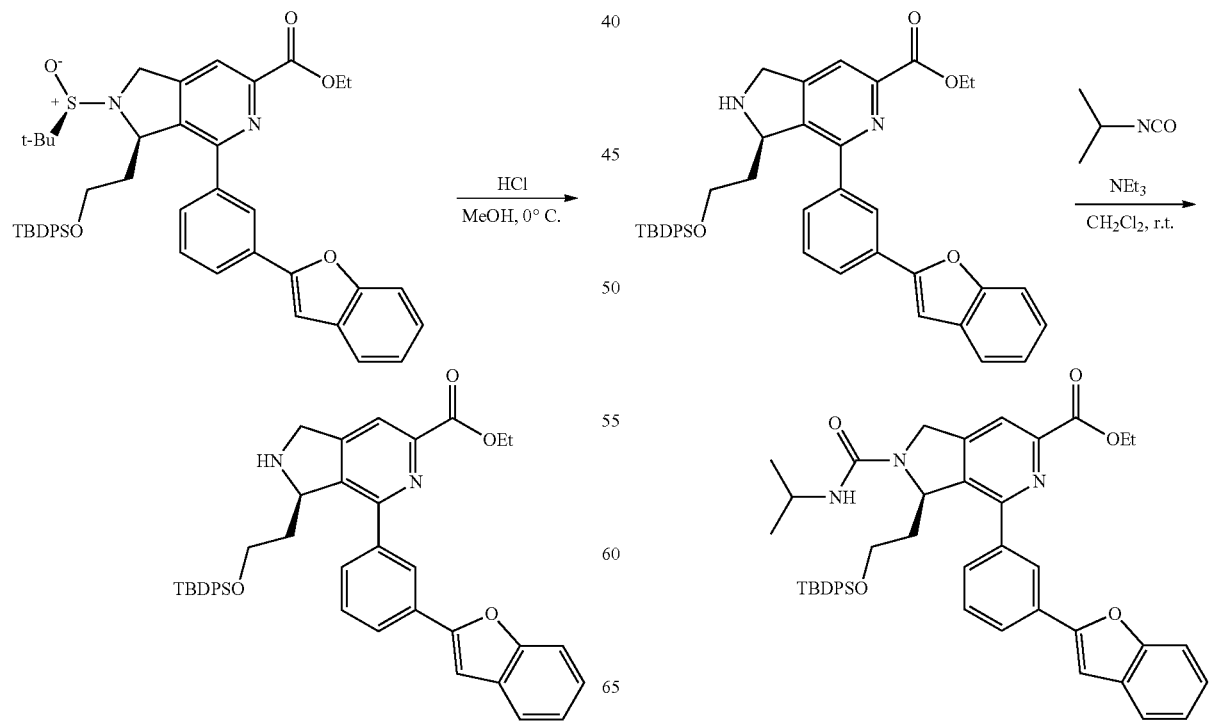

In a 20 mL vial, ethyl (R)-4-(3-(benzofuran-2-yl)phenyl)-3-(2-((tert-butyldiphenylsilyl)oxy)ethyl)-2,3-dihydro-1H-pyrrolo[3,4-c]pyridine-6-carboxylate (451 mg, 0.676 mmol, 1.0 equiv) was dissolved in 6.8 mL of CH$_2$Cl$_2$ and cooled to 0° C. NEt$_3$ (141 L, 1.41 mmol, 1.5 equiv) was added, followed by 2-isocyanatopropane (80 µL, 0.812 mmol, 1.2 equiv), and the mixture was stirred at 0° C. for 1 hour. The reaction mixture was quenched by addition of 5 mL saturated aqueous NaHCO$_3$, then the aqueous layer was extracted with CH$_2$Cl$_2$ (3×5 mL). The combined organic extracts were washed with brine (1×5 mL), dried (Na$_2$SO$_4$), filtered, and concentrated by rotary evaporation. Purification by silica flash chromatography yielded ethyl (R)-4-(3-(benzofuran-2-yl)phenyl)-3-(2-((tert-butyldiphenylsilyl)oxy)ethyl)-2-(isopropylcarbamoyl)-2,3-dihydro-1H-pyrrolo[3,4-c]pyridine-6-carboxylate as a colorless film (465 mg, 91%).

TLC: R$_f$0.37 (50% EtOAc/hexanes). [α]$_D$$^{20}$: +144.0° (c 1.0, CHCl$_3$). IR (ATR): 3378, 3070, 2965, 2932, 2858, 1722, 1641, 1527, 1453, 1371, 1234, 1107, 739, 703. $^1$H-NMR (600 MHz): δ 8.22 (s, 1H), 8.01 (s, 1H), 7.92 (d, J=7.9 Hz, 1H), 7.64 (d, J=7.7 Hz, 1H), 7.61 (d, J=7.6 Hz, 1H), 7.53 (d, J=8.1 Hz, 1H), 7.42-7.26 (m, 9H), 7.25-7.22 (m, 2H), 7.20 (t, J=7.5 Hz, 2H), 7.09 (s, 1H), 5.84 (s, 1H), 5.17 (d, J=15.7 Hz, 1H), 4.94 (s, 1H), 4.54 (dq, J=10.9, 7.1 Hz, 1H), 4.50-4.40 (m, 2H), 4.15-4.04 (m, 1H), 3.71-3.57 (m, 1H), 3.55-3.44 (m, 1H), 1.94-1.78 (m, 1H), 1.46 (t, J=7.1 Hz, 3H), 1.41-1.28 (m, 1H), 1.17 (dd, J=9.5, 6.6 Hz, 6H), 0.87 (s, 9H). $^{13}$C-NMR (151 MHz): δ 165.1, 156.5, 155.2, 154.9, 153.6, 149.2, 147.6, 139.3, 139.1, 135.3, 135.3, 133.0, 133.0, 131.3, 129.7, 129.7, 129.3, 129.1, 128.1, 127.6, 127.6, 125.5, 125.2, 124.5, 123.0, 121.0, 118.3, 111.2, 102.1, 62.0, 60.2, 59.4, 53.4, 50.9, 42.7, 27.0, 23.4, 23.4, 19.0, 14.3. HRMS m/z calcd for C$_{46}$H$_{49}$N$_3$O$_5$SiNa ([M+Na]$^+$) 774.3339; found 774.3307.

(R)-4-(3-(benzofuran-2-yl)phenyl)-3-(2-((tert-butyldiphenylsilyl)oxy)ethyl)-N$^2$-isopropyl-N$^6$-(2,2,2-trifluoroethylyl)-1,3-dihydro-2H-pyrrolo[3,4-c]pyridine-2,6-dicarboxamide In a 20 mL vial, ethyl (R)-4-(3-(benzofuran-2-yl)phenyl)-3-(2-((tert-butyldiphenylsilyl)oxy)ethyl)-2-(isopropylcarbamoyl)-2,3-dihydro-1H-pyrrolo[3,4-c]pyridine-6-carboxylate (465 mg, 0.618 mmol, 1.0 equiv, azeotroped 3× with toluene) was dissolved in 6.2 mL CH$_2$Cl$_2$ at room temperature. A pre-stirred (>2 h) stock solution of dimethylaluminum 2,2,2-trifluoroethylamide (0.2 M solution in CH$_2$Cl$_2$/toluene, 6.2 mL, 1.24 mmol, 2.0 equiv) was slowly added and the mixture was stirred at room temperature for 17 h, then carefully quenched by dropwise addition of 2 mL MeOH followed by dilution with 10 mL of CH$_2$Cl$_2$ and careful addition of 5 mL saturated aqueous NaHCO$_3$. The aqueous layer was extracted with CH$_2$Cl$_2$ (3×10 mL), then the combined organic layers were dried (Na$_2$SO$_4$), filtered, and concentrated by rotary evaporation. Purification by silica flash chromatography (20% EtOAc/CH$_2$Cl$_2$) yielded (R)-4-(3-(benzofuran-2-yl)phenyl)-3-(2-((tert-butyldiphenylsilyl)oxy)ethyl)-N$^2$-isopropyl-N$^6$-(2,2,2-trifluoroethyl)-1,3-dihydro-2H-pyrrolo[3,4-c]pyridine-2,6-dicarboxamide as a colorless film (454 mg, 91%).

TLC: R$_f$0.23 (20% EtOAc/CH$_2$Cl$_2$). [α]$_D$$^{20}$: +144.3° (c 1.0, CHCl$_3$). IR (ATR): 3380, 3071, 2962, 2932, 2859, 1685, 1641, 1522, 1383, 1274, 1162, 1056, 751, 702. $^1$H-NMR (600 MHz): δ 8.42 (t, J=6.8 Hz, 1H), 8.17 (s, 1H), 8.11 (s, 1H), 7.96 (d, J=7.9 Hz, 1H), 7.62 (d, J=7.6 Hz, 1H), 7.60 (d, J=7.7 Hz, 1H), 7.53 (d, J=8.1 Hz, 1H), 7.44 (t, J=7.7 Hz, 1H), 7.41-7.36 (m, 2H), 7.35-7.31 (m, 4H), 7.31-7.27 (m, 2H), 7.25-7.22 (m, 2H), 7.22-7.17 (m, 2H), 7.09 (s, 1H), 5.87 (s, 1H), 5.09 (d, J=15.5 Hz, 1H), 4.77 (s, 1H), 4.47 (dd, J=15.5, 1.7 Hz, 2H), 4.34-4.16 (m, 1H), 4.11-3.98 (m, 2H), 3.66-3.55 (m, 1H), 3.54-3.44 (m, 1H), 1.94 (s, 1H), 1.40 (s, 1H), 1.18 (t, J=6.8 Hz, 6H), 0.85 (s, 9H). $^{13}$C-NMR (151 MHz): δ 164.3, 156.3, 156.3, 155.0, 154.9, 152.3, 149.9, 147.9, 139.2, 139.0, 135.3, 135.3, 133.0, 133.0, 131.3, 129.7, 129.7, 129.4, 129.0, 127.8, 127.6, 127.6, 125.6, 124.9, 124.7, 124.1 (q, J=277.6 Hz), 123.1, 121.1, 116.0, 111.3, 102.3, 60.1, 59.6, 51.0, 42.7, 40.8 (q, J=34.7 Hz), 26.9, 23.4, 23.4, 19.0. HRMS m/z calcd for C$_{46}$H$_{47}$N$_4$O$_4$SiF$_3$Na ([M+Na]$^+$) 827.3216; found 827.3246.

Preparation of dimethylaluminum 2,2,2-trifluoroethylamide Stock Solution

To a 10 mL roundbottom flask containing 2,2,2-trifluoroethylamine (78 µL, 1.0 mmol, 1.0 equiv) in 9.5 mL of CH2Cl2 was slowly added trimethylaluminum solution (2 M in toluene, 0.5 mL, 1.0 mmol, 1.0 equiv) at rt. The mixture was stirred for >2 h before use. Solution can be stored at −20° C. for at least 1 month.

(R)-4-(3-(benzofuran-2-yl)phenyl)-3-(2-hydroxyethyl)-N$^2$-isopropyl-N$^6$-(2,2,2-trifluoroethyl)-1,3-dihydro-2H-pyrrolo[3,4-c]pyridine-2,6-dicarboxamide (Tan003-M03)

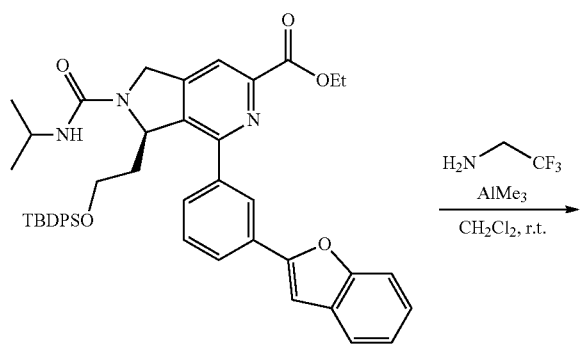

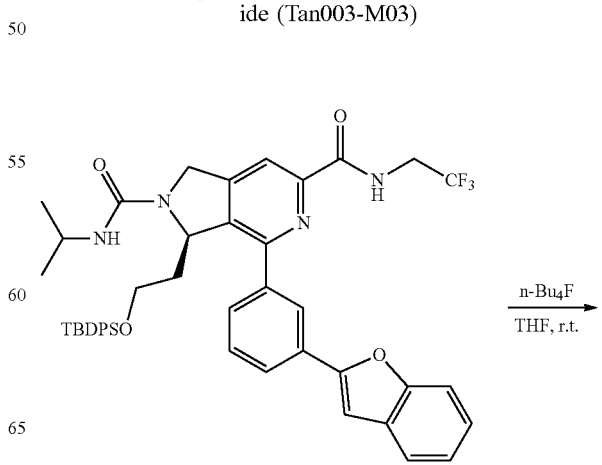

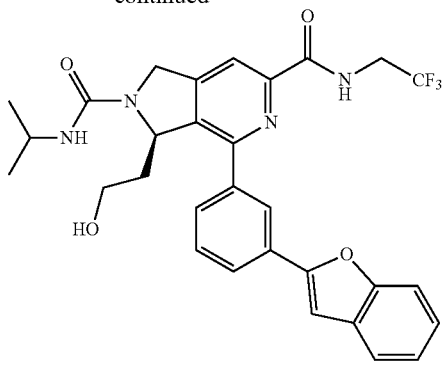

In a 20 mL vial, (R)-4-(3-(benzofuran-2-yl)phenyl)-3-(2-((tert-butyldiphenylsilyl)oxy)ethyl)-$N^2$-isopropyl-$N^6$-(2,2,2-trifluoroethyl)-1,3-dihydro-2H-pyrrolo[3,4-c]pyridine-2,6-dicarboxamide (454 mg, 0.564 mmol, 1.0 equiv) was dissolved in 5.6 mL of THF and cooled to 0° C. n-Bu$_4$NF solution (1.0 M in THF, 846 µL, 0.846 mmol, 1.5 equiv) was added dropwise and the mixture was stirred at 0° C. for 1 hour, then allowed to warm to room temperature over 4.5 h. The reaction mixture was diluted with 10 mL EtOAc and 5 mL saturated aqueous NaHCO$_3$, then the aqueous layer was extracted with EtOAc (3×5 mL). The combined organic extracts were washed with brine (1×5 mL), dried (Na$_2$SO$_4$), filtered, and concentrated by rotary evaporation. Purification by silica flash chromatography yielded Tan003-M03 as a colorless film (313 mg, 98%).

TLC: R$_f$ 0.31 (80% EtOAc/hexanes). $[\alpha]_D^{19}$: +180.4° (c 1.0, CHCl$_3$). IR (ATR): 3317, 3068, 2971, 1683, 1630, 1525, 1420, 1274, 1162, 802, 751. $^1$H-NMR (600 MHz): δ 8.44 (t, J=6.8 Hz, 1H), 8.24 (s, 1H), 8.14 (s, 1H), 7.99 (d, J=7.9 Hz, 1H), 7.73 (d, J=7.7 Hz, 1H), 7.67-7.60 (m, 2H), 7.54 (d, J=8.1 Hz, 1H), 7.31 (t, J=7.1 Hz, 1H), 7.26-7.24 (m, 1H), 7.15 (s, 1H), 6.06 (d, J=10.1 Hz, 1H), 4.93 (d, J=14.7 Hz, 1H), 4.81-4.48 (m, 2H), 4.35-4.16 (m, 1H), 4.16-3.99 (m, 2H), 3.58-3.49 (m, 1H), 3.49-3.38 (m, 1H), 1.91-1.73 (m, 1H), 1.32-1.17 (m, 7H). $^{13}$C-NMR (151 MHz): δ 164.3, 157.3, 155.0, 152.2, 148.9, 148.1, 148.1, 139.4, 138.4, 131.3, 129.5, 129.0, 128.0, 126.0, 124.7, 124.7, 124.1 (q, J=279.1 Hz), 121.1, 115.9, 111.2, 102.3, 59.2, 58.5, 50.9, 43.0, 40.8 (q, J=34.9 Hz), 37.8, 23.4, 23.4. HRMS m/z calcd for C$_{30}$H$_{29}$N$_4$O$_4$F$_3$Na ([M+Na]$^+$) 589.2039; found 589.2026.

Preparation of ent-Tan003-M03

The synthesis of enantiomer ent-Tan003-M03 is analogous to the synthesis of Tan003-M03.

Synthesis of Tan003—O08: [Synthesis of ent-Tan003—O08 is Analogous]

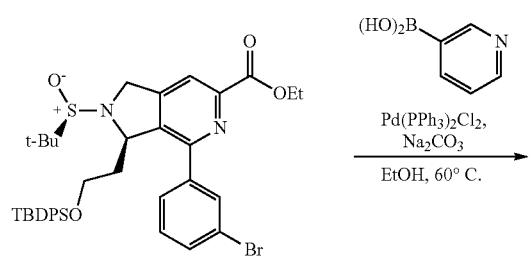

To a 40 mL vial was added ethyl (R)-4-(3-bromophenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate (876 mg, 1.19 mmol, 1.0 equiv), pyridin-3-ylboronic acid (293 mg, 2.39 mmol, 2.0 equiv), and Na$_2$CO$_3$ (122 mg, 1.15 mmol, 3.0 equiv). Degassed ethanol (11.9 mL) was added, and the whole solution purged with argon for ~10 minutes. Bis(triphenylphosphine)palladium dichloride (42 mg, 0.0597 mmol, 0.05 equiv) was quickly added to the reaction, then it was capped with a teflon-lined cap and

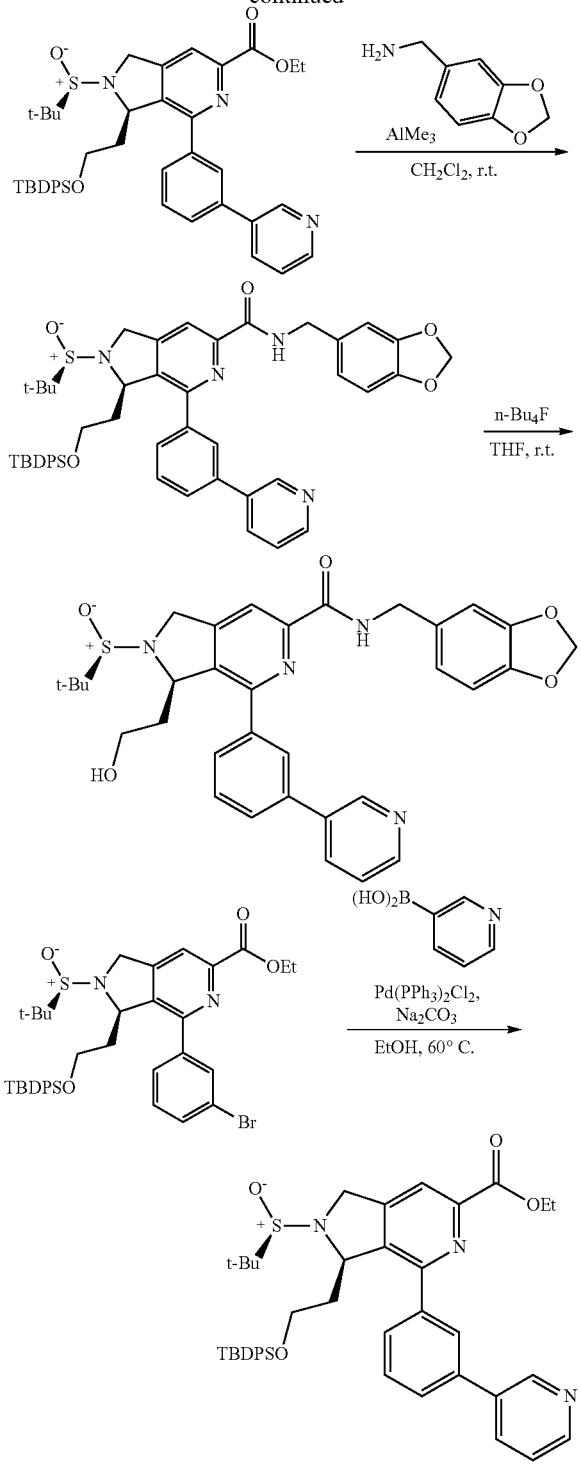

stirred at 60° C. After 12 hours, the reaction was cooled to room temperature, then diluted with EtOAc, filtered through Celite, and concentrated by rotary evaporation. Purification by silica flash chromatography (50-80% EtOAc/hexanes) yielded ethyl (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxylate as a white foam (819 mg, 94%).

TLC: $R_f$ 0.13 (60% EtOAc/hexanes). $[\alpha]_D^{20}$: +61.8° (c 1.0, CHCl$_3$). IR (ATR): 3398, 3070, 2958, 2931, 2858, 1741, 1718, 1578, 1472, 1428, 1225, 1108, 1076, 758, 705. $^1$H-NMR (600 MHz): δ 8.89 (s, 1H), 8.61 (d, J=4.0 Hz, 1H), 7.99 (s, 1H), 7.97 (s, 1H), 7.89 (dt, J=7.9, 1.9 Hz, 1H), 7.73 (d, J=7.7 Hz, 1H), 7.65 (d, J=7.9 Hz, 1H), 7.47-7.34 (m, 8H), 7.30-7.28 (m, 2H), 7.28-7.26 (m, 2H), 5.79 (d, J=7.0 Hz, 1H), 5.20 (d, J=15.8 Hz, 1H), 4.52 (dq, J=10.9, 7.1 Hz, 1H), 4.44 (dq, J=10.9, 7.1 Hz, 1H), 4.02 (d, J=15.0 Hz, 1H), 3.66 (ddd, J=10.4, 8.5, 5.0 Hz, 1H), 3.48 (ddd, J=10.5, 6.1, 4.5 Hz, 1H), 1.85-1.73 (m, 1H), 1.61-1.52 (m, 1H), 1.44 (t, J=7.1 Hz, 3H), 1.22 (s, 9H), 0.93 (s, 9H). $^{13}$C-NMR (151 MHz): δ 164.9, 153.2, 151.2, 148.6, 148.3, 147.6, 139.5, 139.1, 138.4, 136.0, 135.3, 135.2, 134.4, 133.2, 133.1, 129.6, 129.6, 129.4, 127.8, 127.6, 127.5, 127.5, 127.5, 123.5, 118.2, 68.6, 61.8, 59.3, 58.4, 45.7, 37.5, 26.6, 23.6, 18.9, 14.3. HRMS m/z calcd for C$_{43}$H$_{50}$N$_3$O$_4$SSi ([M+H]$^+$) 732.3291; found 732.3293.

(R)—N-(benzo[d][1,3]dioxol-5-ylmethyl)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide

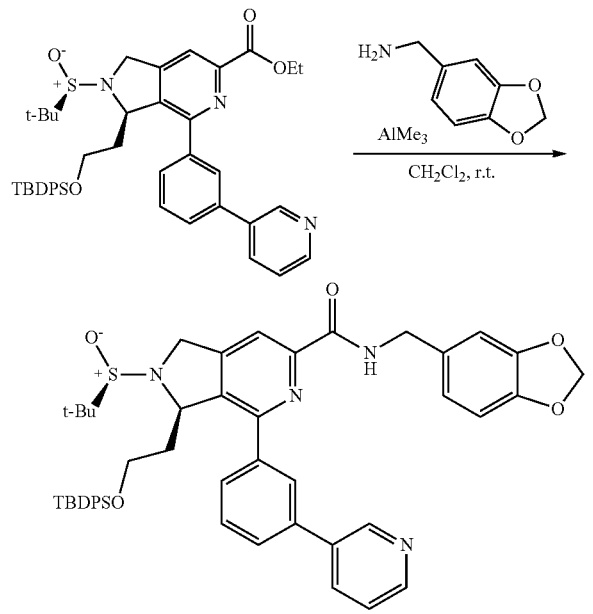

In a 20 mL vial, ethyl (R)-3-(2-((tert-butyldiphenylsilyl) oxy)ethyl)-2-((R)-tert-butylsulfinyl)-4-(3-(pyridin-3-yl) phenyl)-2,3-dihydro-1H-pyrrolo[3,4-c]pyridine-6-carboxylate (410 mg, 0.560 mmol, 1.0 equiv, azeotroped 3× with toluene) was dissolved in 2.8 mL CH$_2$Cl$_2$ at room temperature. A pre-stirred (>2 h) stock solution of dimethylaluminum piperonylamide (0.2 M solution in CH$_2$Cl$_2$/toluene, 2.8 mL, 1.12 mmol, 2.0 equiv) was slowly added and the mixture was stirred at room temperature for 17 h, then carefully quenched by dropwise addition of 2 mL MeOH followed by dilution with 5 mL of CH$_2$Cl$_2$ and careful addition of 5 mL saturated aqueous NaHCO$_3$. The aqueous layer was extracted with CH$_2$Cl$_2$ (3×10 mL), then the combined organic layers were dried (Na$_2$SO$_4$), filtered, and concentrated by rotary evaporation. Purification by silica flash chromatography (80% EtOAc/hexanes→100% EtOAc) yielded (R)—N-(benzo[d][1,3]dioxol-5-ylmethyl)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide as a light yellow foam (440 mg, 94%).

TLC: $R_f$ 0.50 (100% EtOAc). $[\alpha]_D^{19}$: +62.5° (c 1.0, CHCl$_3$). IR (ATR): 3396, 3069, 3047, 2957, 2930, 2896, 2858, 1673, 1575, 1523, 1504, 1490, 1445, 1428, 1253, 1111, 1075, 1041, 930, 740, 705. $^1$H-NMR (600 MHz): δ 8.86 (s, 1H), 8.63 (d, J=3.9 Hz, 1H), 8.33 (t, J=6.1 Hz, 1H), 8.10 (s, 1H), 7.86-7.80 (m, 2H), 7.66 (d, J=7.8 Hz, 2H), 7.49-7.33 (m, 8H), 7.30-7.23 (m, 5H), 6.85 (s, 1H), 6.81 (d, J=8.0 Hz, 1H), 6.75 (d, J=7.9 Hz, 1H), 5.92 (s, 2H), 5.75 (d, J=6.4 Hz, 1H), 5.19 (d, J=15.8 Hz, 1H), 4.60 (dd, J=14.8, 6.2 Hz, 1H), 4.55 (dd, J=14.8, 6.1 Hz, 1H), 4.02 (d, J=15.6 Hz, 1H), 3.64 (ddd, J=10.3, 8.2, 5.0 Hz, 1H), 3.47 (dt, J=10.7, 5.4 Hz, 1H), 1.83-1.61 (m, 1H), 1.62-1.49 (m, 1H), 1.21 (s, 9H), 0.91 (s, 9H). $^{13}$C-NMR (151 MHz): δ 163.8, 151.8, 151.6, 149.2, 148.8, 148.3, 147.9, 146.9, 139.5, 138.5, 138.4, 135.9, 135.4, 135.3, 134.5, 133.3, 133.2, 132.1, 129.6, 129.6, 129.6, 127.8, 127.7, 127.6, 127.1, 123.6, 121.0, 115.7, 108.4, 108.2, 101.0, 68.6, 59.4, 58.5, 45.9, 43.2, 37.7, 26.7, 23.7, 19.0; 1 C not observed. HRMS m/z calcd for C$_{49}$H$_{53}$N$_4$O$_5$SSi ([M+H]$^+$) 837.3506; found 837.3474.

Preparation of Dimethylaluminum Piperonylamide Stock Solution

To a 10 mL roundbottom flask containing piperonylamine (125 μL, 1.0 mmol, 1.0 equiv) in 9.5 mL of CH2Cl2 was slowly added trimethylaluminum solution (2 M in toluene, 0.5 mL, 1.0 mmol, 1.0 equiv) at rt. The mixture was stirred for >2 h before use. Solution can be stored at −20° C. for at least 1 month.

(R)—N-(benzo[d][1,3]dioxol-5-ylmethyl)-2-((R)-tert-butylsulfinyl)-3-(2-hydroxyethyl)-4-(3-(pyridin-3-yl)phenyl)-2,3-dihydro-1H-pyrrolo[3,4-c]pyridine-6-carboxamide (Tan003—O08)

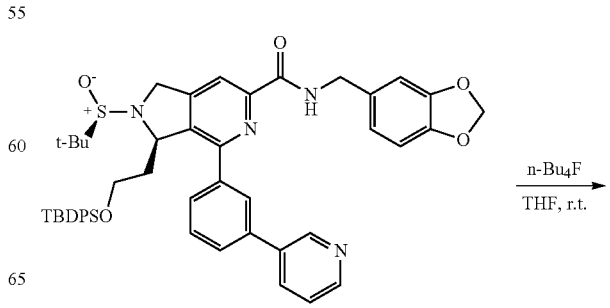

177
-continued

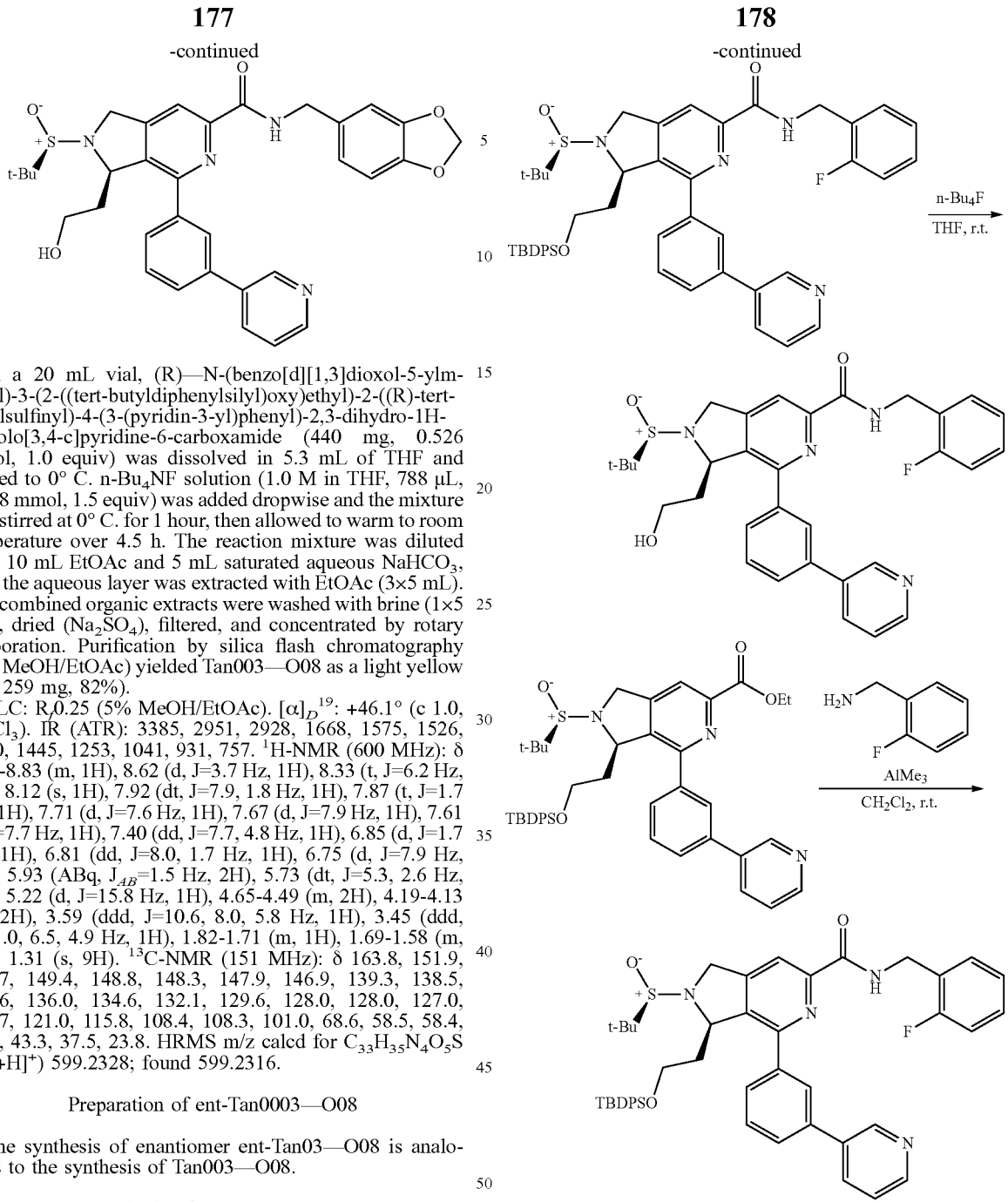

In a 20 mL vial, (R)—N-(benzo[d][1,3]dioxol-5-ylm-ethyl)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide (440 mg, 0.526 mmol, 1.0 equiv) was dissolved in 5.3 mL of THF and cooled to 0° C. n-Bu$_4$NF solution (1.0 M in THF, 788 μL, 0.788 mmol, 1.5 equiv) was added dropwise and the mixture was stirred at 0° C. for 1 hour, then allowed to warm to room temperature over 4.5 h. The reaction mixture was diluted with 10 mL EtOAc and 5 mL saturated aqueous NaHCO$_3$, then the aqueous layer was extracted with EtOAc (3×5 mL). The combined organic extracts were washed with brine (1×5 mL), dried (Na$_2$SO$_4$), filtered, and concentrated by rotary evaporation. Purification by silica flash chromatography (5% MeOH/EtOAc) yielded Tan003—O08 as a light yellow film 259 mg, 82%).

TLC: R$_f$0.25 (5% MeOH/EtOAc). [α]$_D^{19}$: +46.1° (c 1.0, CHCl$_3$). IR (ATR): 3385, 2951, 2928, 1668, 1575, 1526, 1490, 1445, 1253, 1041, 931, 757. $^1$H-NMR (600 MHz): δ 8.95-8.83 (m, 1H), 8.62 (d, J=3.7 Hz, 1H), 8.33 (t, J=6.2 Hz, 1H), 8.12 (s, 1H), 7.92 (dt, J=7.9, 1.8 Hz, 1H), 7.87 (t, J=1.7 Hz, 1H), 7.71 (d, J=7.6 Hz, 1H), 7.67 (d, J=7.9 Hz, 1H), 7.61 (t, J=7.7 Hz, 1H), 7.40 (dd, J=7.7, 4.8 Hz, 1H), 6.85 (d, J=1.7 Hz, 1H), 6.81 (dd, J=8.0, 1.7 Hz, 1H), 6.75 (d, J=7.9 Hz, 1H), 5.93 (ABq, J$_{AB}$=1.5 Hz, 2H), 5.73 (dt, J=5.3, 2.6 Hz, 1H), 5.22 (d, J=15.8 Hz, 1H), 4.65-4.49 (m, 2H), 4.19-4.13 (m, 2H), 3.59 (ddd, J=10.6, 8.0, 5.8 Hz, 1H), 3.45 (ddd, J=11.0, 6.5, 4.9 Hz, 1H), 1.82-1.71 (m, 1H), 1.69-1.58 (m, 1H), 1.31 (s, 9H). $^{13}$C-NMR (151 MHz): δ 163.8, 151.9, 151.7, 149.4, 148.8, 148.3, 147.9, 146.9, 139.3, 138.5, 137.6, 136.0, 134.6, 132.1, 129.6, 128.0, 128.0, 127.0, 123.7, 121.0, 115.8, 108.4, 108.3, 101.0, 68.6, 58.5, 58.4, 46.0, 43.3, 37.5, 23.8. HRMS m/z calcd for C$_{33}$H$_{35}$N$_4$O$_5$S ([M+H]$^+$) 599.2328; found 599.2316.

Preparation of ent-Tan0003—O08

The synthesis of enantiomer ent-Tan03—O08 is analogous to the synthesis of Tan003—O08.

Synthesis of ent-Tan003-D20

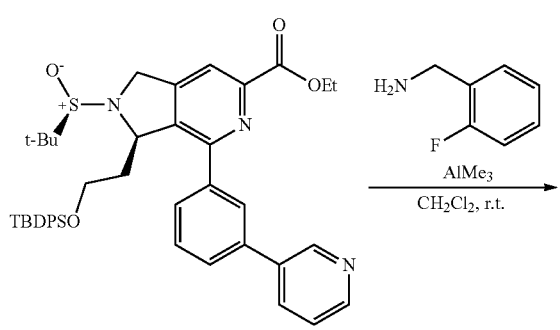

178
-continued (R)-3-(2-((tert-butyldiphenylsilyl)oxy)ethyl)-2-((R)-tert-butylsulfinyl)-N-(2-fluorobenzyl)-4-(3-(pyridin-3-yl)phenyl)-2,3-dihydro-1H-pyrrolo[3,4-c]pyridine-6-carboxamide In a 20 mL vial, ethyl (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxylate (410 mg, 0.560 mmol, 1.0 equiv, azeotroped 3× with toluene) was dissolved in 2.8 mL CH$_2$Cl$_2$ at room temperature. A pre-stirred (>2 h) stock solution of dimethylaluminum (2-fluorobenzyl)amide (0.2 M solution in CH$_2$Cl$_2$/toluene, 2.8 mL, 1.12 mmol, 2.0 equiv) was slowly added and the mixture was stirred at room temperature for 17 h, then carefully quenched by dropwise addition of 2 mL MeOH followed by dilution with 5 mL of CH$_2$Cl$_2$ and careful addition of 5 mL saturated aqueous NaHCO$_3$. The aqueous layer was extracted with CH$_2$Cl$_2$ (3×10 mL), then the combined organic layers were dried (Na$_2$SO$_4$), filtered, and concentrated by rotary evaporation. Purification by silica flash chromatography (80% EtOAc/hexanes→100% EtOAc) yielded (R)-3-(2-((tert-butyldiphenylsilyl)oxy)ethyl)-2-((R)-tert-butylsulfinyl)-N-(2-fluorobenzyl)-4-(3-(pyridin-3-yl)phenyl)-2,3-dihydro-1H-pyrrolo[3,4-c]pyridine-6-carboxamide as a light yellow foam (386 mg, 85%).

TLC: R$_f$ 0.53 (100% EtOAc). [α]$_D^{20}$: +58.7° (c 1.0, CHCl$_3$). IR (ATR): 3392, 3049, 2958, 2930, 2858, 1674, 1576, 1523, 1427, 1266, 1229, 1107, 1073, 940, 736, 701. $^1$H-NMR (600 MHz): δ 8.88 (s, 1H), 8.64 (s, 1H), 8.46 (t, J=6.3 Hz, 1H), 8.08 (s, 1H), 7.91-7.83 (m, 2H), 7.68 (dd, J=11.5, 7.9 Hz, 2H), 7.47-7.32 (m, 9H), 7.28-7.27 (m, 1H), 7.26-7.23 (m, 3H), 7.10 (t, J=7.5 Hz, 1H), 7.06 (t, J=9.4, 9.0 Hz, 1H), 5.77 (d, J=6.5 Hz, 1H), 5.18 (d, J=15.8 Hz, 1H), 4.76 (dd, J=15.2, 6.4 Hz, 1H), 4.71 (dd, J=15.2, 6.2 Hz, 1H), 4.01 (d, J=15.5 Hz, 1H), 3.64 (ddd, J=10.2, 8.5, 5.1 Hz, 2H), 3.47 (dt, J=10.5, 5.4 Hz, 1H), 1.81-1.74 (m, 1H), 1.61-1.50 (m, 1H), 1.21 (s, 9H), 0.91 (s, 9H). $^{13}$C-NMR (151 MHz): δ 163.9, 161.0 (d, J=246.1 Hz), 160.9, 151.9, 151.6, 149.1, 148.8, 148.3, 139.5, 138.5, 138.4, 136.0, 135.4, 135.3, 134.4, 133.3, 133.2, 130.0 (d, J=4.3 Hz), 129.6, 129.6, 129.6, 129.2 (d, J=8.1 Hz), 127.7, 127.6, 127.2, 125.2 (d, J=14.8 Hz), 124.3 (d, J=3.6 Hz), 123.6, 115.7, 115.4 (d, J=21.2 Hz), 68.6, 59.4, 58.5, 45.9, 37.7, 37.4 (d, J=4.0 Hz), 26.7, 23.7, 19.0; 1 C not observed. HRMS m/z calcd for C$_{48}$H$_{52}$FN$_4$O$_3$SSi ([M+H]$^+$) 811.3513; found 811.3505.

Preparation of dimethylaluminum (2-fluorobenzyl)amide Stock Solution

To a 10 mL roundbottom flask containing 2-fluorobenzyl amine (114 µL, 1.0 mmol, 1.0 equiv) in 9.5 mL of CH$_2$Cl$_2$ was slowly added trimethylaluminum solution (2 M in toluene, 0.5 mL, 1.0 mmol, 1.0 equiv) at rt. The mixture was stirred for >2 h before use. Solution can be stored at −20° C. for at least 1 month.

(R)-2-((R)-tert-butylsulfinyl)-N-(2-fluorobenzyl)-3-(2-hydroxyethyl)-4-(3-(pyridin-3-yl)phenyl)-2,3-dihydro-1H-pyrrolo[3,4-c]pyridine-6-carboxamide (ent-Tan003-D20)

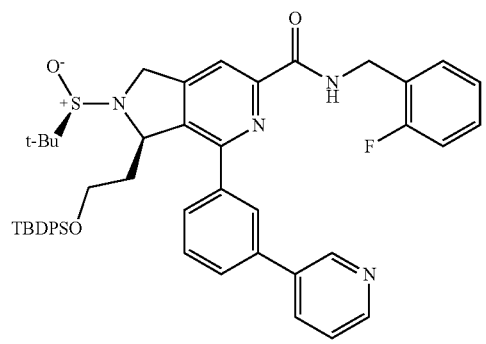

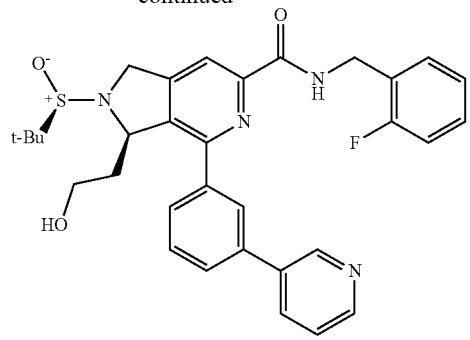

In a 20 mL vial, (R)-3-(2-((tert-butyldiphenylsilyl)oxy)ethyl)-2-((R)-tert-butylsulfinyl)-N-(2-fluorobenzyl)-4-(3-(pyridin-3-yl)phenyl)-2,3-dihydro-1H-pyrrolo[3,4-c]pyridine-6-carboxamide (386 mg, 0.476 mmol, 1.0 equiv) was dissolved in 4.6 mL of THF and cooled to 0° C. n-Bu$_4$NF solution (1.0 M in THF, 714 µL, 0.714 mmol, 1.5 equiv) was added dropwise and the mixture was stirred at 0° C. for 1 hour, then allowed to warm to room temperature over 4.5 h. The reaction mixture was diluted with 10 mL EtOAc and 5 mL saturated aqueous NaHCO$_3$, then the aqueous layer was extracted with EtOAc (3×5 mL). The combined organic extracts were washed with brine (1×5 mL), dried (Na$_2$SO$_4$), filtered, and concentrated by rotary evaporation. Purification by silica flash chromatography (100% EtOAc→10% MeOH/EtOAc) yielded ent-Tan003-D20 as a light yellow foam (189 mg, 69%).

TLC: R$_f$ 0.28 (5% MeOH/EtOAc). [α]$_D^{19}$: +49.1° (c 1.0, CHCl$_3$). IR (ATR): 3388, 2958, 1670, 1575, 1526, 1475, 1230, 1063, 756. $^1$H-NMR (600 MHz): δ 8.91 (s, 1H), 8.64 (d, J=4.1 Hz, 1H), 8.45 (t, J=6.3 Hz, 1H), 8.11 (s, 1H), 7.94 (dt, J=7.9, 1.9 Hz, 1H), 7.91 (s, 1H), 7.74 (d, J=7.6 Hz, 1H), 7.69 (d, J=7.9 Hz, 1H), 7.62 (t, J=7.7 Hz, 1H), 7.45-7.37 (m, 2H), 7.26-7.23 (m, 1H), 7.10 (t, J=7.5 Hz, 1H), 7.06 (t, J=9.7, 8.8 Hz, 1H), 5.74 (dt, J=6.1, 2.8 Hz, 2H), 5.22 (d, J=15.8 Hz, 1H), 4.84-4.64 (m, 2H), 4.15 (d, J=16.7 Hz, 1H), 3.59 (ddd, J=10.6, 8.0, 5.8 Hz, 1H), 3.45 (dt, J=11.0, 5.7 Hz, 1H), 1.85-1.70 (m, 1H), 1.68-1.60 (m, 2H), 1.31 (s, 9H). $^{13}$C-NMR (151 MHz): δ 163.9, 161.0 (d, J=246.2 Hz), 151.9, 151.6, 149.4, 148.9, 148.4, 139.3, 138.5, 137.6, 136.0, 134.5, 130.0 (d, J=4.3 Hz), 129.6, 129.2 (d, J=8.2 Hz), 128.0, 127.9, 127.1, 125.2 (d, J=14.8 Hz), 124.3 (d, J=3.5 Hz), 123.7, 115.7, 115.4 (d, J=21.3 Hz), 68.7, 58.5, 58.4, 46.0, 37.5, 37.5 (d, J=4.0 Hz), 23.8. HRMS m/z calcd for C$_{32}$H$_{34}$FN$_4$O$_3$S ([M+H]$^+$) 573.2336; found 573.2330.

Preparation of Tan003-D20

The synthesis of enantiomer Tan003-D20 is analogous to the synthesis of ent-Tan003-D20.

Synthesis of Tan002—O12

Ethyl (R)-2-((R)-tert-butylsulfinyl)-3-(2-hydroxyethyl)-4-phenyl-2,3-dihydro-1H-pyrrolo[3,4-c]pyridine-6-carboxylate (Tan002—O12)

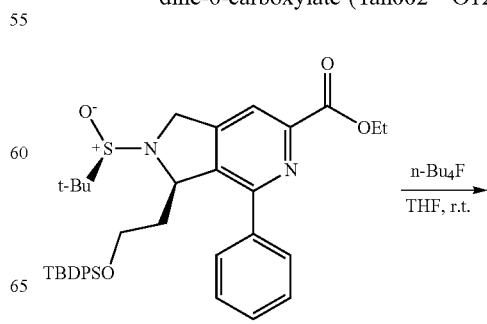

181

-continued

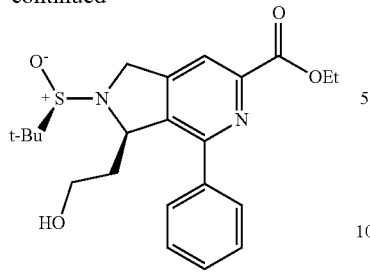

In a 20 mL vial, ethyl (R)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxylate (387 mg, 0.591 mmol, 1.0 equiv) was dissolved in 5.9 mL of THF and cooled to 0° C. n-Bu$_4$NF solution (1.0 M in THF, 886 μL, 0.886 mmol, 1.5 equiv) was added dropwise and the mixture was stirred at 0° C. for 1 hour, then allowed to warm to room temperature over 4.5 h. The reaction mixture was diluted with 10 mL EtOAc and 5 mL saturated aqueous NaHCO$_3$, then the aqueous layer was extracted with EtOAc (3×5 mL). The combined organic extracts were washed with brine (1×5 mL), dried (Na$_2$SO$_4$), filtered, and concentrated by rotary evaporation. Purification by silica flash chromatography (70% EtOAc/hexanes) yielded Tan002—O12 as a white foam (191 mg, 77%).

TLC: R$_f$ 0.22 (70% EtOAc/hexanes). [α]$_D^{20}$: +30.5° (c 1.0, CHCl$_3$). IR (ATR): 3410, 2982, 1737, 1577, 1456, 1429, 1394, 1370, 1229, 1051, 756. $^1$H-NMR (600 MHz): δ 7.97 (s, 1H), 7.72 (d, J=6.9 Hz, 2H), 7.48 (t, J=7.3 Hz, 2H), 7.46-7.42 (m, 1H), 5.74-5.62 (m, 1H), 5.20 (d, J=15.7 Hz, 1H), 4.51 (dq, J=10.8, 7.1 Hz, 1H), 4.44 (dq, J=10.8, 7.1 Hz, 1H), 4.13 (d, J=15.5 Hz, 1H), 3.58-3.46 (m, 1H), 3.45-3.31 (m, 1H), 1.75-1.67 (m, 1H), 1.65-1.55 (m, 1H), 1.43 (t, J=7.1 Hz, 3H), 1.30 (s, 9H), 1.08 (s, 1H). $^{13}$C-NMR (151 MHz): δ 165.1, 153.9, 151.0, 147.8, 138.5, 138.0, 129.3, 128.8, 128.5, 118.1, 68.9, 62.0, 58.6, 58.3, 45.8, 37.3, 23.7, 14.3. HRMS m/z calcd for C$_{22}$H$_{28}$N$_2$O$_4$SNa ([M+Na]$^+$) 439.1667; found 439.1660.

Ethyl (R)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxylate was prepared according to literature procedure: Bauer, R. A.; DiBlasi, C. M.; Tan, D. S. Org. Lett. 2010, 12, 2084-2087.

Preparation of Compound 247

(R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide

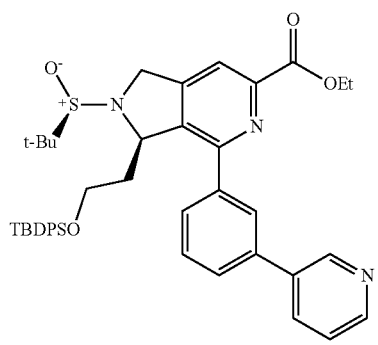

182

-continued

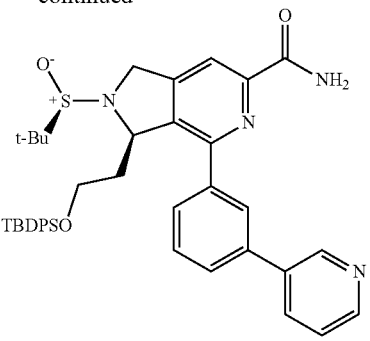

In a 4 mL vial, ethyl (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxylate (38 mg, 0.0519 mmol, 1.0 equiv) was dissolved in 0.13 mL THF and 0.13 mL MeOH at room temperature. Aq. NH$_3$ (~30% solution, 0.26 mL, 5.19 mmol, 100 equiv) was added and the mixture was stirred at room temperature for 18 h, then diluted with 1 mL EtOAc and 1 mL sat. aq. NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (1% NEt$_3$/EtOAc) yielded (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide as a light yellow foam (31 mg, 84%).

TLC: R$_f$ 0.32 (5% MeOH/EtOAc). [α]$_D^{21}$: +73.9° (c 1.0, CHCl$_3$). IR (ATR): 3400, 3224, 3070, 2958, 2958, 2931, 2858, 1690, 1646, 1574, 1471, 1382, 1111, 1087, 943, 756, 703. $^1$H-NMR (600 MHz): δ 8.89 (s, 1H), 8.64 (s, 1H), 8.08 (s, 1H), 7.90 (s, 1H), 7.87 (dq, J=3.9, 2.0 Hz, 2H), 7.71 (d, J=7.6 Hz, 1H), 7.67 (d, J=7.8 Hz, 1H), 7.47-7.35 (m, 8H), 7.30-7.28 (m, 1H), 7.27-7.24 (m, 2H), 5.85 (d, J=4.6 Hz, 1H), 5.82-5.75 (m, 1H), 5.19 (d, J=15.8 Hz, 1H), 4.02 (d, J=15.5 Hz, 1H), 3.66 (ddd, J=10.4, 8.3, 5.0 Hz, 1H), 3.49 (dt, J=10.5, 5.1 Hz, 1H), 1.83-1.70 (m, 1H), 1.67-1.52 (m, 1H), 1.22 (s, 9H), 0.92 (s, 9H). $^{13}$C NMR (151 MHz): δ 166.3, 151.9, 151.7, 148.8, 148.8, 148.3, 139.5, 138.8, 138.4, 136.0, 135.4, 135.3, 134.5, 133.3, 133.2, 129.7, 129.6, 129.5, 127.7, 127.6, 127.6, 127.2, 123.6, 115.8, 68.6, 59.4, 58.5, 45.8, 37.7, 26.7, 23.7, 19.0; 1 C not observed. HRMS m/z calcd for C$_{41}$H$_{47}$N$_4$O$_3$SSi ([M+H]$^+$) 703.3138; found 703.3160.

(R)-2-((R)-tert-butylsulfinyl)-3-(2-hydroxyethyl)-4-(3-(pyridin-3-yl)phenyl)-2,3-dihydro-1H-pyrrolo[3,4-c]pyridine-6-carboxamide (Compound 247)

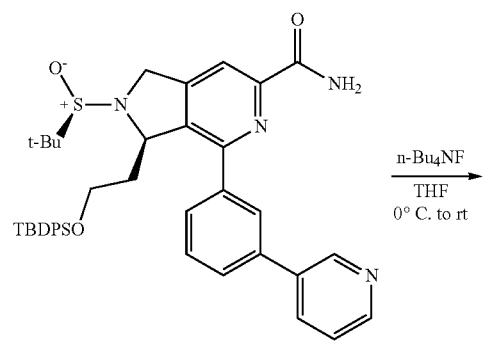

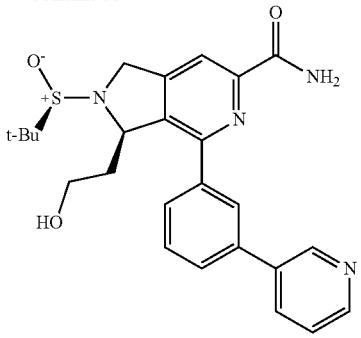

In a small vial, (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide (30 mg, 0.0427 mmol, 1.0 equiv) was dissolved in 0.43 mL of THF and cooled to 0° C. n-Bu$_4$NF solution (1.0 M in THF, 64 μL, 0.064 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (4% MeOH/EtOAc) yielded the compound 247 as a light yellow solid (16 mg, 79%). TLC: R$_f$ 0.08 (5% MeOH/EtOAc). [α]$_D^{20}$: −18.1° (c 0.48, CHCl$_3$). IR (ATR): 3443, 3297, 3053, 2958, 1682, 1574, 1455, 1390, 1266, 1048, 945, 753, 703. $^1$H-NMR (600 MHz): δ 8.88 (s, 1H), 8.59 (d, J=4.1 Hz, 1H), 8.07 (s, 1H), 7.95 (dt, J=8.0, 1.9 Hz, 1H), 7.91 (s, 1H), 7.88 (d, J=4.4 Hz, 1H), 7.75 (d, J=7.6 Hz, 1H), 7.66 (d, J=7.8 Hz, 1H), 7.60 (t, J=7.6 Hz, 1H), 7.39 (dd, J=7.9, 4.8 Hz, 1H), 5.90 (d, J=4.1 Hz, 1H), 5.83-5.70 (m, 1H), 5.21 (d, J=15.7 Hz, 1H), 4.15 (d, J=14.9 Hz, 1H), 3.60 (ddd, J=10.7, 8.0, 5.8 Hz, 1H), 3.45 (ddd, J=11.0, 6.5, 4.9 Hz, 1H), 1.85-1.72 (m, 1H), 1.72-1.59 (m, 1H), 1.30 (s, 9H). $^{13}$C-NMR (151 MHz): δ 166.2, 151.9, 151.7, 149.0, 148.7, 148.2, 139.2, 138.4, 137.9, 136.0, 134.6, 129.5, 128.0, 127.9, 127.0, 123.7, 115.8, 68.7, 58.5, 58.2, 45.9, 37.6, 23.8. HRMS m/z calcd for C$_{25}$H$_{29}$N$_4$O$_3$S ([M+H]$^+$) 465.1960; found 465.1959.

Preparation of Compound 237

(R)-3-(2-((tert-butyldiphenylsilyl)oxy)ethyl)-2-((R)-tert-butylsulfinyl)-4-(3-(pyridin-3-yl)phenyl)-N-(2,2,2-trifluoroethyl)-2,3-dihydro-1H-pyrrolo[3,4-c]pyridine-6-carboxamide To a vial containing ethyl (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxylate (34 mg, 0.0464 mmol, 1.0 equiv, azeotroped 3× with toluene) at room temperature was slowly added a pre-stirred (>2 h) stock solution of dimethylaluminum 2,2,2-trifluoroethylamide (0.2 M solution in CH$_2$Cl$_2$/toluene, 0.46 mL, 0.0929 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (50% EtOAc/hexanes) yielded (R)-3-(2-((tert-butyldiphenylsilyl)oxy)ethyl)-2-((R)-tert-butylsulfinyl)-4-(3-(pyridin-3-yl)phenyl)-N-(2,2,2-trifluoroethyl)-2,3-dihydro-1H-pyrrolo[3,4-c]pyridine-6-carboxamide as a sticky yellow foam (30 mg, 82%).TLC: R$_f$ 0.44 (50% EtOAc/CH$_2$Cl$_2$). [α]$_D^{20}$: +56.8° (c 1.0, CHCl$_3$). IR (ATR): 3331, 3071, 2956, 2931, 2859, 1687, 1523, 1273, 1162, 1076, 740, 705. $^1$H-NMR (600 MHz): δ 8.89 (s, 1H), 8.65 (s, 1H), 8.36 (t, J=6.8 Hz, 1H), 8.08 (s, 1H), 7.91-7.82 (m, 2H), 7.75-7.64 (m, 2H), 7.48 (t, J=7.7 Hz, 1H), 7.44-7.33 (m, 7H), 7.29-7.27 (m, 3H), 7.26-7.24 (m, 1H), 5.76 (ddd, J=7.7, 3.4, 1.8 Hz, 1H), 5.19 (d, J=15.9 Hz, 1H), 4.37-4.15 (m, 1H), 4.06-3.90 (m, 2H), 3.64 (ddd, J=10.4, 8.2, 5.0 Hz, 1H), 3.49 (dt, J=10.6, 5.4 Hz, 1H), 1.84-1.72 (m, 1H), 1.62-1.48 (m, 1H), 1.22 (s, 9H), 0.91 (s, 9H). $^{13}$C-NMR (151 MHz): δ 164.2, 152.1, 151.9, 148.9, 148.3, 148.0, 139.3, 138.5, 135.9, 135.4, 135.3, 134.4, 133.3, 133.1, 129.7, 129.7, 129.7, 127.9, 127.8, 127.6, 127.1, 124.1 (q, J=278.7 Hz), 123.7, 116.0, 68.6, 59.4, 58.5, 45.9, 40.8 (q, J=34.9 Hz), 37.6, 26.7, 23.7, 19.0; 2 C not observed. HRMS m/z calcd for C$_{43}$H$_{48}$F$_3$N$_4$O$_3$SSi ([M+H]$^+$) 785.3169; found 785.3158.

(R)-2-((R)-tert-butylsulfinyl)-3-(2-hydroxyethyl)-4-(3-(pyridin-3-yl)phenyl)-N-(2,2,2-trifluoroethyl)-2,3-dihydro-1H-pyrrolo[3,4-c]pyridine-6-carboxamide (Compound 237)

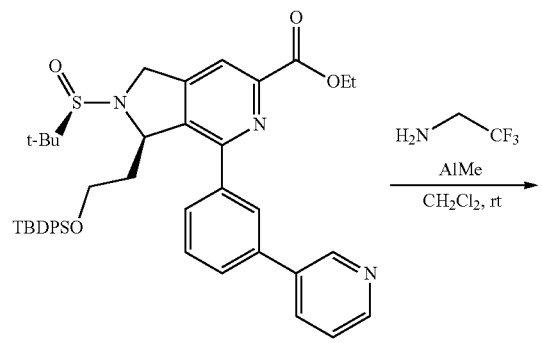

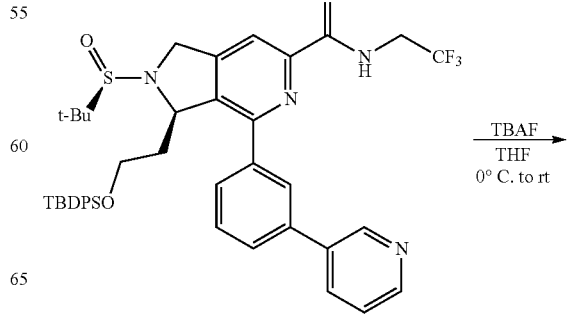

TBAF
THF
0° C. to rt

185

-continued

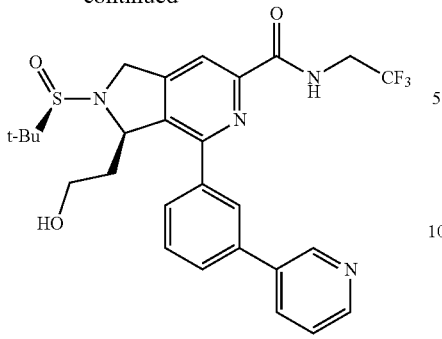

In a small vial, (R)-3-(2-((tert-butyldiphenylsilyl)oxy)ethyl)-2-((R)-tert-butylsulfinyl)-4-(3-(pyridin-3-yl)phenyl)-N-(2,2,2-trifluoroethyl)-2,3-dihydro-1H-pyrrolo[3,4-c]pyridine-6-carboxamide (29 mg, 0.0369 mmol, 1.0 equiv) was dissolved in 0.37 mL of THF and cooled to 0° C. n-Bu$_4$NF solution (1.0 M in THF, 55 μL, 0.0554 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (1% MeOH/EtOAc) yielded compound 237 as a light yellow solid (10 mg, 50%). TLC: R$_f$ 0.06 (5% MeOH/CH$_2$Cl$_2$). [α]$_D^{20}$: +59.0° (c 1.0, CHCl$_3$). IR (ATR): 3389, 2957, 2926, 2872, 1682, 1576, 1524, 1475, 1422, 1392, 1272, 1159, 1056, 755, 712. $^1$H-NMR (600 MHz): δ 8.91 (s, 1H), 8.63 (d, J=4.8 Hz, 1H), 8.38 (t, J=6.8 Hz, 1H), 8.10 (s, 1H), 7.95 (d, J=8.0 Hz, 1H), 7.90 (s, 1H), 7.75 (d, J=7.5 Hz, 1H), 7.70 (d, J=7.7 Hz, 1H), 7.64 (t, J=7.6 Hz, 1H), 7.41 (dd, J=7.9, 4.8 Hz, 1H), 5.75 (d, J=7.0 Hz, 1H), 5.23 (d, J=15.8 Hz, 1H), 4.23 (dq, J=15.8, 8.3, 7.7 Hz, 1H), 4.16 (d, J=15.6 Hz, 1H), 4.02 (ddd, J=15.1, 8.9, 6.3 Hz, 1H), 3.61 (ddd, J=10.6, 8.1, 5.6 Hz, 1H), 3.47 (ddd, J=10.9, 6.3, 4.9 Hz, 1H), 1.86-1.67 (m, 1H), 1.70-1.59 (m, 1H), 1.31 (s, 9H). $^{13}$C-NMR (151 MHz): δ 164.2, 152.1, 151.9, 148.8, 148.3, 148.3, 139.1, 138.5, 138.5, 135.9, 134.6, 129.7, 128.1, 128.0, 127.0, 124.1 (q, J=278.6 Hz), 123.7, 116.0, 68.7, 58.5, 58.3, 45.9, 40.8 (q, J=34.9 Hz), 37.6, 23.8. HRMS m/z calcd for C$_{27}$H$_{30}$F$_3$N$_4$O$_3$S ([M+H]+) 547.1991; found 547.1979.

Preparation of Compound 264

(R)—N-(benzo[d][1,3]dioxol-5-ylmethyl)-3-(2-hydroxyethyl)-4-(3-(pyridin-3-yl)phenyl)-2,3-dihydro-1H-pyrrolo[3,4-c]pyridine-6-carboxamide (Compound 264)

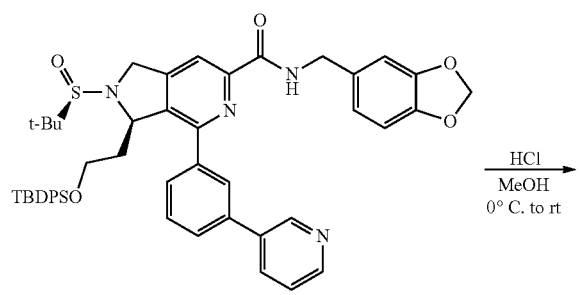

186

-continued

In a small vial, (R)—N-(benzo[d][1,3]dioxol-5-ylmethyl)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxamide (26 mg, 0.0311 mmol, 1.0 equiv) was dissolved in 0.31 mL of anhyd MeOH and cooled to 0° C. HCl solution (4.0 M in dioxane, 31 μL, 0.124 mmol, 4 equiv) was added dropwise and the mixture was stirred at 0° C. for 5 min, then allowed to warm to room temperature and stirred for 10 h. The reaction was quenched by addition of sat. aq. NaHCO$_3$ and then diluted with EtOAc. The aqueous layer was extracted with EtOAc (3×1 mL), then the combined organic layers were dried (Na$_2$SO$_4$), filtered, and concentrated by rotary evaporation. Purification by silica flash chromatography (10% MeOH/CH$_2$Cl$_2$) yielded compound 264 as a light yellow film (7 mg, 46%). TLC: R$_f$ 0.08 (5% MeOH/CH$_2$Cl$_2$). [α]$_D^{20}$: −88.9° (c 0.22, CHCl$_3$). IR (ATR): 3378, 3053, 2893, 1664, 1524, 1490, 1444, 1253, 1039, 928, 802, 736, 712. $^1$H-NMR (600 MHz): δ 8.88 (d, J=2.4 Hz, 1H), 8.63 (dd, J=4.9, 1.6 Hz, 1H), 8.37 (t, J=6.2 Hz, 1H), 8.18 (s, 1H), 7.90 (dt, J=8.0, 2.0 Hz, 1H), 7.84 (s, 1H), 7.74-7.63 (m, 2H), 7.60 (t, J=7.6 Hz, 1H), 7.40 (dd, J=7.9, 4.8 Hz, 1H), 6.85 (d, J=1.7 Hz, 1H), 6.82 (dd, J=7.9, 1.7 Hz, 1H), 6.75 (d, J=7.9 Hz, 1H), 5.93 (s, 2H), 5.19 (dd, J=9.6, 3.5 Hz, 1H), 4.67-4.53 (m, 2H), 4.40 (d, J=16.2 Hz, 1H), 4.31 (d, J=16.2 Hz, 1H), 3.72 (ddd, J=11.3, 8.8, 2.7 Hz, 1H), 3.61 (ddd, J=10.9, 5.4, 3.2 Hz, 1H), 1.58-1.40 (m, 2H). $^{13}$C-NMR (151 MHz): δ 164.0, 154.3, 151.9, 149.1, 148.9, 148.3, 147.9, 146.9, 141.0, 139.7, 138.5, 136.0, 134.5, 132.1, 129.5, 127.8, 127.7, 126.9, 123.7, 121.0, 115.9, 108.4, 108.3, 101.0, 63.7, 62.0, 50.8, 43.2, 33.7. HRMS m/z calcd for C$_{29}$H$_{27}$N$_4$O$_4$ ([M+H]$^+$) 495.2032; found 495.2035.

Preparation of Compound 265

(R)—N-(2-fluorobenzyl)-3-(2-hydroxyethyl)-4-(3-(pyridin-3-yl)phenyl)-2,3-dihydro-1H-pyrrolo[3,4-c]pyridine-6-carboxamide (Compound 265)

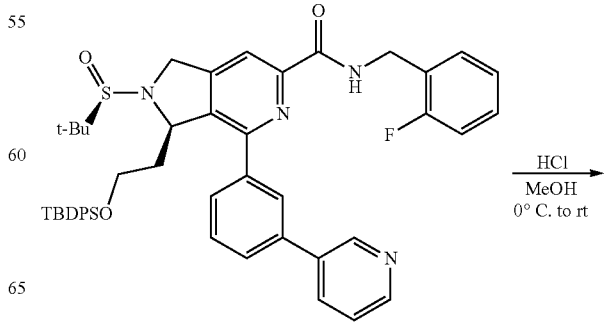

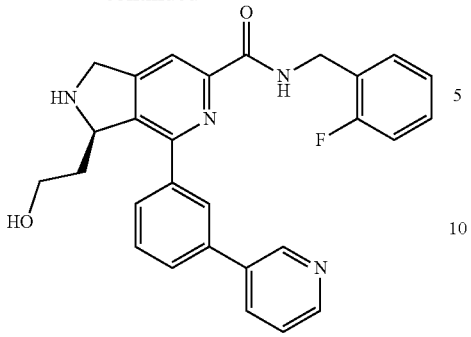

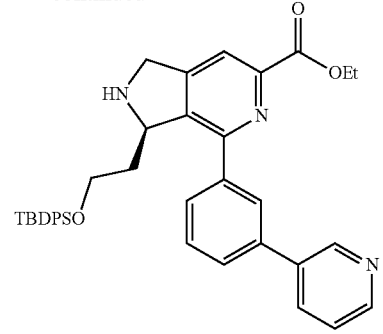

In a small vial, (R)-3-(2-((tert-butyldiphenylsilyl)oxy)ethyl)-2-((R)-tert-butylsulfinyl)-N-(2-fluorobenzyl)-4-(3-(pyridin-3-yl)phenyl)-2,3-dihydro-1H-pyrrolo[3,4-c]pyridine-6-carboxamide (18 mg, 0.0222 mmol, 1.0 equiv) was dissolved in 0.22 mL of anhyd MeOH and cooled to 0° C. HCl solution (4.0 M in dioxane, 22 μL, 0.0888 mmol, 4 equiv) was added dropwise and the mixture was stirred at 0° C. for 5 min, then allowed to warm to room temperature and stirred for 10 h. The reaction was quenched by addition of sat. aq. NaHCO₃ and then diluted with EtOAc. The aqueous layer was extracted with EtOAc (3×1 mL), then the combined organic layers were dried (Na₂SO₄), filtered, and concentrated by rotary evaporation. Purification by silica flash chromatography (10% MeOH/CH₂Cl₂) yielded compound 265 as a light yellow film (5.5 mg, 53%). TLC: $R_f$ 0.08 (5% MeOH/CH₂Cl₂). $[\alpha]_D^{19}$: +17.5° (c 0.53, CHCl₃). IR (ATR): 3377, 3319, 3050, 2918, 2850, 2363, 1668, 1571, 1524, 1491, 1472, 1422, 1266, 1229, 1062, 758, 737, 712. ¹H-NMR (600 MHz): δ 8.90 (d, J=2.2 Hz, 1H), 8.64 (dd, J=4.8, 1.3 Hz, 1H), 8.49 (t, J=6.2 Hz, 1H), 8.17 (s, 1H), 7.92 (dt, J=7.9, 1.9 Hz, 1H), 7.89 (s, 1H), 7.75-7.66 (m, 2H), 7.61 (t, J=7.7 Hz, 1H), 7.47-7.37 (m, 2H), 7.26-7.23 (m, 1H), 7.10 (t, J=7.5 Hz, 1H), 7.08-7.03 (m, 1H), 5.21 (dd, J=9.7, 3.4 Hz, 1H), 4.82-4.69 (m, 2H), 4.39 (d, J=16.2 Hz, 1H), 4.30 (d, J=16.2 Hz, 1H), 3.73 (ddd, J=11.3, 8.9, 2.5 Hz, 1H), 3.62 (ddd, J=10.9, 5.5, 3.2 Hz, 1H), 1.60-1.42 (m, 2H). ¹³C-NMR (151 MHz): δ 164.1, 161.0 (d, J=246.2 Hz), 154.4, 151.8, 149.0, 148.9, 148.3, 141.0, 139.6, 138.5, 136.0, 134.5, 130.0 (d, J=4.2 Hz), 129.6, 129.2 (d, J=8.1 Hz), 127.8, 127.6, 127.0, 125.2 (d, J=14.7 Hz), 124.3 (d, J=3.6 Hz), 123.7, 115.8, 115.4 (d, J=21.2 Hz), 63.8, 62.0, 50.7, 37.5 (d, J=4.0 Hz), 33.7. HRMS m/z calcd for C₂₈H₂₆FN₄O₄ ([M+H]⁺) 469.2040; found 469.2053.

Preparation of Compound 253

Ethyl (R)-3-(2-((tert-butyldiphenylsilyl)oxy)ethyl)-4-(3-(pyridin-3-yl)phenyl)-2,3-dihydro-1H-pyrrolo[3,4-c]pyridine-6-carboxylate In a vial, ethyl (R)-3-(2-((tert-butyldiphenylsilyl)oxy)ethyl)-2-((R)-tert-butylsulfinyl)-4-(3-(pyridin-3-yl)phenyl)-2,3-dihydro-1H-pyrrolo[3,4-c]pyridine-6-carboxylate (303 mg, 0.414 mmol, 1.0 equiv) was dissolved in 4.1 mL of anhyd MeOH and cooled to 0° C. HCl solution (4.0 M in dioxane, 124 μL, 0.497 mmol, 1.2 equiv) was added dropwise and the mixture was stirred at 0° C. for 2 h. The reaction was quenched by addition of sat. aq. NaHCO₃ and then diluted with EtOAc. The aqueous layer was extracted with EtOAc (3×10 mL), then the combined organic layers were dried (Na₂SO₄), filtered, and concentrated by rotary evaporation. Purification by silica flash chromatography (100% EtOAc→1% MeOH/EtOAc) yielded ethyl (R)-3-(2-((tert-butyldiphenylsilyl)oxy)ethyl)-4-(3-(pyridin-3-yl)phenyl)-2,3-dihydro-1H-pyrrolo[3,4-c]pyridine-6-carboxylate as a light yellow foam (225 mg, 86%). TLC: $R_f$ 0.53 (5% MeOH/CH₂Cl₂). $[\alpha]_D^{21}$: +138.3° (c 1.0, CHCl₃). IR (ATR): 3049, 2957, 2932, 2857, 1737, 1716, 1572, 1472, 1268, 1224, 1109, 739, 704. ¹H-NMR (600 MHz): δ 8.87 (s, 1H), 8.60 (d, J=4.8 Hz, 1H), 8.02 (s, 1H), 7.95 (s, 1H), 7.88 (d, J=7.9 Hz, 1H), 7.69 (d, J=7.7 Hz, 1H), 7.61 (d, J=7.8 Hz, 1H), 7.56-7.49 (m, 4H), 7.47 (t, J=7.7 Hz, 1H), 7.43-7.37 (m, 2H), 7.37-7.29 (m, 5H), 5.21 (d, J=9.3 Hz, 1H), 4.53 (dq, J=10.8, 7.1 Hz, 1H), 4.45 (dq, J=10.8, 7.1 Hz, 1H), 4.34-4.26 (m, 2H), 3.74-3.64 (m, 1H), 3.64-3.54 (m, 1H), 1.80-1.65 (m, 1H), 1.45 (t, J=7.1 Hz, 3H), 1.41-1.31 (m, 1H), 0.99 (s, 9H). ¹³C-NMR (151 MHz): δ 165.4, 154.0, 153.7, 148.6, 148.3, 147.3, 142.1, 139.9, 138.3, 136.2, 135.4, 135.4, 134.5, 133.2, 133.2, 129.7, 129.7, 129.3, 127.9, 127.7, 127.6, 127.6, 127.5, 123.5, 118.4, 61.9, 61.4, 60.9, 51.1, 35.4, 26.9, 26.8, 19.1, 14.34. HRMS m/z calcd for C₃₉H₄₂N₃O₃Si ([M+H]⁺) 628.2995; found 628.2974.

Ethyl (R)-3-(2-((tert-butyldiphenylsilyl)oxy)ethyl)-2-(isopropylcarbamoyl)-4-(3-(pyridin-3-yl)phenyl)-2,3-dihydro-1H-pyrrolo[3,4-c]pyridine-6-carboxylate

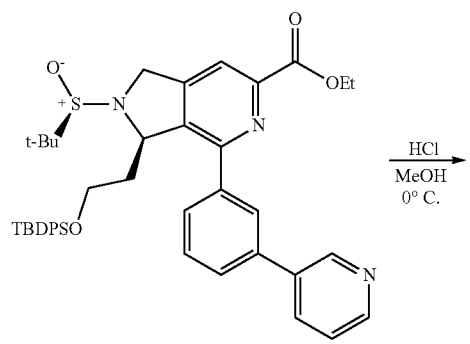

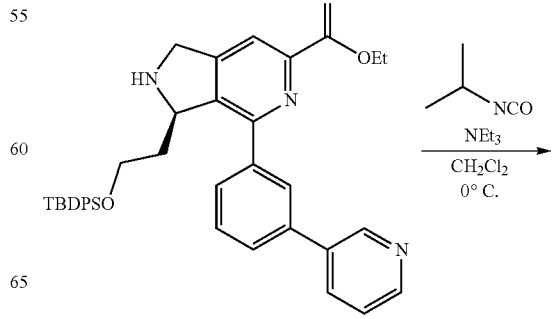

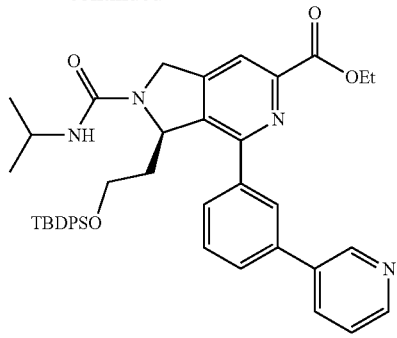

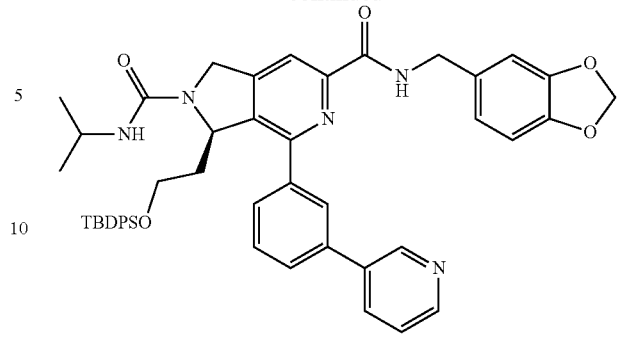

In a vial, ethyl (R)-3-(2-((tert-butyldiphenylsilyl)oxy) ethyl)-4-(3-(pyridin-3-yl)phenyl)-2,3-dihydro-1H-pyrrolo [3,4-c]pyridine-6-carboxylate (218 mg, 0.347 mmol, 1.0 equiv) was dissolved in 3.7 mL of $CH_2Cl_2$ and cooled to 0° C. $NEt_3$ (73 μL, 0.521 mmol, 1.5 equiv) was added, followed by 2-isocyanatopropane (38 μL, 0.382 mmol, 1.2 equiv), and the mixture was stirred at 0° C. for 1 hour. The reaction mixture was quenched by addition of 2 mL saturated aqueous $NaHCO_3$, then the aqueous layer was extracted with $CH_2Cl_2$ (3×3 mL). The combined organic extracts were washed with brine (1×3 mL), dried ($Na_2SO_4$), filtered, and concentrated by rotary evaporation. Purification by silica flash chromatography yielded ethyl (R)-3-(2-((tert-butyldiphenylsilyl)oxy)ethyl)-2-(isopropylcarbamoyl)-4-(3-(pyridin-3-yl)phenyl)-2,3-dihydro-1H-pyrrolo[3,4-c]pyridine-6-carboxylate as an white solid film (214 mg, 86%).TLC: $R_f$ 0.21 (80% EtOAc/$CH_2Cl_2$). $[α]_D^{21}$: +100.8° (c 1.0, $CHCl_3$). IR (ATR): 3369, 3071, 2967, 2932, 2858, 1724, 1638, 1579, 1530, 1371, 1233, 1108, 756, 704. $^1$H-NMR (600 MHz): δ 8.89 (d, J=2.3 Hz, 1H), 8.63 (dd, J=4.8, 1.6 Hz, 1H), 8.00 (s, 1H), 7.96 (s, 1H), 7.90 (dt, J=7.9, 1.8 Hz, 1H), 7.70 (d, J=7.7 Hz, 1H), 7.64 (d, J=7.9 Hz, 1H), 7.43-7.31 (m, 9H), 7.29-7.27 (m, 1H), 7.22 (t, J=7.6 Hz, 2H), 5.85 (s, 1H), 5.10 (d, J=14.8 Hz, 1H), 4.53 (dq, J=10.8, 7.1 Hz, 1H), 4.50-4.40 (m, 2H), 4.17-3.95 (m, 1H), 3.66-3.58 (m, 1H), 3.53 (dt, J=10.8, 4.9 Hz, 1H), 2.04-1.88 (m, 1H), 1.45 (t, J=7.1 Hz, 3H), 1.42-1.34 (m, 1H), 1.16 (d, J=6.6 Hz, 6H), 0.89 (s, 9H). $^{13}$C-NMR (151 MHz): δ 165.1, 156.4, 153.6, 149.2, 148.7, 148.3, 147.7, 139.6, 139.0, 138.6, 136.1, 135.3, 135.3, 134.6, 133.1, 133.0, 129.8, 129.7, 129.6, 127.8, 127.7, 127.6, 127.6, 127.6, 123.6, 118.2, 62.0, 60.2, 59.6, 50.9, 42.7, 27.0, 23.4, 23.3, 19.1, 14.3. HRMS m/z calcd for $C_{43}H_{49}N_4O_4Si$ ([M+H]$^+$) 713.3523; found 713.3540.

(R)—N$^6$-(benzo[d][1,3]dioxol-5-ylmethyl)-3-(2-((tert-butyldiphenylsilyl)oxy)ethyl)-N$^2$-isopropyl-4-(3-(pyridin-3-yl)phenyl)-1,3-dihydro-2H-pyrrolo[3,4-c]pyridine-2,6-dicarboxamide To a vial containing ethyl (R)-3-(2-((tert-butyldiphenylsilyl)oxy)ethyl)-2-(isopropylcarbamoyl)-4-(3-(pyridin-3-yl)phenyl)-2,3-dihydro-1H-pyrrolo[3,4-c]pyridine-6-carboxylate (82 mg, 0.115 mmol, 1.0 equiv, azeotroped 3× with toluene) at room temperature was slowly added a pre-stirred (>2 h) stock solution of dimethylaluminum piperonylamide (0.2 M solution in $CH_2Cl_2$/toluene, 1.15 mL, 0.230 mmol, 2.0 equiv). The mixture was stirred at room temperature for 15 h, then carefully quenched by addition of a few drops of MeOH followed by dilution with 1 mL of $CH_2Cl_2$ and careful addition of 1 mL saturated aqueous $NaHCO_3$. The aqueous layer was extracted with EtOAc (3×1 mL), then the combined organic layers were dried ($Na_2SO_4$), filtered, and concentrated by rotary evaporation. Purification by silica flash chromatography (70% EtOAc/$CH_2Cl_2$→100% EtOAc) yielded (R)—N$^6$-(benzo[d][1,3]dioxol-5-ylmethyl)-3-(2-((tert-butyldiphenylsilyl)oxy)ethyl)-N$^2$-isopropyl-4-(3-(pyridin-3-yl)phenyl)-1,3-dihydro-2H-pyrrolo[3,4-c]pyridine-2,6-dicarboxamide as a sticky yellow foam (49 mg, 52%). TLC: $R_f$ 0.24 (80% EtOAc/$CH_2Cl_2$). $[α]_D^{19}$: +94.1° (c 1.0, $CHCl_3$). IR (ATR): 3367, 3050, 2963, 2931, 2858, 1642, 1521, 1445, 1378, 1252, 1110, 1040, 938, 735, 702. $^1$H-NMR (600 MHz): δ 8.86 (s, 1H), 8.64 (d, J=4.2 Hz, 1H), 8.35 (t, J=6.1 Hz, 1H), 8.13 (s, 1H), 7.89-7.77 (m, 2H), 7.71-7.61 (m, 2H), 7.46 (t, J=7.6 Hz, 1H), 7.43-7.29 (m, 7H), 7.26-7.23 (m, 2H), 7.21 (t, J=7.5 Hz, 2H), 6.86 (d, J=1.7 Hz, 1H), 6.82 (dd, J=7.9, 1.6 Hz, 1H), 6.75 (d, J=7.9 Hz, 1H), 5.88-5.82 (m, 1H), 5.01 (d, J=15.3 Hz, 1H), 4.72-4.53 (m, 3H), 4.48 (dd, J=15.2, 2.4 Hz, 1H), 4.04 (dq, J=13.5, 6.7 Hz, 1H), 3.60-3.45 (m, 2H), 2.08-1.95 (m, 1H), 1.52-1.40 (m, 1H), 1.16 (d, J=6.6 Hz, 8H), 0.86 (s, 9H). $^{13}$C-NMR (151 MHz): δ 163.8, 156.1, 152.1, 149.5, 149.1, 148.9, 148.3, 147.9, 146.9, 139.6, 138.5, 138.3, 135.9, 135.3, 135.2, 134.5, 133.1, 133.1, 132.1, 129.7, 129.7, 129.6, 127.8, 127.6, 127.6, 127.6, 127.1, 123.7, 121.0, 115.7, 108.4, 108.3, 101.0, 60.2, 59.7, 51.1, 43.2, 42.6, 26.9, 23.5, 23.4, 19.0. HRMS m/z calcd for $C_{49}H_{52}N_5O_5Si$ ([M+H]$^+$) 818.3738; found 818.3715.

(R)—N$^6$-(benzo[d][1,3]dioxol-5-ylmethyl)-3-(2-hydroxyethyl)-N$^2$-isopropyl-4-(3-(pyridin-3-yl)phenyl)-1,3-dihydro-2H-pyrrolo[3,4-c]pyridine-2,6-dicarboxamide (Compound 253)

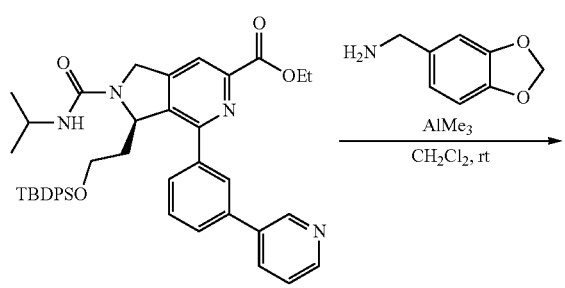

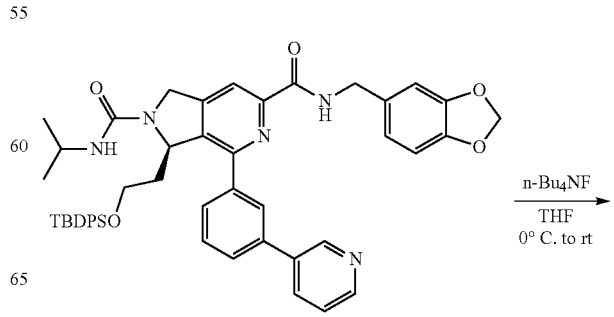

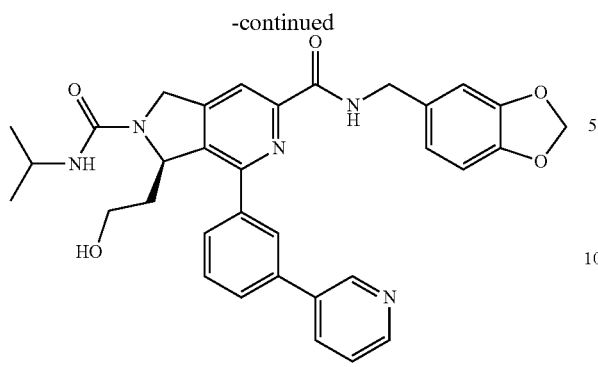

In a small vial, (R)—N[6]-(benzo[d][1,3]dioxol-5-ylmethyl)-3-(2-((tert-butyldiphenylsilyl)oxy)ethyl)-N[2]-isopropyl-4-(3-(pyridin-3-yl)phenyl)-1,3-dihydro-2H-pyrrolo[3,4-c]pyridine-2,6-dicarboxamide (39 mg, 0.0477 mmol, 1.0 equiv) was dissolved in 0.48 mL of THF and cooled to 0° C. n-Bu$_4$NF solution (1.0 M in THF, 72 μL, 0.0715 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (3% MeOH/EtOAc) yielded compound 253 as a light yellow solid (18 mg, 66%). TLC: R$_f$ 0.21 (3% MeOH/EtOAc). $[\alpha]_D^{20}$: +116.9° (c 1.0, CHCl$_3$). IR (ATR): 3308, 3052, 2970, 2930, 2877, 1663, 1629, 1524, 1444, 1380, 1252, 1238, 1186, 1038, 735, 712. $^1$H-NMR (600 MHz): δ 8.88 (s, 1H), 8.61 (d, J=4.1 Hz, 1H), 8.39 (t, J=6.1 Hz, 1H), 8.15 (s, 1H), 7.99 (dt, J=7.9, 1.7 Hz, 1H), 7.90 (s, 1H), 7.77 (d, J=7.5 Hz, 1H), 7.67 (d, J=7.8 Hz, 1H), 7.63 (t, J=7.6 Hz, 1H), 7.39 (dd, J=7.8, 4.8 Hz, 1H), 6.85 (s, 1H), 6.82 (d, J=8.0 Hz, 1H), 6.75 (d, J=7.9 Hz, 1H), 6.06 (d, J=10.1 Hz, 1H), 5.93 (d, J=1.4 Hz, 2H), 4.89 (d, J=14.6 Hz, 1H), 4.78-4.51 (m, 4H), 4.06 (h, J=6.7 Hz, 1H), 3.65-3.48 (m, 1H), 3.44 (d, J=11.9 Hz, 1H), 1.92-1.75 (m, 1H), 1.27-1.10 (m, 7H). $^{13}$C-NMR (151 MHz): δ 163.8, 157.4, 152.0, 149.3, 148.8, 148.6, 148.3, 147.9, 146.9, 138.9, 138.7, 138.6, 136.1, 134.8, 132.0, 129.7, 128.2, 127.9, 127.0, 123.7, 121.0, 115.6, 108.3, 108.3, 101.0, 59.1, 58.4, 51.0, 43.3, 43.0, 37.8, 23.4, 23.3. HRMS m/z calcd for C$_{33}$H$_{34}$N$_5$O$_5$ ([M+H]$^+$) 580.2560; found 580.2545.

Preparation of Compound 254

(R)-3-(2-((tert-butyldiphenylsilyl)oxy)ethyl)-N[6]-(2-fluorobenzyl)-N[2]-isopropyl-4-(3-(pyridin-3-yl)phenyl)-1,3-dihydro-2H-pyrrolo[3,4-c]pyridine-2,6-dicarboxamide

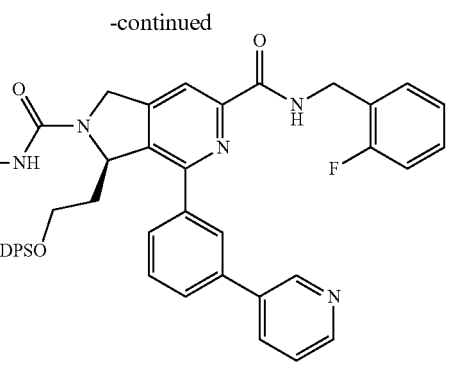

To a vial containing ethyl (R)-3-(2-((tert-butyldiphenylsilyl)oxy)ethyl)-2-(isopropylcarbamoyl)-4-(3-(pyridin-3-yl)phenyl)-2,3-dihydro-1H-pyrrolo[3,4-c]pyridine-6-carboxylate (82 mg, 0.115 mmol, 1.0 equiv, azeotroped 3× with toluene) at room temperature was slowly added a pre-stirred (>2 h) stock solution of dimethylaluminum (2-fluorobenzyl) amide (0.2 M solution in CH$_2$Cl$_2$/toluene, 1.15 mL, 0.230 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (70% EtOAc/CH$_2$Cl$_2$→100% EtOAc) yielded (R)-3-(2-((tert-butyldiphenylsilyl)oxy)ethyl)-N[6]-(2-fluorobenzyl)-N[2]-isopropyl-4-(3-(pyridin-3-yl)phenyl)-1,3-dihydro-2H-pyrrolo[3,4-c]pyridine-2,6-dicarboxamide as a sticky yellow foam (47 mg, 52%). TLC: R$_f$ 0.26 (80% EtOAc/CH$_2$Cl$_2$). $[\alpha]_D^{19}$: +83.2° (c 1.0, CHCl$_3$). IR (ATR): 3381, 3071, 3050, 2965, 2930, 2854, 1669, 1638, 1577, 1521, 1457, 1427, 1380, 1265, 1178, 1109, 1058, 894, 735, 702. $^1$H-NMR (600 MHz): δ 8.89 (s, 1H), 8.65 (s, 1H), 8.48 (t, J=6.0 Hz, 1H), 8.11 (s, 1H), 7.90-7.83 (m, 2H), 7.68 (d, J=7.8 Hz, 2H), 7.51-7.37 (m, 5H), 7.36-7.27 (m, 4H), 7.26-7.23 (m, 3H), 7.19 (t, J=7.5 Hz, 2H), 7.12-7.03 (m, 2H), 5.88 (s, 1H), 5.00 (d, J=15.4 Hz, 1H), 4.77 (dd, J=15.1, 6.4 Hz, 1H), 4.71 (dd, J=15.1, 6.2 Hz, 1H), 4.64 (bs, 1H), 4.47 (d, J=15.1 Hz, 1H), 4.09-4.00 (m, 1H), 3.60-3.44 (m, 2H), 2.06-1.94 (m, 1H), 1.52-1.38 (m, 1H), 1.17 (d, J=6.5 Hz, 6H), 0.85 (s, 9H). $^{13}$C-NMR (151 MHz): δ 163.9, 161.0 (d, J=246.2 Hz), 156.1, 152.0, 149.6, 149.0, 148.8, 148.2, 139.5, 138.6, 138.3, 135.9, 135.3, 135.2, 134.5, 133.1, 133.0, 130.1 (d, J=4.3 Hz), 129.7, 129.6, 129.6, 129.3 (d, J=8.1 Hz), 127.8, 127.6, 127.5, 127.2, 125.2 (d, J=14.8 Hz), 124.3 (d, J=3.6 Hz), 123.7, 115.6, 115.4 (d, J=21.2 Hz), 60.1, 59.8, 51.1, 42.6, 37.5 (d, J=4.1 Hz), 29.4, 26.9, 23.5, 23.4, 19.0. HRMS m/z calcd for C$_{48}$H$_{51}$FN$_5$O$_3$Si ([M+H]$^+$) 792.3745; found 792.3755.

(R)—N[6]-(2-fluorobenzyl)-3-(2-hydroxyethyl)-N[2]-isopropyl-4-(3-(pyridin-3-yl)phenyl)-1,3-dihydro-2H-pyrrolo[3,4-c]pyridine-2,6-dicarboxamide (Compound 254)

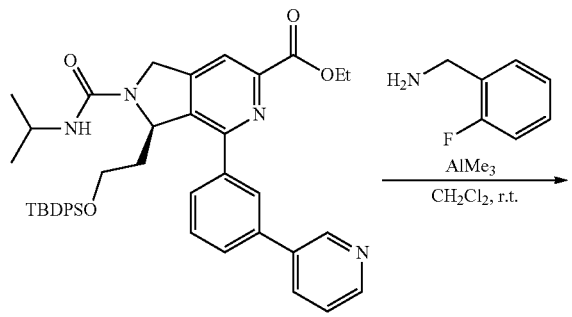

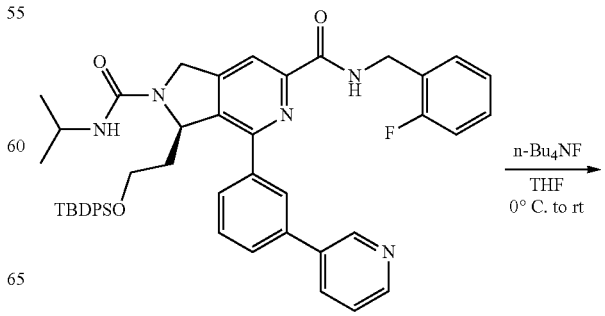

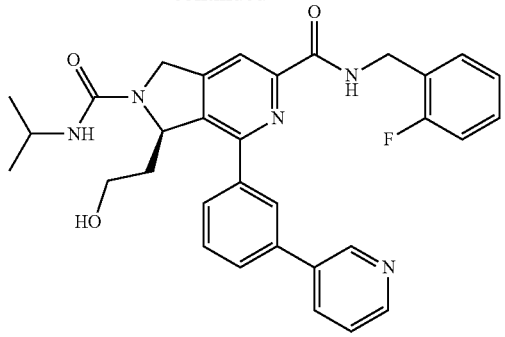

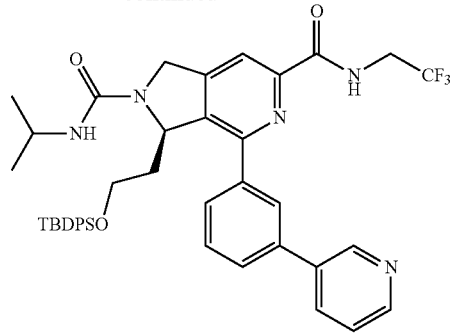

In a small vial, (R)-3-(2-((tert-butyldiphenylsilyl)oxy)ethyl)-N⁶-(2-fluorobenzyl)-N²-isopropyl-4-(3-(pyridin-3-yl)phenyl)-1,3-dihydro-2H-pyrrolo[3,4-c]pyridine-2,6-dicarboxamide (42 mg, 0.0530 mmol, 1.0 equiv) was dissolved in 0.53 mL of THF and cooled to 0° C. n-Bu₄NF solution (1.0 M in THF, 80 µL, 0.0795 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO₃, then the aqueous layer was extracted with EtOAc (3×2 mL). The combined organic extracts were washed with brine (1×1 mL), dried (Na₂SO₄), filtered, and concentrated by rotary evaporation. Purification by silica flash chromatography (3% MeOH/EtOAc) yielded compound 254 as a light yellow solid (21 mg, 70%). TLC: $R_f$ 0.21 (3% MeOH/EtOAc). $[\alpha]_D^{20}$: +119.8° (c 1.0, CHCl₃). IR (ATR): 3319, 3066, 2969, 2874, 1668, 1630, 1525, 1457, 1382, 1292, 1230, 1178, 1058, 758, 713. ¹H-NMR (600 MHz): δ 8.90 (s, 1H), 8.62 (d, J=4.3 Hz, 1H), 8.51 (t, J=6.3 Hz, 1H), 8.13 (s, 1H), 8.01 (d, J=7.9 Hz, 1H), 7.94 (s, 1H), 7.79 (d, J=7.5 Hz, 1H), 7.71-7.66 (m, 1H), 7.64 (t, J=7.6 Hz, 1H), 7.43-7.37 (m, 2H), 7.26-7.23 (m, 1H), 7.10 (t, J=7.5 Hz, 1H), 7.08-7.04 (m, 1H), 6.08 (d, J=10.2 Hz, 1H), 4.89 (d, J=14.6 Hz, 1H), 4.80-4.56 (m, 4H), 4.35 (bs, 1H), 4.05 (dq, J=13.3, 6.6 Hz, 1H), 3.55 (t, J=10.4 Hz, 1H), 3.51-3.38 (m, 1H), 1.91-1.72 (m, 1H), 1.27-1.15 (m, 7H). ¹³C-NMR (151 MHz): δ 163.9, 161.0 (d, J=246.2 Hz), 157.4, 151.9, 149.2, 148.7, 148.7, 148.3, 138.9, 138.7, 138.6, 136.1, 134.8, 130.0 (d, J=4.3 Hz), 129.7, 129.3 (d, J=8.2 Hz), 128.2, 127.8, 127.0, 125.0 (d, J=14.7 Hz), 124.3 (d, J=3.6 Hz), 123.7, 115.5, 115.4 (d, J=20.5 Hz), 59.1, 58.3, 51.0, 43.0, 37.8, 37.5 (d, J=4.0 Hz), 23.4, 23.3. HRMS m/z calcd for C₃₂H₃₃FN₅O₃ ([M+H]⁺) 554.2567; found 554.2559.

Preparation of Compound 255

(R)-3-(2-((tert-butyldiphenylsilyl)oxy)ethyl)-N²-isopropyl-4-(3-(pyridin-3-yl)phenyl)-N⁶-(2,2,2-trifluoroethyl)-1,3-dihydro-2H-pyrrolo[3,4-c]pyridine-2,6-dicarboxamide To a vial containing ethyl (R)-3-(2-((tert-butyldiphenylsilyl)oxy)ethyl)-2-(isopropylcarbamoyl)-4-(3-(pyridin-3-yl)phenyl)-2,3-dihydro-1H-pyrrolo[3,4-c]pyridine-6-carboxylate (41 mg, 0.0575 mmol, 1.0 equiv, azeotroped 3× with toluene) at room temperature was slowly added a pre-stirred (>2 h) stock solution of dimethylaluminum 2,2,2-trifluoroethylamide (0.2 M solution in CH₂Cl₂/toluene, 0.58 mL, 0.115 mmol, 2.0 equiv). The mixture was stirred at room temperature for 15 h, then carefully quenched by addition of a few drops of MeOH followed by dilution with 1 mL of CH₂Cl₂ and careful addition of 1 mL saturated aqueous NaHCO₃. The aqueous layer was extracted with EtOAc (3×1 mL), then the combined organic layers were dried (Na₂SO₄), filtered, and concentrated by rotary evaporation. Purification by silica flash chromatography (70% EtOAc/CH₂Cl₂→100% EtOAc) yielded (R)-3-(2-((tert-butyldiphenylsilyl)oxy)ethyl)-N²-isopropyl-4-(3-(pyridin-3-yl)phenyl)-N⁶-(2,2,2-trifluoroethyl)-1,3-dihydro-2H-pyrrolo[3,4-c]pyridine-2,6-dicarboxamide as a sticky yellow foam (28 mg, 64%). TLC: $R_f$ 0.29 (80% EtOAc/CH₂Cl₂). $[\alpha]_D^{20}$: +89.0° (c 1.0, CHCl₃). IR (ATR): 3367, 3075, 3050, 2963, 2933, 2859, 1684, 1639, 1520, 1382, 1268, 1158, 1110, 736, 702. ¹H-NMR (600 MHz): δ 8.89 (s, 1H), 8.66 (s, 1H), 8.38 (t, J=6.7 Hz, 1H), 8.10 (s, 1H), 7.91-7.83 (m, 2H), 7.69 (dd, J=13.6, 7.8 Hz, 2H), 7.49 (t, J=7.7 Hz, 1H), 7.42-7.29 (m, 7H), 7.28-7.27 (m, 1H), 7.26-7.24 (m, 1H), 7.21 (t, J=7.6 Hz, 2H), 5.88 (s, 1H), 5.02 (d, J=14.7 Hz, 1H), 4.65 (bs, 1H), 4.48 (dd, J=15.3, 2.0 Hz, 1H), 4.31-4.17 (m, 1H), 4.07-3.98 (m, 2H), 3.64-3.43 (m, 2H), 2.03-1.95 (m, 1H), 1.56-1.37 (m, 1H), 1.17 (d, J=6.6 Hz, 6H), 0.86 (s, 9H). ¹³C-NMR (151 MHz): δ 164.2, 156.1, 152.3, 149.8, 148.9, 148.3, 147.9, 139.3, 139.1, 138.6, 135.8, 135.3, 135.2, 135.1, 134.4, 133.1, 133.0, 129.8, 129.7, 128.0, 127.6, 127.6, 127.1, 124.1 (q, J=278.7 Hz), 123.7, 116.0, 60.1, 59.8, 51.1, 42.7, 40.8 (q, J=34.9 Hz), 35.2, 26.9, 23.5, 23.4, 19.0; 1 C not observed. HRMS m/z calcd for C₄₃H₄₇F₃N₅O₃Si ([M+H]⁺) 766.3400; found 766.3396.

(R)-3-(2-hydroxyethyl)-N2-isopropyl-4-(3-(pyridin-3-yl)phenyl)-N6-(2,2,2-trifluoroethyl)-1,3-dihydro-2H-pyrrolo[3,4-c]pyridine-2,6-dicarboxamide (Compound 255)

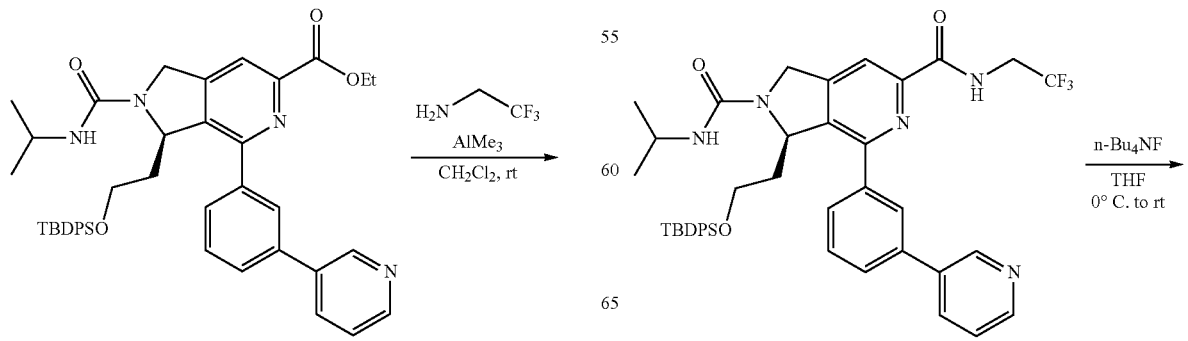

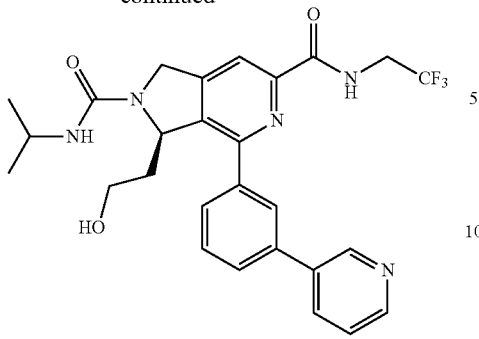

In a small vial, (R)-3-(2-(((tert-butyldiphenylsilyl)oxy)ethyl)-$N^2$-isopropyl-4-(3-(pyridin-3-yl)phenyl)-$N^6$-(2,2,2-trifluoroethyl)-1,3-dihydro-2H-pyrrolo[3,4-c]pyridine-2,6-dicarboxamide (28 mg, 0.0366 mmol, 1.0 equiv) was dissolved in 0.36 mL of THF and cooled to 0° C. n-Bu$_4$NF solution (1.0 M in THF, 55 μL, 0.0548 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (3% MeOH/EtOAc) yielded compound 255 as a light yellow solid (10 mg, 54%).

TLC: R$_f$ 0.21 (3% MeOH/EtOAc). $[\alpha]_D^{20}$: +139.9° (c 1.0, CHCl$_3$). IR (ATR): 3319, 1681, 1631, 1523, 1383, 1273, 1158, 1057, 736. $^1$H-NMR (600 MHz): δ 8.90 (d, J=1.9 Hz, 1H), 8.62 (d, J=3.8 Hz, 1H), 8.42 (t, J=6.7 Hz, 1H), 8.13 (s, 1H), 8.01 (d, J=7.9 Hz, 1H), 7.93 (s, 1H), 7.79 (d, J=7.4 Hz, 1H), 7.72-7.60 (m, 2H), 7.41 (dd, J=7.8, 4.8 Hz, 1H), 6.08 (d, J=10.2 Hz, 1H), 4.92 (d, J=14.6 Hz, 1H), 4.84-4.60 (m, 2H), 4.26-4.14 (m, 2H), 4.14-3.96 (m, 2H), 3.56 (td, J=11.4, 2.6 Hz, 1H), 3.50-3.43 (m, 1H), 1.86-1.76 (m, 1H), 1.26-1.17 (m, 7H). $^{13}$C-NMR (151 MHz): δ 164.2, 157.4, 152.2, 148.9, 148.8, 148.3, 148.1, 139.3, 138.7, 136.0, 134.8, 129.8, 128.3, 127.9, 126.9, 124.0 (q, J=278.7, 278.1 Hz), 123.8, 115.9, 59.1, 58.3, 50.9, 43.0, 40.8 (q, J=35.0 Hz), 37.7, 23.4, 23.3. HRMS m/z calcd for C$_{27}$H$_{29}$F$_3$N$_5$O$_3$ ([M+H]$^+$) 528.2222; found 528.2227.

Preparation of Compound 248

(R)-4-(3-(benzofuran-2-yl)phenyl)-3-(2-((tert-butyldiphenylsilyl)oxy)ethyl)-$N^2$-isopropyl-1,3-dihydro-2H-pyrrolo[3,4-c]pyridine-2,6-dicarboxamide In a 4 mL vial, ethyl (R)-4-(3-(benzofuran-2-yl)phenyl)-3-(2-((tert-butyldiphenylsilyl)oxy)ethyl)-2-(isopropylcarbamoyl)-2,3-dihydro-1H-pyrrolo[3,4-c]pyridine-6-carboxylate (23 mg, 0.0310 mmol, 1.0 equiv) was dissolved in 0.15 mL 1:1 THF/MeOH at room temperature. Aq. NH$_3$ (~30% solution, 0.15 mL, 8.01 mmol, 250 equiv) was added and the mixture was stirred at room temperature for 12 h, then diluted with 1 mL EtOAc and 1 mL sat. aq. NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (70% EtOAc/hexanes) yielded (R)-4-(3-(benzofuran-2-yl)phenyl)-3-(2-((tert-butyldiphenylsilyl)oxy)ethyl)-$N^2$-isopropyl-1,3-dihydro-2H-pyrrolo[3,4-c]pyridine-2,6-dicarboxamide as a light yellow solid film (19 mg, 83%). TLC: R$_f$ 0.29 (70% EtOAc/hexanes). $[\alpha]_D^{19}$: +135.5° (c 1.0, CHCl$_3$). IR (ATR): 3449, 3360, 3070, 2963, 2930, 2857, 1688, 1638, 1573, 1528, 1452, 1378, 1260, 1109, 798, 739, 702. $^1$H-NMR (600 MHz): δ 8.17 (s, 1H), 8.11 (s, 1H), 8.00-7.81 (m, 2H), 7.62 (d, J=7.2 Hz, 2H), 7.54 (d, J=7.9 Hz, 1H), 7.46-7.37 (m, 3H), 7.36-7.30 (m, 4H), 7.30-7.27 (m, 2H), 7.25-7.23 (m, 2H), 7.20 (t, J=7.4 Hz, 2H), 7.10 (s, 1H), 5.87 (s, 1H), 5.69 (d, J=4.5 Hz, 1H), 5.09 (d, J=15.5 Hz, 1H), 4.80 (bs, 1H), 4.47 (dd, J=15.5, 2.3 Hz, 1H), 4.17-3.98 (m, J=6.5 Hz, 1H), 3.68-3.55 (m, 1H), 3.55-3.45 (m, 1H), 2.05-1.84 (m, 1H), 1.47-1.32 (m, 1H), 1.18 (t, J=6.4 Hz, 6H), 0.86 (s, 9H). $^{13}$C-NMR (151 MHz): δ 166.3, 156.3, 155.0, 155.0, 152.2, 149.7, 148.7, 139.3, 138.7, 135.3, 135.3, 133.1, 133.0, 131.3, 129.7, 129.7, 129.3, 129.0, 127.9, 127.6, 27.6, 125.5, 124.9, 124.6, 123.1, 121.1, 115.7, 111.3, 102.2, 60.2, 59.6, 51.0, 42.7, 35.6, 26.9, 23.4, 23.4, 19.0. HRMS m/z calcd for C$_{44}$H$_{46}$N$_4$O$_4$SiNa ([M+Na]$^+$) 745.3186; found 745.3162.

(R)-4-(3-(benzofuran-2-yl)phenyl)-3-(2-hydroxyethyl)-$N^2$-isopropyl-1,3-dihydro-2H-pyrrolo[3,4-c]pyridine-2,6-dicarboxamide (Compound 248)

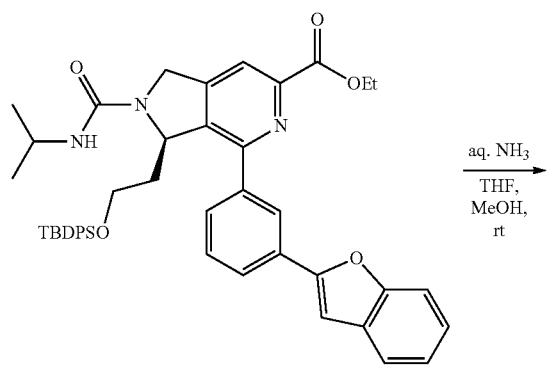

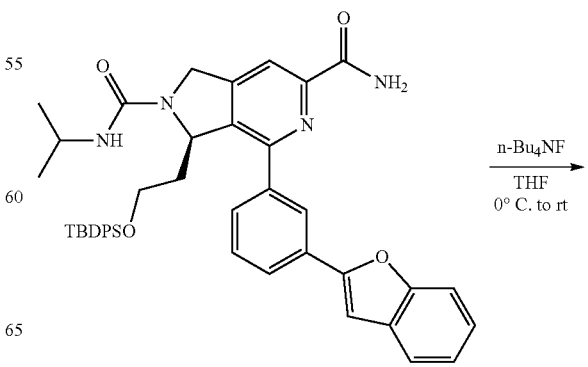

197

-continued

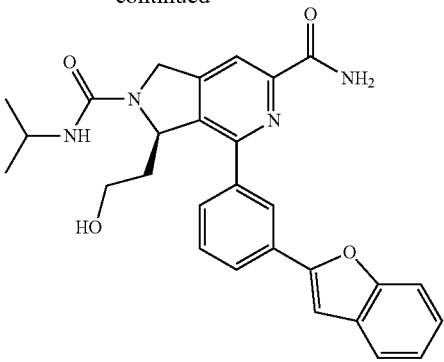

In a small vial, (R)-4-(3-(benzofuran-2-yl)phenyl)-3-(2-((tert-butyldiphenylsilyl)oxy)ethyl)-N²-isopropyl-1,3-dihydro-2H-pyrrolo[3,4-c]pyridine-2,6-dicarboxamide (18 mg, 0.0249 mmol, 1.0 equiv) was dissolved in 0.25 mL of THF and cooled to 0° C. n-Bu$_4$NF solution (1.0 M in THF, 37 μL, 0.0373 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (100% EtOAc) yielded the compound 248 as a light yellow solid film (6 mg, 53%). TLC: R$_f$ 0.17 (100% EtOAc). [α]$_D^{19}$: +177.0° (c 0.64, CHCl$_3$). IR (ATR): 3445, 3305, 2968, 2931, 2873, 1685, 1629, 1573, 1541, 1452, 1381, 1299, 1258, 1173, 1058, 800,750. $^1$H-NMR (600 MHz): δ 8.23 (s, 1H), 8.13 (s, 1H), 8.04-7.91 (m, 2H), 7.74 (d, J=7.7 Hz, 1H), 7.68-7.56 (m, 2H), 7.54 (d, J=7.9 Hz, 1H), 7.31 (ddd, J=8.2, 7.2, 1.3 Hz, 1H), 7.25-7.23 (m, 1H), 7.15 (s, 1H), 6.06 (d, J=10.1 Hz, 1H), 5.73 (d, J=4.4 Hz, 1H), 4.91 (d, J=14.6 Hz, 1H), 4.77-4.60 (m, 2H), 4.07 (h, J=6.7 Hz, 1H), 3.61-3.48 (m, 1H), 3.49-3.36 (m, 1H), 1.89-1.76 (m, 1H), 1.65 (s, 1H), 1.32-1.17 (m, 7H). $^{13}$C-NMR (151 MHz): δ 166.2, 157.4, 155.1, 154.9, 152.1, 148.9, 148.6, 138.9, 138.7, 131.3, 129.4, 129.0, 128.0, 125.9, 124.7, 124.6, 123.1, 121.1, 115.6, 111.2, 102.3, 59.2, 58.5, 50.9, 43.0, 37.9, 23.4, 23.3. HRMS m/z calcd for C$_{28}$H$_{28}$N$_4$O$_4$Na ([M+Na]$^+$) 507.2008; found 507.2021.

Preparation of Compound 241

(R)—N$^6$-(benzo[d][1,3]dioxol-5-ylmethyl)-4-(3-(benzofuran-2-yl)phenyl)-3-(2-((tert-butyldiphenylsilyl)oxy)ethyl)-N²-isopropyl-1,3-dihydro-2H-pyrrolo[3,4-c]pyridine-2,6-dicarboxamide

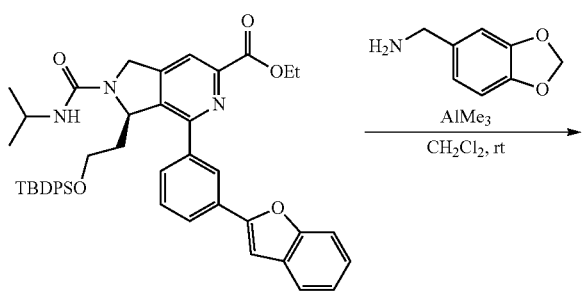

198

-continued

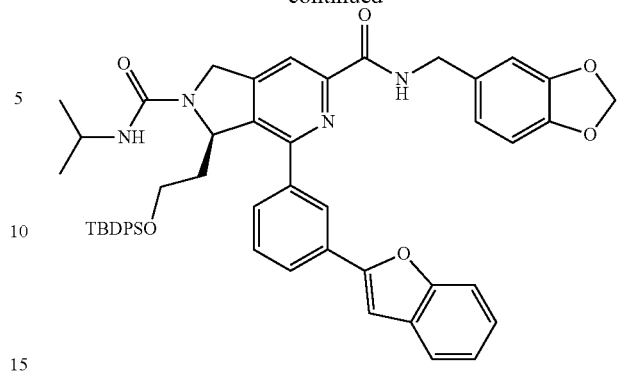

To a vial containing ethyl (R)-4-(3-(benzofuran-2-yl)phenyl)-3-(2-((tert-butyldiphenylsilyl)oxy)ethyl)-2-(isopropylcarbamoyl)-2,3-dihydro-1H-pyrrolo[3,4-c]pyridine-6-carboxylate (16 mg, 0.0209 mmol, 1.0 equiv, azeotroped 3× with toluene) at room temperature was slowly added a pre-stirred (>2 h) stock solution of dimethylaluminum piperonylamide (0.2 M solution in CH$_2$Cl$_2$/toluene, 0.21 mL, 0.0417 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (40% EtOAc/hexanes) yielded (R)—N$^6$-(benzo[d][1,3]dioxol-5-ylmethyl)-4-(3-(benzofuran-2-yl)phenyl)-3-(2-((tert-butyldiphenylsilyl)oxy)ethyl)-N²-isopropyl-1,3-dihydro-2H-pyrrolo[3,4-c]pyridine-2,6-dicarboxamide as a white foam (15 mg, 83%). TLC: R$_f$0.19 (25% EtOAc/CH$_2$Cl$_2$). [α]$_D^{20}$: +139.0° (c 1.0, CHCl$_3$). IR (ATR): 3376, 3069, 2930, 1667, 1521, 1490, 1446, 1379, 1256, 1110, 1042, 929, 738, 703. $^1$H-NMR (600 MHz): δ 8.39 (t, J=6.2 Hz, 1H), 8.13 (d, J=5.7 Hz, 2H), 7.93 (d, J=7.9 Hz, 1H), 7.61 (d, J=7.5 Hz, 1H), 7.58 (d, J=7.7 Hz, 1H), 7.52 (d, J=8.2 Hz, 1H), 7.43-7.37 (m, 3H), 7.34-7.26 (m, 6H), 7.24 (t, J=7.6 Hz, 2H), 7.19 (t, J=7.5 Hz, 2H), 7.05 (s, 1H), 6.88 (d, J=1.7 Hz, 1H), 6.83 (dd, J=8.0, 1.7 Hz, 1H), 6.76 (d, J=7.9 Hz, 1H), 5.91 (s, 2H), 5.88-5.81 (m, 1H), 5.08 (d, J=15.4 Hz, 1H), 4.77 (bs, 1H), 4.63 (dd, J=14.9, 6.3 Hz, 1H), 4.56 (dd, J=14.9, 6.1 Hz, 1H), 4.47 (dd, J=15.7, 2.3 Hz, 1H), 4.07 (dq, J=13.5, 6.7 Hz, 1H), 3.64-3.51 (m, 1H), 3.52-3.43 (m, 1H), 2.00-1.86 (m, 1H), 1.44-1.32 (m, 1H), 1.17 (dd, J=6.6, 5.2 Hz, 6H), 0.85 (s, 9H). $^{13}$C-NMR (151 MHz): δ 163.9, 156.3, 155.0, 154.9, 152.0, 149.6, 149.1, 147.9, 146.9, 139.3, 138.4, 135.3, 135.3, 133.1, 133.0, 132.2, 131.2, 129.7, 129.6, 129.3, 129.0, 127.9, 127.6, 127.6, 125.4, 124.9, 124.6, 123.1, 121.1, 121.0, 115.7, 111.3, 108.4, 108.3, 102.2, 101.0, 60.2, 59.6, 53.4, 51.1, 43.2, 42.6, 26.9, 23.4, 23.4, 19.0. HRMS m/z calcd for C$_{52}$H$_{52}$N$_4$O$_6$SiNa ([M+Na]$^+$) 879.3554; found 879.3517.

(R)—N[6]-(benzo[d][1,3]dioxol-5-ylmethyl)-4-(3-(benzofuran-2-yl)phenyl)-3-(2-hydroxyethyl)-N[2]-isopropyl-1,3-dihydro-2H-pyrrolo[3,4-c]pyridine-2,6-dicarboxamide (Compound 241)

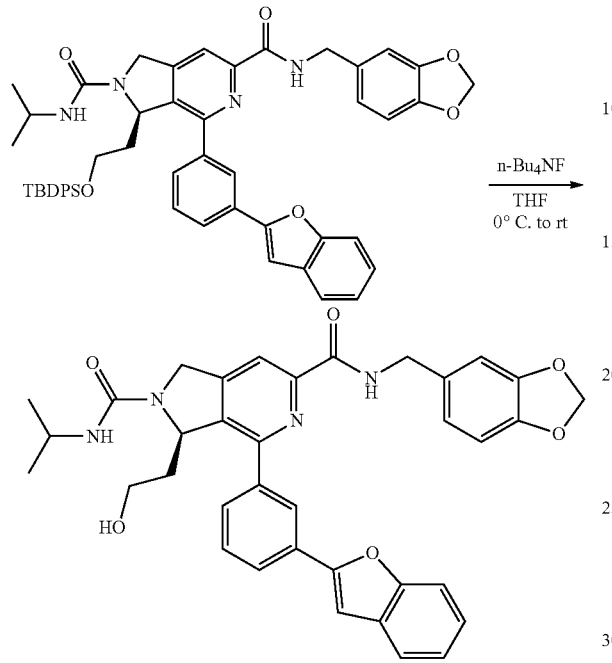

In a small vial, (R)—N[6]-(benzo[d][1,3]dioxol-5-ylmethyl)-4-(3-(benzofuran-2-yl)phenyl)-3-(2-((tert-butyldiphenylsilyl)oxy)ethyl)-N[2]-isopropyl-1,3-dihydro-2H-pyrrolo[3,4-c]pyridine-2,6-dicarboxamide (15 mg, 0.0173 mmol, 1.0 equiv) was dissolved in 0.17 mL of THF and cooled to 0° C. n-Bu$_4$NF solution (1.0 M in THF, 26 µL, 0.0259 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (70% EtOAc/hexanes) yielded the compound 241 as a light yellow solid film (7 mg, 70%).

TLC: $R_f$ 0.41 (2% MeOH/EtOAc). $[\alpha]_D^{19}$: +150.1° (c 1.0, CHCl$_3$). IR (ATR): 3313, 3062, 2969, 2929, 2778, 1733, 1666, 1627, 1524, 1445, 1380, 1255, 1039, 928, 800, 750, 699. $^1$H-NMR (600 MHz): δ 8.42 (t, J=6.2 Hz, 1H), 8.19 (s, 1H), 8.15 (s, 1H), 7.95 (d, J=7.8 Hz, 1H), 7.70 (d, J=7.7 Hz, 1H), 7.63-7.57 (m, 2H), 7.52 (d, J=8.2 Hz, 1H), 7.30 (t, J=8.3 Hz, 1H), 7.26-7.22 (m, 1H), 7.12 (s, 1H), 6.88 (d, J=1.7 Hz, 1H), 6.84 (dd, J=7.9, 1.7 Hz, 1H), 6.76 (d, J=7.9 Hz, 1H), 6.04 (d, J=10.2 Hz, 1H), 5.91 (s, 2H), 4.90 (d, J=14.7 Hz, 1H), 4.78-4.50 (m, 4H), 4.07 (dq, J=13.3, 6.7 Hz, 1H), 3.60-3.48 (m, 1H), 3.48-3.39 (m, 1H), 1.89-1.74 (m, 1H), 1.25 (t, J=6.4 Hz, 6H), 1.23-1.17 (m, 1H). $^{13}$C-NMR (151 MHz): δ 163.8, 157.4, 155.0, 154.9, 152.0, 149.2, 148.6, 147.9, 146.9, 138.7, 138.7, 132.0, 131.2, 129.4, 129.0, 128.0, 125.8, 124.7, 124.6, 123.1, 121.1, 121.0, 115.6, 111.2, 108.4, 108.3, 102.2, 101.0. HRMS m/z calcd for C$_{36}$H$_{34}$N$_4$O$_6$Na ([M+Na]$^+$) 641.2376; found 641.2397.

Preparation of Compound 268

(R)-4-(3-(benzofuran-2-yl)phenyl)-3-(2-((tert-butyldiphenylsilyl)oxy)ethyl)-N[6]-(2-fluorobenzyl)-N[2]-isopropyl-1,3-dihydro-2H-pyrrolo[3,4-c]pyridine-2,6-dicarboxamide

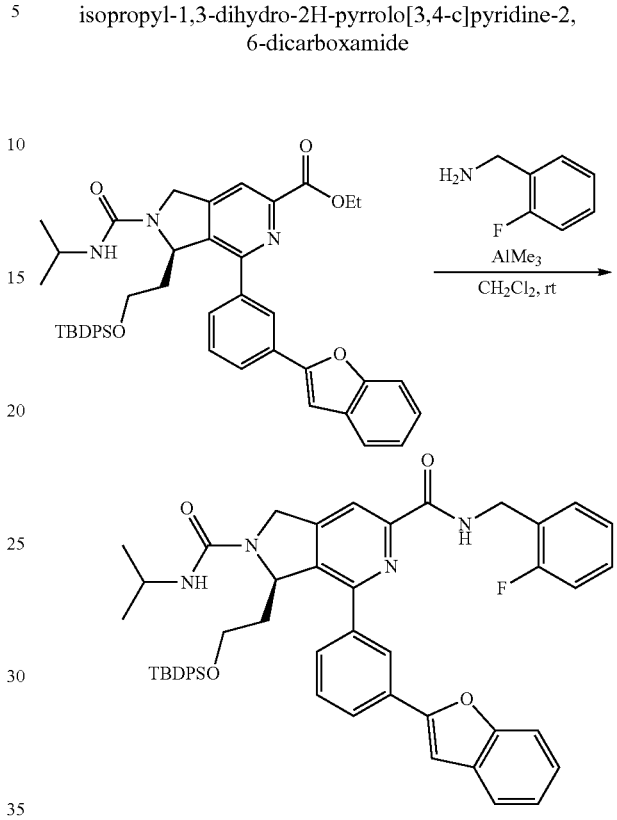

To a vial containing ethyl (R)-4-(3-(benzofuran-2-yl)phenyl)-3-(2-((tert-butyldiphenylsilyl)oxy)ethyl)-2-(isopropylcarbamoyl)-2,3-dihydro-1H-pyrrolo[3,4-c]pyridine-6-carboxylate (19 mg, 0.0247 mmol, 1.0 equiv, azeotroped 3× with toluene) at room temperature was slowly added a pre-stirred (>2 h) stock solution of dimethylaluminum (2-fluorobenzyl)amide (0.2 M solution in CH$_2$Cl$_2$/toluene, 0.25 mL, 0.0495 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (40% EtOAc/hexanes) yielded (R)-4-(3-(benzofuran-2-yl)phenyl)-3-(2-((tert-butyldiphenylsilyl)oxy)ethyl)-N[6]-(2-fluorobenzyl)-N[2]-isopropyl-1,3-dihydro-2H-pyrrolo[3,4-c]pyridine-2,6-dicarboxamide as a light yellow foam (11 mg, 53%). TLC: $R_f$ 0.22 (25% EtOAc/CH$_2$Cl$_2$). $[\alpha]_D^{20}$: +149.4° (c 1.0, CHCl$_3$). IR (ATR): 3386, 3071, 2963, 2932, 2858, 1673, 1524, 1456, 1456, 1383, 1258, 1177, 1110, 1059, 798, 751, 740, 703. $^1$H-NMR (600 MHz): δ 8.50 (t, J=6.3 Hz, 1H), 8.17 (s, 1H), 8.12 (s, 1H), 7.93 (d, J=7.9 Hz, 1H), 7.65-7.58 (m, 2H), 7.53 (d, J=8.1 Hz, 1H), 7.46-7.37 (m, 4H), 7.35-7.30 (m, 4H), 7.30-7.27 (m, 2H), 7.25-7.21 (m, 3H), 7.18 (t, J=7.4 Hz, 2H), 7.11 (td, J=7.5, 1.2 Hz, 1H), 7.08-7.03 (m, 2H), 5.93-5.78 (m, 1H), 5.07 (d, J=15.2 Hz, 1H), 4.85-4.63 (m, 3H), 4.46 (dd, J=15.5, 1.7 Hz, 2H), 4.16-3.98 (m, 1H), 3.63-3.54 (m, 1H), 3.54-3.41 (m, 1H), 2.01-1.83 (m, 1H), 1.48-1.34 (m, 1H), 1.18 (t, J=6.2 Hz, 6H), 0.84 (s, 9H). $^{13}$C-NMR (151 MHz): δ 163.99, 161.0 (d, J=246.3 Hz), 156.3, 155.1, 155.0, 152.0, 149.6, 149.0, 139.2, 138.4, 135.3, 135.3, 133.1, 133.0, 131.2, 130.1 (d, J=4.2 Hz), 129.7, 129.6, 129.3, 129.2 (d, J=8.2 Hz), 129.1, 127.9, 127.6, 127.5, 125.5, 125.2 (d, J=14.7 Hz), 124.9, 124.6, 124.3 (d, J=3.6 Hz), 123.1, 121.1, 115.6, 115.4 (d, J=21.2 Hz), 111.3, 102.2, 60.2, 59.6, 51.0, 42.6, 37.4 (d, J=4.1 Hz), 35.6, 26.9, 23.5, 23.4, 19.0. HRMS m/z calcd for $C_{51}H_{51}FN_4O_4SiNa$ ([M+Na]$^+$) 853.3561; found 853.3563.

(R)-4-(3-(benzofuran-2-yl)phenyl)-N$^6$-(2-fluorobenzyl)-3-(2-hydroxyethyl)-N$^2$-isopropyl-1,3-dihydro-2H-pyrrolo[3,4-c]pyridine-2,6-dicarboxamide (Compound 268)

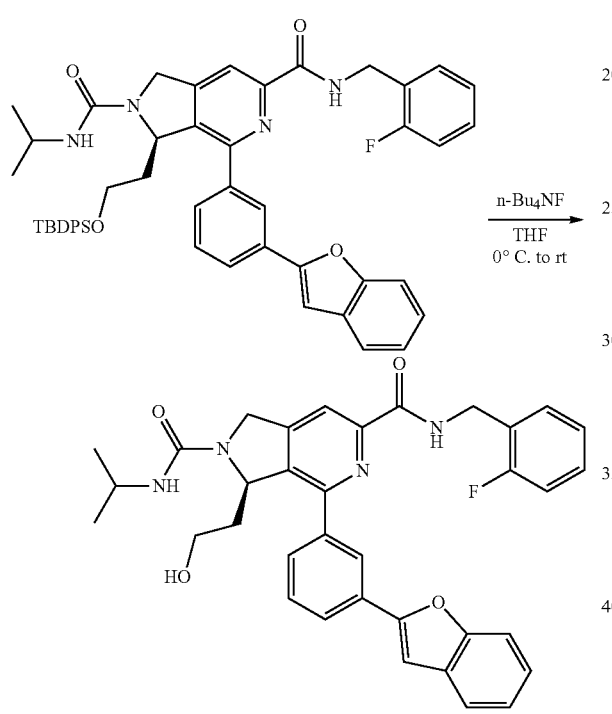

In a small vial, (R)-4-(3-benzofuran-2-yl)phenyl)-3-(2-tert-butyldiphenylsilyl)oxy)ethyl)-N$^6$-(2-fluorobenzyl)-N$^2$-isopropyl-1,3-dihydro-2H-pyrrolo[3,4-c]pyridine-2,6-dicarboxamide (11 mg, 0.0129 mmol, 1.0 equiv) was dissolved in 0.13 mL of THF and cooled to 0° C. n-Bu$_4$NF solution (1.0 M in THF, 19 µL, 0.0193 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (70% EtOAc/hexanes) yielded the compound 268 as a light yellow solid film (4 mg, 57%).

TLC: R$_f$ 0.46 (2% MeOH/EtOAc). IR (ATR): 3319, 3067, 2964, 2874, 1669, 1629, 1524, 1455, 1382, 1261, 1175, 1097, 1034, 800, 751, 700. $^1$H-NMR (600 MHz): δ 8.53 (t, J=6.3 Hz, 1H), 8.24 (s, 1H), 8.14 (s, 1H), 7.97 (d, J=7.9 Hz, 1H), 7.73 (d, J=7.7 Hz, 1H), 7.61 (t, J=7.4 Hz, 2H), 7.53 (d, J=8.1 Hz, 1H), 7.43 (t, J=7.6 Hz, 1H), 7.31 (t, J=7.2 Hz, 1H), 7.29-7.27 (m, 1H), 7.25-7.23 (m, 1H), 7.14 (s, 1H), 7.12 (t, J=7.2 Hz, 1H), 7.07 (t, J=9.7, 8.7 Hz, 2H), 6.06 (d, J=10.0 Hz, 1H), 4.90 (d, J=14.6 Hz, 1H), 4.82-4.72 (m, 2H), 4.69-4.50 (m, 2H), 4.12-4.01 (m, 1H), 3.58-3.49 (m, 1H), 3.49-3.40 (m, 1H), 1.88-1.78 (m, 1H), 1.25 (t, J=6.7 Hz, 6H), 1.19-1.13 (m, 1H). $^{13}$C-NMR (151 MHz): δ 163.9, 161.0 (d, J=246.3 Hz), 157.3, 155.1, 155.0, 151.9, 149.2, 148.6, 138.7, 138.6, 135.3, 135.2, 131.3, 130.0 (d, J=4.2 Hz), 129.5, 129.3 (d, J=8.1 Hz), 129.1, 128.0, 127.6, 125.9, 125.1 (d, J=14.7 Hz), 124.8, 124.6, 124.3 (d, J=3.6 Hz), 123.1, 121.1, 115.5 (d, J=4.0 Hz), 115.4, 111.2, 102.2, 59.2, 58.6, 50.9, 43.0, 37.9, 37.5 (d, J=4.0 Hz), 23.4, 23.4. HRMS m/z calcd for $C_{35}H_{34}FN_4O_4$ ([M+H]$^+$) 593.2564; found 593.2571.

Preparation of Compound 219

(R)—N-(benzo[d][1,3]dioxol-5-ylmethyl)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxamide

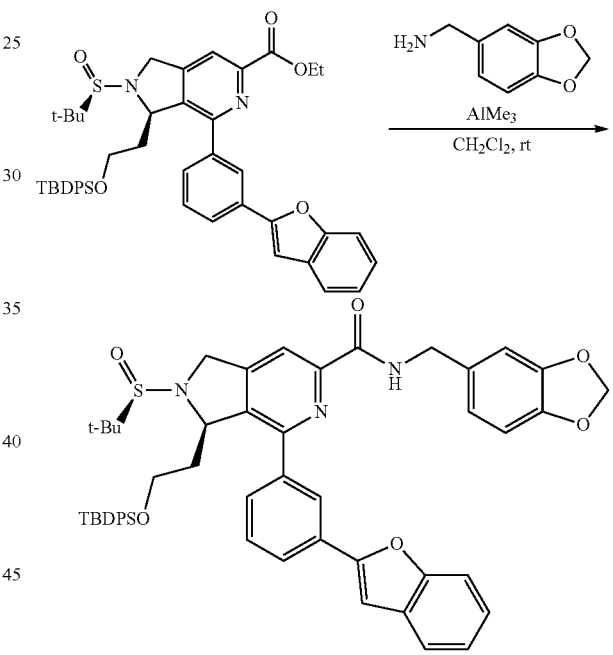

To a vial containing ethyl (R)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate (25 mg, 0.0324 mmol, 1.0 equiv, azeotroped 3× with toluene) at room temperature was slowly added a pre-stirred (>2 h) stock solution of dimethylaluminum piperonylamide (0.2 M solution in CH$_2$Cl$_2$/toluene, 0.32 mL, 0.0648 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (50% EtOAc/hexanes) yielded (R)—N-(benzo[d][1,3]dioxol-5-ylmethyl)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxamide as a white foam (25 mg, 90%). TLC: $R_f$ 0.22 (50% EtOAc/hexanes). $[\alpha]_D^{19}$: +100.3° (c 1.0, CHCl$_3$). IR (ATR): 3386, 3070, 2959, 2930, 2850, 1673, 1574, 1524, 1490, 1445, 1256, 1110, 1074, 1043, 929, 799, 754, 703. $^1$H-NMR (600 MHz): δ 8.39 (t, J=6.2 Hz, 1H), 8.13 (s, 1H), 8.10 (s, 1H), 7.92 (d, J=7.8 Hz, 1H), 7.62-7.56 (m, 2H), 7.53 (d, J=8.2 Hz, 1H), 7.46-7.36 (m, 5H), 7.36-7.28 (m, 3H), 7.28-7.26 (m, 2H), 7.26-7.23 (m, 3H), 7.05 (s, 1H), 6.88 (s, 1H), 6.83 (d, J=8.0 Hz, 1H), 6.76 (d, J=7.9 Hz, 1H), 5.91 (s, 2H), 5.76 (d, J=6.3 Hz, 1H), 5.19 (d, J=15.8 Hz, 1H), 4.64 (dd, J=14.9, 6.4 Hz, 1H), 4.54 (dd, J=14.9, 6.0 Hz, 1H), 4.01 (d, J=15.5 Hz, 1H), 3.63 (ddd, J=10.4, 8.3, 5.1 Hz, 1H), 3.45 (dt, J=10.6, 5.4 Hz, 1H), 1.84-1.69 (m, 1H), 1.60-1.48 (m, 1H), 1.21 (s, 9H), 0.89 (s, 9H). $^{13}$C-NMR (151 MHz): δ 163.9, 155.1, 154.9, 151.7, 151.7, 149.2, 147.9, 146.9, 139.3, 138.5, 135.4, 135.4, 133.3, 133.2, 132.2, 131.1, 129.6, 129.6, 129.3, 129.0, 128.1, 127.5, 127.5, 125.4, 124.9, 124.5, 123.0, 121.0, 121.0, 115.7, 111.3, 108.4, 108.3, 102.1, 101.0, 68.5, 59.4, 58.5, 45.9, 43.2, 37.7, 26.7, 23.8, 18.9. HRMS m/z calcd for C$_{52}$H$_{53}$N$_3$O$_6$SSiNa ([M+Na]$^+$) 898.3322; found 898.3364.

(R)—N-(benzo[d][1,3]dioxol-5-ylmethyl)-4-(3-(benzofuran-2-yl)phenyl)-2-((R)-tert-butylsulfinyl)-3-(2-hydroxyethyl)-2,3-dihydro-1H-pyrrolo[3,4-c]pyridine-6-carboxamide (Compound 219)

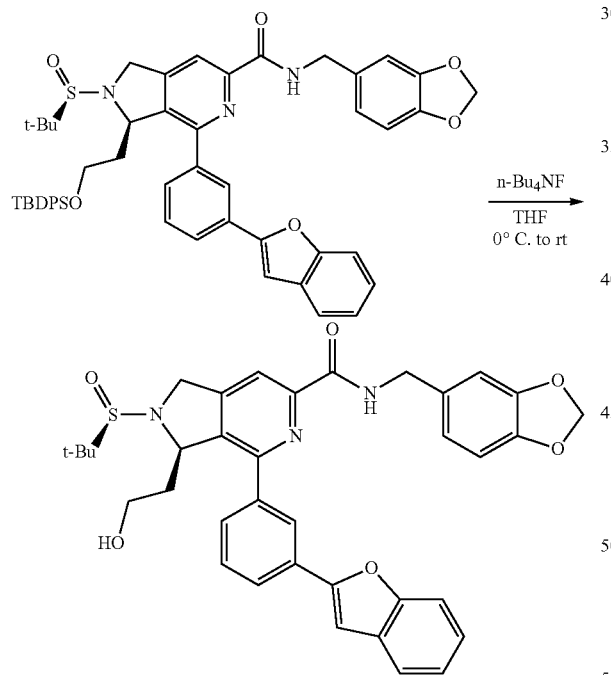

In a small vial, (R)—N-(benzo[d][1,3]dioxol-5-ylmethyl)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxamide (25 mg, 0.0285 mmol, 1.0 equiv) was dissolved in 0.29 mL of THF and cooled to 0° C. n-Bu$_4$NF solution (1.0 M in THF, 43 μL, 0.0428 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (80% EtOAc/hexanes) yielded compound 219 as a light yellow foam (15 mg, 84%). TLC: $R_f$ 0.08 (60% EtOAc/hexanes). $[\alpha]_D^{20}$: +77.4° (c 1.0, CHCl$_3$). IR (ATR): 3385, 2926, 1668, 1574, 1490, 1256, 1041, 928, 800, 753. $^1$H-NMR (600 MHz): δ 8.38 (t, J=6.1 Hz, 1H), 8.14 (s, 1H), 8.13 (s, 1H), 7.95 (d, J=7.8 Hz, 1H), 7.63 (d, J=7.7 Hz, 1H), 7.61 (d, J=7.6 Hz, 1H), 7.59-7.52 (m, 2H), 7.31 (t, J=8.3 Hz, 1H), 7.26-7.23 (m, 1H), 7.10 (s, 1H), 6.87 (d, J=1.6 Hz, 1H), 6.83 (dd, J=7.9, 1.7 Hz, 1H), 6.76 (d, J=7.9 Hz, 1H), 5.91 (s, 2H), 5.73 (ddd, J=5.9, 3.2, 1.8 Hz, 1H), 5.23 (d, J=15.7 Hz, 1H), 4.62 (dd, J=14.8, 6.3 Hz, 1H), 4.55 (dd, J=14.9, 6.1 Hz, 1H), 4.16 (d, J=16.8 Hz, 1H), 3.61-3.50 (m, 1H), 3.47-3.35 (m, 1H), 1.83-1.69 (m, 1H), 1.68-1.59 (m, 1H), 1.31 (s, 9H). $^{13}$C-NMR (151 MHz): δ 163.8, 155.0, 154.9, 151.8, 151.8, 149.4, 147.9, 146.9, 139.1, 137.5, 132.1, 131.1, 129.3, 129.0, 128.2, 125.6, 124.7, 124.6, 123.1, 121.1, 121.0, 115.7, 111.3, 108.4, 108.3, 102.2, 101.0, 68.6, 58.5, 58.4, 46.0, 43.3, 37.5, 23.8. HRMS m/z calcd for C$_{36}$H$_{35}$N$_3$O$_6$SNa ([M+Na]$^+$) 660.2144; found 660.2147.

Preparation of Compound 220

(R)-4-(3-(benzofuran-2-yl)phenyl)-3-(2-((tert-butyldiphenylsilyl)oxy)ethyl)-2-((R)-tert-butylsulfinyl)-N-(2-fluorobenzyl)-2,3-dihydro-1H-pyrrolo[3,4-c]pyridine-6-carboxamide

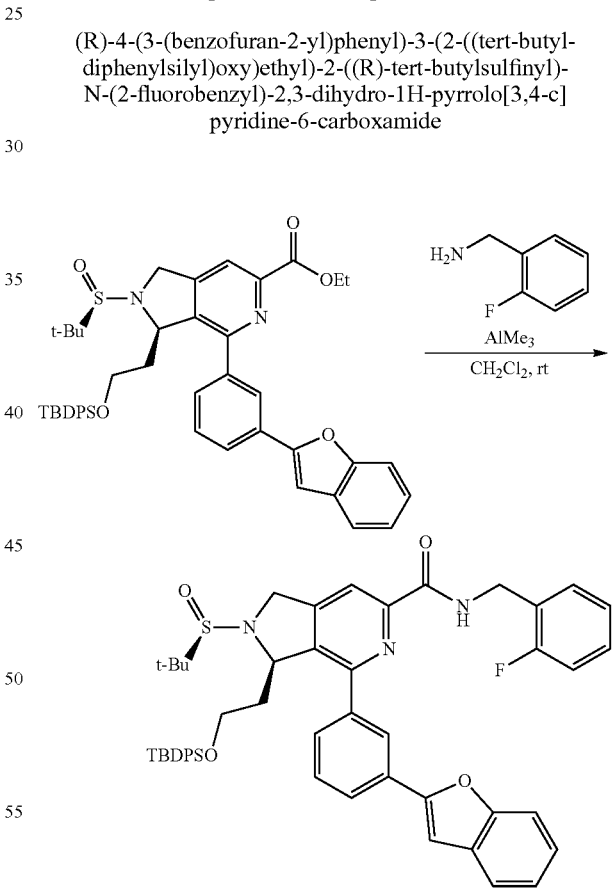

To a vial containing ethyl (R)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate (24 mg, 0.0311 mmol, 1.0 equiv, azeotroped 3× with toluene) at room temperature was slowly added a pre-stirred (>2 h) stock solution of dimethylaluminum (2-fluorobenzyl)amide (0.2 M solution in CH$_2$Cl$_2$/toluene, 0.31 mL, 0.0623 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (40% EtOAc/hexanes) yielded (R)-4-(3-(benzofuran-2-yl)phenyl)-3-(2-((tert-butyldiphenylsilyl)oxy)ethyl)-2-((R)-tert-butylsulfinyl)-N-(2-fluorobenzyl)-2,3-dihydro-1H-pyrrolo[3,4-c]pyridine-6-carboxamide as a light yellow foam (23 mg, 88%). TLC: R$_f$ 0.32 (50% EtOAc/hexanes). [α]$_D^{20}$: +94.8° (c 1.0, CHCl$_3$). IR (ATR): 3395, 3070, 2958, 2858, 1676, 1574, 1524, 1490, 1455, 1428, 1310, 1176, 1109, 1075, 942, 757, 703. $^1$H-NMR (600 MHz): 8.49 (t, J=6.3 Hz, 1H), 8.17 (s, 1H), 8.09 (s, 1H), 7.93 (d, J=7.9 Hz, 1H), 7.64-7.57 (m, 2H), 7.54 (d, J=8.2 Hz, 1H), 7.46-7.36 (m, 6H), 7.35-7.29 (m, 3H), 7.29-7.26 (m, 2H), 7.26-7.23 (m, 4H), 7.11 (t, J=7.5 Hz, 1H), 7.08-7.03 (m, 2H), 5.83-5.73 (m, 1H), 5.19 (d, J=15.8 Hz, 1H), 4.78 (dd, J=15.2, 6.4 Hz, 1H), 4.72 (dd, J=15.2, 6.2 Hz, 1H), 4.00 (d, J=15.0 Hz, 1H), 3.63 (ddd, J=10.4, 8.3, 5.1 Hz, 1H), 3.45 (ddd, J=10.6, 6.0, 4.7 Hz, 1H), 1.85-1.72 (m, 1H), 1.60-1.49 (m, 1H), 1.21 (s, 9H), 0.89 (s, 9H). $^{13}$C-NMR (151 MHz): δ 164.0, 161.0 (d, J=246.3 Hz), 155.1, 154.9, 151.8, 151.7, 149.1, 139.2, 138.5, 135.4, 135.4, 133.3, 133.2, 131.1, 130.0 (d, J=4.2 Hz), 129.6, 129.6, 129.3, 129.2 (d, J=8.1 Hz), 129.1, 128.0, 127.5, 127.5, 125.4, 125.2 (d, J=14.8 Hz), 124.9, 124.5, 124.3 (d, J=3.6 Hz), 123.0, 121.0, 115.7, 115.4 (d, J=21.2 Hz), 111.3, 102.1, 68.6, 59.4, 58.5, 45.9, 37.7, 37.4 (d, J=4.2 Hz), 26.7, 23.8, 18.9. HRMS m/z calcd for C$_{51}$H$_{52}$FN$_3$O$_4$SSiNa ([M+Na]$^+$) 872.3330; found 872.3337.

(R)-4-(3-(benzofuran-2-yl)phenyl)-2-((R)-tert-butylsulfinyl)-N-(2-fluorobenzyl)-3-(2-hydroxyethyl)-2,3-dihydro-1H-pyrrolo[3,4-c]pyridine-6-carboxamide (Compound 220)

In a small vial, ((R)-4-(3-(benzofuran-2-yl)phenyl)-3-(2-((tert-butyldiphenylsilyl)oxy)ethyl)-2-((R)-tert-butylsulfinyl)-N-(2-fluorobenzyl)-2,3-dihydro-1H-pyrrolo[3,4-c]pyridine-6-carboxamide (20 mg, 0.0235 mmol, 1.0 equiv) was dissolved in 0.24 mL of THF and cooled to 0° C. n-Bu$_4$NF solution (1.0 M in THF, 35 μL, 0.0353 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (80% EtOAc/hexanes) yielded compound 220 as a light yellow foam (12 mg, 85%). TLC: R$_f$ 0.08 (60% EtOAc/hexanes). [α]$_D^{20}$: +79.5° (c 1.0, CHCl$_3$). IR (ATR): 3393, 2959, 1671, 1574, 1526, 1491, 1454, 1258, 1230, 1176, 1047, 924, 799, 753. $^1$H-NMR (600 MHz): δ 8.49 (t, J=6.3 Hz, 1H), 8.17 (s, 1H), 8.11 (s, 1H), 7.95 (d, J=7.8 Hz, 1H), 7.66 (d, J=7.7 Hz, 1H), 7.64-7.52 (m, 3H), 7.42 (t, J=7.2 Hz, 1H), 7.32 (t, J=7.6 Hz, 1H), 7.28-7.26 (m, 1H), 7.26-7.23 (m, 1H), 7.15-7.08 (m, 2H), 7.08-7.01 (m, 1H), 5.80-5.69 (m, 1H), 5.22 (d, J=15.6 Hz, 1H), 4.82-4.66 (m, 2H), 4.15 (d, J=15.5 Hz, 1H), 3.55 (ddd, J=10.8, 7.7, 6.0 Hz, 1H), 3.42 (ddd, J=11.2, 6.6, 5.0 Hz, 1H), 1.82-1.71 (m, 1H), 1.71-1.59 (m, 1H), 1.31 (s, 9H), 0.92 (t, J=7.3 Hz, 1H). $^{13}$C-NMR (151 MHz): δ 163.9, 161.0 (d, J=246.3 Hz), 155.0, 154.9, 151.8, 151.7, 149.3, 139.0, 137.5, 131.1, 130.0 (d, J=4.2 Hz), 129.3, 129.2 (d, J=8.2 Hz), 129.0, 128.2, 127.7, 125.6, 125.2 (d, J=14.7 Hz), 124.6, 124.3 (d, J=3.6 Hz), 123.1, 121.1, 115.7, 115.4 (d, J=21.2 Hz), 111.3, 102.2, 68.7, 58.5, 58.4, 46.0, 37.5, 37.4 (d, J=4.1 Hz), 23.8. HRMS m/z calcd for C$_{35}$H$_{34}$FN$_3$O$_4$SNa ([M+Na]$^+$) 634.2152; found 634.2154.

Preparation of Compound 226

(R)-4-(3-(benzofuran-2-yl)phenyl)-3-(2-((tert-butyldiphenylsilyl)oxy)ethyl)-2-((R)-tert-butylsulfinyl)-N-(2,2,2-trifluoroethyl)-2,3-dihydro-1H-pyrrolo[3,4-c]pyridine-6-carboxamide

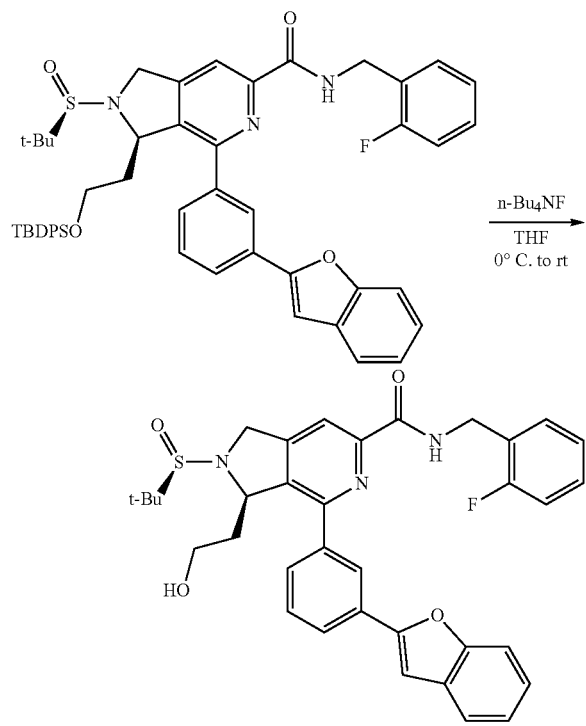

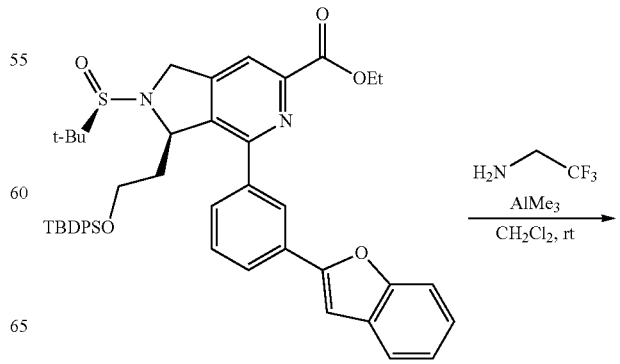

-continued

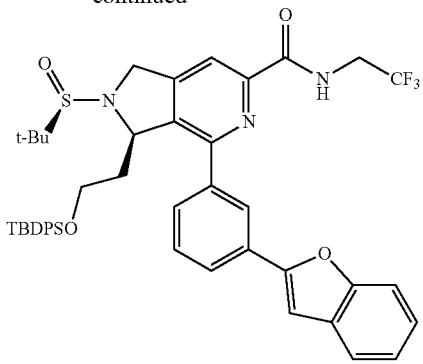

To a vial containing ethyl (R)-4-(3-(benzofuran-2-yl)phenyl)-3-(2-((tert-butyldiphenylsilyl)oxy)ethyl)-2-((R)-tert-butylsulfinyl)-2,3-dihydro-1H-pyrrolo[3,4-c]pyridine-6-carboxylate (59 mg, 0.0765 mmol, 1.0 equiv, azeotroped 3× with toluene) at room temperature was slowly added a pre-stirred (>2 h) stock solution of dimethylaluminum 2,2,2-trifluoroethylamide (0.2 M solution in $CH_2Cl_2$/toluene, 0.77 mL, 0.153 mmol, 2.0 equiv). The mixture was stirred at room temperature for 15 h, then carefully quenched by addition of a few drops of MeOH followed by dilution with 1 mL of $CH_2Cl_2$ and careful addition of 1 mL saturated aqueous $NaHCO_3$. The aqueous layer was extracted with EtOAc (3×1 mL), then the combined organic layers were dried ($Na_2SO_4$), filtered, and concentrated by rotary evaporation. Purification by silica flash chromatography (40% EtOAc/hexanes) yielded (R)-4-(3-(benzofuran-2-yl)phenyl)-3-(2-((tert-butyldiphenylsilyl)oxy)ethyl)-2-((R)-tert-butylsulfinyl)-N-(2,2,2-trifluoroethyl)-2,3-dihydro-1H-pyrrolo[3,4-c]pyridine-6-carboxamide as a sticky yellow foam (35 mg, 56%). TLC: $R_f$ 0.52 (30% EtOAc/$CH_2Cl_2$). $[\alpha]_D^{20}$: +90.7° (c 1.0, $CHCl_3$). IR (ATR): 3328, 3071, 2958, 2931, 2859, 1688, 1574, 1524, 1473, 1452, 1428, 1391, 1273, 1216, 1162, 1109, 1074, 943, 753, 702. $^1$H-NMR (600 MHz): δ 8.43 (t, J=6.8 Hz, 1H), 8.18 (s, 1H), 8.08 (s, 1H), 7.95 (d, J=7.8 Hz, 1H), 7.61 (t, J=7.8 Hz, 2H), 7.54 (d, J=8.2 Hz, 1H), 7.45-7.38 (m, 5H), 7.37-7.30 (m, 3H), 7.28-7.24 (m, 5H), 7.08 (s, 1H), 5.78 (d, J=6.5 Hz, 1H), 5.20 (d, J=15.8 Hz, 1H), 4.29 (ddd, J=18.1, 15.9, 8.5 Hz, 1H), 4.04-3.90 (m, 2H), 3.64 (ddd, J=10.4, 8.2, 5.0 Hz, 1H), 3.47 (dt, J=10.6, 5.4 Hz, 1H), 1.83-1.71 (m, 1H), 1.62-1.50 (m, 1H), 1.22 (s, 9H), 0.90 (s, 9H). $^{13}$C-NMR (151 MHz): δ 164.3, 155.0, 154.9, 152.0, 151.9, 148.0, 139.3, 139.0, 135.4, 135.4, 133.2, 133.1, 131.2, 129.6, 129.6, 129.3, 129.0, 128.0, 127.6, 127.5, 125.5, 124.8, 124.6, 124.1 (q, J=278.6 Hz), 123.1, 121.1, 116.0, 111.3, 102.2, 68.6, 59.3, 58.5, 45.8, 40.7 (q, J=34.9 Hz), 37.6, 26.6, 23.7, 18.9. HRMS m/z calcd for $C_{46}H_{49}F_3N_3O_4SSi$ ([M+H]$^+$) 824.3165; found 824.3143.

(R)-4-(3-(benzofuran-2-yl)phenyl)-2-((R)-tert-butylsulfinyl)-3-(2-hydroxyethyl)-N-(2,2,2-trifluoroethyl)-2,3-dihydro-1H-pyrrolo[3,4-c]pyridine-6-carboxamide (Compound 226)

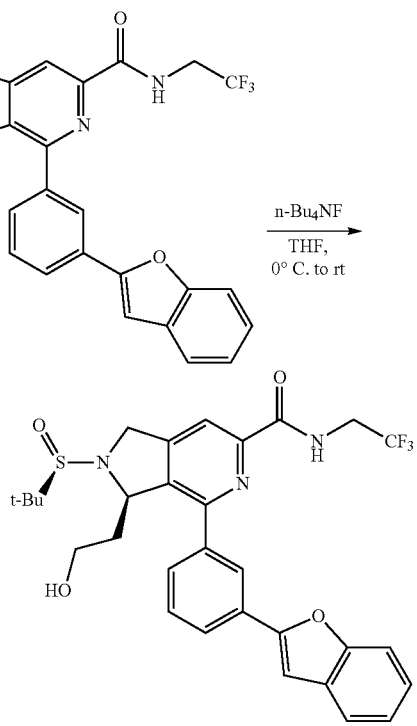

In a small vial, (R)-4-(3-(benzofuran-2-yl)phenyl)-3-(2-((tert-butyldiphenylsilyl)oxy)ethyl)-2-((R)-tert-butylsulfinyl)-N-(2,2,2-trifluoroethyl)-2,3-dihydro-1H-pyrrolo[3,4-c]pyridine-6-carboxamide (18 mg, 0.0215 mmol, 1.0 equiv) was dissolved in 0.22 mL of THF and cooled to 0° C. n-Bu$_4$NF solution (1.0 M in THF, 32 µL, 0.0322 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq $NaHCO_3$, then the aqueous layer was extracted with EtOAc (3×2 mL). The combined organic extracts were washed with brine (1×1 mL), dried ($Na_2SO_4$), filtered, and concentrated by rotary evaporation. Purification by silica flash chromatography (60% EtOAc/hexanes) yielded compound 226 as a light yellow foam (12 mg, 85%).

TLC: $R_f$ 0.37 (80% EtOAc/hexanes). $[\alpha]_D^{20}$: +101.3° (c 1.0, $CHCl_3$). IR (ATR): 3377, 2960, 1685, 1574, 1526, 1453, 1422, 1400, 1273, 1216, 1162, 1046, 801, 754. $^1$H-NMR (600 MHz): δ 8.41 (t, J=6.7 Hz, 1H), 8.18 (s, 1H), 8.11 (s, 1H), 7.98 (d, J=7.7 Hz, 1H), 7.67 (d, J=7.7 Hz, 1H), 7.64-7.59 (m, 2H), 7.56 (d, J=8.2 Hz, 1H), 7.32 (t, J=8.1 Hz, 1H), 7.29-7.23 (m, 1H), 7.14 (s, 1H), 5.82-5.68 (m, 1H), 5.24 (d, J=15.8 Hz, 1H), 4.33-4.21 (m, 1H), 4.17 (d, J=15.5 Hz, 1H), 4.10-3.94 (m, 1H), 3.64-3.52 (m, 1H), 3.51-3.38 (m, 1H), 1.81-1.72 (m, 1H), 1.72-1.63 (m, 1H), 1.31 (s, 9H), 1.11 (s, 1H). $^{13}$C-NMR (151 MHz): δ 164.2, 154.9, 154.9, 152.1, 152.0, 148.2, 138.8, 138.3, 131.2, 129.4, 129.0, 128.2, 125.8, 124.7, 124.6, 124.1 (q, J=278.6 Hz), 123.2, 121.1, 116.0, 111.3, 102.3, 68.7, 58.5, 46.0, 40.8 (q, J=35.0 Hz), 37.5, 23.8; 1 C not observed. HRMS m/z calcd for $C_{30}H_{30}F_3N_3O_4SNa$ ([M+Na]$^+$) 608.1807; found 608.1790.

Preparation of Compound 225

(R)-4-(3-(benzofuran-2-yl)phenyl)-3-(2-hydroxyethyl)-N-(2,2,2-trifluoroethyl)-2,3-dihydro-1H-pyrrolo[3,4-c]pyridine-6-carboxamide (Compound 225)

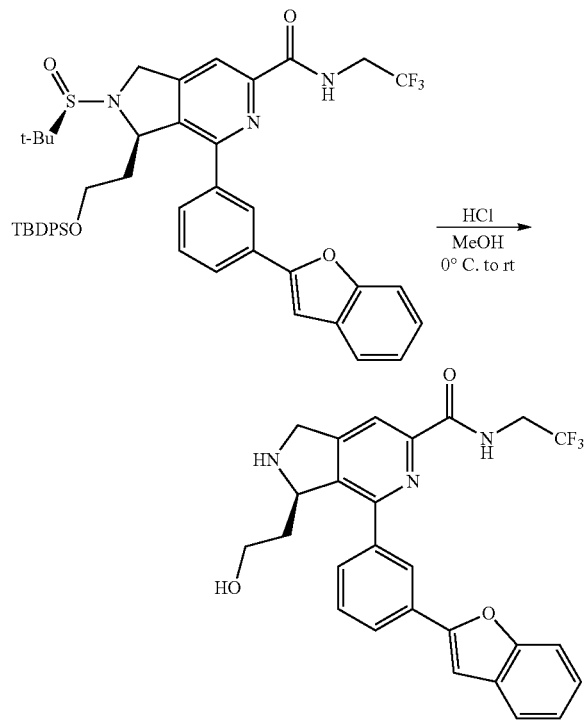

In a small vial, (R)-4-(3-(benzofuran-2-yl)phenyl)-3-(2-((tert-butyldiphenylsilyl)oxy)ethyl)-2-((R)-tert-butylsulfinyl)-N-(2,2,2-trifluoroethyl)-2,3-dihydro-1H-pyrrolo[3,4-c]pyridine-6-carboxamide (18 mg, 0.0215 mmol, 1.0 equiv) was dissolved in 0.21 mL of anhyd MeOH and cooled to 0° C. HCl solution (4.0 M in dioxane, 16 µL, 0.0644 mmol, 3 equiv) was added dropwise and the mixture was stirred at 0° C. for 5 min, then allowed to warm to room temperature and stirred for 6 h. The reaction was quenched by addition of sat. aq. NaHCO$_3$ and then diluted with EtOAc. The aqueous layer was extracted with EtOAc (3×1 mL), then the combined organic layers were dried (Na$_2$SO$_4$), filtered, and concentrated by rotary evaporation. Purification by silica flash chromatography (10% MeOH/EtOAc) yielded compound 225 as a light yellow film (5.1 mg, 51%). TLC: R$_f$ 0.06 (80% EtOAc/hexanes). [α]$_D^{20}$: +147.6° (c 0.53, CHCl$_3$). IR (ATR): 3332, 3011, 2929, 1684, 1569, 1526, 1452, 1420, 1307, 1272, 1161, 1062, 803, 754. $^1$H-NMR (600 MHz): δ 8.45 (t, J=6.7 Hz, 1H), 8.21-8.13 (m, 2H), 7.96 (d, J=7.7 Hz, 1H), 7.66-7.57 (m, 3H), 7.54 (d, J=8.2 Hz, 1H), 7.32 (t, J=7.7 Hz, 1H), 7.28-7.24 (m, 1H), 7.12 (s, 1H), 5.23 (dd, J=9.9, 3.4 Hz, 1H), 4.41 (d, J=16.3 Hz, 1H), 4.32 (d, J=16.3 Hz, 1H), 4.26-4.15 (m, 1H), 4.15-4.04 (m, 1H), 3.74 (ddd, J=11.3, 9.0, 2.5 Hz, 1H), 3.61 (ddd, J=11.0, 5.4, 3.2 Hz, 1H), 1.59-1.42 (m, 2H). $^{13}$C-NMR (151 MHz): δ 164.5, 155.0, 154.9, 154.6, 152.1, 148.0, 141.8, 139.1, 131.1, 129.4, 129.0, 128.0, 125.6, 124.7, 124.5, 124.1 (q, J=278.6 Hz), 123.2, 121.1, 116.2, 111.2, 102.2, 63.9, 62.1, 50.8, 40.8 (q, J=34.9 Hz), 33.6. HRMS m/z calcd for $C_{26}H_{23}F_3N_3O_3$ ([M+H]$^+$) 482.1692; found 482.1678.

Preparation of Compound 267

Ethyl (R)-3-(2-((tert-butyldiphenylsilyl)oxy)ethyl)-4-phenyl-2,3-dihydro-1H-pyrrolo[3,4-c]pyridine-6-carboxylate

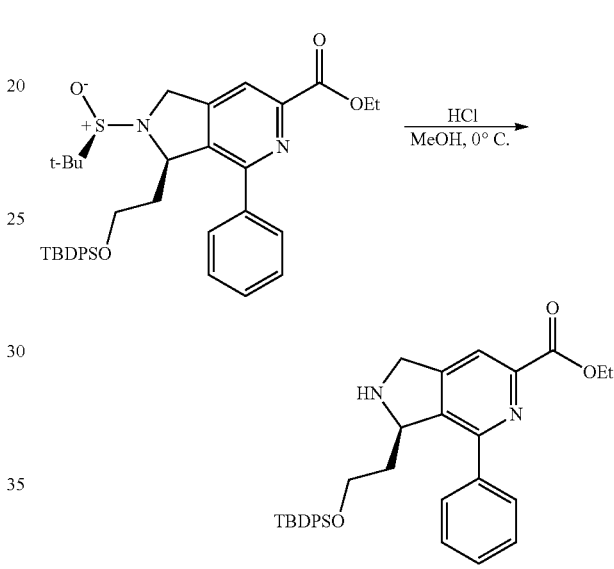

In a vial, ethyl (R)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxylate (64 mg, 0.0997 mmol, 1.0 equiv) was dissolved in 1.0 mL of anhyd MeOH and cooled to 0° C. HCl solution (4.0 M in dioxane, 27 µL, 0.107 mmol, 1.1 equiv) was added dropwise and the mixture was stirred at 0° C. for 2.5 h. The reaction was quenched by addition of sat. aq. NaHCO$_3$ and then diluted with EtOAc. The aqueous layer was extracted with EtOAc (3×3 mL), then the combined organic layers were dried (Na$_2$SO$_4$), filtered, and concentrated by rotary evaporation. Purification by silica flash chromatography (50% EtOAc/hexanes) yielded ethyl (R)-3-(2-((tert-butyldiphenylsilyl)oxy)ethyl)-4-phenyl-2,3-dihydro-1H-pyrrolo[3,4-c]pyridine-6-carboxylate as a light yellow foam (37 mg, 69%).

TLC: R$_f$ 0.58 (80% EtOAc/hexanes). [α]$_D^{20}$: +101.1° (c 1.0, CHCl$_3$). IR (ATR): 3337, 3071, 2958, 2932, 2857, 1738, 1716, 1571, 1472, 1428, 1392, 1334, 1226, 1110, 757, 702. $^1$H-NMR (600 MHz): δ 7.97 (s, 1H), 7.76-7.69 (m, 2H), 7.59-7.52 (m, 4H), 7.44-7.37 (m, 5H), 7.37-7.31 (m, 4H), 5.21 (d, J=9.5 Hz, 1H), 4.52 (dq, J=10.8, 7.1 Hz, 1H), 4.44 (dq, J=10.8, 7.1 Hz, 1H), 4.34-4.11 (m, 2H), 3.71 (td, J=9.9, 3.4 Hz, 1H), 3.59 (dt, J=10.3, 4.6 Hz, 1H), 2.66 (s, 1H), 1.78-1.66 (m, 1H), 1.45 (t, J=7.1 Hz, 3H), 1.38-1.22 (m, 1H), 1.03 (s, 9H). $^{13}$C-NMR (151 MHz): δ 165.5, 154.0, 153.8, 147.1, 142.0, 138.9, 135.4, 135.4, 133.3, 129.6, 129.6, 128.8, 128.6, 128.5, 127.6, 127.6, 118.1, 61.8, 61.3, 60.7, 51.0, 35.3, 26.8, 19.1, 14.3; 1 C not observed. HRMS m/z calcd for $C_{34}H_{39}N_2O_3Si$ ([M+H]$^+$) 551.2730; found 551.2723.

Ethyl (R)-3-(2-((tert-butyldiphenylsilyl)oxy)ethyl)-2-(isopropylcarbamoyl)-4-phenyl-2,3-dihydro-1H-pyrrolo[3,4-c]pyridine-6-carboxylate

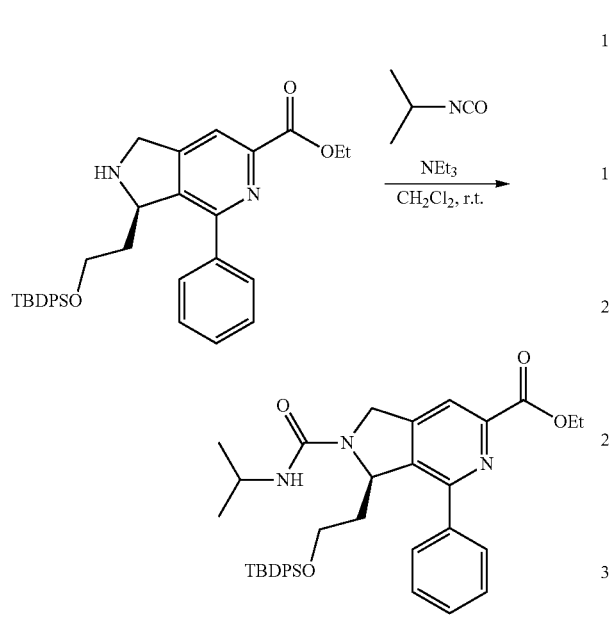

In a vial, ethyl (R)-3-(2-((tert-butyldiphenylsilyl)oxy) ethyl)-4-phenyl-2,3-dihydro-1H-pyrrolo[3,4-c]pyridine-6-carboxylate (96 mg, 0.174 mmol, 1.0 equiv) was dissolved in 1.7 mL of $CH_2Cl_2$ and cooled to 0° C. $NEt_3$ (36 µL, 0.261 mmol, 1.5 equiv) was added, followed by 2-isocyanatopropane (21 µL, 0.209 mmol, 1.2 equiv), and the mixture was stirred at 0° C. for 1 h. The reaction mixture was quenched by addition of 2 mL saturated aqueous $NaHCO_3$, then the aqueous layer was extracted with $CH_2Cl_2$ (3×3 mL). The combined organic extracts were washed with brine (1×3 mL), dried ($Na_2SO_4$), filtered, and concentrated by rotary evaporation. Purification by silica flash chromatography (40% EtOAc/hexanes) yielded ethyl (R)-3-(2-((tert-butyldiphenylsilyl)oxy)ethyl)-2-(isopropylcarbamoyl)-4-phenyl-2,3-dihydro-1H-pyrrolo[3,4-c]pyridine-6-carboxylate as an white solid film (48 mg, 43%).TLC: $R_f$0.32 (50% EtOAc/hexanes). $[\alpha]_D^{20}$: +81.3° (c 1.0, $CHCl_3$). IR (ATR): 3371, 3071, 2965, 2932, 2858, 1724, 1632, 1579, 1534, 1460, 1429, 1388, 1370, 1299, 1235, 1108, 740, 703. $^1$H-NMR (600 MHz): δ 7.95 (s, 1H), 7.77-7.67 (m, 2H), 7.42-7.35 (m, 9H), 7.33-7.27 (m, 4H), 5.82 (d, J=6.9 Hz, 1H), 5.14 (d, J=12.7 Hz, 1H), 4.95 (bs, 1H), 4.58-4.48 (m, 1H), 4.48-4.38 (m, 2H), 4.07 (dq, J=13.6, 6.8 Hz, 1H), 3.63 (t, J=8.0 Hz, 1H), 3.50 (dt, J=10.4, 4.7 Hz, 1H), 1.90-1.70 (m, 1H), 1.44 (t, J=7.1 Hz, 3H), 1.30-1.22 (m, 1H), 1.17 (dd, J=6.6, 2.5 Hz, 6H), 0.93 (s, 9H). $^{13}$C-NMR (151 MHz): δ 165.2, 156.6, 154.0, 149.1, 147.6, 138.9, 138.6, 135.4, 135.3, 135.3, 133.2, 133.0, 129.8, 129.7, 129.1, 128.9, 128.4, 127.7, 117.9, 61.9, 60.3, 50.8, 42.7, 27.1, 23.4, 23.4, 19.1, 14.3. HRMS m/z calcd for $C_{38}H_{45}N_3O_4SiNa$ ([M+Na]$^+$) 658.3077; found 658.3049.

(R)-3-(2-((tert-butyldiphenylsilyl)oxy)ethyl)-N$^2$-isopropyl-4-phenyl-N$^6$-(2,2,2-trifluoroethyl)-1,3-dihydro-2H-pyrrolo[3,4-c]pyridine-2,6-dicarboxamide

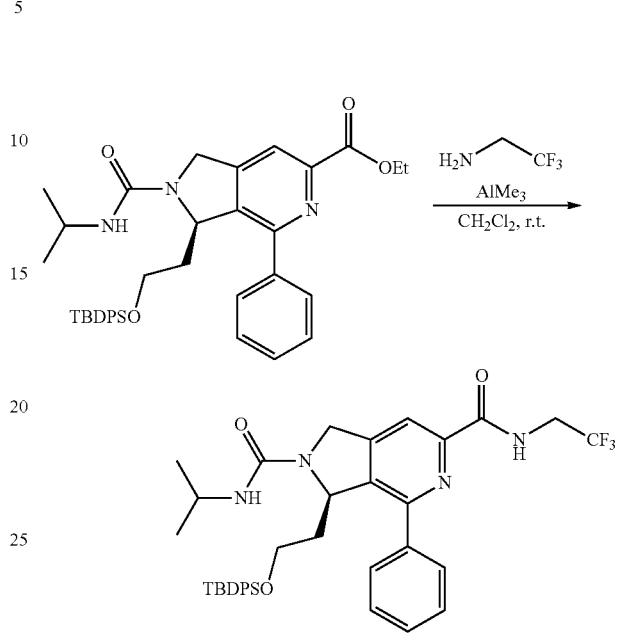

To a vial containing ethyl (R)-3-(2-((tert-butyldiphenylsilyl)oxy)ethyl)-2-(isopropylcarbamoyl)-4-phenyl-2,3-dihydro-1H-pyrrolo[3,4-c]pyridine-6-carboxylate (48 mg, 0.0755 mmol, 1.0 equiv, azeotroped 3× with toluene) at room temperature was slowly added a pre-stirred (>2 h) stock solution of dimethylaluminum 2,2,2-trifluoroethylamide (0.2 M solution in $CH_2Cl_2$/toluene, 0.75 mL, 0.151 mmol, 2.0 equiv). The mixture was stirred at room temperature for 17 h, then carefully quenched by addition of a few drops of MeOH followed by dilution with 1 mL of $CH_2Cl_2$ and careful addition of 1 mL saturated aqueous $NaHCO_3$. The aqueous layer was extracted with EtOAc (3×1 mL), then the combined organic layers were dried ($Na_2SO_4$), filtered, and concentrated by rotary evaporation. Purification by silica flash chromatography (40% EtOAc/hexanes) yielded (R)-3-(2-((tert-butyldiphenylsilyl)oxy)ethyl)-N$^2$-isopropyl-4-phenyl-N$^6$-(2,2,2-trifluoroethyl)-1,3-dihydro-2H-pyrrolo[3,4-c]pyridine-2,6-dicarboxamide as a sticky yellow foam (34 mg, 66%).

TLC: $R_f$0.41 (30% EtOAc/$CH_2Cl_2$). $[\alpha]_D^{20}$: +64.5° (c 1.0, $CHCl_3$). IR (ATR): 3376, 3071, 3051, 2963, 2932, 2859, 1686, 1639, 1578, 1521, 1459, 1428, 1383, 1274, 1162, 1111, 987, 758, 742, 702. $^1$H-NMR (600 MHz): δ 8.40 (t, J=6.8 Hz, 1H), 8.06 (s, 1H), 7.74-7.60 (m, 2H), 7.49-7.33 (m, 9H), 7.33-7.24 (m, 4H), 5.85 (s, 1H), 5.07 (d, J=15.5 Hz, 1H), 4.80 (bs, 1H), 4.45 (d, J=15.4 Hz, 1H), 4.35-4.15 (m, 1H), 4.13-3.94 (m, 2H), 3.69-3.54 (m, 1H), 3.54-3.44 (m, 1H), 1.98-1.80 (m, 1H), 1.40-1.26 (m, 1H), 1.18 (dd, J=6.6, 2.1 Hz, 6H), 0.90 (s, 9H). $^{13}$C-NMR (151 MHz): δ 164.3, 156.3, 152.6, 149.8, 147.8, 139.0, 138.3, 135.3, 133.1, 133.0, 129.7, 129.7, 129.3, 128.9, 128.2, 127.7, 127.6, 127.6, 124.1 (q, J=278.6 Hz), 115.6, 60.2, 59.5, 51.0, 42.6, 40.7 (q, J=34.9 Hz), 27.0, 23.4, 23.4, 19.0. HRMS m/z calcd for C$_{38}$H$_{43}$F$_3$N$_4$O$_3$SiNa ([M+Na]$^+$) 711.2954; found 711.2957.

(R)-3-(2-hydroxyethyl)-N$^2$-isopropyl-4-phenyl-N$^6$-(2,2,2-trifluoroethyl)-1,3-dihydro-2H-pyrrolo[3,4-c]pyridine-2,6-dicarboxamide (Compound 267)

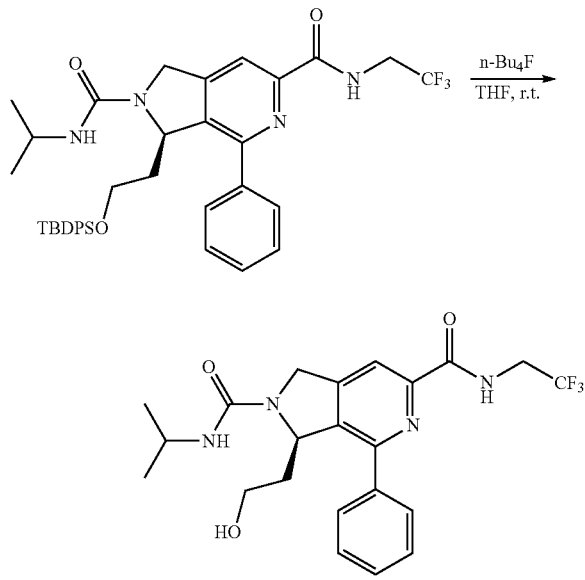

In a small vial, (R)-3-(2-((tert-butyldiphenylsilyl)oxy)ethyl)-N$^2$-isopropyl-4-phenyl-N$^6$-(2,2,2-trifluoroethyl)-1,3-dihydro-2H-pyrrolo[3,4-c]pyridine-2,6-dicarboxamide (34 mg, 0.0494 mmol, 1.0 equiv) was dissolved in 0.49 mL of THF and cooled to 0° C. n-Bu$_4$NF solution (1.0 M in THF, 74 µL, 0.0740 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (70% EtOAc/hexanes) yielded compound 267 as a light yellow film (10 mg, 47%). TLC: R$_f$ 0.08 (50% EtOAc/hexanes). [α]$_D^{20}$: +17.1° (c 0.56, CHCl$_3$). IR (ATR): 3313, 3061, 2971, 2877, 1682, 1627, 1578, 1523, 1458, 1384, 1273, 1158, 1057, 987, 738, 699. $^1$H-NMR (600 MHz): δ 8.42 (t, J=6.8 Hz, 1H), 8.10 (s, 1H), 7.82-7.70 (m, 2H), 7.57-7.52 (m, 2H), 7.52-7.46 (m, 1H), 5.99 (d, J=10.1 Hz, 1H), 4.88 (d, J=14.7 Hz, 1H), 4.72-4.39 (m, 2H), 4.31-4.16 (m, 1H), 4.14-3.89 (m, 3H), 3.57-3.45 (m, 1H), 3.45-3.33 (m, 1H), 1.79-1.69 (m, 1H), 1.23 (t, J=7.0 Hz, 6H), 1.19-1.10 (m, 1H). $^{13}$C-NMR (151 MHz): δ 164.3, 157.3, 152.8, 148.6, 148.0, 139.3, 137.9, 129.6, 129.0, 128.1, 124.1 (q, J=278.6 Hz), 115.5, 59.2, 58.5, 50.9, 43.0, 40.8 (q, J=35.0 Hz), 37.8, 23.4, 23.3. HRMS m/z calcd for C$_{22}$H$_{25}$F$_3$N$_4$O$_3$Na ([M+Na]$^+$) 473.1776; found 473.1797.

Preparation of Compound 217

(R)—N-(benzo[d][1,3]dioxol-5-ylmethyl)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxamide

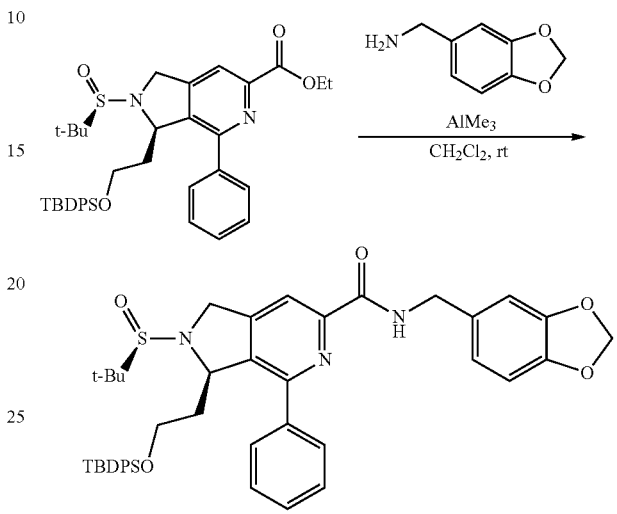

To a vial containing ethyl (R)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxylate (31 mg, 0.0473 mmol, 1.0 equiv, azeotroped 3× with toluene) at room temperature was slowly added a pre-stirred (>2 h) stock solution of dimethylaluminum piperonylamide (0.2 M solution in CH$_2$Cl$_2$/toluene, 0.47 mL, 0.0947 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (40% EtOAc/hexanes) yielded (R)—N-(benzo[d][1,3]dioxol-5-ylmethyl)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxamide as a white foam (35 mg, 97%). TLC: R$_f$ 0.27 (50% EtOAc/hexanes). [α]$_D^{20}$: +42.5° (c 1.0, CHCl$_3$). IR (ATR): 3387, 3071, 2958, 2931, 2859, 1673, 1576, 1523, 1503, 1490, 1253, 1239, 1075, 1042, 930, 757, 702. $^1$H-NMR (600 MHz): δ 8.36 (t, J=6.3 Hz, 1H), 8.06 (s, 1H), 7.72-7.61 (m, 2H), 7.49-7.45 (m, 2H), 7.45-7.36 (m, 7H), 7.33-7.28 (m, 4H), 6.85 (d, J=1.7 Hz, 1H), 6.81 (dd, J=7.9, 1.6 Hz, 1H), 6.76 (d, J=7.9 Hz, 1H), 5.94 (d, J=1.6 Hz, 2H), 5.78 (d, J=8.1 Hz, 1H), 5.17 (d, J=15.7 Hz, 1H), 4.62 (dd, J=14.9, 6.4 Hz, 1H), 4.52 (dd, J=14.8, 6.1 Hz, 1H), 4.00 (d, J=15.5 Hz, 1H), 3.75-3.58 (m, 1H), 3.43 (ddd, J=10.4, 6.0, 4.2 Hz, 1H), 1.78-1.66 (m, 1H), 1.51-1.38 (m, 1H), 1.22 (s, 9H), 0.97 (s, 9H). $^{13}$C-NMR (151 MHz): δ 164.0, 152.1, 151.7, 149.1, 147.9, 146.9, 138.5, 138.5, 135.5, 135.4, 133.4, 133.3, 132.2, 129.7, 129.6, 129.1, 128.8, 128.3, 127.6, 127.6, 121.0, 115.4, 108.4, 108.3, 101.0, 68.5, 59.4, 58.6, 45.8, 43.2, 37.6, 26.8, 23.8, 19.1. HRMS m/z calcd for C$_{44}$H$_{49}$N$_3$O$_6$SSiNa ([M+Na]$^+$) 782.3060; found 782.3507.

(R)—N-(benzo[d][1,3]dioxol-5-ylmethyl)-2-((R)-tert-butylsulfinyl)-3-(2-hydroxyethyl)-4-phenyl-2,3-dihydro-1H-pyrrolo[3,4-c]pyridine-6-carboxamide (Compound 217)

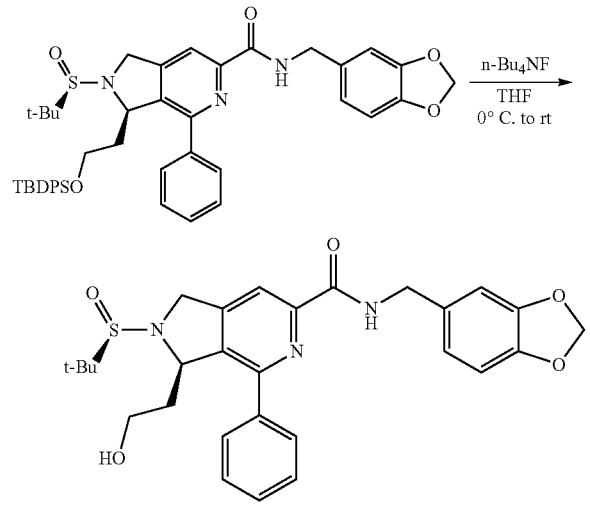

In a small vial, (R)—N-(benzo[d][1,3]dioxol-5-ylmethyl)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxamide (33 mg, 0.0434 mmol, 1.0 equiv) was dissolved in 0.43 mL of THF and cooled to 0° C. n-Bu$_4$NF solution (1.0 M in THF, 65 µL, 0.0651 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (75% EtOAc/hexanes) yielded compound 217 as a white solid foam (13 mg, 57%). TLC: R$_f$ 0.24 (80% EtOAc/hexanes). [α]$_D^{20}$: +23.9° (c 1.0, CHCl$_3$). IR (ATR): 3389, 2949, 1666, 1576, 1527, 1503, 1491, 1445, 1254, 1239, 1041, 930, 758. $^1$H-NMR (600 MHz): δ 8.36 (t, J=6.2 Hz, 1H), 8.08 (s, 1H), 7.69-7.60 (m, 2H), 7.55-7.39 (m, 3H), 6.85 (d, J=1.6 Hz, 1H), 6.81 (dd, J=7.9, 1.7 Hz, 1H), 6.76 (d, J=7.9 Hz, 1H), 5.93 (d, J=2.0 Hz, 2H), 5.71-5.62 (m, 1H), 5.20 (d, J=15.6 Hz, 1H), 4.60 (dd, J=14.9, 6.3 Hz, 1H), 4.53 (dd, J=14.8, 6.1 Hz, 1H), 4.13 (d, J=15.6 Hz, 1H), 3.59-3.44 (m, 1H), 3.38 (dt, J=11.3, 5.9 Hz, 1H), 1.76-1.63 (m, 1H), 1.63-1.54 (m, 1H), 1.30 (s, 9H), 1.16 (s, 1H). $^{13}$C-NMR (151 MHz): δ 163.9, 152.2, 151.6, 149.3, 147.8, 146.9, 138.4, 137.3, 132.1, 129.3, 128.8, 128.2, 121.0, 115.5, 108.4, 108.3, 101.0, 68.7, 58.5, 58.3, 46.0, 43.2, 37.4, 23.8. HRMS m/z calcd for C$_{28}$H$_{31}$N$_3$O$_5$SNa ([M+Na]$^+$) 544.1882; found 544.1864.

Preparation of Compound 218

(R)-3-(2-((tert-butyldiphenylsilyl)oxy)ethyl)-2-((R)-tert-butylsulfinyl)-N-(2-fluorobenzyl)-4-phenyl-2,3-dihydro-1H-pyrrolo[3,4-c]pyridine-6-carboxamide

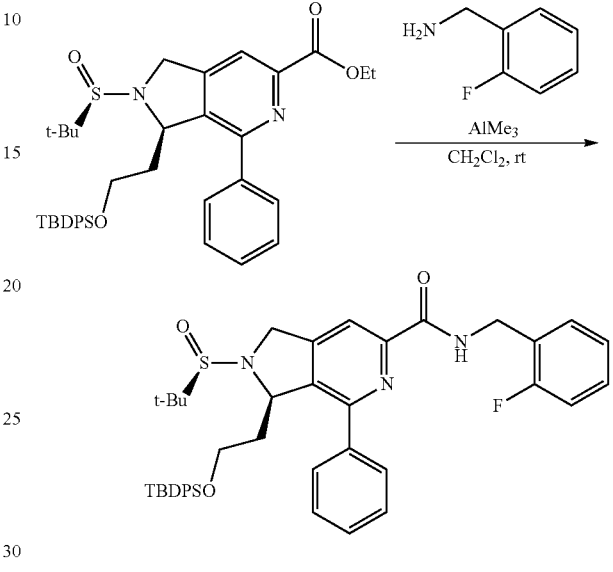

To a vial containing ethyl (R)-3-(2-((tert-butyldiphenylsilyl)oxy)ethyl)-2-((R)-tert-butylsulfinyl)-4-phenyl-2,3-dihydro-1H-pyrrolo[3,4-c]pyridine-6-carboxylate (31 mg, 0.0473 mmol, 1.0 equiv, azeotroped 3× with toluene) at room temperature was slowly added a pre-stirred (>2 h) stock solution of dimethylaluminum (2-fluorobenzyl)amide (0.2 M solution in CH$_2$Cl$_2$/toluene, 0.47 mL, 0.0947 mmol, 2.0 equiv). The mixture was stirred at room temperature for 15 h, then carefully quenched by addition of a few drops of MeOH followed by dilution with 1 mL of CH$_2$Cl$_2$ and careful addition of 1 mL saturated aqueous NaHCO$_3$. The aqueous layer was extracted with EtOAc (3×1 mL), then the combined organic layers were dried (Na$_2$SO$_4$), filtered, and concentrated by rotary evaporation. Purification by silica flash chromatography (40% EtOAc/hexanes) yielded (R)-3-(2-((tert-butyldiphenylsilyl)oxy)ethyl)-2-((R)-tert-butylsulfinyl)-N-(2-fluorobenzyl)-4-phenyl-2,3-dihydro-1H-pyrrolo[3,4-c]pyridine-6-carboxamide as a light yellow foam (34 mg, 99%).

TLC: R$_f$ 0.38 (50% EtOAc/hexanes). [α]$_D^{21}$: +80.9° (c 1.0, CHCl$_3$). IR (ATR): 3394, 3071, 2958, 2931, 2858, 1676, 1577, 1523, 1491, 1473, 1427, 1391, 1230, 1110, 1075, 943, 758, 702. $^1$H-NMR (600 MHz): δ 8.44 (t, J=6.4 Hz, 1H), 8.05 (s, 1H), 7.73-7.65 (m, 2H), 7.49-7.45 (m, 2H), 7.45-7.35 (m, 8H), 7.32-7.28 (m, 4H), 7.25-7.22 (m, 1H), 7.14-7.03 (m, 2H), 5.79 (d, J=7.6 Hz, 1H), 5.17 (d, J=15.8 Hz, 1H), 4.76 (dd, J=15.2, 6.4 Hz, 1H), 4.70 (dd, J=15.3, 6.3 Hz, 1H), 3.99 (d, J=15.1 Hz, 1H), 3.65 (td, J=9.9, 9.5, 4.8 Hz, 1H), 3.43 (ddd, J=10.4, 6.1, 4.2 Hz, 1H), 1.78-1.69 (m, 1H), 1.50-1.41 (m, 1H), 1.21 (s, 10H), 0.97 (s, 9H). $^{13}$C-NMR (151 MHz): δ 164.1, 161.0 (d, J=246.4 Hz), 152.0, 151.7, 149.0, 138.5, 138.5, 135.5, 135.4, 133.4, 133.2, 130.0 (d, J=4.2 Hz), 129.7, 129.6, 129.1 (d, J=7.9 Hz), 129.1, 128.8, 128.3, 127.6, 127.6, 125.3 (d, J=14.7 Hz), 124.3 (d, J=3.6 Hz), 115.4, 115.3 (d, J=21.2 Hz), 68.5, 59.4, 58.6, 45.8, 37.6, 37.3 (d, J=4.2 Hz), 26.8, 23.8, 19.1. HRMS m/z calcd for $C_{43}H_{49}FN_3O_3SSi$ ([M+H]$^+$) 734.3248; found 734.3220.

(R)-2-((R)-tert-butylsulfinyl)-N-(2-fluorobenzyl)-3-(2-hydroxyethyl)-4-phenyl-2,3-dihydro-1H-pyrrolo[3,4-c]pyridine-6-carboxamide (Compound 218)

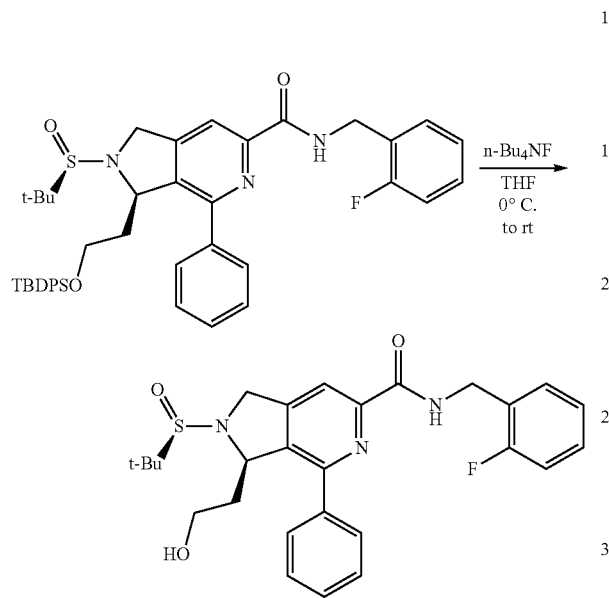

In a small vial, (R)-3-(2-((tert-butyldiphenylsilyl)oxy)ethyl)-2-((R)-tert-butylsulfinyl)-N-(2-fluorobenzyl)-4-phenyl-2,3-dihydro-1H-pyrrolo[3,4-c]pyridine-6-carboxamide (28 mg, 0.0381 mmol, 1.0 equiv) was dissolved in 0.38 mL of THF and cooled to 0° C. n-Bu$_4$NF solution (1.0 M in THF, 57 μL, 0.0572 mmol, 1.5 equiv) was added dropwise and the mixture was stirred at 0° C. for 1 h, then allowed to warm to room temperature over 4 h. The reaction mixture was diluted with 1 mL EtOAc and 1 mL sat aq NaHCO$_3$, then the aqueous layer was extracted with EtOAc (3×2 mL). The combined organic extracts were washed with brine (1×1 mL), dried (Na$_2$SO$_4$), filtered, and concentrated by rotary evaporation. Purification by silica flash chromatography (75% EtOAc/hexanes) yielded compound 218 as a white solid foam (14 mg, 76%). TLC: R$_f$ 0.32 (80% EtOAc/hexanes). [α]$_D^{20}$: +28.4° (c 1.0, CHCl$_3$). IR (ATR): 3393, 2955, 1669, 1577, 1527, 1491, 1457, 1423, 1364, 1230, 1049, 931, 758. $^1$H-NMR (600 MHz): δ 8.44 (t, J=6.4 Hz, 1H), 8.07 (s, 1H), 7.68 (d, J=6.9 Hz, 2H), 7.53-7.45 (m, 3H), 7.40 (td, J=7.6, 1.7 Hz, 1H), 7.25-7.22 (m, 1H), 7.10 (t, J=7.4 Hz, 1H), 7.08-7.02 (m, 1H), 5.74-5.62 (m, 1H), 5.19 (d, J=15.7 Hz, 1H), 4.79-4.61 (m, 2H), 4.13 (dd, J=15.7, 2.0 Hz, 1H), 3.52 (ddd, J=10.8, 7.6, 6.2 Hz, 1H), 3.38 (ddd, J=11.2, 6.7, 5.2 Hz, 1H), 1.76-1.64 (m, 1H), 1.64-1.53 (m, 1H), 1.30 (s, 9H). $^{13}$C-NMR (151 MHz): δ 164.0, 160.9 (d, J=246.3 Hz), 152.2, 151.6, 149.2, 138.4, 137.4, 130.0 (d, J=4.2 Hz), 129.3, 129.2 (d, J=8.1 Hz), 128.8, 128.2, 125.2 (d, J=14.7 Hz), 124.3 (d, J=3.6 Hz), 115.4, 115.3 (d, J=21.2 Hz), 68.7, 58.6, 58.4, 46.0, 37.4, 37.3 (d, J=4.3 Hz), 23.8. HRMS m/z calcd for $C_{27}H_{30}FN_3O_3SNa$ ([M+Na]$^+$) 518.1890; found 518.1907.

Preparation of Compound 223

Ethyl (S)-4-(3-(benzofuran-2-yl)phenyl)-2-(tert-butylsulfinyl)-2,3-dihydro-1H-pyrrolo[3,4-c]pyridine-6-carboxylate

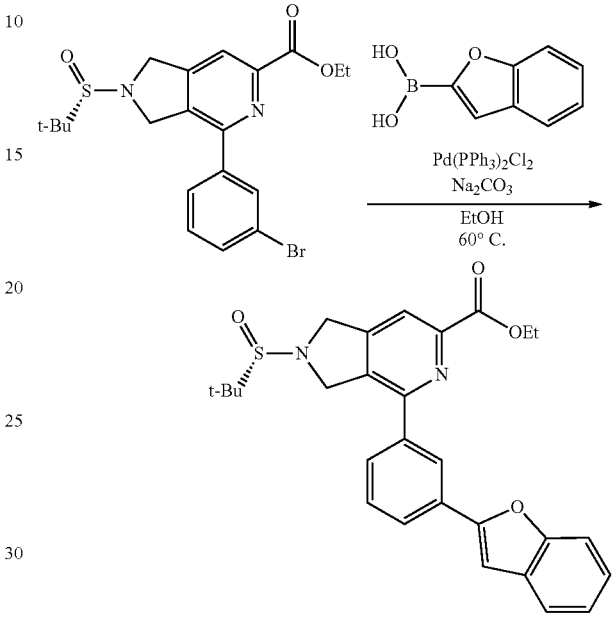

To a vial was added ethyl (S)-4-(3-bromophenyl)-2-(tert-butylsulfinyl)-2,3-dihydro-1H-pyrrolo[3,4-c]pyridine-6-carboxylate (57 mg, 0.126 mmol, 1.0 equiv), benzofuran-2-ylboronic acid (51 mg, 0.316 mmol, 2.0 equiv), and Na$_2$CO$_3$ (47 mg, 0.442 mmol, 3.0 equiv). Degassed ethanol (1.3 mL) was added, and the whole solution purged with argon for ~10 minutes. Bis(triphenylphosphine)palladium dichloride (4.4 mg, 0.00631 mmol, 0.05 equiv) was quickly added to the reaction, then it was capped with a teflon-lined cap and stirred at 60° C. After 16 h, the reaction was cooled to room temperature, then diluted with EtOAc, filtered through Celite, and concentrated by rotary evaporation. Purification by silica flash chromatography (30% EtOAc/hexanes) yielded ethyl (S)-4-(3-(benzofuran-2-yl)phenyl)-2-(tert-butylsulfinyl)-2,3-dihydro-1H-pyrrolo[3,4-c]pyridine-6-carboxylate as a light yellow foam (49 mg, 80%). TLC: R$_f$ 0.31 (40% EtOAc/hexanes). [α]$_D^{20}$: +71.0° (c 1.0, CHCl$_3$). IR (ATR): 2981, 2860, 1740, 1716, 1575, 1452, 1419, 1391, 1369, 1335, 1302, 1258, 1224, 1068, 1021, 937, 796, 750. $^1$H-NMR (600 MHz): δ 8.26 (s, 1H), 8.02 (s, 1H), 7.94 (d, J=7.8 Hz, 1H), 7.75 (d, J=7.7 Hz, 1H), 7.61 (d, J=7.6 Hz, 1H), 7.57 (t, J=7.7 Hz, 1H), 7.54 (d, J=8.1 Hz, 1H), 7.31 (t, J=7.6 Hz, 1H), 7.26-7.23 (m, 1H), 7.11 (s, 1H), 5.14 (d, J=15.0 Hz, 1H), 5.02 (d, J=15.2 Hz, 1H), 4.77 (d, J=14.9 Hz, 1H), 4.58-4.41 (m, 3H), 1.47 (t, J=7.1 Hz, 3H), 1.28 (s, 9H). $^{13}$C-NMR (151 MHz): δ 165.1, 155.3, 154.9, 152.9, 150.5, 147.7, 139.0, 135.6, 131.0, 129.2, 129.1, 128.2, 125.7, 124.7, 124.5, 123.0, 121.0, 118.0, 111.2, 101.9, 62.0, 58.2, 23.3, 14.3. HRMS m/z calcd for $C_{28}H_{28}N_2O_4SNa$ ([M+Na]$^+$) 511.1667; found 511.1686.

Ethyl 4-(3-(benzofuran-2-yl)phenyl)-2,3-dihydro-1H-pyrrolo[3,4-c]pyridine-6-carboxylate

Ethyl 4-(3-(benzofuran-2-yl)phenyl)-2-(isopropylcarbamoyl)-2,3-dihydro-1H-pyrrolo[3,4-c]pyridine-6-carboxylate

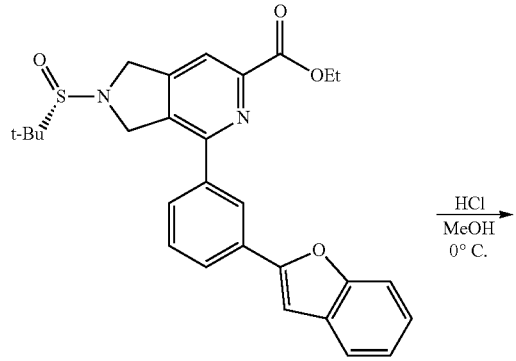

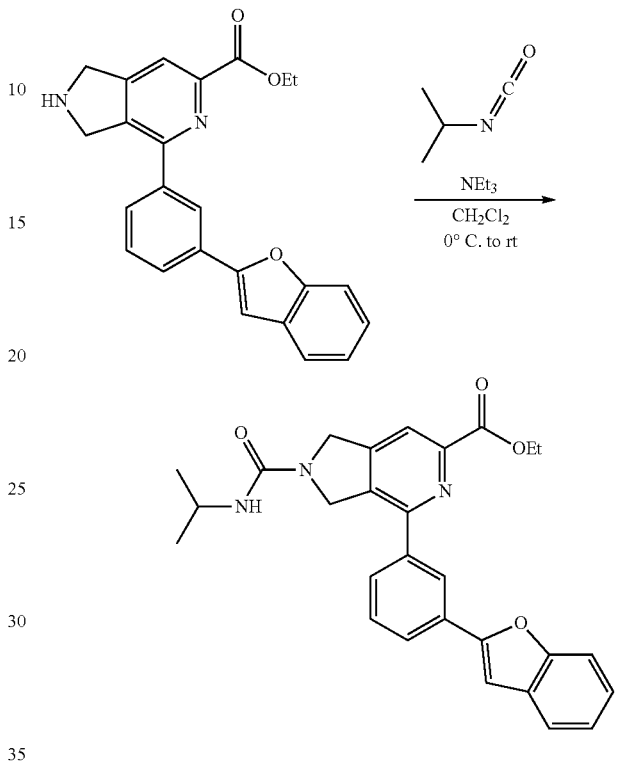

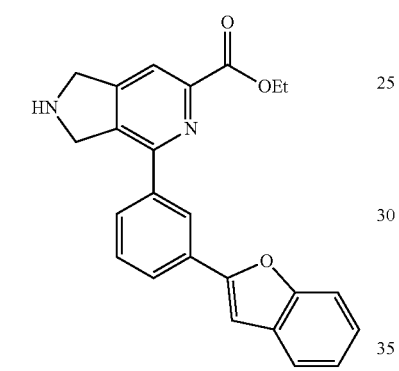

In a vial, ethyl (S)-4-(3-(benzofuran-2-yl)phenyl)-2-(tert-butylsulfinyl)-2,3-dihydro-1H-pyrrolo[3,4-c]pyridine-6-carboxylate (46 mg, 0.0941 mmol, 1.0 equiv) was dissolved in 0.94 mL of anhyd MeOH and cooled to 0° C. HCl solution (4.0 M in dioxane, 47 µL, 0.188 mmol, 2 equiv) was added dropwise and the mixture was stirred at 0° C. for 3 h. The reaction was quenched by addition of sat. aq. NaHCO$_3$ and then diluted with EtOAc. The aqueous layer was extracted with EtOAc (3×3 mL), then the combined organic layers were dried (Na$_2$SO$_4$), filtered, and concentrated by rotary evaporation. Purification by silica flash chromatography (10% MeOH/EtOAc) yielded ethyl 4-(3-(benzofuran-2-yl)phenyl)-2,3-dihydro-1H-pyrrolo[3,4-c]pyridine-6-carboxylate as a light yellow foam (26 mg, 73%). TLC: R$_f$ 0.22 (5% MeOH/CH$_2$Cl$_2$). IR (ATR): 3327, 2983, 2850, 1733, 1571, 1451, 1391, 1371, 1335, 1309, 1287, 1258, 1223, 1169, 1023, 798, 750. $^1$H-NMR (600 MHz): δ 8.27 (s, 1H), 8.02 (s, 1H), 7.91 (d, J=7.8 Hz, 1H), 7.76 (d, J=7.7 Hz, 1H), 7.59 (d, J=7.6 Hz, 1H), 7.57-7.50 (m, 2H), 7.30 (t, J=8.1 Hz, 1H), 7.24 (t, J=7.4 Hz, 1H), 7.09 (s, 1H), 4.54 (s, 2H), 4.50 (q, J=7.1 Hz, 2H), 4.37 (s, 2H), 2.79 (bs, 1H), 1.47 (t, J=7.1 Hz, 3H). $^{13}$C-NMR (151 MHz): δ 165.4, 155.4, 154.9, 154.1, 152.5, 147.2, 139.3, 139.1, 130.8, 129.1, 129.1, 128.3, 125.4, 124.7, 124.4, 123.0, 121.0, 118.1, 111.2, 101.8, 61.9, 52.7, 14.3; 1 C not observed. HRMS m/z calcd for C$_{24}$H$_{21}$N$_2$O$_3$ ([M+H]$^+$) 385.1552; found 385.1552.

In a vial, ethyl 4-(3-(benzofuran-2-yl)phenyl)-2,3-dihydro-1H-pyrrolo[3,4-c]pyridine-6-carboxylate (25 mg, 0.0650 mmol, 1.0 equiv) was dissolved in 0.65 mL of CH$_2$Cl$_2$ and cooled to 0° C. NEt$_3$ (23 µL, 0.163 mmol, 1.5 equiv) was added, followed by 2-isocyanatopropane (7 µL, 0.0715 mmol, 1.1 equiv), and the mixture was stirred at 0° C. for 1.5 h. The reaction mixture was quenched by addition of 1 mL saturated aqueous NaHCO$_3$, then the aqueous layer was extracted with CH$_2$Cl$_2$ (3×3 mL). The combined organic extracts were washed with brine (1×1 mL), dried (Na$_2$SO$_4$), filtered, and concentrated by rotary evaporation. Purification by silica flash chromatography (100% CH$_2$Cl$_2$→50% EtOAc/CH$_2$Cl$_2$) and filtration of insoluble byproducts with Et$_2$O yielded ethyl 4-(3-(benzofuran-2-yl)phenyl)-2-(isopropylcarbamoyl)-2,3-dihydro-1H-pyrrolo[3,4-c]pyridine-6-carboxylate as an white solid film (15 mg, 51%). TLC: R$_f$ 0.81 (10% MeOH/EtOAc). IR (ATR): 3386, 3093, 2964, 2950, 2908, 2860, 1722, 1650, 1580, 1522, 1463, 1382, 1296, 1236, 1108, 789, 751. $^1$H-NMR (600 MHz): δ 8.26 (s, 1H), 8.03 (s, 1H), 7.94 (d, J=7.8 Hz, 1H), 7.72 (d, J=7.7 Hz, 1H), 7.60 (d, J=7.6 Hz, 1H), 7.57 (t, J=7.7 Hz, 1H), 7.53 (d, J=8.1 Hz, 1H), 7.30 (t, J=7.2 Hz, 1H), 7.24 (t, J=7.5 Hz, 1H), 7.11 (s, 1H), 4.94 (s, 1H), 4.82 (d, J=2.5 Hz, 2H), 4.50 (q, J=7.1 Hz, 2H), 4.22 (d, J=7.6 Hz, 1H), 4.06 (dq, J=13.4, 6.7 Hz, 1H), 1.47 (t, J=7.1 Hz, 3H), 1.21 (d, J=6.5 Hz, 6H). $^{13}$C-NMR (151 MHz): δ 165.0, 155.6, 155.2, 154.9, 153.3, 149.0, 147.9, 138.8, 134.4, 131.0, 129.2, 129.0, 128.1, 125.7, 124.7, 124.5, 123.0, 121.0, 118.3, 111.2, 102.0, 62.1, 51.7, 51.3, 42.7, 23.6, 14.3. HRMS m/z calcd for C$_{28}$H$_{27}$N$_3$O$_4$Na ([M+Na]$^+$) 492.1899; found 492.1889.

4-(3-(benzofuran-2-yl)phenyl)-N2-isopropyl-N6-(2,2-trifluoroethyl)-1,3-dihydro-2H-pyrrolo[3,4-c]pyridine-2,6-dicarboxamide (Compound 223)

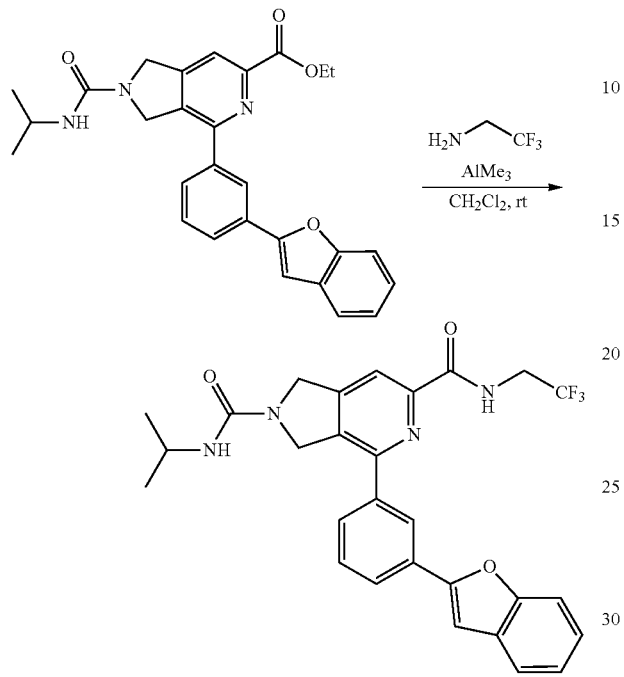

To a vial containing ethyl 4-(3-(benzofuran-2-yl)phenyl)-2-(isopropylcarbamoyl)-2,3-dihydro-1H-pyrrolo[3,4-c]pyridine-6-carboxylate (14 mg, 0.0300 mmol, 1.0 equiv, azeotroped 3× with toluene) at room temperature was slowly added a pre-stirred (>2 h) stock solution of dimethylaluminum 2,2,2-trifluoroethylamide (0.2 M solution in $CH_2Cl_2$/toluene, 0.30 mL, 0.0601 mmol, 2.0 equiv). The mixture was stirred at room temperature for 15 h, then carefully quenched by addition of a few drops of MeOH followed by dilution with 1 mL of $CH_2Cl_2$ and careful addition of 1 mL saturated aqueous $NaHCO_3$. The aqueous layer was extracted with EtOAc (3×1 mL), then the combined organic layers were dried ($Na_2SO_4$), filtered, and concentrated by rotary evaporation. Purification by silica flash chromatography (60% EtOAc/hexanes) yielded compound 223 as a sticky yellow foam (13 mg, 81%).

TLC: $R_f$ 0.26 (30% EtOAc/$CH_2Cl_2$). IR (ATR): 3320, 2966, 2924, 2854, 1678, 1639, 1578, 1528, 1456, 1385, 1274, 1260, 1164, 749. $^1$H-NMR (600 MHz): δ 8.47 (t, J=6.7 Hz, 1H), 8.23 (s, 1H), 8.15 (s, 1H), 7.97 (d, J=7.8 Hz, 1H), 7.67 (d, J=7.7 Hz, 1H), 7.64-7.59 (m, 2H), 7.54 (d, J=8.2 Hz, 1H), 7.32 (t, J=7.2 Hz, 1H), 7.29-7.21 (m, 4H), 7.12 (s, 1H), 4.97 (s, 2H), 4.81 (s, 2H), 4.24-4.11 (m, 3H), 4.06 (h, J=6.7 Hz, 1H), 1.21 (d, J=6.5 Hz, 6H). $^{13}$C-NMR (151 MHz): δ 164.3, 155.6, 154.9, 154.9, 152.0, 149.7, 148.2, 138.4, 134.5, 131.2, 129.4, 129.0, 127.8, 125.9, 124.7, 124.5, 124.1 (q, J=278.7 Hz), 123.2, 121.1, 116.0, 111.2, 102.2, 51.6, 51.4, 42.7, 40.8 (q, J=34.9 Hz), 23.6. HRMS m/z calcd for $C_{28}H_{25}F_3N_4O_3Na$ ([M+Na]$^+$) 545.1776; found 545.1763.

Preparation of Compound 212

Ethyl (R)-2-(tert-butylsulfinyl)-4-(3-(pyridin-3-yl)phenyl)-2,3-dihydro-1H-pyrrolo[3,4-c]pyridine-6-carboxylate

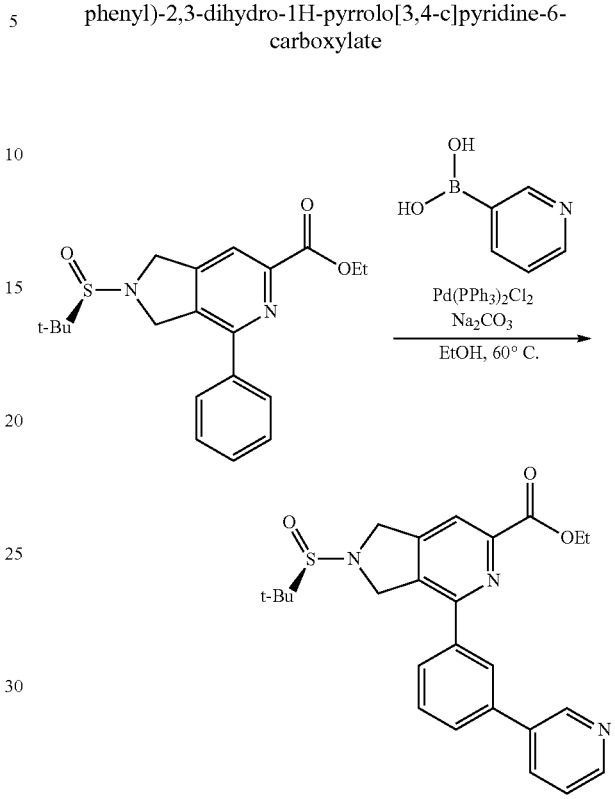

To a vial was added ethyl (R)-4-(3-bromophenyl)-2-(tert-butylsulfinyl)-2,3-dihydro-1H-pyrrolo[3,4-c]pyridine-6-carboxylate (53 mg, 0.117 mmol, 1.0 equiv), pyridin-3-ylboronic acid (29 mg, 0.235 mmol, 2.0 equiv), and $Na_2CO_3$ (37 mg, 0.352 mmol, 3.0 equiv). Degassed ethanol (1.2 mL) was added, and the whole solution purged with argon for ~10 minutes. Bis(triphenylphosphine)palladium dichloride (4.1 mg, 0.00587 mmol, 0.05 equiv) was quickly added to the reaction, then it was capped with a teflon-lined cap and stirred at 60° C. After 21 h, the reaction was cooled to room temperature, then diluted with EtOAc, filtered through Celite, and concentrated by rotary evaporation. Purification by silica flash chromatography (2.5% MeOH/$CH_2Cl_2$) yielded ethyl (R)-2-(tert-butylsulfinyl)-4-(3-(pyridin-3-yl)phenyl)-2,3-dihydro-1H-pyrrolo[3,4-c]pyridine-6-carboxylate as a light yellow foam (43 mg, 82%). TLC: $R_f$ 0.19 (2.5% MeOH/$CH_2Cl_2$). $[α]_D^{19}$: -67.1° (c 1.0, CHCl$_3$). IR (ATR): 3404, 2982, 2866, 1738, 1718, 1576, 1473, 1392, 1369, 1333, 1301, 1271, 1067, 1022, 752. $^1$H-NMR (600 MHz): δ 8.90 (d, J=1.5 Hz, 19H), 8.63 (d, J=4.1 Hz, 1H), 8.01 (s, 1H), 7.99 (s, 1H), 7.93 (dt, J=7.9, 1.8 Hz, 1H), 7.77 (d, J=7.7 Hz, 1H), 7.66 (d, J=7.7 Hz, 1H), 7.60 (t, J=7.7 Hz, 1H), 7.40 (dd, J=7.8, 4.8 Hz, 1H), 5.12 (d, J=15.3 Hz, 1H), 5.01 (d, J=15.4 Hz, 1H), 4.74 (d, J=14.9 Hz, 1H), 4.53 (d, J=15.2 Hz, 1H), 4.49 (q, J=7.1 Hz, 2H), 1.45 (t, J=7.1 Hz, 3H), 1.27 (s, 9H). $^{13}$C-NMR (151 MHz): δ 165.1, 152.9, 150.6, 148.8, 148.4, 147.8, 139.3, 138.5, 136.3, 135.6, 134.6, 129.4, 128.1, 127.7, 127.3, 123.6, 118.0, 62.0, 58.2, 23.2, 14.3; 2 C not observed. HRMS m/z calcd for $C_{25}H_{28}N_3O_3S$ ([M+H]$^+$) 450.1851; found 450.1834.

(R)—N-(benzo[d][1,3]dioxol-5-ylmethyl)-2-(tert-butylsulfinyl)-4-(3-(pyridin-3-yl)phenyl)-2,3-dihydro-1H-pyrrolo[3,4-c]pyridine-6-carboxamide (Compound 212)

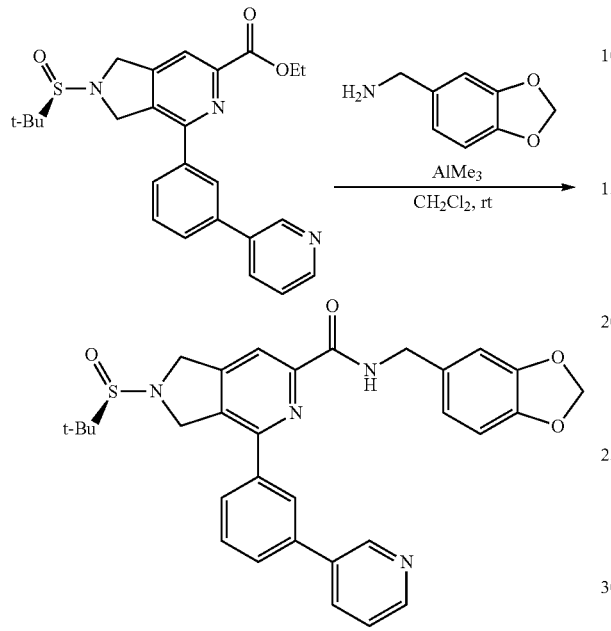

To a vial containing ethyl (R)-2-(tert-butylsulfinyl)-4-(3-(pyridin-3-yl)phenyl)-2,3-dihydro-1H-pyrrolo[3,4-c]pyridine-6-carboxylate (20 mg, 0.0445 mmol, 1.0 equiv, azeotroped 3× with toluene) at room temperature was slowly added a pre-stirred (>2 h) stock solution of dimethylaluminum piperonylamide (0.2 M solution in $CH_2Cl_2$/toluene, 0.44 mL, 0.0890 mmol, 2.0 equiv). The mixture was stirred at room temperature for 15 h, then carefully quenched by addition of a few drops of MeOH followed by dilution with 1 mL of $CH_2Cl_2$ and careful addition of 1 mL saturated aqueous $NaHCO_3$. The aqueous layer was extracted with EtOAc (3×1 mL), then the combined organic layers were dried ($Na_2SO_4$), filtered, and concentrated by rotary evaporation. Purification by silica flash chromatography (50% EtOAc/$CH_2Cl_2$) yielded compound 212 as a white foam (18 mg, 74%). TLC: $R_f$ 0.33 (3% MeOH/EtOAc). $[\alpha]_D^{20}$: −49.1° (c 1.0, $CHCl_3$). IR (ATR): 3387, 2979, 1669, 1575, 1524, 1504, 1490, 1445, 1362, 1335, 1253, 1189, 1040, 935, 757. $^1$H-NMR (600 MHz): δ 8.88 (s, 1H), 8.65 (s, 1H), 8.36 (t, J=6.1 Hz, 1H), 8.14 (s, 1H), 7.95-7.83 (m, 2H), 7.71 (d, J=7.6 Hz, 1H), 7.67 (d, J=7.8 Hz, 1H), 7.61 (t, J=7.7 Hz, 1H), 7.41 (dd, J=7.9, 4.8 Hz, 1H), 6.86 (d, J=1.7 Hz, 1H), 6.82 (dd, J=7.9, 1.7 Hz, 1H), 6.76 (d, J=7.9 Hz, 1H), 5.93 (s, 2H), 5.10 (d, J=14.9 Hz, 1H), 5.00 (d, J=15.4 Hz, 1H), 4.70 (d, J=14.8 Hz, 1H), 4.60 (d, J=6.2 Hz, 2H), 4.55 (d, J=15.3 Hz, 1H), 1.26 (s, 9H). $^{13}$C-NMR (151 MHz): δ 163.9, 151.3, 151.2, 149.3, 148.9, 148.3, 147.9, 146.9, 139.2, 138.5, 136.1, 135.0, 134.5, 132.1, 129.5, 128.1, 127.6, 126.9, 123.7, 121.0, 115.5, 108.4, 108.3, 101.0, 58.2, 43.3, 23.2; 2 C not observed. HRMS m/z calcd for $C_{31}H_{31}N_4O_4S$ ([M+H]$^+$) 555.2066; found 555.2043.

Preparation of Compound 213

(R)-2-(tert-butylsulfinyl)-N-(2-fluorobenzyl)-4-(3-(pyridin-3-yl)phenyl)-2,3-dihydro-1H-pyrrolo[3,4-c]pyridine-6-carboxamide (Compound 213)

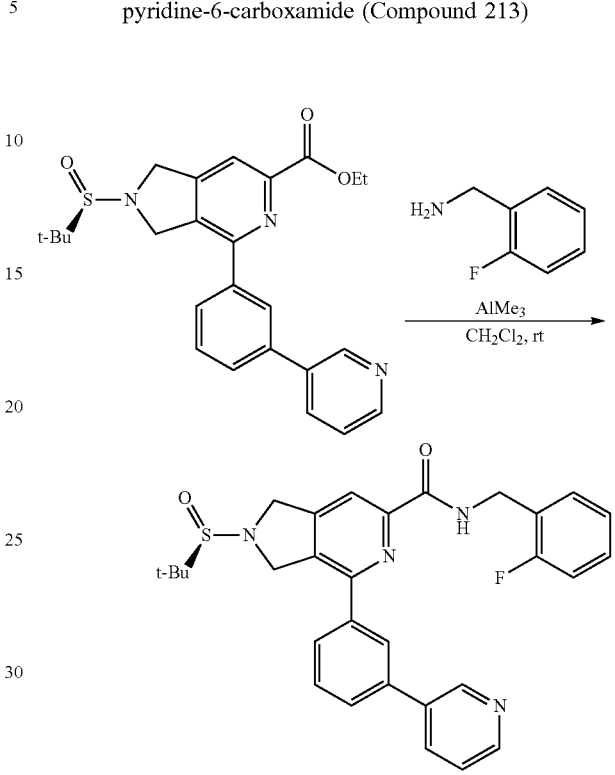

To a vial containing ethyl (R)-2-(tert-butylsulfinyl)-4-(3-(pyridin-3-yl)phenyl)-2,3-dihydro-1H-pyrrolo[3,4-c]pyridine-6-carboxylate (20 mg, 0.0445 mmol, 1.0 equiv, azeotroped 3× with toluene) at room temperature was slowly added a pre-stirred (>2 h) stock solution of dimethylaluminum (2-fluorobenzyl)amide (0.2 M solution in $CH_2Cl_2$/toluene, 0.44 mL, 0.0890 mmol, 2.0 equiv). The mixture was stirred at room temperature for 15 h, then carefully quenched by addition of a few drops of MeOH followed by dilution with 1 mL of $CH_2Cl_2$ and careful addition of 1 mL saturated aqueous $NaHCO_3$. The aqueous layer was extracted with EtOAc (3×1 mL), then the combined organic layers were dried ($Na_2SO_4$), filtered, and concentrated by rotary evaporation. Purification by silica flash chromatography (50% EtOAc/$CH_2Cl_2$) yielded compound 213 as a light yellow foam (18 mg, 76%). TLC: $R_f$ 0.39 (3% MeOH/EtOAc). $[\alpha]_D^{20}$: −57.6° (c 1.0, $CHCl_3$). IR (ATR): 3388, 2960, 1672, 1575, 1524, 1491, 1456, 1422, 1363, 1335, 1230, 1178, 1064, 1022, 937, 758. $^1$H-NMR (600 MHz): δ 8.92 (s, 1H), 8.67 (s, 1H), 8.50 (t, J=6.2 Hz, 1H), 8.12 (s, 1H), 7.95-7.89 (m, 2H), 7.73 (d, J=7.6 Hz, 1H), 7.68 (d, J=7.8 Hz, 1H), 7.62 (t, J=7.7 Hz, 1H), 7.45-7.39 (m, 2H), 7.26-7.24 (m, 1H), 7.11 (t, J=7.5 Hz, 1H), 7.08-7.04 (m, 1H), 5.12 (d, J=14.8 Hz, 1H), 5.00 (d, J=15.4 Hz, 1H), 4.75 (d, J=6.3 Hz, 2H), 4.71 (d, J=14.9 Hz, 1H), 4.55 (d, J=15.3 Hz, 1H), 1.26 (s, 9H). $^{13}$C-NMR (151 MHz): δ 164.0, 161.0 (d, J=246.1 Hz), 151.2, 151.2, 149.2, 148.7, 148.2, 139.1, 138.5, 136.2, 135.0, 134.6, 130.0 (d, J=4.2 Hz), 129.5, 129.2 (d, J=8.1 Hz), 128.1, 127.5, 126.9, 125.1 (d, J=14.7 Hz), 124.3 (d, J=3.6 Hz), 123.7, 115.4 (d, J=21.3 Hz), 115.33, 58.2, 37.5 (d, J=4.0 Hz), 23.2; 2 C not observed. HRMS m/z calcd for $C_{30}H_{30}FN_4O_2S$ ([M+H]$^+$) 529.2074; found 529.2090.

Select compounds described herein were evaluated for structure-activity analyses in vitro. The $IC_{50}$ value was measured after infection with *Trypanosoma cruzi* parasites for 72 hours and treatment with the compound for 72 hours.

TABLE 1

$IC_{50}$ values and cytotoxicity data of exemplary compounds described herein.

| Compound # | $IC_{50}$ (μM) | Cytotoxicity (μM) |
|---|---|---|
| 21 | 0.054 | >10 |
| 37 | 0.048 | >10 |
| 49 | 0.862 | >10 |
| 50 | 0.230 | >10 |
| 51 | >10 | >10 |
| 57 | 0.495 | >10 |
| 58 | 0.301 | >10 |
| 77 | >10 | >10 |
| 78 | >10 | >10 |
| 79 | 1.40 | >10 |
| 84 | 1.51 | >10 |
| 85 | 0.0437 | >10 |
| 86 | 2.85 | >10 |
| 87 | 7.18 | >10 |
| 88 | 1.51 | >10 |
| 89 | 0.028 | >10 |
| 90 | 8.50 | >10 |
| 91 | >10 | >10 |

Example 1. In Vivo Efficacy Assay of Exemplary Compounds Described Herein

Figure 2:
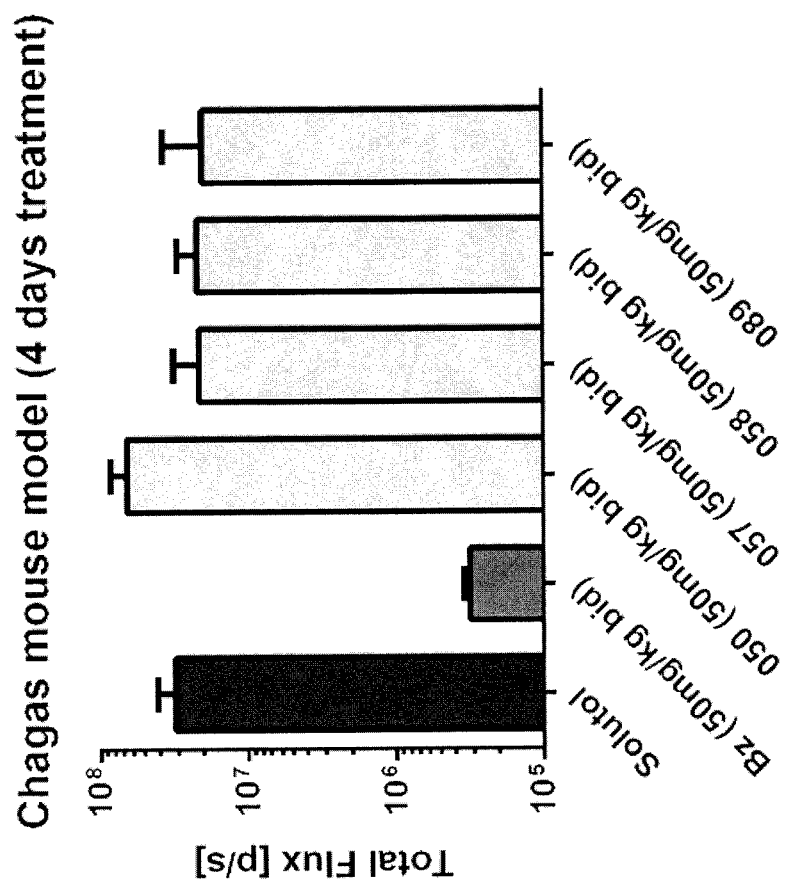
FIG. 2 shows exemplary results of compounds 50, 57, 58, and 89 in an initial in vivo efficacy assay in a mouse model. The efficacy of compounds 50, 57, 58, and 89 in *T. cruzi* parasite reduction was measured as a luminescence reading, using an In Vivo Imaging System (IVIS) for *T. cruzi* parasites expressing luciferase after treatment with compound 1 for four consecutive days, with 2 doses per day (bid) at 12 hours between the doses.

The efficacy of compounds on *T. cruzi* infection in a mouse model (*T. cruzi* strain CA-I/72 grown in mouse C2C12 myoblast cells) was determined. Exemplary results for compounds 21 (2015-FoleyC-021) and 37 (2015-FoleyC-037) are shown in FIG. 1, and exemplary results for compounds 50, 57, 58, and 89 are shown in FIG. 2.

6-week old female BALB/c mice were infected with $2 \times 10^6$ *Trypanosoma cruzi* (*T. cruzi*) Brazil strain parasites expressing luciferase. Each tested group had five individual mice. Three days post-infection with *T. cruzi* parasites, the mice were treated with the compounds for four consecutive days, with two doses per day (bid) with approximately a 12 hour difference between the doses. Compounds were administered intraperitoneally at 50 mg/kg diluted in 10% DMSO in water. On the seventh day after infection (12 hours after the last dose), 2.5 mg of luciferin (intraperitoneal) was administered, followed by a reading of the luminescence using an In Vivo Imaging System (IVIS, Perkin Elmer). The average luminescence signal per group was compared and normalized to the control groups: treated with reference drug (50 mg/kg Benznidazole (Bz), 100% efficacy) and compared with the vehicle alone (10% DMSO in water or 20% Solutol, 0% efficacy).

Example 2. In Vitro Assay

Select compounds described herein were evaluated for structure-activity analyses for anti-trypanosomal activity, plasma stability, microsomal stability, Parallel artificial membrane permeability assay (PAMPA) Permeability, Caco-2 Bi-directional Permeability, plasma protein binding, cytotoxicity, pharmacokinetics assays, and relative bioavailability, in vitro and in vivo. Exemplary results for compounds 21 (2015-FoleyC-021) and 37 (2015-FoleyC-037) are shown in Table 2.

TABLE 2

$IC_{50}$ and $EC_{50}$, values, logS data, permeability data, plasma stability, protein binding, toxicity, and microsomal stability data of exemplary compounds described herein.

| Compound # | 2015-foleyc-021 | 2015-foleyc-037 |
|---|---|---|
| In Vitro Assays | | |
| plasma stability ($t_{1/2}$, mouse) | >4 h | >4 h |
| microsomal stability ($t_{1/2}$, mouse): | | |
| 1 mg/mL hepatic microsomes | 3.9 min | 1.3 min |
| 0.25 mg/mL hepatic microsomes | 46 min | 13 min |
| Parallel artificial membrane permeability assay (PAMPA) Permeability (log Pe [cm/s]) | −7.26 | −5.24 |
| Caco-2 Bi-directional Permeability (Efflux ratio) | 24.9 | 13.2 |
| plasma protein binding (mouse) | 95.5% | 91.9% |
| Cytotoxicity Screening | | |
| HepG2 $IC_{50}$ (μM) | | |
| Cellular ATP | 52.5 | 54.2 |
| Membrane Integrity | 62.1 | 90.6 |

TABLE 2-continued

IC$_{50}$ and EC$_{50}$, values, logS data, permeability data, plasma stability, protein binding, toxicity, and microsomal stability data of exemplary compounds described herein.

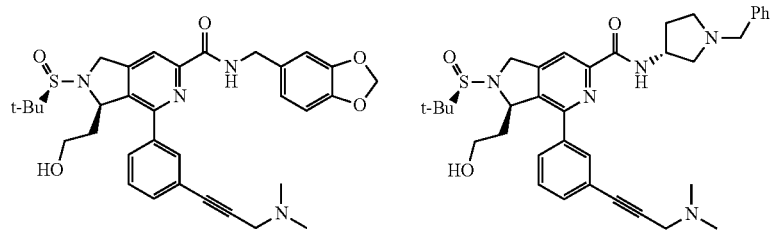

| Compound # | 2015-foleyc-021 | 2015-foleyc-037 |
|---|---|---|
| Cell Count | 51.3 | 56.2 |
| MRC5 IC$_{50}$ (μM) | | |
| Cellular ATP | 44.7 | 54.1 |
| Membrane Integrity | 24.4 | 13.4 |
| Cell Count | 63.7 | 64.2 |
| In Vivo Pharmacokinetic (PK) Studies | | |
| PK (ip, 50 mg/kg) | | |
| t$_{1/2}$ | 2.8 h | 6.3 h |
| C$_{max}$ | 19.8 μM | 6.8 μM |
| Area under the curve (AUC) | 50.1 μM·h | 11.1 μM·h |
| PK (po, 50 mg/kg) | | |
| t$_{1/2}$ | 3.5 h | 4.3 h |
| C$_{max}$ | 11.8 μM | 1.7 μM |
| AUC | 24.3 μM·h | 5.2 μM·h |
| Relative Bioavailability, F$_{rel}$ (po/ip) | 48% | 47% |

To evaluate the hepatic microsomal stability of selected compounds, 1 μM of each selected compound was incubated with 1 mg/mL hepatic microsomes in 100 mM KPi, pH 7.4. The microsomes were obtained from C57BL/6 mice. The reaction was initiated by adding NADPH (1 mM final concentration). Aliquots were removed at 0, 5, 10, 20, 40, and 60 minutes and added to acetonitrile (5× v:v) to stop the reaction and precipitate the protein. NADPH dependence of the reaction is evaluated with —NADPH samples. At the end of the assay, the samples were centrifuged through a Millipore Multiscreen Solvinter 0.45 micron low binding PTFE hydrophilic filter plate and analyzed by LC-MS/MS. Data was log transformed and represented as half-life.

To evaluate the plasma stability of selected compounds, 10 μM of each selected compound was incubated with undiluted plasma. Plasma was freshly obtained from C57BBl\6 mice drawn in the vivarium and used immediately. Plasma was brought to 37° C. within a 96-well plate and then the compound is introduced via a DMSO stock solution. The sample was continually shaken at 37° C. and aliquots are removed at multiple time points out to four hours. Aliquots were added to acetonitrile (5× v:v) to stop any enzymatic activity and held on ice. At the end of the assay, the samples were centrifuged through a Millipore Multiscreen Solvinter 0.45 micron low binding PTFE hydrophilic filter plate and analyzed by LC-MS/MS. Data was log transformed and represented as half-life.

To evaluate the plasma protein binding of selected compounds, equilibrium dialysis was used. All samples of the selected compounds were tested in triplicate using the RED Rapid Equilibrium Dialysis Device (Thermo Scientific). The initial drug concentration in the plasma chamber was 5 μM and phosphate buffered saline was added to the receiver chamber. The plate was covered and allowed to shake in a 37° C. incubator for 6 hours. 25 μl was sampled from the plasma and PBS chambers which were then diluted with either blank PBS or plasma to achieve a 1:1 ratio or plasma:PBS for all samples. The concentration of drug in the plasma and PBS chambers were determined by LC-MS/MS. The fraction bound was calculated as ([plasma]−[PBS])/[plasma].

To evaluate the Parallel Artificial Membrane Permeability Assay (PAMPA) of selected compounds, an assessment of permeability was done using a commercial PAMPA kit. Selected compounds were evaluated over a range of concentrations by 300 μl of PBS containing the compound to the bottom donor plate. Selected compounds were from DMSO stocks and the final DMSO concentration in the donor wells was one percent. 200 μl of blank PBS was added to the top receiver plate. The plates were allowed to incubate at room temperature. After 5 hours, aliquots were taken from the donor and receiver plates and the concentration of drug was determined. Compound permeability was calculated using the equation $$P_e = -\frac{\ln\left[1 - \frac{C_A(t)}{C_{eq}}\right]}{\left(A * \left(\frac{1}{V_D} + \frac{1}{V_A}\right) * t\right)}$$

where $P_e$ is expressed in units of cm/s, $C_A(t)$ is drug concentration in the acceptor at time t, $V_D$ is donor well volume, $V_A$ is acceptor well volume, A is the area of the filter (0.3 cm$^2$), t is time in seconds, and $C_{eq}=[C_D(t)*V_D+C_A(t)*V_A]/(V_D+V_A)$.

To evaluate the plasma pharmacokinetics of selected compounds, a group of eighteen female mice were administered divided into two groups; Group 1 (intraperitoneal (i.p.)) and Group 2 (oral administration (p.o.)) with compound 21 or compound 37 solution formulation at a dose of 50 mg/kg by both the routes in 5% NMP, 5% Solutol and 90% Normal saline. Blood samples (approximately 60 mL) were collected from retro orbital plexus of each mouse under light isoflurane anesthesia such that the samples were obtained at 0.083, 0.25, 0.5, 1, 2, 4, 8, 12 and 24 hours (i.p.); and pre-dose, 0.25, 0.5, 1, 2, 4, 8, 12 and 24 hour (p.o.). The blood samples were collected from a set of three mice at each time point in labeled micro centrifuge tube containing K2EDTA as anticoagulant. Plasma samples were separated by centrifugation at 4000 rpm for 10 min and stored below $-70°$ C. until bioanalysis. After collection of blood sample, animals were humanely euthanized by carbon dioxide asphyxiation to collect liver and heart from Group 1 and Group 2 at 1, 8 and 24 hours. The collected tissues were rinsed in PBS and were homogenized with cold phosphate buffer saline (pH 7.4) of nine times the weight of liver and two times the weight of heart tissue and stored below $-70°$ C. until bio-analysis. Total volume was ten and three times the tissue weights of liver and heart, respectively. All samples were processed for analysis by protein precipitation using acetonitrile and analyzed with fit-for-purpose LC-MS/MS method (LLOQ: 1.01 ng/mL for plasma; 20.20 ng/g for liver and 6.06 ng/g for heart tissue). Following a single intraperitoneal dose administration to female BALB/c mice, plasma concentrations of compound 21 or compound 37 were quantifiable till 24 hours with $T_{max}$ at 0.25 hour. Following a single oral dose administration to female BALB/c mice, plasma concentrations of compound 21 or compound 37 were quantifiable till 24 hours with $T_{max}$ at 1.00 hour. Exemplary results for compounds 21 (2015-FoleyC-021) and 37 (2015-FoleyC-037) are shown above in Table 2.

To evaluate the metabolic stability of compounds 21 and 37 in mice liver microsomes (MLM), a 1120 µL aliquot of potassium phosphate buffer (50 mM, pH 7.4) containing mice liver microsomes (0.357 mg/mL) was added to individual 2 mL tubes (final concentration 0.25 mg/mL). Imipramine in MLM was run as positive controls. Test compounds (compound 21 or compound 37) and positive control compounds (1 mM DMSO stocks) were directly spiked into respective tubes to prepare a concentration of 1.428 µM (final concentration 1 µM). From the above mix, 70 µL was added to individual wells of 96 well reaction plates and pre-incubated in a 37° C. water bath for 5 min. All the reactions were initiated by adding 30 µL of 3.33 mM NADPH (final concentration 1 mM). Reactions without NADPH and heat inactivated microsomes minus NADPH (0 min and 60 min) were also incubated to rule out non-NADPH metabolism or chemical instability in the incubation buffer. All reactions were terminated using 100 µL of ice-cold acetonitrile containing internal standard (glipizide—2 µM) at 0, 5, 15 and 60 min. The plates were centrifuged at 4000 RPM for 15 min and 100 µL aliquots were submitted for analysis by LC-M/MS. Samples were monitored for parent compound disappearance in Multiple reaction monitoring (MRM) mode using LC-MS/MS.

To evaluate the bi-directional Caco-2 permeability of compounds 21 and 37, Caco-2 cells were grown in Dulbecco's Modified Eagle Medium (DMEM) (20% Fetal bovine serum (FBS)) until 85-90% confluence. After attaining required confluence, cells were trypsinized and seeded into 24 well millcell plates at a density of 0.6×105 cells/insert. The plates were maintained for 21 days at 37° C. in CO2 incubator with change of medium every alternative day. Monolayer integrity was monitored by measuring Trans-epithelial electrical resistance (TEER) from day 15. Caco-2 cell monolayer was washed twice with HBSS and incubated for 30 min in CO2 incubator. TEER values were measured and wells showing TEER values above 230 ohms.cm2 were taken for experiments. Bi-directional permeability study was initiated by adding appropriate volume of HBSS containing the test compounds or probe P-gp substrate loperamide to either the apical (A-B transport) or basal side (B-A transport) of the monolayer. At selected time points (0, 15, 30, 60 and 90 mins) an aliquot of 50 µL was collected from the receiver compartment for determination of test compound concentrations. The volume withdrawn was replaced immediately with plain HBSS buffer (pH 7.4). TEER was measure at the end of the experiment to test the post experiment monolayer integrity. A 50 µL sample of loperamide, compound 21 and compound 37 were mixed with 100 µL internal standard followed by mixing. Finally samples were vortexed for 5 minutes and transferred to 96-well plates for LC MS/MS analysis.

To evaluate the cytotoxicity of selected compounds, cell viability assays (CellTiter Glo) were conducted. Each compound (compound 21 or compound 37) was plated in triplicate starting at their respective stock concentration. They were serially diluted column-wise for ten 3x dilutions using DMSO as the diluent. Staurosporine was used as positive control for DRC (dose response curve), and was plated starting at 1.25 mM. This plate was used as a source plate to make the assay plates by transferring 0.1 µl into 25 µl assay volume to reach the right working concentration for each compound. HepG2 and MRC5 were plated at a density of 1500 cells/25 µl in well in the assay plate and allowed to settle overnight. 0.1 µL of compounds was then transferred from the source plate, into the cell assay plates. The cells were left to incubate with the compounds for 48 hours, after which, 25 µL of Promega Cell Titer-Glo was added to each well, and allowed to incubate at room temperature with shaking for 20 minutes. RLU's (Relative Light Units) for each well were then recorded on a BioTek Synergy NEO. Fluorescence microscopy was also used to evaluate the cytotoxicity of selected compounds. Cells were plated at a density of 1500 cells/25 µl in well in a 384 wells plate the day before incubation with the drugs. The following day, 0.1 µl of the source plate are added to the assay plate. Then, 25 µl of a fluorophores mixture containing Hoechst 33342, Syto17 diluted in Eagle's Minimum Essential Medium (EMEM) was added to each well. Plates are read after 48 hours of incubation in the ImageXpress instrument (Molecular Devices) using the appropriate filters.

Example 3. In Vitro Assay of Exemplary Compounds Described Herein

Select compounds described herein were evaluated for structure-activity analyses for anti-plasmodial activity in vitro. For Dd2 EC50 (µM), calculations were for n=3. For HepG2 EC50 (µM), calculations were for n=1. For the human microsomal stability determination, t was 60 minutes.

TABLE 3

IC$_{50}$ and EC$_{50}$, values, logS data, permeability data, and microsomal stability data of exemplary compounds described herein.

| Compound # | Compound Structure | Dd2 EC$_{50}$ (μM) | Hep G2 EC$_{50}$ (μM) | Solubility LogS, at pH 1.2; pH 6.5; or pH 7.4 | Predicted logS | Predicted logD | Permeability (log Pe, in [cm/s]) | Human microsomal stability (%) |
|---|---|---|---|---|---|---|---|---|
| Tan003-M03 | 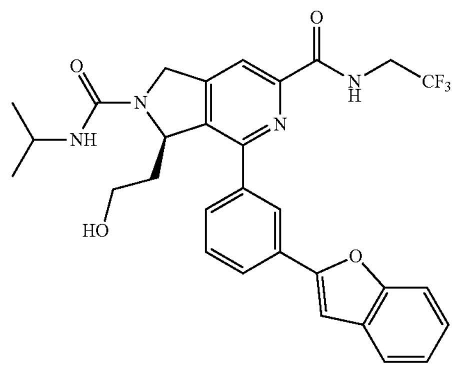 [SMILES: CC(C)NC(=O)N1Cc2cc(C(=O)NCC(F)(F)F)nc(-c3cccc(-c4cc5ccccc5o4)c3)c2[C@H]1CCO] | 0.24 ± 0.07 | 45 | 5.1; −5.2; −5.1 | −4.37 | 3.94 | −5.40 | 61.5 |
| ent-Tan003-M03 | 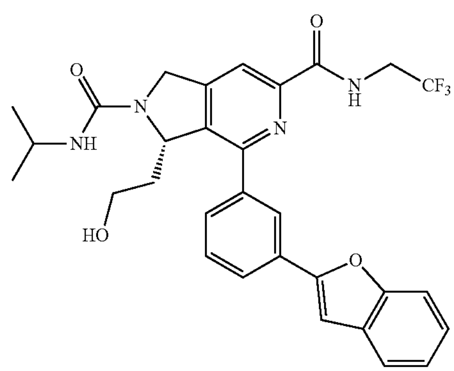 [SMILES: CC(C)NC(=O)N1Cc2cc(C(=O)NCC(F)(F)F)nc(-c3cccc(-c4cc5ccccc5o4)c3)c2[C@@H]1CCO] | 0.20 ± 0.02 | — | −5.2 (at pH 7.4) | — | — | — | 62.7 |
| Tan003-O08 | 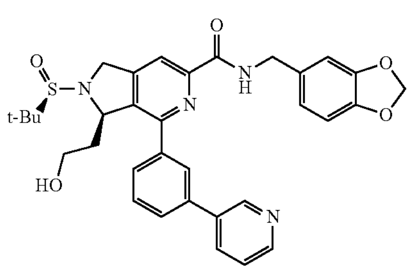 [SMILES: CC(C)(C)[S@@](=O)N1Cc2cc(C(=O)NCc3ccc4c(c3)OCO4)nc(-c3cccc(-c4cccnc4)c3)c2[C@H]1CCO] | 0.53 ± 0.11 | 41 | 3.8; −5.0; −4.9 | −4.20 | 3.59 | −5.74 | <1 |
| ent-Tan003-O08 | 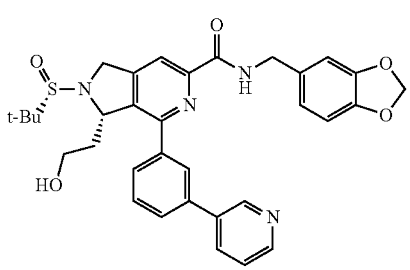 [SMILES: CC(C)(C)[S@](=O)N1Cc2cc(C(=O)NCc3ccc4c(c3)OCO4)nc(-c3cccc(-c4cccnc4)c3)c2[C@@H]1CCO] | 0.86 ± 0.08 | — | — | — | — | — | — |

TABLE 3-continued

IC$_{50}$ and EC$_{50}$, values, logS data, permeability data, and microsomal stability data of exemplary compounds described herein.

| Compound # | Compound Structure | Dd2 EC$_{50}$ (μM) | Hep G2 EC$_{50}$ (μM) | Solubility LogS, at pH 1.2; pH 6.5; or pH 7.4 | Predicted logS | Predicted logD | Permeability (log Pe, in [cm/s]) | Human microsomal stability (%) |
|---|---|---|---|---|---|---|---|---|
| ent-Tan003-D20 | 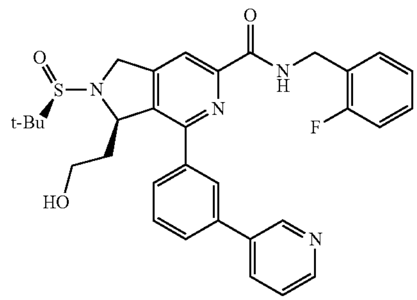 [SMILES: CC(C)(C)[S@@](=O)N1Cc2cc(C(=O)NCc3ccccc3F)nc(-c3cccc(-c4cccnc4)c3)c2[C@H]1CCO] | 0.38 ± 0.09 | 60 | — | — | — | — | — |
| Tan003-D20 | 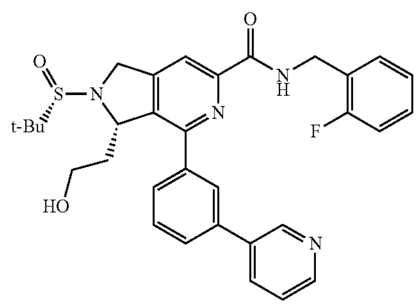 [SMILES: CC(C)(C)[S@](=O)N1Cc2cc(C(=O)NCc3ccccc3F)nc(-c3cccc(-c4cccnc4)c3)c2[C@@H]1CCO] | 0.38 ± 0.02 | — | 3.8; −5.2; −5.1 | −4.57 | 4.05 | −5.62 | <1 |
| Tan002-O12; 2015-foleyc-216 | 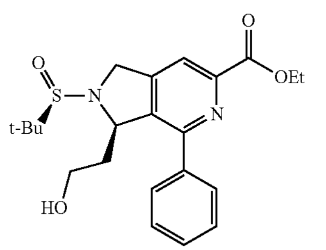 [SMILES: CCOC(=O)c1cc2c(c(-c3ccccc3)n1)[C@@H](CCO)N([S@](=O)C(C)(C)C)C2] | 0.89 ± 0.13 | >100 | — | −3.06 | 2.75 | — | — |
| 2015-foleyc-223 | 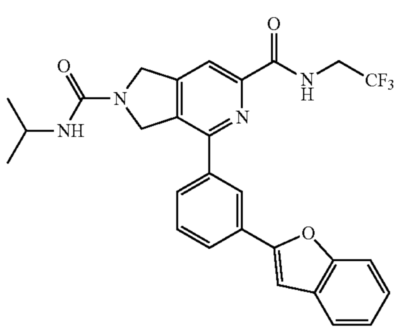 [SMILES: CC(C)NC(=O)N1Cc2cc(C(=O)NCC(F)(F)F)nc(-c3cccc(-c4cc5ccccc5o4)c3)c2C1] | >25 | 57 | — | −4.44 | 4.51 | — | — |
| 2015-foleyc-212 | 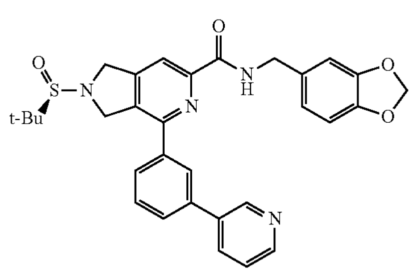 [SMILES: CC(C)(C)[S@@](=O)N1Cc2cc(C(=O)NCc3ccc4c(c3)OCO4)nc(-c3cccc(-c4cccnc4)c3)c2C1] | >25 | >100 | — | −4.30 | 4.21 | — | — |

TABLE 3-continued

IC$_{50}$ and EC$_{50}$, values, logS data, permeability data, and microsomal stability data of exemplary compounds described herein.

| Compound # | Compound Structure | Dd2 EC$_{50}$ (μM) | Hep G2 EC$_{50}$ (μM) | Solubility LogS, at pH 1.2; pH 6.5; or pH 7.4 | Predicted logS | Predicted logD | Permeability (log Pe, in [cm/s]) | Human microsomal stability (%) |
|---|---|---|---|---|---|---|---|---|
| 2015-foleyc-213 | 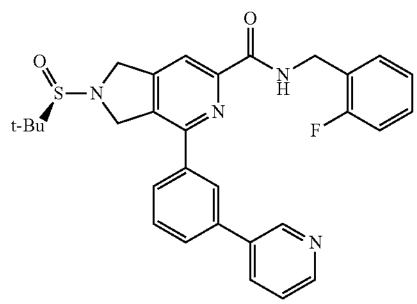 [SMILES: CC(C)(C)[S@@](=O)N1Cc2cc(C(=O)NCc3ccccc3F)nc(-c3cccc(-c4cccnc4)c3)c2C1] | >25 | >100 | — | −4.59 | 4.67 | — | — |
| 2015-foleyc-225 | 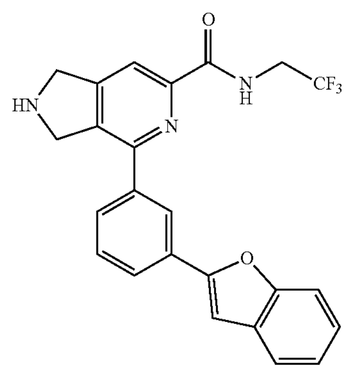 [SMILES: O=C(NCC(F)(F)F)c1cc2c(c(-c3cccc(-c4cc5ccccc5o4)c3)n1)CNC2] | 4.92 ± 0.62 | >100 | — | −4.37 | 2.44 | — | — |
| 2015-foleyc-264 | 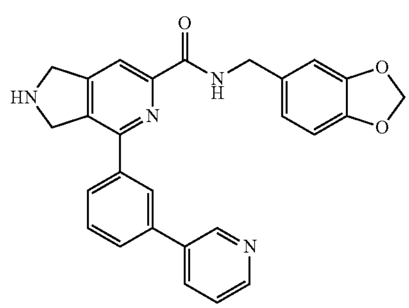 [SMILES: O=C(NCc1ccc2c(c1)OCO2)c1cc2c(c(-c3cccc(-c4cccnc4)c3)n1)CNC2] | >25 | >100 | — | −4.82 | 1.54 | — | — |
| 2015-foleyc-265 | 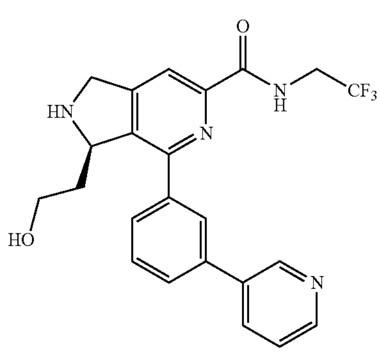 [SMILES: O=C(NCC(F)(F)F)c1cc2c(c(-c3cccc(-c4cccnc4)c3)n1)[C@@H](CCO)NC2] | 6.69 ± 0.35 | 77 | — | −5.01 | 2.05 | — | — |

TABLE 3-continued

IC$_{50}$ and EC$_{50}$, values, logS data, permeability data, and microsomal stability data of exemplary compounds described herein.

| Compound # | Compound Structure | Dd2 EC$_{50}$ (μM) | Hep G2 EC$_{50}$ (μM) | Solubility LogS, at pH 1.2; pH 6.5; or pH 7.4 | Predicted logS | Predicted logD | Permeability (log Pe, in [cm/s]) | Human microsomal stability (%) |
|---|---|---|---|---|---|---|---|---|
| 2015-foleyc-226 | 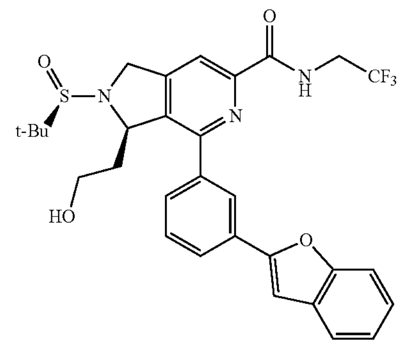 [SMILES: CC(C)(C)[S@@](=O)N1Cc2cc(C(=O)NCC(F)(F)F)nc(-c3cccc(-c4cc5ccccc5o4)c3)c2[C@H]1CCO] | >25 | >100 | — | −3.91 | 4.46 | — | — |
| 2015-foleyc-253 | 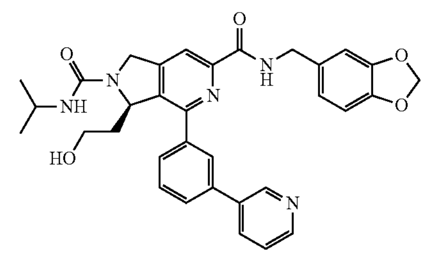 [SMILES: CC(C)NC(=O)N1Cc2cc(C(=O)NCc3ccc4c(c3)OCO4)nc(-c3cccc(-c4cccnc4)c3)c2[C@H]1CCO] | 5.73 ± 0.33 | 62 | — | −4.52 | 3.04 | — | — |
| 2015-foleyc-254 | 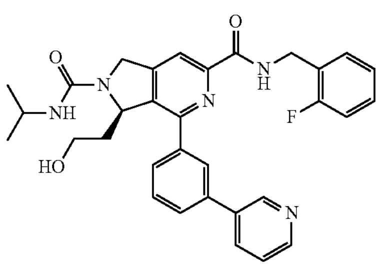 [SMILES: CC(C)NC(=O)N1Cc2cc(C(=O)NCc3ccccc3F)nc(-c3cccc(-c4cccnc4)c3)c2[C@H]1CCO] | 9.95 ± 0.89 | 71 | — | −4.75 | 3.56 | — | — |
| 2015-foleyc-267 | 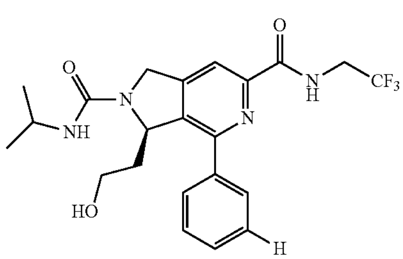 [SMILES: CC(C)NC(=O)N1Cc2cc(C(=O)NCC(F)(F)F)nc(-c3ccccc3)c2[C@H]1CCO] | 3.50 ± 0.97 | >100 | — | −3.98 | 2.22 | — | — |
| 2015-foleyc-217 | 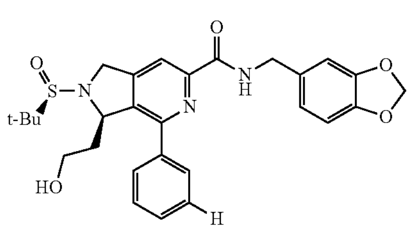 [SMILES: CC(C)(C)[S@@](=O)N1Cc2cc(C(=O)NCc3ccc4c(c3)OCO4)nc(-c3ccccc3)c2[C@H]1CCO] | 2.19 ± 0.32 | 63 | — | 3.73 | 3.22 | — | — |

TABLE 3-continued

IC$_{50}$ and EC$_{50}$, values, logS data, permeability data, and microsomal stability data of exemplary compounds described herein.

| Compound # | Compound Structure | Dd2 EC$_{50}$ (μM) | Hep G2 EC$_{50}$ (μM) | Solubility LogS, at pH 1.2; pH 6.5; or pH 7.4 | Predicted logS | Predicted logD | Permeability (log Pe, in [cm/s]) | Human microsomal stability (%) |
|---|---|---|---|---|---|---|---|---|
| 2015-foleyc-218 | 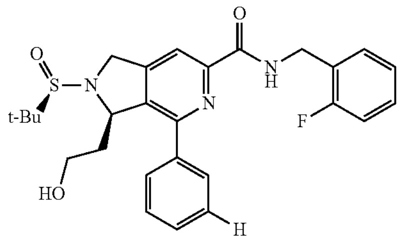 [SMILES: CC(C)(C)[S@@](=O)N1Cc2cc(C(=O)NCc3ccccc3F)nc(-c3ccccc3)c2[C@H]1CCO] | 1.45 ± 0.28 | >100 | — | −4.09 | 3.68 | — | — |
| 2015-foleyc-255 | 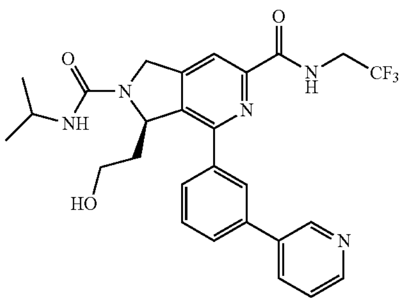 [SMILES: CC(C)NC(=O)N1Cc2cc(C(=O)NCC(F)(F)F)nc(-c3cccc(-c4cccnc4)c3)c2[C@H]1CCO] | 15.50 ± 0.75 | >100 | — | −4.44 | 2.65 | — | — |
| 2015-foleyc-219 | 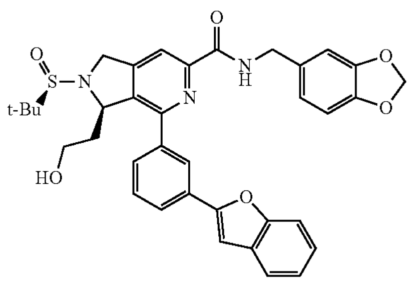 [SMILES: CC(C)(C)[S@@](=O)N1Cc2cc(C(=O)NCc3ccc4c(c3)OCO4)nc(-c3cccc(-c4cc5ccccc5o4)c3)c2[C@H]1CCO] | 1.39 ± 0.13 | >100 | — | −3.90 | 4.95 | — | — |
| 2015-foleyc-220 | 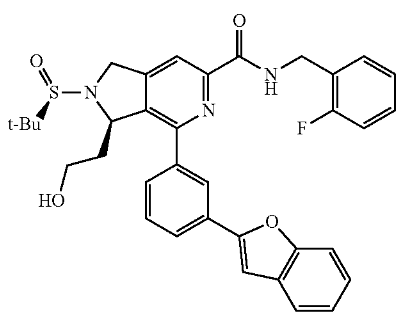 [SMILES: CC(C)(C)[S@@](=O)N1Cc2cc(C(=O)NCc3ccccc3F)nc(-c3cccc(-c4cc5ccccc5o4)c3)c2[C@H]1CCO] | >25 | >100 | — | −4.09 | 5.40 | — | — |
| 2015-foleyc-248 | 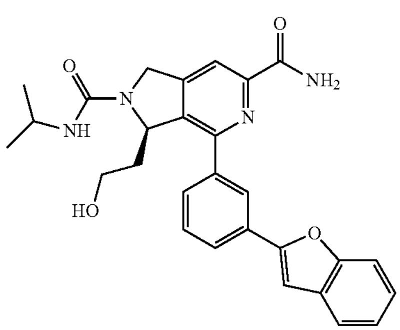 [SMILES: CC(C)NC(=O)N1Cc2cc(C(N)=O)nc(-c3cccc(-c4cc5ccccc5o4)c3)c2[C@H]1CCO] | >25 | >100 | — | −3.96 | 2.76 | — | — |

TABLE 3-continued

IC$_{50}$ and EC$_{50}$ values, logS data, permeability data, and microsomal stability data of exemplary compounds described herein.

| Compound # | Compound Structure | Dd2 EC$_{50}$ (µM) | Hep G2 EC$_{50}$ (µM) | Solubility LogS, at pH 1.2; pH 6.5; or pH 7.4 | Predicted logS | Predicted logD | Permeability (log Pe, in [cm/s]) | Human microsomal stability (%) |
|---|---|---|---|---|---|---|---|---|
| 2015-foleyc-248 | 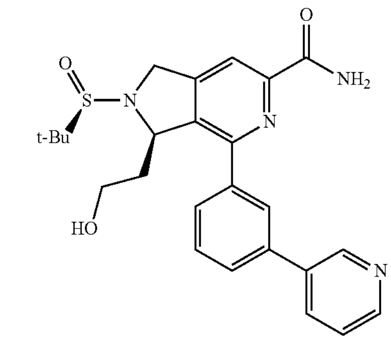 [SMILES: CC(C)(C)[S@@](=O)N1Cc2cc(C(N)=O)nc(-c3cccc(-c4cccnc4)c3)c2[C@H]1CCO] | 1.48 ± 0.14 | >100 | — | −3.57 | 1.89 | — | — |
| 2015-foleyc-241 | 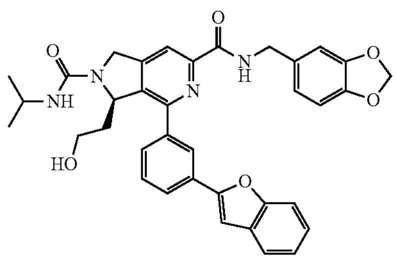 [SMILES: CC(C)NC(=O)N1Cc2cc(C(=O)NCc3ccc4c(c3)OCO4)nc(-c3cccc(-c4cc5ccccc5o4)c3)c2[C@H]1CCO] | 4.99 ± 0.59 | >100 | — | −4.21 | 4.34 | — | — |
| 2015-foleyc-268 | 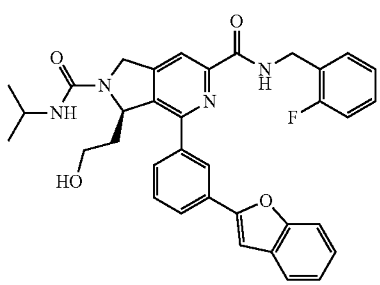 [SMILES: CC(C)NC(=O)N1Cc2cc(C(=O)NCc3ccccc3F)nc(-c3cccc(-c4cc5ccccc5o4)c3)c2[C@H]1CCO] | 10.2 ± 0.94 | >100 | — | −4.45 | 4.85 | — | — |
| 2015-foleyc-237 | 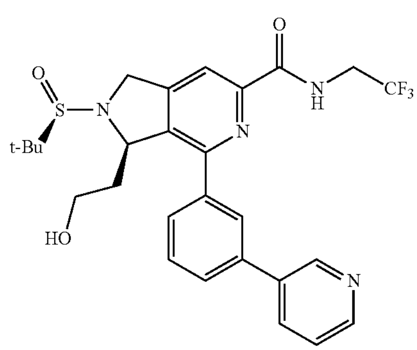 [SMILES: CC(C)(C)[S@@](=O)N1Cc2cc(C(=O)NCC(F)(F)F)nc(-c3cccc(-c4cccnc4)c3)c2[C@H]1CCO] | 5.84 ± 0.94 | >100 | — | −3.99 | 3.11 | — | — |

To determine EC$_{50}$ for selected compounds, *P. falciparum* Dd2 and 3D7 strains were maintained at 37° C. in 5% CO$_2$ and 95% air using a modified Trager and Jensen (Trager et al., 1976, *Science*, 193, 673-675) method in RPMI media with L-glutamine (Invitrogen) and supplemented with 25 mM HEPES, 26 mM NaHCO$_3$, 2% dextrose, 15 mg/L hypoxanthine (Sigma-Aldrich), 25 mg/L gentamicin (Life Technologies), and 0.5% Albumax II (Life Technologies). Different dilutions of the compound in RPMI 1640 (Life Technologies) from a stock of 10 mM in dimethyl sulfoxide (DMSO) were added to the culture at a 1% parasitemia and 2% hematocrit in 96-well black plates (Santa Cruz Biotechnology). Maximum DMSO concentration in the culture never exceeded 0.25%. Chloroquine at 1 µM was used as a positive control to determine the baseline value. Following 72 h incubation at 37° C., the ability of the compounds to inhibit growth of the parasite was determined by a SYBR green I-based DNA quantification assay (See Bennett et al., 2004, Chemother. 48, 1807-1810; see also Johnson et al., 2007, Antimicrob. Agents. Chemother. 51, 1926-1933; Smilkstein et al., 2004, Antimicrob. Agents. Chemother. 48, 1803-1806). $EC_{50}$ was calculated (n=3) from a dose response curve that was generated from a concentration range of 0-20 μM using GraphPad Prism v5.0.

To determine microsomal stability for selected compounds, a reaction plate was prepared by adding 691.25 μL, pre-warmed (37° C.) microsomal solution (0.63 mg/mL protein in 100 mM KPO4 with 1.3 mM EDTA) to an empty well of a 96 well plate and maintained at 37° C. The diluted 0.1 mM compound (8.75 μL) is added to the microsomal solution in the reaction plate and mixed thoroughly by repeated pipetting. The resulting solutions were pre-incubated for 5 minutes at 37° C. before preparing the T=0 plates. For the T=0 plates, an aliquot (160 μL) of each reaction solution was added to an empty well of a 96 well plate, as an exact replicate of the Reaction Plate. Cold (4° C.) MeOH (400 μL) is added to each well and mixed thoroughly by repeated pipetting. NADPH Regeneration solution (40 μL) is added to each well and mixed thoroughly by repeated pipetting. For the T=60 minute Incubation Plates (without NADPH), an aliquot (160 μL) of each reaction solution was added to an empty well of a 96 well plate, as an exact replicate of the Reaction Plate. LC-MS grade H2O (40 μL) is added to each well and mixed thoroughly by repeated pipetting. The plate was sealed and incubated at 37° C. for the incubation period. After incubation, cold (4° C.) MeOH (400 μL) is added to each well and mixed thoroughly by repeated pipetting. For the T=60 minute Incubation Plates, NADPH (95 μL) was added to the remaining solution (microsomes+test compound) in each well in the previously-prepared reaction plate to initiate the reaction. The plate was sealed and incubated at 37° C. for the incubation period. An aliquot (100 μL) was removed from each well at the desired time point and dispensed into a well of a 96-well plate. 200 μL of cold (4° C.) MeOH was to quench the reaction.

For selected compounds (Tan003-M03, ent-Tan003-M03, Tan003—O08, and Tan003-D20, kinetic solubility assays were performed. The selected compound samples were supplied as DMSO dissolved stocks for analysis in SGF pH 1.2, 50 mM NaPO4 pH6.5 and 1×PBS pH7.4 buffers. A final DMSO concentration of 2.0% and maximum theoretical compound concentrations of 200 μM (assuming a 10 mM DMSO stock) was achieved by diluting a 6 μl aliquot of DMSO stock with 294 μl of the appropriate buffer using Hamilton Starlet liquid handling and incubated directly in a Millipore solubility filter plate. Following 24 hour incubation at ambient temperature (23.3-24.2° C.), the samples were vacuum filtered.

For selected compounds, a Parallel artificial membrane permeability assay (PAMPA) analysis was conducted. The 10 mM DMSO stock solutions for selected compounds (Tan003-M03, ent-Tan003-M03, Tan003—O08, and Tan003-D20) were diluted 50 fold with 1×PBS, pH 7.4, for a dose concentration of 200 μM and a volume of 300 μL in the Donor compartment of the Corning Gentest Pre-coated PAMPA plate. After preparation of the Donor plate, any precipitation was noted. The Acceptor compartment was filled with 1×PBS (200 μL), pH 7.4. After careful assembly of the PAMPA plate, it was left to incubate for five hours in the dark at ambient temperature. The previously prepared solubility assay was used to measure the initial concentration of the sample in buffer (C0). After the incubation was complete, the PAMPA plate was disassembled, and the samples were transferred from the Donor and Acceptor plates to 96-well plates for analysis by chemiluminescent nitrogen detection (CLND. The C0 plate was filtered prior to analysis by CLND.

Selected compounds were evaluated for cytotoxicity using HepG2 human hepatoma cells. A 384-well clear bottom plate was seeded with 2,500 cells/well and incubated for 24 h. Serial dilutions of the compound (were added to the plate and plates were incubated for an additional 48 h. Viability of cells were assessed by MTS [(3-(4,5-dimethyl-thiazol-2-yl)-5-(3-carboxymethoxyphenyl)-2-(4-sulfophenyl)-2H-tetrazolium) cell proliferation assay (CellTiter 96® Aqueous non-radioactive cell proliferation assay, Promega) (See Cory et al., Cancer Communications, 3, 1991, p. 207-212).

Example 4. In Vivo Assay of Exemplary Compounds Described Herein

Select Compounds Described Herein were Evaluated for Structure-Activity Analyses for Anti-Plasmodial Activity In Vivo.

TABLE 4

In vivo PK and liver distribution data for exemplary compounds described herein.

| Compound # | Tan003-M03 | Tan003-O08 | ent-Tan003-D20 |
|---|---|---|---|
| PK (ip, plasma/liver) | (Dose: 50 mg/kg) | (Dose: 100 mg/kg) | (Dose: 100 mg/kg) |
| | 1.2 h/2.2 h | 2.4 h/3.5 h | 1.9 h/4.6 h |
| | 1.0 h/0.1 h | 0.5 h/0.5 h | 1.0 h/0.25 h |
| $t_{1/2}$ | 14.0 μM/58.6 μM | 33.4 μM/87.6 μM | 72.6 μM/111.3 μM |
| $T_{max}$ | 52.7 μM·h/186.0 μM·h | 157.9 μM·h/666.8 μM·h | 167.9 μM·h/306.4 μM·h |
| $C_{max}$ | | | |
| $AUC_{inf}$ | | | |

TABLE 4-continued

In vivo PK and liver distribution data for exemplary compounds described herein.

| Compound # | Tan003-M03 | Tan003-O08 | ent-Tan003-D20 |
|---|---|---|---|
| PK (po, plasma/liver) | (Dose: 50 mg/kg) | (Dose: 100 mg/kg) | (Dose: 100 mg/kg) |
| $t_{1/2}$ | 8.2 h/3.1 h | 1.1 h/16.9 h | 2.1 h/6.4 h |
| $T_{max}$ | 0.25 h/0.25 h | 1.0 h/4.0 h | 0.5 h/0.5 h |
| $C_{max}$ | 10.9 μM/53.8 μM | 27.6 μM/39.6 μM | 56.4 μM/49.2 μM |
| Area under the curve ($AUC_{inf}$) | 29.9 μM·h/107.9 μM·h | 77.1 μM·h/238.1 μM·h | 36.7 μM·h/124.9 μM·h |
| Relative Bioavailability, $F_{rel}$ ($AUC_{inf}$ po/ $AUC_{inf}$ ip) | 57% | 49% | 22% |

A plasma pharmacokinetics and liver distribution study of selected compounds, including Pyrrolopyridine-O08 (2015-foleyc-216), Pyrrolopyridine-D20-ent (2015-foleyc-217), and Pyrrolopyridine-M03 (2015-foleyc-218), in female BALB/c mice was conducted following a single intraperitoneal and oral administration. To determine in vivo PK data for selected compounds, a group of fifty four female mice were divided into two groups as; Group 1 (100 mg/kg; intraperitoneal (i.p.)) and Group 2 (100 mg/kg; oral administration (p.o.)). Following a single intraperitoneal dose administration to female BALB/c mice, plasma concentrations of the selected compound (2015-foleyc-216, 2015-foleyc-217, or 2015-foleyc-218) were quantifiable till 12 hours with $T_{max}$ at 1.00 hour. Following a single oral dose administration to female BALB/c mice, plasma concentrations of the selected compound ((2015-foleyc-216, 2015-foleyc-217, or 2015-foleyc-218) were quantifiable till 12 hours with $T_{max}$ at 0.50 hour. Animals in Group 1 and Group 2 were administered with solution formulation of the selected compound ((2015-foleyc-216, 2015-foleyc-217, or 2015-foleyc-218) in 5% NMP, 5% Solutol HS, 30% PEG-400 and 60% HPβCD (20% w/v) at 100 mg/kg dose by intraperitoneal and oral route respectively. Blood samples (approximately 60 μL) were collected from retro orbital plexus of each mouse under light isoflurane anesthesia such that the samples were obtained at 0.08, 0.25, 0.5, 1, 2, 4, 8, 12 and 24 hours (i.p.); and pre-dose, 0.25, 0.5, 1, 2, 4, 8, 12 and 24 hours (p.o.). The blood samples were collected from a set of thoursee mice at each time point in labeled micro centrifuge tube containing K2EDTA as anticoagulant. Plasma samples were separated by centrifugation at 4000 rpm for 10 min and stored below −70° C. until bioanalysis. After collection of blood sample, animals were humanely euthanized by carbon dioxide asphyxiation to collect liver from Group 1 and Group 2 at all the time points. The collected tissues were rinsed in PBS and were homogenized with nine times of liver weight in ice cold phosphate buffer saline (pH 7.4) and stored below −70° C. until bio-analysis. Total homogenate volume was ten times the tissue weight. All samples were processed for analysis by protein precipitation using acetonitrile and analyzed with fit-for-purpose LC-MS/MS method (LLOQ: 2.01 ng/mL for plasma and 50.30 ng/g for liver). Pharmacokinetic parameters were calculated using the non-compartmental analysis tool of Phoenix WinNonlin® (Version 6.3). Mean pharmacokinetic parameters are summarized in Table 4.

Figure 3:
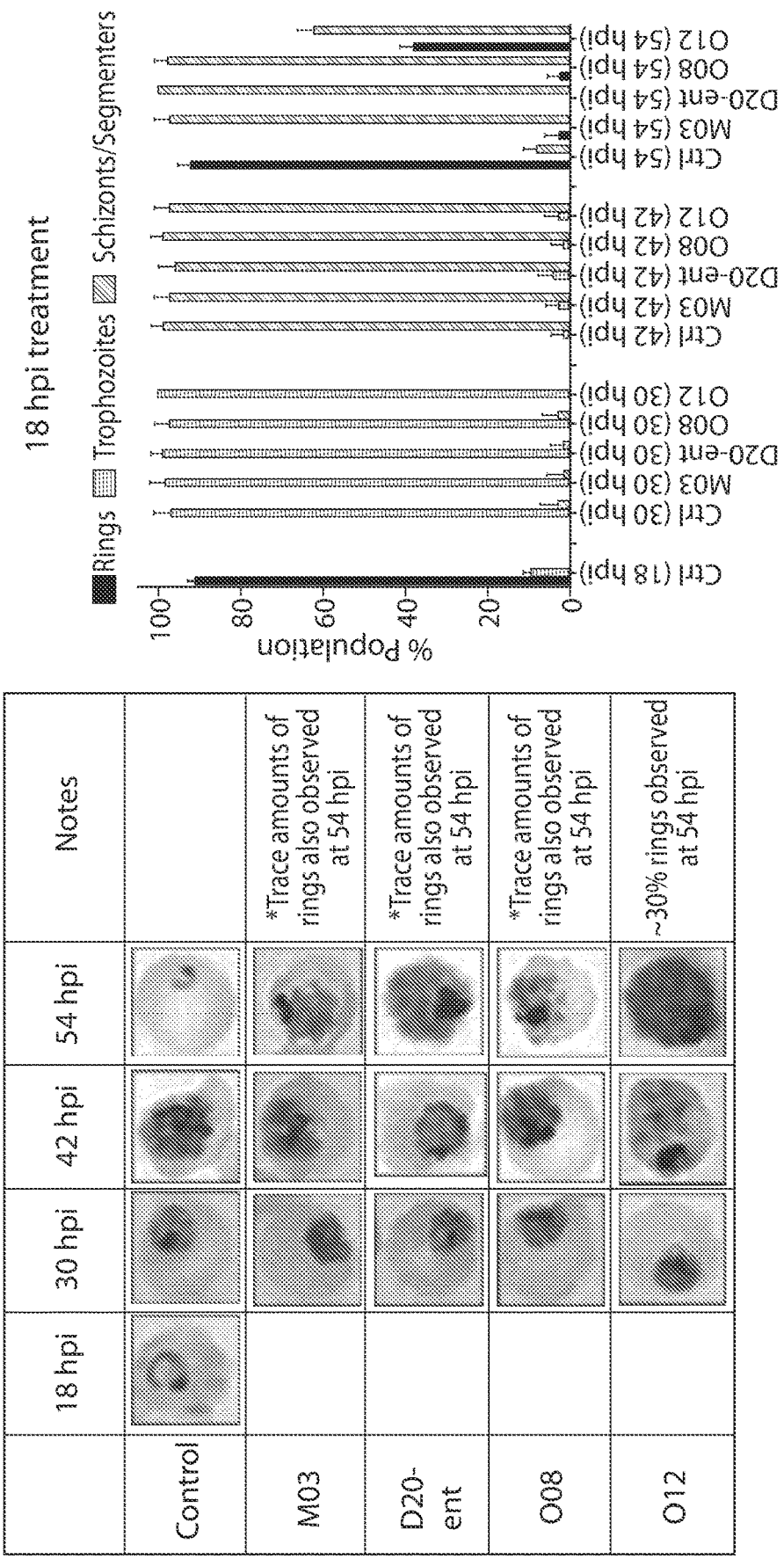
FIG. 3 shows exemplary results of Giemsa staining that reveals exemplary compounds (Tan003-M03, ent-Tan003-D20, Tan003—O08 ("O08") and Tan002—O12) inhibit parasite development before egress.
Figure 4A:
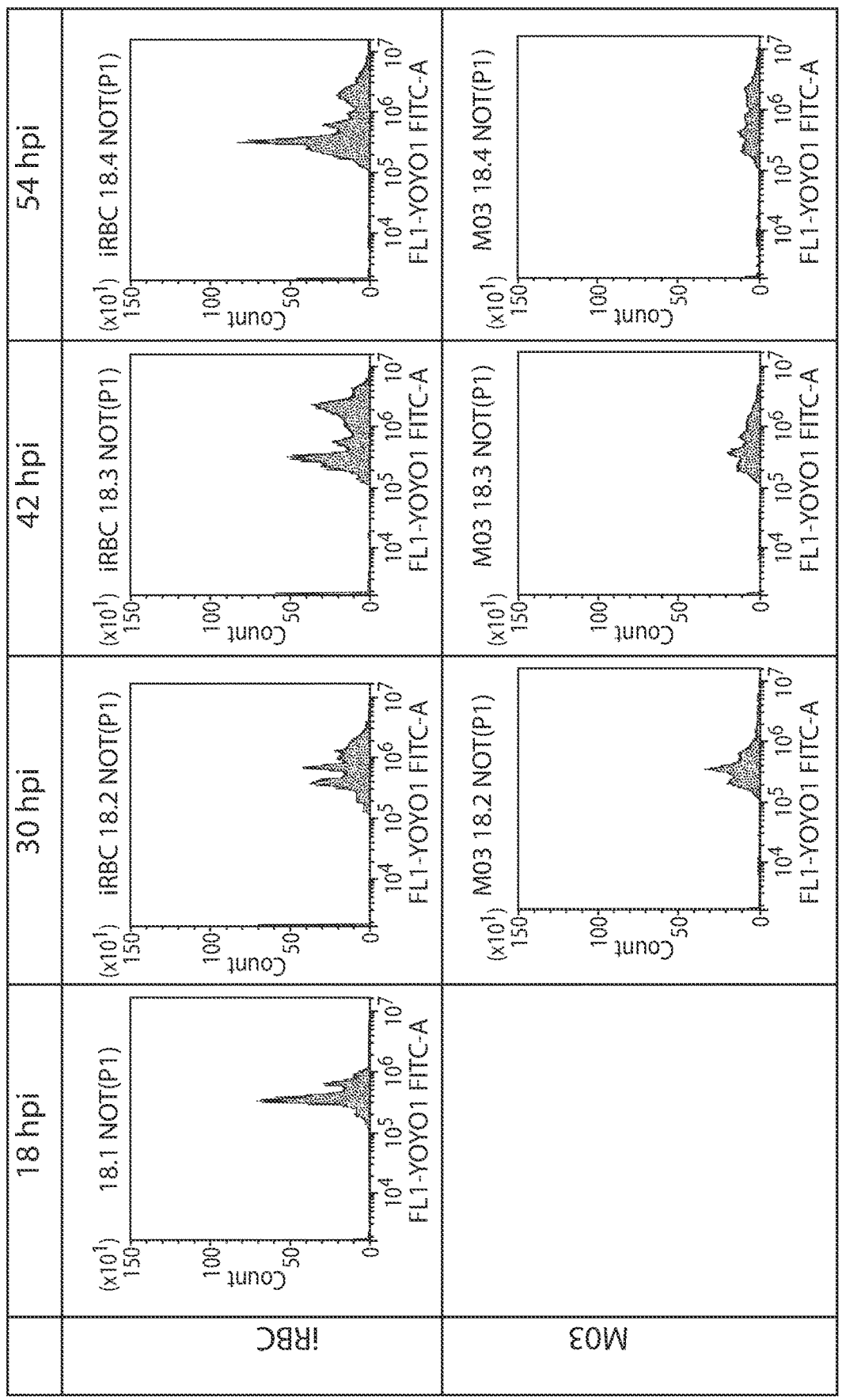
FIGS. 4A-4D show flow cytometry results showing exemplary compounds (Tan003-M03, ent-Tan003-D20, Tan003—O08, and Tan002—O12) block parasite stage progression prior to egress.
Figure 4B:
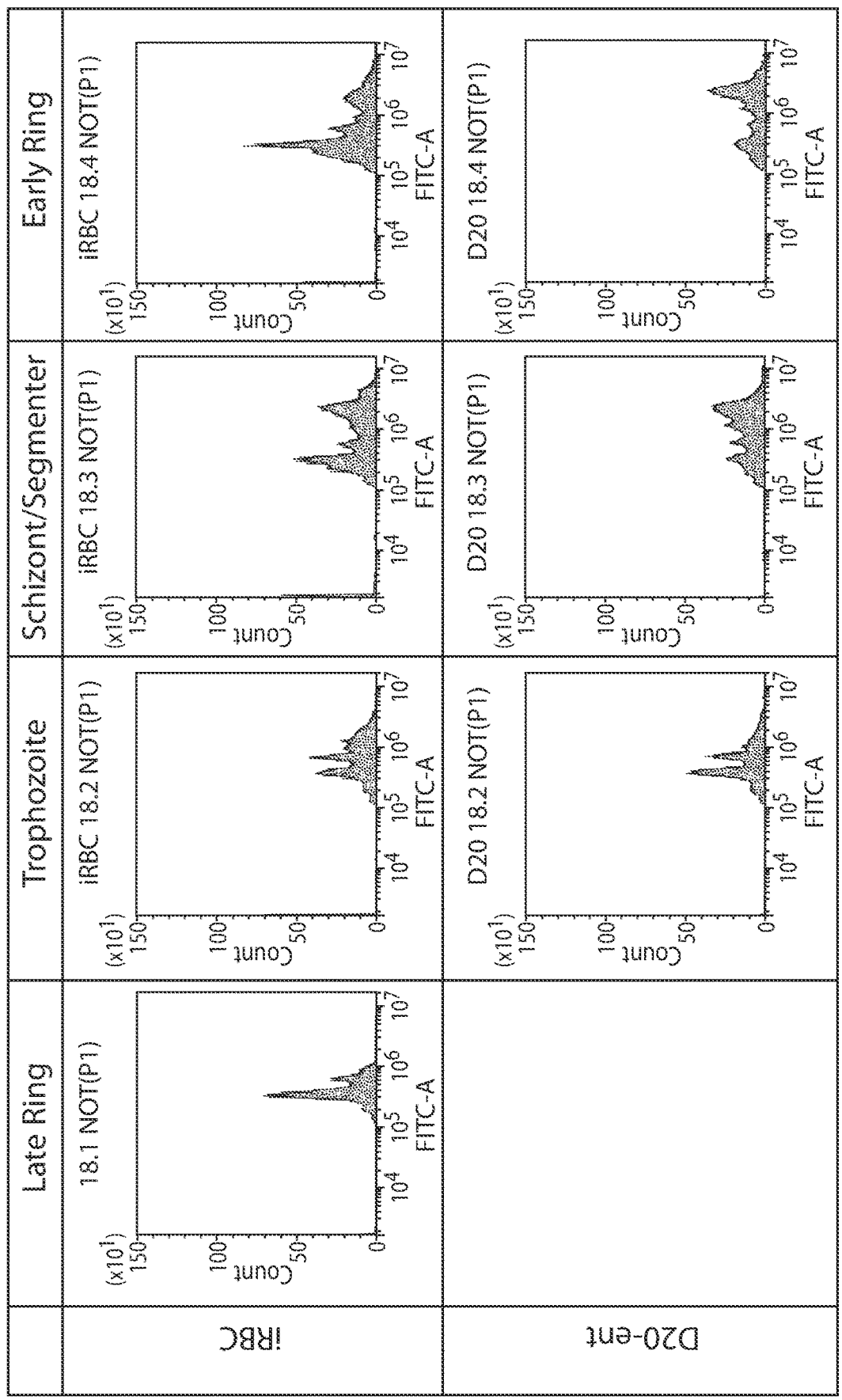
Figure 4C:
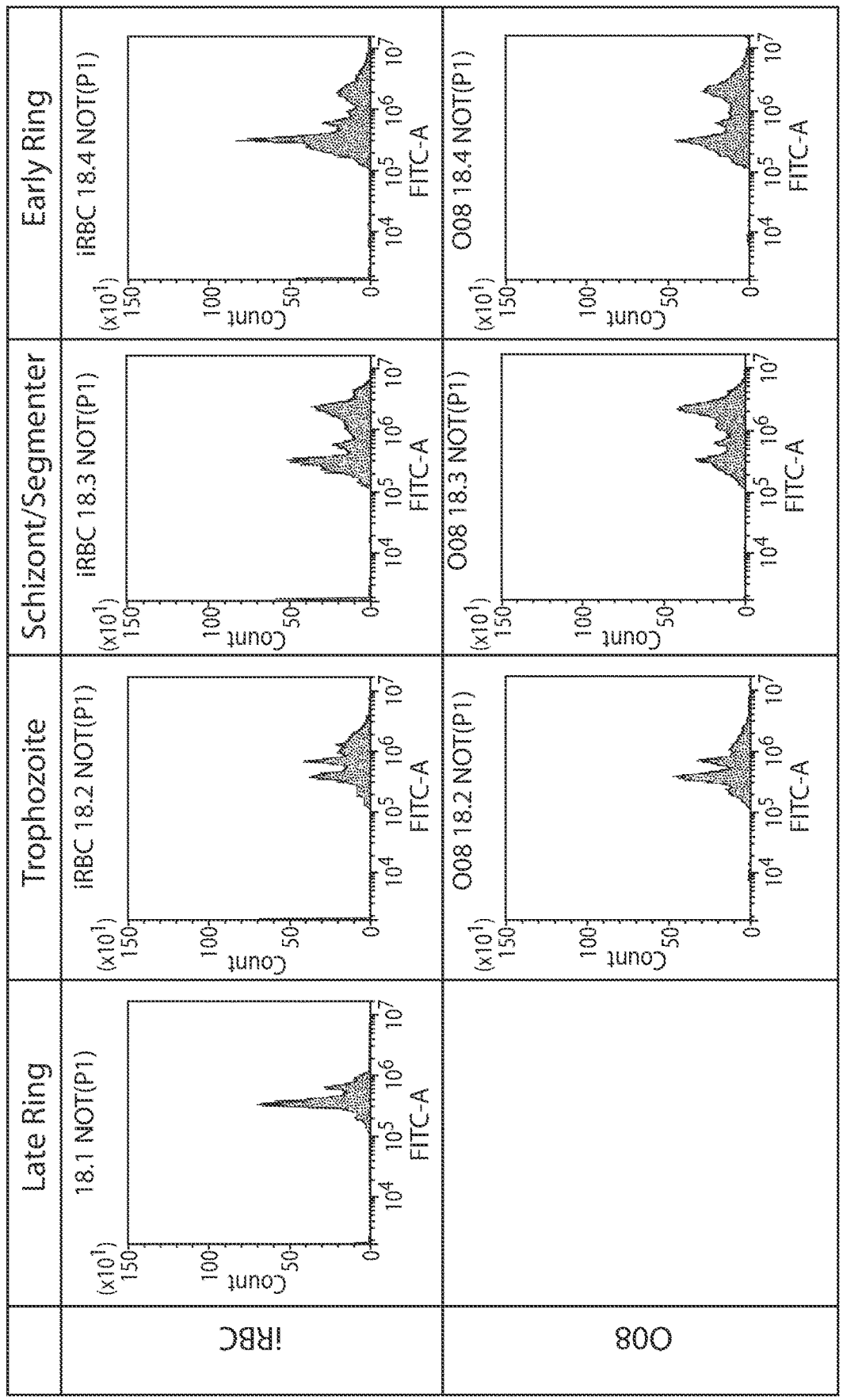
Figure 4D:
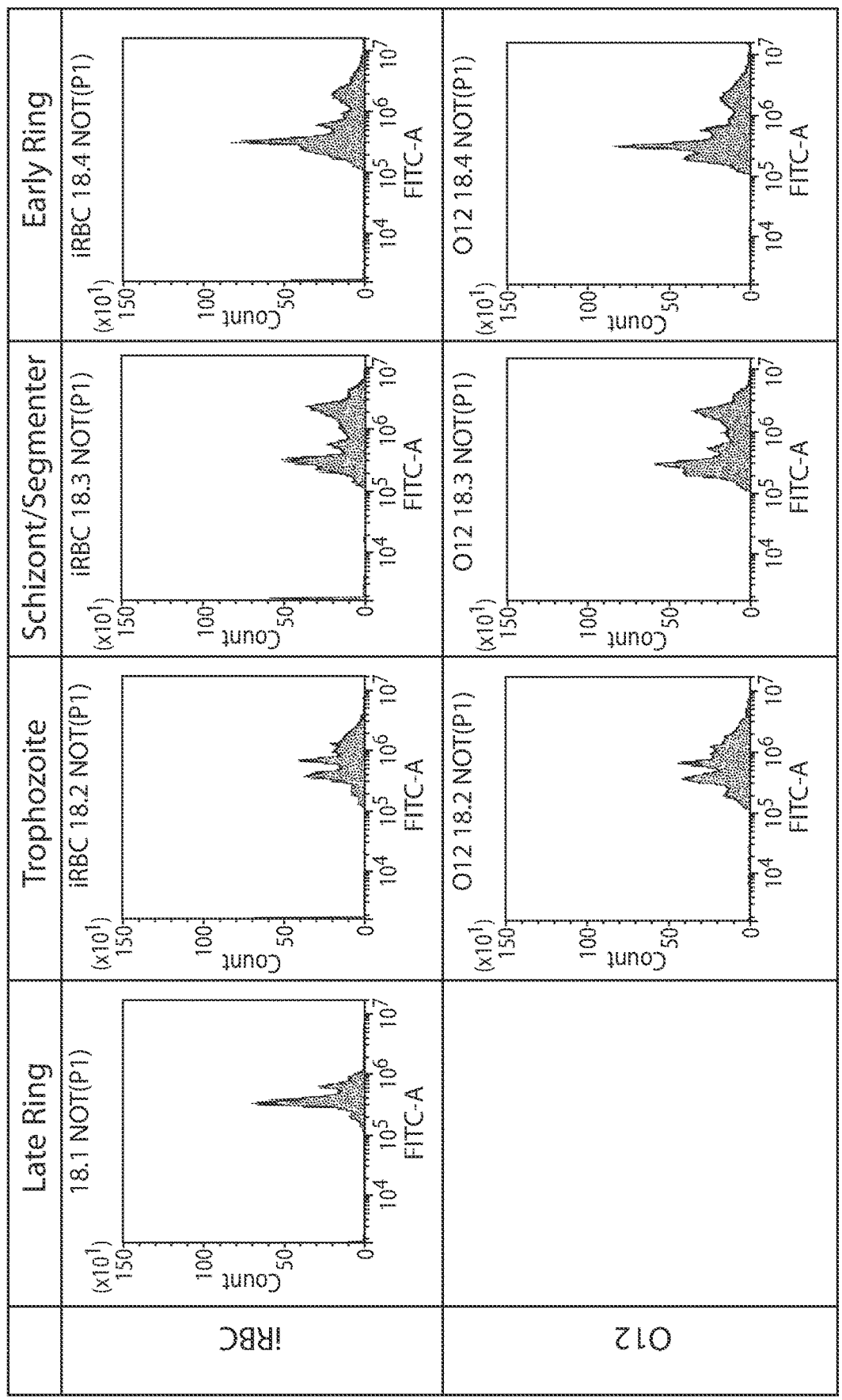

Example 5. Assessment of Stage Specific Parasite Inhibition by Exemplary Compounds Described Herein Select compounds described herein were evaluated for stage specific inhibition of parasite development. Tightly synchronized parasite cultures (Dd2) were treated with $3 \times IC_{50}$ concentrations of compound Tan003-M03 ("M03"), compound ent-Tan003-D20 ("D20-ent"), compound Tan003—O08 ("O08") or compound Tan002—O12 ("O12") at early ring, late ring, trophozoite, and schizont stages. Every 12 hours, Giemsa smears were made for treated cultures and samples were also collected and fixed for flow cytometry. Giemsa staining revealed All exemplary compounds predominantly inhibit parasite stage development prior to egress when treated at Ring (FIG. 3), Trophozoite or Schizont stages (not shown). These results were also confirmed via flow cytometry (FIGS. 4A-4D). Prior to flow analysis, fixed samples were permeabilized, RNase treated, and stained with YoYo-I as described in Bouillon et al., 2013. As seen in FIG. 4, at 18 hours post invasion (late ring) in the control culture the peaks represent singly, and multiple-infected cells based on DNA content. As the parasite matures, the DNA content increases and peaks start to spread to the right because of schizogony. Following reinvasion parasitemia increases in the next growth cycle, which is represented by an increase in peak height. At 54 hpi, parasites are at the early ring stage of the next cycle, parasitemia is significantly higher, and three distinct peaks reappear. In contrast, exposure to all exemplary compounds at the late ring stage the maturation is blocked and as a result parasitemia does not increase. This suggests a block of intraerythrocytic maturation of parasite late in schizont stages of development just prior to egress when treated with any of these exemplary compounds.

Figure 5:
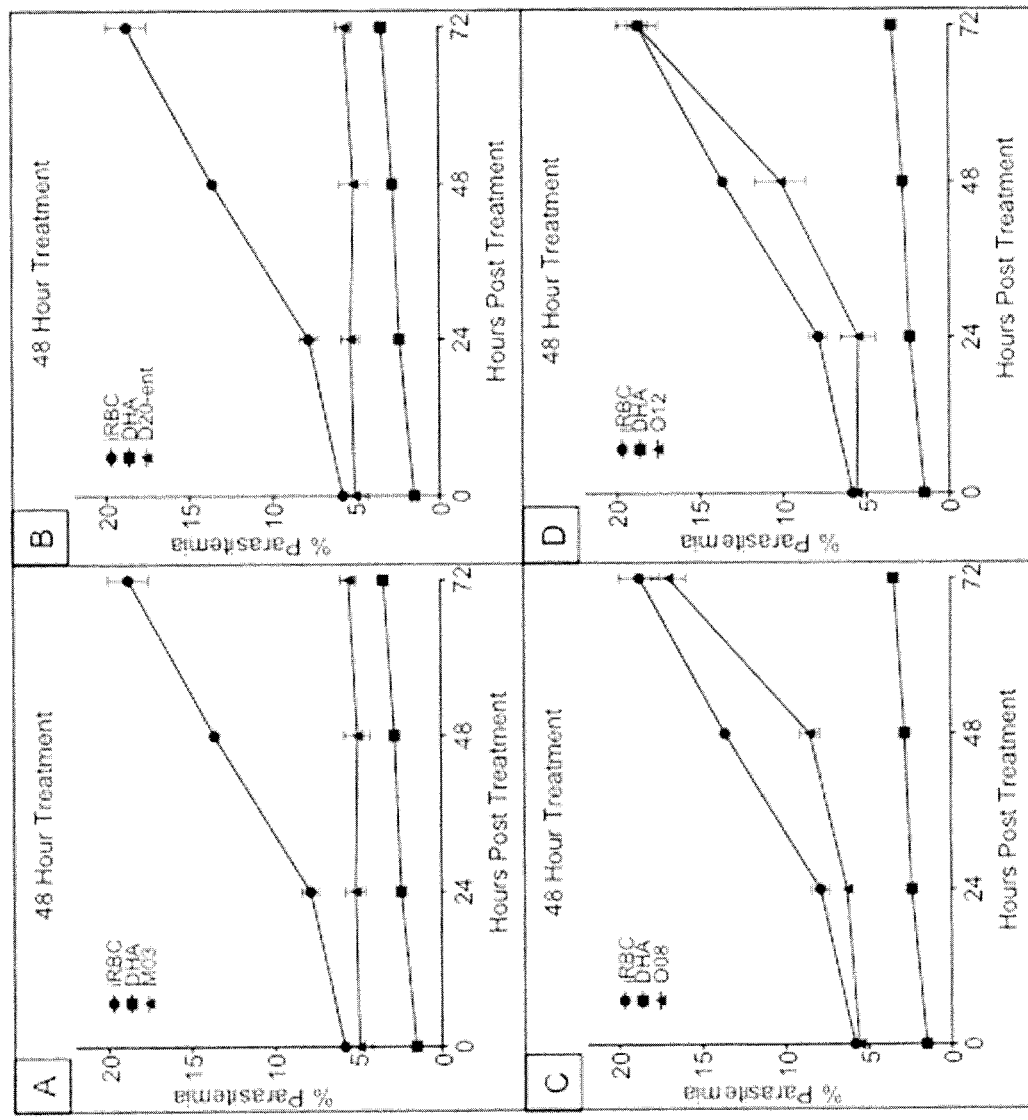
FIGS. 5A-5D show a rate of killing study showing that compounds Tan003-M03 and ent-Tan003-D20 are parasitocidal and prohibit progression beyond segmenter stages in asynchronous cultures when treated for at least 48 hours.
Figure 6:
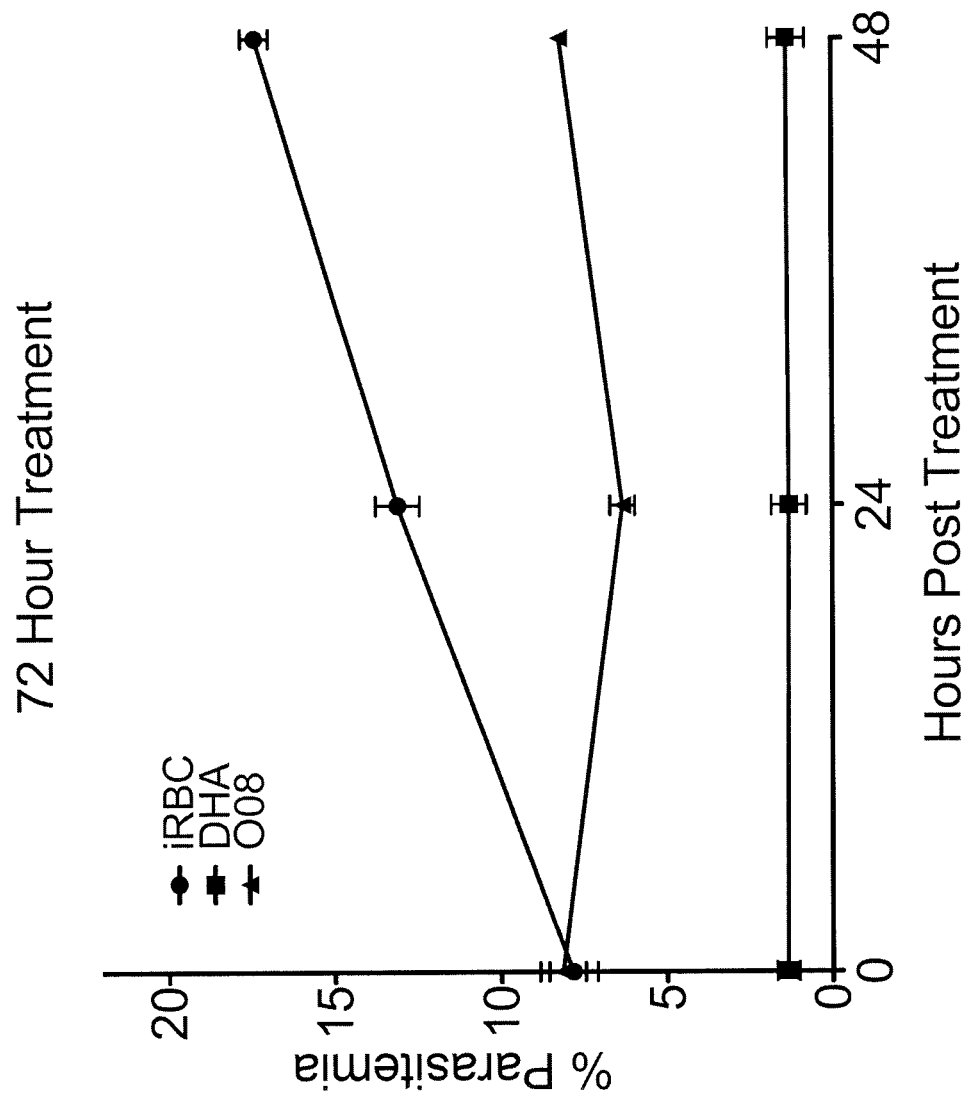
FIG. 6 shows exemplary results after treatment with compound Tan003—O08 for 72 hours, which significantly decreases viable parasites in asynchronous culture.

Example 6. Parasitocidal or Parasitostatic Determination of Exemplary Compounds Described Herein Asynchronous cultures were grown and treated with compounds, vehicle control or Dihydroartemisinin at 3×IC$_{50}$ to determine their respective rate of killing curves. Cultures were treated for 12, 24, 48, or 72 hours with compound, washed several times to remove any inhibitor, and monitored for continued growth for several days. As shown in FIG. 5, compounds Tan003-M03 and ent-Tan003-D20 are parasitocidal and prevent any parasite development beyond the schizont stage when treated for at least 48 hours. Compound Tan003—O08 demonstrates potent parasitocidal activity beginning at 72 hours of treatment (FIG. 6), and compound Tan002—O12 did not show any parasitocidal activity in this study. Overall, the exemplary compounds including, but not limited to, Tan003-M03 and ent-Tan003-D20 are parasitocidal agents blocking parasite maturation at the segmenter stage preventing egress, a novel mechanism of action absent among current antimalarials.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

REFERENCES

1. Bouillon, A., Gorgette, O., Mercereau-Puijalon, O., Barale, J. C., 2013. Screening and evaluation of inhibitors of *Plasmodium falciparum* merozoite egress and invasion using cytometry.

What is claimed is:
1. A compound of Formula (I'):

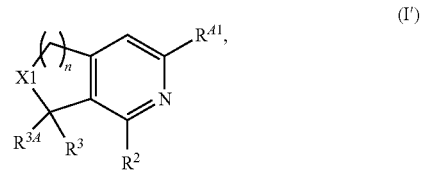

or a pharmaceutically acceptable salt thereof, wherein:
n is 1;
X1 is NR$^4$;
R$^{41}$ is hydrogen, halogen, C(=O)R$^1$, substituted or unsubstituted carbocyclyl, substituted or unsubstituted heteroaryl, —OR, —N(R$^4$)$_2$, —SR, —CN, —SCN, or —NO$_2$;
R$^1$ is hydrogen, substituted or unsubstituted alkyl, substituted or unsubstituted aryl, substituted or unsubstituted heteroaryl, —NH$_2$,

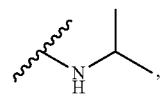 , 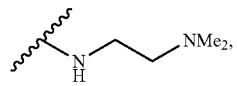

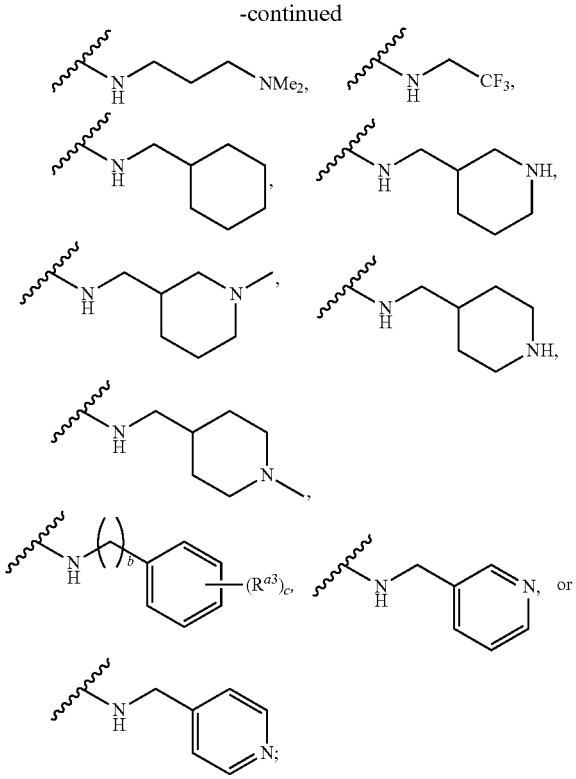

b is 0, 1, 2, 3, 4, 5, or 6;

c is 0, 1, 2, 3, 4, or 5;

$R^{a3}$ is independently substituted or unsubstituted alkyl, halogen, —$OR^{a4}$, —$N_3$, —$N(R^{a4})_2$, —$SR^{a4}$, —CN, —SCN, —$SO_2R^{a4}$, —$C(=O)R^{a4}$, $C(=O)OR^{a4}$, —$C(=O)N(R^{a4})_2$, or —$NO_2$;

$R^{a4}$ is independently hydrogen or substituted or unsubstituted $C_{1-6}$ alkyl;

R is hydrogen, substituted or unsubstituted alkyl, substituted or unsubstituted carbocyclyl, substituted or unsubstituted heterocyclyl, substituted or unsubstituted aryl, substituted or unsubstituted heteroaryl, or oxygen protecting group;

$R^2$ is of the formula:

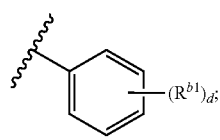

d is 0, 1, 2, 3, 4, or 5;

each instance of $R^{b1}$ is independently hydrogen, halogen, substituted or unsubstituted alkyl, substituted or unsubstituted heterocyclyl, substituted or unsubstituted 5-membered monocyclic heteroaryl, substituted or unsubstituted 9- to 10-membered bicyclic heteroaryl, —$OR^{b2}$, —$N_3$, —$N(R^{b3})_2$, —$SR^{b2}$, —CN, —SCN, —$SO_2R^{b2}$, $C(=O)R^{b2}$, $C(=O)OR^{b2}$, —$C(=O)N(R^{b3})_2$, or —$NO_2$;

$R^{b2}$ is hydrogen, or substituted or unsubstituted $C_{1-6}$ alkyl;

each instance of $R^{b3}$ is independently hydrogen, or substituted or unsubstituted $C_{1-6}$ alkyl;

$R^3$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^{3A}$ is hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$R^4$ is halogen, hydrogen, —$C(=O)R^{D2}$, —$C(=O)OR^D$, —$C(=O)N(R^{d1})_2$, substituted or unsubstituted alkyl, substituted or unsubstituted imine, substituted or unsubstituted thiocarbonyl, substituted or unsubstituted aryl, substituted or unsubstituted heteroaryl,

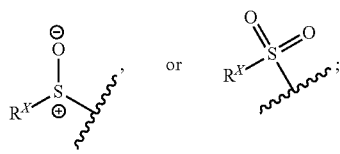

$R^{D2}$ is hydrogen or substituted or unsubstituted $C_{2-6}$ alkyl;

$R^D$ is hydrogen or substituted or unsubstituted $C_{1-6}$ alkyl;

each instance of $R^{d1}$ is independently hydrogen, substituted or unsubstituted $C_{1-6}$ alkyl, or nitrogen protecting group, or two instances of $R^{d1}$ are taken together with the intervening atoms to form a substituted or unsubstituted, heterocyclic ring;

$R^X$ is hydrogen, substituted or unsubstituted $C_{2-10}$ alkyl, substituted or unsubstituted carbocyclyl, substituted or unsubstituted heterocyclyl, substituted or unsubstituted aryl, or substituted or unsubstituted heteroaryl; and each instance of $R^A$ is independently hydrogen, substituted or unsubstituted acyl, substituted or unsubstituted alkyl, substituted or unsubstituted carbocyclyl, substituted or unsubstituted heterocyclyl, substituted or unsubstituted aryl, substituted or unsubstituted heteroaryl, or nitrogen protecting group, or optionally two $R^A$ are taken together with the intervening atoms to form substituted or unsubstituted heterocyclyl or substituted or unsubstituted heteroaryl;

wherein carbocyclyl is non-aromatic;

wherein the compound is not of the formula:

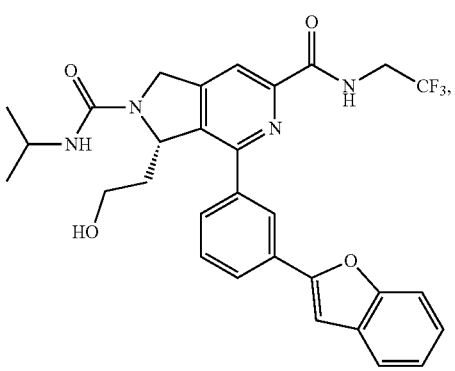

-continued

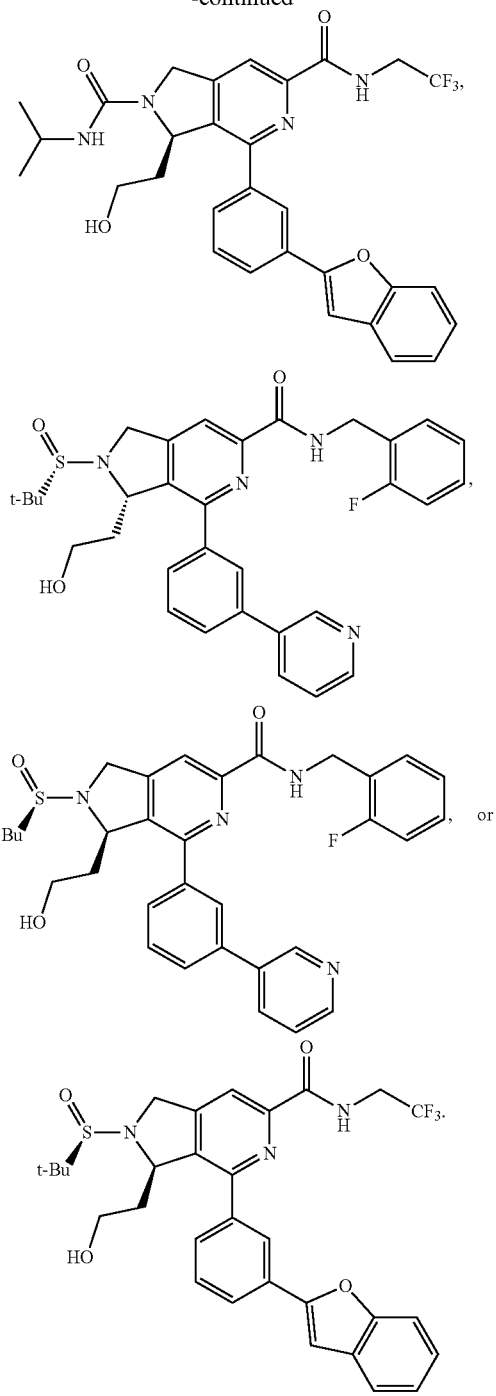

2. The compound of claim 1, or a pharmaceutically acceptable salt thereof, wherein the compound is of Formula (I):

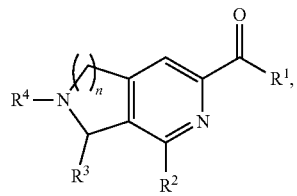

(I)

or a pharmaceutically acceptable salt thereof, wherein:

R³ is hydrogen, substituted or unsubstituted alkyl, substituted or unsubstituted aryl, or substituted or unsubstituted heteroaryl;

R⁴ is hydrogen, —C(=O)R$^{D2}$, —C(=O)OR$^D$, —C(=O)N(R$^{d1}$)$_2$, substituted or unsubstituted alkyl, substituted or unsubstituted imine, substituted or unsubstituted thiocarbonyl group, substituted or unsubstituted aryl, substituted or unsubstituted heteroaryl,

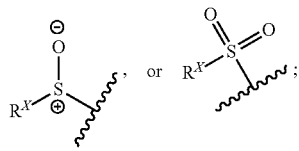

R$^{D2}$ is hydrogen or substituted or unsubstituted C$_{2-6}$ alkyl;
R$^D$ is hydrogen or substituted or unsubstituted C$_{1-6}$ alkyl; and each instance of R$^{d1}$ is independently hydrogen, substituted or unsubstituted C$_{1-6}$ alkyl, or nitrogen protecting group, or two instances of R$^{d1}$ are taken together with the intervening atoms to form a substituted or unsubstituted, heterocyclic ring.

3. The compound of claim 1, or a pharmaceutically acceptable salt thereof, wherein R$^{A1}$ is —C(=O)R¹.

4. The compound of claim 1, or a pharmaceutically acceptable salt thereof, wherein R$^{3A}$ is hydrogen.

5. The compound of claim 2, or a pharmaceutically acceptable salt thereof, wherein:
n is 1; and
R¹ is —NH₂,

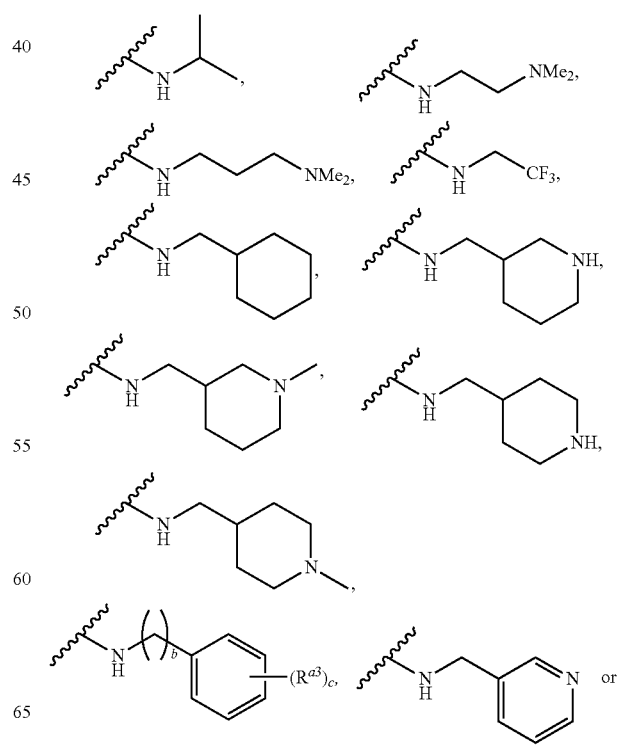

253

-continued

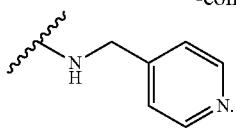

6. The compound of claim 2, or a pharmaceutically acceptable salt thereof, wherein R¹ is

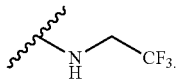

7. The compound of claim 1, or a pharmaceutically acceptable salt thereof, wherein R² is of the formula:

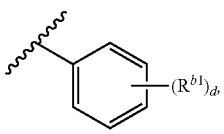

wherein:
d is 0, 1, 2, or 3; and
each instance of $R^{b1}$ is independently substituted or unsubstituted heterocyclyl, substituted or unsubstituted 5-membered monocyclic heteroaryl, or substituted or unsubstituted 9- to 10-membered bicyclic heteroaryl.

8. The compound of claim 1, or a pharmaceutically acceptable salt thereof, wherein R³ is hydrogen.

9. The compound of claim 1, or a pharmaceutically acceptable salt thereof, wherein R³ is of the formula:

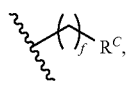

wherein:
f is 1, 2, 3, 4, 5, or 6;
$R^C$ is independently substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{c1}$, $-N(R^{c2})_2$, $-NR^{c2}C(=O)R^{c1}$, or $SR^{c1}$;
$R^{c1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or oxygen protecting group; and
each instance of $R^{c2}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl,

254 substituted or unsubstituted aryl, substituted or unsubstituted heteroaryl, or nitrogen protecting group, or two $R^{c2}$ are taken together with the intervening atoms to form substituted or unsubstituted heterocyclyl or substituted or unsubstituted heteroaryl.

10. The compound of claim 1, or a pharmaceutically acceptable salt thereof, wherein R⁴ is of the formula:

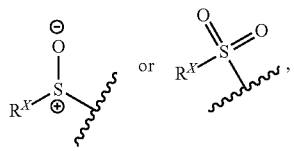

and $R^X$ is substituted or unsubstituted $C_{2-6}$ alkyl.

11. The compound of claim 1, or a pharmaceutically acceptable salt thereof, wherein R⁴ is of the formula: $-C(=O)R^{D2}$ or $-C(=O)OR^D$; $R^{D2}$ is hydrogen or substituted or unsubstituted $C_{2-6}$ alkyl; and $R^D$ is hydrogen or substituted or unsubstituted $C_{1-6}$ alkyl.

12. The compound of claim 1, or a pharmaceutically acceptable salt thereof, wherein R⁴ is of the formula: $-C(=O)N(R^{d1})_2$, and each instance of $R^{d1}$ is independently hydrogen, substituted or unsubstituted $C_{1-6}$ alkyl, or nitrogen protecting group, or two instances of $R^{d1}$ are taken together with the intervening atoms to form a substituted or unsubstituted, heterocyclic ring.

13. The compound of claim 1, or a pharmaceutically acceptable salt thereof, wherein R⁴ is hydrogen.

14. The compound of claim 1, wherein the compound is of the formula:

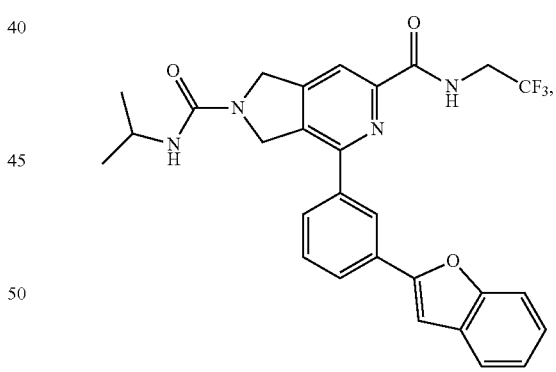

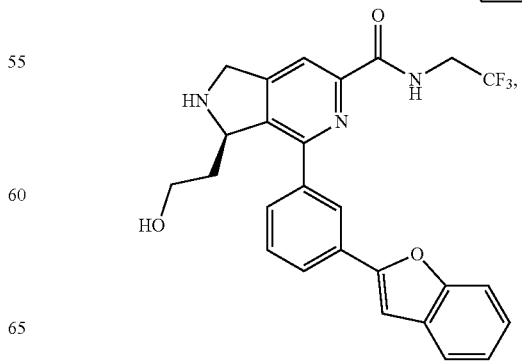

-continued

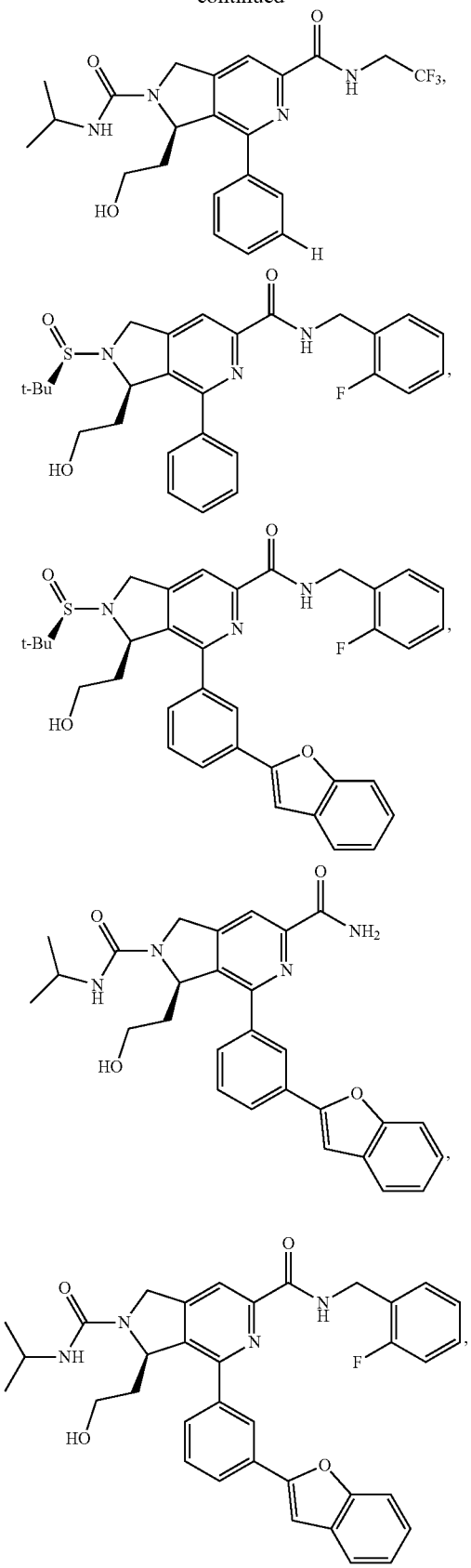

or a pharmaceutically acceptable salt thereof.

15. A pharmaceutical composition comprising a compound of claim 1, or a pharmaceutically acceptable salt thereof, and optionally a pharmaceutically acceptable excipient.

16. A method of treating a parasitic infectious disease in a subject in need thereof, the method comprising administering to the subject an effective amount of a compound of claim 1, a pharmaceutically acceptable salt thereof.

17. The compound of claim 1, or a pharmaceutically acceptable salt thereof, wherein $R^3$ is:

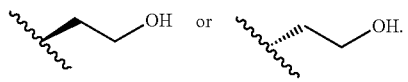

18. The compound of claim 10, or a pharmaceutically acceptable salt thereof, wherein $R^4$ is

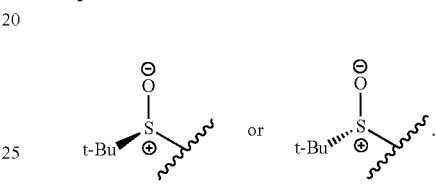

19. The compound of claim 1, or a pharmaceutically acceptable salt thereof, wherein $R^1$ is:

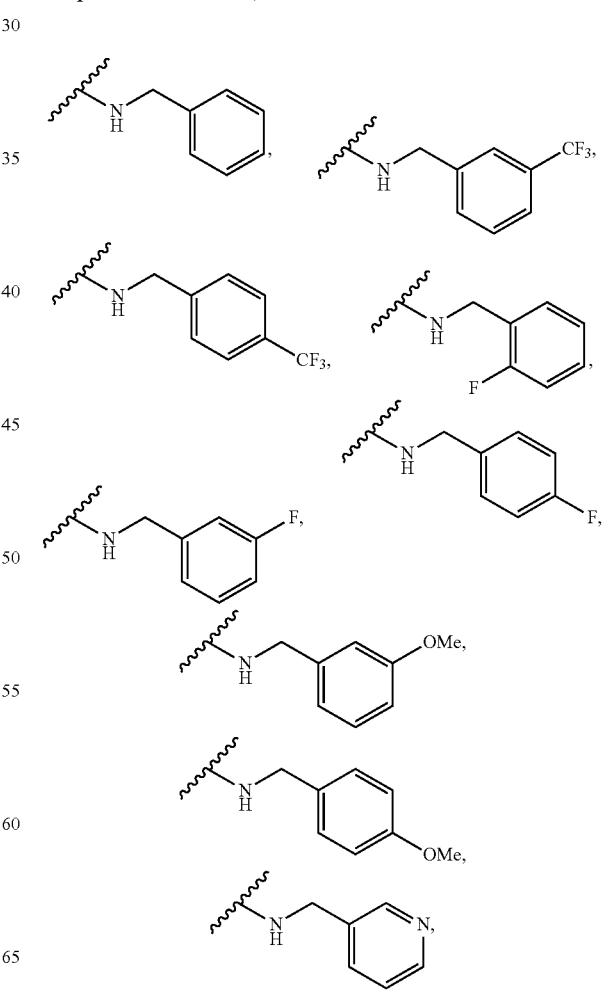

-continued
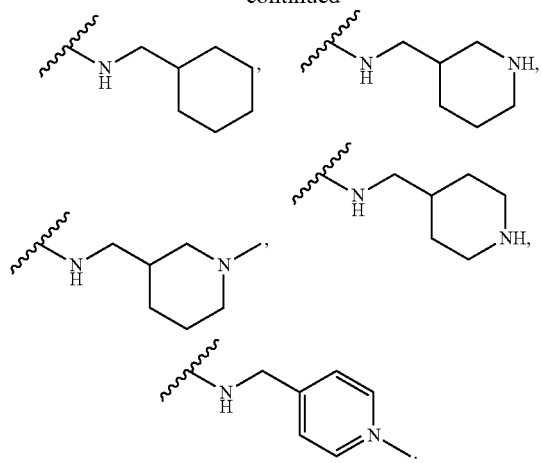
20. The compound of claim 1, or a pharmaceutically acceptable salt thereof, wherein R¹ is
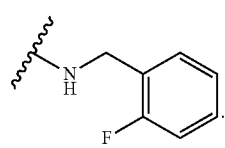 [SMILES: *NCc1ccccc1F]
21. A compound of the formula:
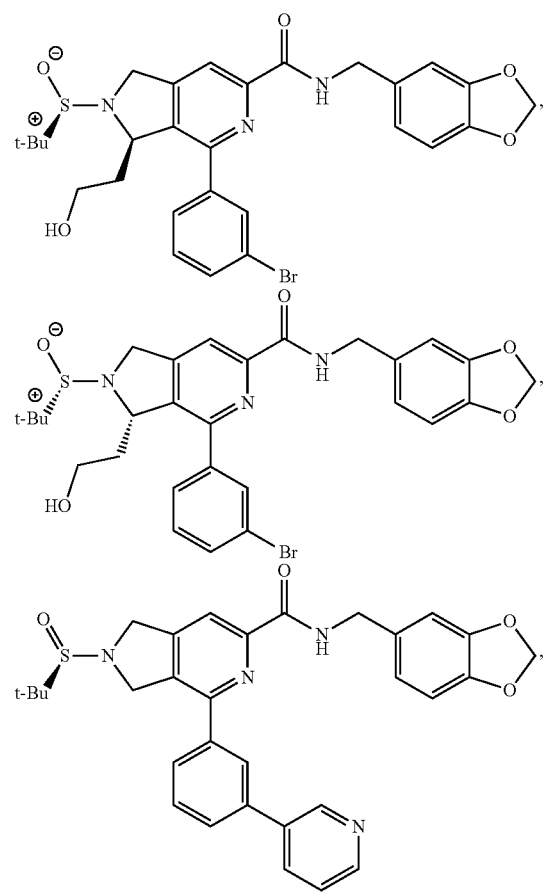
-continued
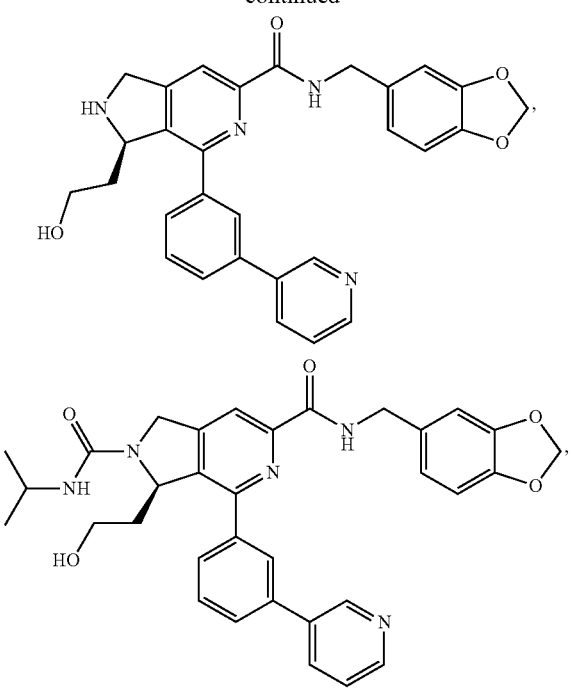

259

-continued

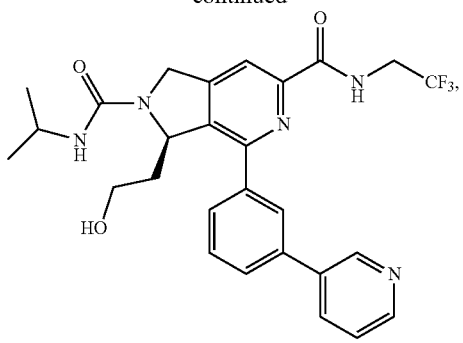

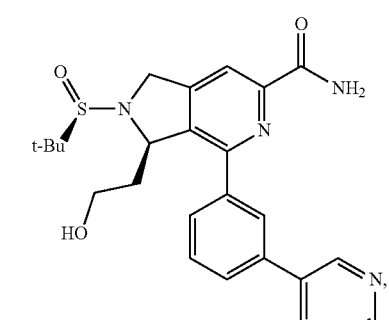

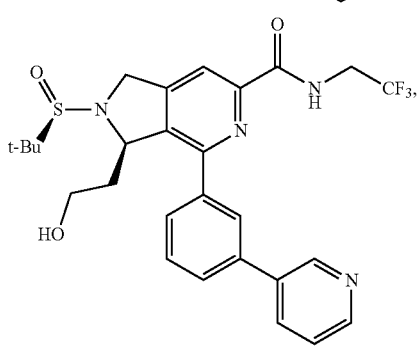

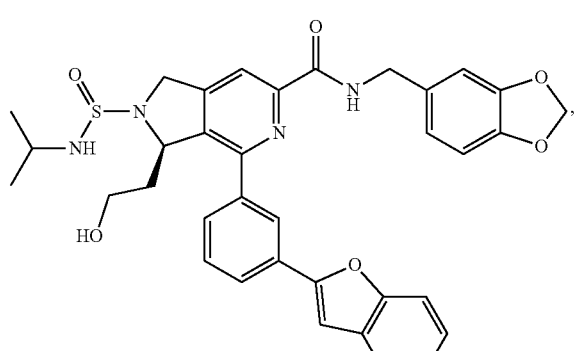

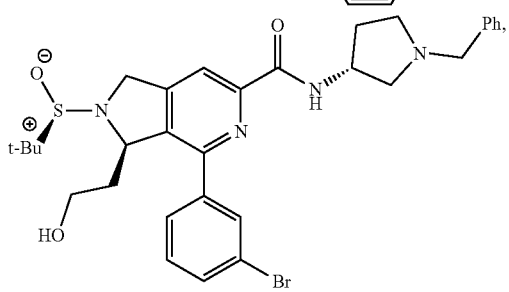

260

-continued

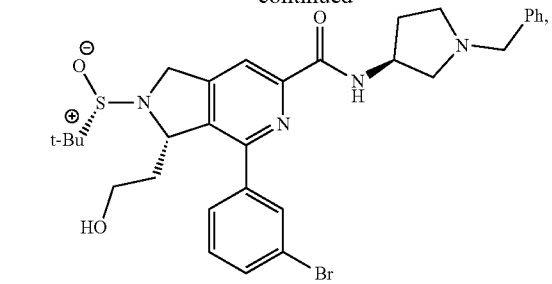

or a pharmaceutically acceptable salt thereof.

22. The compound of claim 1, or a pharmaceutically acceptable salt thereof, wherein $R^1$ is —NH$_2$.

23. The compound of claim 1, or a pharmaceutically acceptable salt thereof, wherein $R^2$ is of the formula:

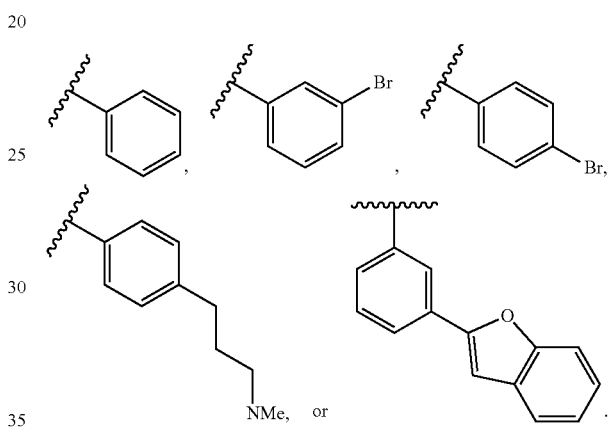

24. A pharmaceutical composition comprising a compound of claim 21, or a pharmaceutically acceptable salt thereof, and optionally a pharmaceutically acceptable excipient.

25. The compound of claim 1, or a pharmaceutically acceptable salt thereof, wherein $R^2$ is of the formula:

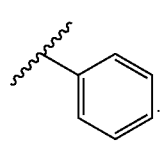

26. The compound of claim 1, or a pharmaceutically acceptable salt thereof, wherein $R^2$ is of the formula:

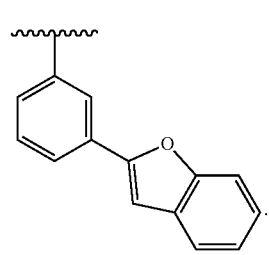 [SMILES: *c1cccc(-c2cc3ccccc3o2)c1]

27. The compound of claim 1, or a pharmaceutically acceptable salt thereof, wherein $R^4$ is

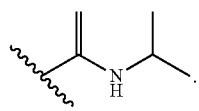 [SMILES: *C(=C)NC(C)C]
28. The compound of claim 1, or a pharmaceutically acceptable salt thereof, wherein $R^3$ is:
29. The compound of claim 1, or a pharmaceutically acceptable salt thereof, wherein X1 is —$NR^4$—;
$R^4$ is hydrogen, —C(=O)N($R^{d1}$)$_2$,
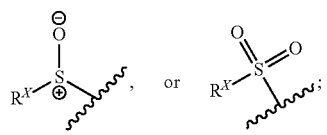
$R^x$ is substituted or unsubstituted $C_{2-6}$ alkyl; and
and each instance of $R^{d1}$ is independently hydrogen or substituted or unsubstituted $C_{1-6}$ alkyl.
* * * * *

UNITED STATES PATENT AND TRADEMARK OFFICE
CERTIFICATE OF CORRECTION

PATENT NO. : 11,180,492 B2  
APPLICATION NO. : 16/070137  
DATED : November 23, 2021  
INVENTOR(S) : Derek Shieh Tan et al.

Page 1 of 3

It is certified that error appears in the above-identified patent and that said Letters Patent is hereby corrected as shown below:

In the Claims

In Claim 19, at Column 257, Lines 14-19, the formula:

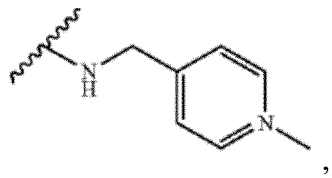

Should be replaced with the formula:

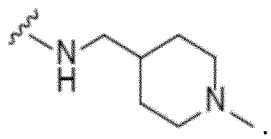

In Claim 21, at Column 257, in Lines 33-43, the formula:

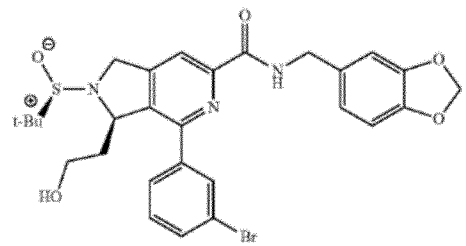

Should be replaced with the formula:

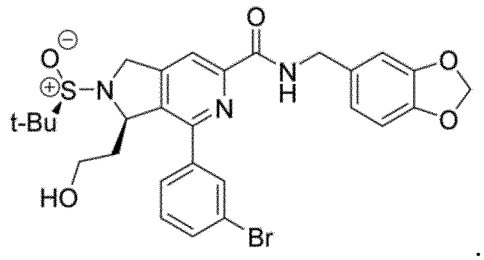

Signed and Sealed this  
Fifteenth Day of March, 2022

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,180,492 B2

In Claim 21, at Column 257, in Lines 44-53, the formula:

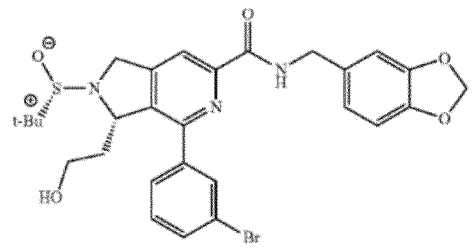

Should be replaced with the formula:

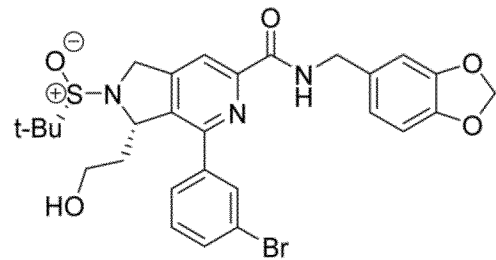

.

In Claim 21, at Column 259, in Lines 42-55, the formula:

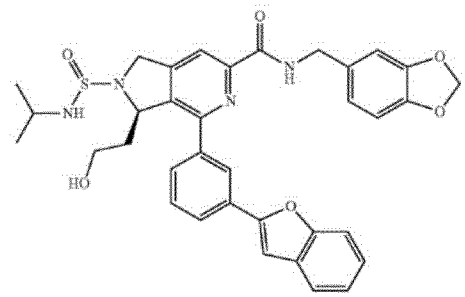

Should be replaced with the formula:

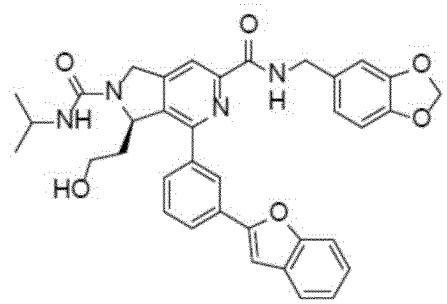

.

In Claim 21, at Column 259, in Lines 56-66, the formula:

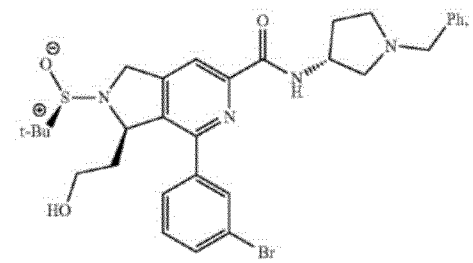

,

CERTIFICATE OF CORRECTION (continued)
U.S. Pat. No. 11,180,492 B2

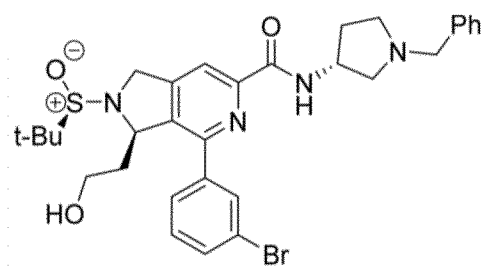

Should be replaced with the formula:

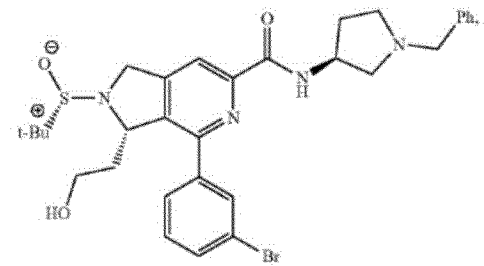

In Claim 21, at Column 260, in Lines 2-12, the formula:

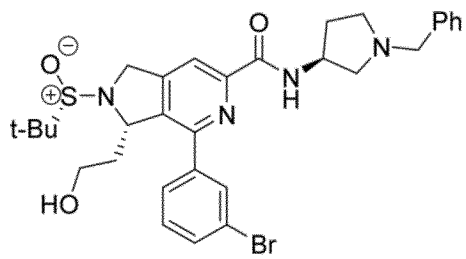

Should be replaced with the formula:

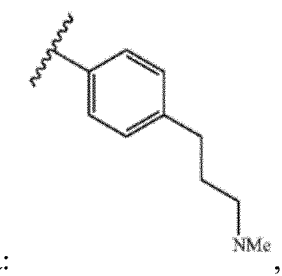

In Claim 23, at Column 260, in Lines 26-35, the formula:

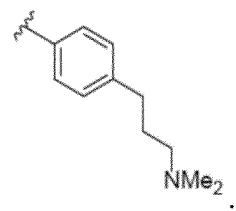

Should be replaced with the formula:

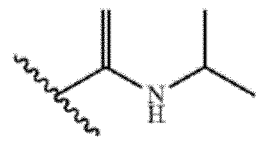

In Claim 27, at Column 261, in Lines 1-5, the formula:

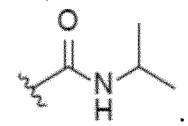

Should be replaced with the formula: